(12) United States Patent
Newberry et al.

(10) Patent No.: US 10,952,682 B2
(45) Date of Patent: *Mar. 23, 2021

(54) SYSTEM AND METHOD OF A BIOSENSOR FOR DETECTION OF HEALTH PARAMETERS

(71) Applicant: Sanmina Corporation, San Jose, CA (US)

(72) Inventors: Robert Steven Newberry, New Hope, AL (US); Matthew Rodencal, Huntsville, AL (US)

(73) Assignee: SANMINA CORPORATION, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/779,453

(22) Filed: Jan. 31, 2020

(65) Prior Publication Data

US 2020/0237317 A1 Jul. 30, 2020

Related U.S. Application Data

(63) Continuation-in-part of application No. 16/711,038, filed on Dec. 11, 2019, and a continuation-in-part of
(Continued)

(51) Int. Cl.
*A61B 5/1455* (2006.01)
*A61B 5/00* (2006.01)
(Continued)

(52) U.S. Cl.
CPC .......... *A61B 5/7275* (2013.01); *A61B 5/0002* (2013.01); *A61B 5/0022* (2013.01); *A61B 5/01* (2013.01); *A61B 5/02416* (2013.01); *A61B 5/1455* (2013.01); *A61B 5/14532* (2013.01); *A61B 5/14551* (2013.01); *A61B 5/4845* (2013.01); *A61B 5/6817* (2013.01);
(Continued)

(58) Field of Classification Search
None
See application file for complete search history.

(56) References Cited

U.S. PATENT DOCUMENTS

| 4,913,150 A | 4/1990 | Cheung et al. |
| 5,115,133 A | 5/1992 | Knudson |

(Continued)

FOREIGN PATENT DOCUMENTS

| CN | 102609627 A | 7/2012 |
| EP | 2017001250 A1 | 1/2017 |

(Continued)

*Primary Examiner* — Marjan Fardanesh
(74) *Attorney, Agent, or Firm* — Loza & Loza LLP; Jessica Smith

(57) ABSTRACT

A photoplethysmography (PPG) circuit obtains PPG signals at a plurality of wavelengths of light reflected from tissue of a user. A processing device generates parameters using the PPG signals to determine a glucose level in blood flow of the user. The parameters include one or more ratio values obtained using the plurality of PPG signals; a phase delay between the plurality of PPG signals; a correlation of phase shape between the plurality of PPG signals or a periodicity of one or more of the plurality of PPG signals.

20 Claims, 55 Drawing Sheets

Related U.S. Application Data application No. 16/433,947, filed on Jun. 6, 2019, now Pat. No. 10,736,580, and a continuation-in-part of application No. 16/391,175, filed on Apr. 22, 2019, and a continuation-in-part of application No. 16/270,268, filed on Feb. 7, 2019, and a continuation-in-part of application No. 16/239,417, filed on Jan. 3, 2019, and a continuation-in-part of application No. 16/208,358, filed on Dec. 3, 2018, and a continuation-in-part of application No. 16/183,354, filed on Nov. 7, 2018, now Pat. No. 10,744,262, and a continuation-in-part of application No. 16/172,661, filed on Oct. 26, 2018, now Pat. No. 10,744,261, and a continuation-in-part of application No. 15/958,620, filed on Apr. 20, 2018, now Pat. No. 10,524,720, and a continuation-in-part of application No. 15/898,580, filed on Feb. 17, 2018, said application No. 16/208,358 is a continuation of application No. 15/859,147, filed on Dec. 29, 2017, now Pat. No. 10,194,871, said application No. 16/270,268 is a continuation of application No. 15/811,479, filed on Nov. 13, 2017, now Pat. No. 10,238,346, said application No. 16/711,038 is a continuation of application No. 15/718,721, filed on Sep. 28, 2017, now Pat. No. 10,517,515, said application No. 15/958,620 is a continuation of application No. 15/680,991, filed on Aug. 18, 2017, now Pat. No. 9,968,289, said application No. 15/718,721 is a continuation of application No. 15/622,941, filed on Jun. 14, 2017, now Pat. No. 9,788,767, said application No. 15/811,479 is a continuation-in-part of application No. 15/490,813, filed on Apr. 18, 2017, now Pat. No. 9,980,676, said application No. 16/183,354 is a continuation of application No. 15/485,816, filed on Apr. 12, 2017, now Pat. No. 10,155,087, application No. 16/779,453, which is a continuation-in-part of application No. 15/404,117, filed on Jan. 11, 2017, and a continuation-in-part of application No. 15/400,916, filed on Jan. 6, 2017, now Pat. No. 10,750,981, said application No. 15/485,816 is a continuation of application No. 15/276,760, filed on Sep. 26, 2016, now Pat. No. 9,636,457, said application No. 15/490,813 is a continuation of application No. 15/275,388, filed on Sep. 24, 2016, now Pat. No. 9,642,578, said application No. 16/391,175 is a continuation of application No. 14/866,500, filed on Sep. 25, 2015, now Pat. No. 10,321,860.

(60) Provisional application No. 62/935,589, filed on Nov. 14, 2019, provisional application No. 62/675,151, filed on May 22, 2018, provisional application No. 62/613,388, filed on Jan. 3, 2018, provisional application No. 62/577,707, filed on Oct. 26, 2017, provisional application No. 62/463,104, filed on Feb. 24, 2017, provisional application No. 62/383,313, filed on Sep. 2, 2016, provisional application No. 62/312,614, filed on Mar. 24, 2016, provisional application No. 62/307,375, filed on Mar. 11, 2016, provisional application No. 62/194,264, filed on Jul. 19, 2015.

(51) Int. Cl.

| | | |
|---|---|---|
| *A61B 5/01* | (2006.01) | |
| *A61B 5/145* | (2006.01) | |
| *A61B 5/024* | (2006.01) | |
| *G16H 40/63* | (2018.01) | |

(52) U.S. Cl.
CPC ............ *A61B 5/6893* (2013.01); *A61B 5/743* (2013.01); *G16H 40/63* (2018.01); *A61B 5/681* (2013.01); *A61B 5/6826* (2013.01); *A61B 5/7225* (2013.01); *A61B 2560/0223* (2013.01)

(56) References Cited

U.S. PATENT DOCUMENTS

| | | |
|---|---|---|
| 5,269,310 A | 12/1993 | Jones et al. |
| 5,358,703 A | 10/1994 | Lai |
| 5,515,847 A | 5/1996 | Braig et al. |
| 5,673,692 A | 10/1997 | Schulze et al. |
| 5,823,966 A | 10/1998 | Buchert |
| 5,947,911 A | 9/1999 | Wong et al. |
| 5,983,121 A | 11/1999 | Tsuchiya |
| 6,087,087 A | 7/2000 | Yonetani et al. |
| 6,280,390 B1 | 8/2001 | Akselrod et al. |
| 6,285,896 B1 | 9/2001 | Tobler et al. |
| 6,305,804 B1 | 10/2001 | Rice et al. |
| 6,537,225 B1 | 3/2003 | Mills |
| 6,694,180 B1 | 2/2004 | Boesen |
| 6,719,705 B2 | 4/2004 | Mills |
| 6,819,950 B2 | 11/2004 | Mills |
| 6,921,367 B2 | 7/2005 | Mills |
| 6,985,763 B2 | 1/2006 | Boas et al. |
| 7,154,592 B2 | 12/2006 | Reynolds et al. |
| 7,167,736 B2 | 1/2007 | Winther |
| 7,171,251 B2 | 1/2007 | Sarussi et al. |
| 7,179,228 B2 | 2/2007 | Banet |
| 7,209,775 B2 | 4/2007 | Bae et al. |
| 7,291,497 B2 | 11/2007 | Holmes et al. |
| 7,371,562 B2 | 5/2008 | Cunningham et al. |
| 7,608,045 B2 | 10/2009 | Mills |
| 7,647,083 B2 | 1/2010 | Al-Ali et al. |
| 7,761,127 B2 | 7/2010 | Al-Ali et al. |
| 7,763,472 B2 | 7/2010 | Doctor et al. |
| 7,764,982 B2 | 7/2010 | Dalke et al. |
| 7,941,199 B2 | 5/2011 | Kiani |
| 8,172,459 B2 * | 5/2012 | Abreu ................ A61B 5/01 374/208 |
| 8,224,411 B2 | 7/2012 | Al-Ali et al. |
| 8,255,027 B2 | 8/2012 | Al-Ali et al. |
| 8,328,420 B2 | 12/2012 | Abreu |
| 8,385,996 B2 | 2/2013 | Smith et al. |
| 8,401,605 B2 | 3/2013 | Huiku |
| 8,483,787 B2 | 7/2013 | Al-Ali et al. |
| 8,494,507 B1 | 7/2013 | Tedesco et al. |
| 8,597,274 B2 | 12/2013 | Sloan et al. |
| 8,652,040 B2 | 2/2014 | Leboeuf et al. |
| 8,676,284 B2 | 3/2014 | He |
| 8,730,047 B2 | 5/2014 | Ridder et al. |
| 8,868,149 B2 | 10/2014 | Eisen et al. |
| 8,888,701 B2 | 11/2014 | Leboeuf et al. |
| 8,906,693 B2 | 12/2014 | Schultz et al. |
| 8,923,918 B2 | 12/2014 | Kreger et al. |
| 8,961,932 B2 | 2/2015 | Silverman |
| 9,022,973 B2 | 5/2015 | Sexton et al. |
| 9,131,882 B2 | 9/2015 | Al-Ali et al. |
| 9,149,216 B2 | 10/2015 | Eisen et al. |
| 9,149,646 B2 | 10/2015 | Keswarpu et al. |
| 9,387,033 B2 | 7/2016 | Yodfat et al. |
| 9,442,092 B2 | 9/2016 | Lane |
| 9,521,970 B2 | 12/2016 | Hoppe et al. |
| 9,554,738 B1 | 1/2017 | Gulati et al. |
| 9,642,578 B2 | 5/2017 | Newberry |
| 9,668,701 B2 | 6/2017 | Maarek |
| 9,713,428 B2 | 7/2017 | Chon et al. |
| 9,739,663 B2 | 8/2017 | Halder et al. |
| 9,820,656 B2 | 11/2017 | Olivier |
| 9,839,381 B1 | 12/2017 | Weber et al. |
| 9,924,895 B2 | 3/2018 | Rawicz et al. |
| 9,949,675 B2 | 4/2018 | Miller |
| 9,999,355 B2 | 6/2018 | Kirenko |
| 10,028,682 B2 | 7/2018 | Thiele |
| D824,937 S | 8/2018 | Sparandara et al. |
| 10,099,554 B2 | 10/2018 | Steeg et al. |

(56) References Cited

U.S. PATENT DOCUMENTS

| | | | |
|---|---|---|---|
| 10,130,285 B1 | 11/2018 | Singamsetty et al. | |
| 10,153,796 B2 | 12/2018 | Fung et al. | |
| 10,181,021 B2 | 1/2019 | Venkatraman et al. | |
| 10,206,619 B1 | 2/2019 | Lee et al. | |
| 10,215,698 B2 | 2/2019 | Han et al. | |
| 10,227,063 B2 | 3/2019 | Abreu | |
| 10,232,156 B2 | 3/2019 | Netzel et al. | |
| 10,278,591 B2 | 5/2019 | Gil | |
| D850,316 S | 6/2019 | Ennis et al. | |
| 10,314,500 B2 | 6/2019 | Olivier | |
| 10,322,728 B1 | 6/2019 | Porikli et al. | |
| 10,342,495 B2 | 7/2019 | Melkoniemi et al. | |
| 10,349,847 B2 | 7/2019 | Kwon et al. | |
| 10,420,470 B2 | 9/2019 | Kwon et al. | |
| 10,420,491 B2 | 9/2019 | Rajan et al. | |
| 10,433,726 B2 | 10/2019 | Ramesh et al. | |
| 10,433,738 B2 | 10/2019 | Thomas et al. | |
| 10,433,739 B2 | 10/2019 | Weekly et al. | |
| 10,463,283 B2 | 11/2019 | Ferber et al. | |
| 2002/0049389 A1 | 4/2002 | Abreu | |
| 2003/0229276 A1* | 12/2003 | Sarussi | A61B 5/0261 600/322 |
| 2004/0078219 A1 | 4/2004 | Kaylor et al. | |
| 2004/0100376 A1 | 5/2004 | Lye et al. | |
| 2004/0157341 A1 | 8/2004 | Reynolds et al. | |
| 2005/0101841 A9 | 5/2005 | Kaylor et al. | |
| 2005/0209516 A1 | 9/2005 | Fraden | |
| 2005/0228244 A1 | 10/2005 | Banet | |
| 2005/0228299 A1 | 10/2005 | Banet | |
| 2005/0245831 A1 | 11/2005 | Banet | |
| 2006/0009698 A1 | 1/2006 | Banet | |
| 2006/0094942 A1 | 5/2006 | Winther | |
| 2006/0287589 A1 | 12/2006 | Wobermin et al. | |
| 2007/0202605 A1 | 8/2007 | Doctor et al. | |
| 2007/0203405 A1 | 8/2007 | Shimomura | |
| 2007/0260132 A1 | 11/2007 | Sterling | |
| 2008/0146890 A1 | 6/2008 | Leboeuf et al. | |
| 2008/0165017 A1 | 7/2008 | Schwartz | |
| 2008/0208019 A1 | 8/2008 | Nitzan | |
| 2008/0241199 A1 | 10/2008 | Silverman | |
| 2009/0043178 A1 | 2/2009 | Belotserkovsky | |
| 2009/0156988 A1 | 6/2009 | Ferren et al. | |
| 2009/0187167 A1 | 7/2009 | Sexton et al. | |
| 2009/0287120 A1 | 11/2009 | Ferren et al. | |
| 2010/0049020 A1 | 2/2010 | Dalke et al. | |
| 2010/0191080 A1 | 7/2010 | Mills | |
| 2010/0274101 A1 | 10/2010 | Lin et al. | |
| 2010/0331631 A1 | 12/2010 | Maclaughlin | |
| 2011/0071376 A1* | 3/2011 | McKenna | G16H 40/40 600/336 |
| 2011/0082355 A1 | 4/2011 | Eisen et al. | |
| 2011/0106050 A1 | 5/2011 | Yodfat et al. | |
| 2011/0137141 A1 | 6/2011 | Razoumov et al. | |
| 2011/0160697 A1 | 6/2011 | Yodfat et al. | |
| 2011/0166553 A1 | 7/2011 | Holmes et al. | |
| 2011/0224518 A1 | 9/2011 | Tindi et al. | |
| 2011/0237464 A1 | 9/2011 | Cunningham et al. | |
| 2011/0275978 A1 | 11/2011 | Hyde et al. | |
| 2012/0010683 A1 | 1/2012 | Keswarpu et al. | |
| 2012/0029363 A1 | 2/2012 | Lund | |
| 2012/0095302 A1 | 4/2012 | Adhikari | |
| 2012/0131507 A1 | 5/2012 | Sparandara et al. | |
| 2012/0136054 A1 | 5/2012 | Schultz et al. | |
| 2012/0156933 A1 | 6/2012 | Kreger et al. | |
| 2012/0203077 A1 | 8/2012 | He et al. | |
| 2012/0238844 A1 | 9/2012 | Grata et al. | |
| 2012/0330126 A1 | 12/2012 | Hoppe et al. | |
| 2013/0030259 A1 | 1/2013 | Thomsen et al. | |
| 2013/0060098 A1 | 3/2013 | Thomsen et al. | |
| 2013/0066176 A1 | 3/2013 | Addison et al. | |
| 2013/0110311 A1 | 5/2013 | Ver Steeg et al. | |
| 2013/0310669 A1 | 11/2013 | Nitzan | |
| 2014/0046160 A1 | 2/2014 | Terashima et al. | |
| 2014/0100432 A1 | 4/2014 | Golda et al. | |
| 2014/0112940 A1 | 4/2014 | Lane | |
| 2014/0194342 A1 | 7/2014 | Zhang et al. | |
| 2014/0243648 A1 | 8/2014 | Dubielczyk | |
| 2014/0253709 A1 | 9/2014 | Bresch et al. | |
| 2014/0275852 A1 | 9/2014 | Hong et al. | |
| 2014/0297313 A1 | 10/2014 | Condurso et al. | |
| 2014/0316226 A1 | 10/2014 | Ferber et al. | |
| 2015/0066238 A1 | 3/2015 | Todd et al. | |
| 2015/0088007 A1 | 3/2015 | Bardy et al. | |
| 2015/0094914 A1 | 4/2015 | Abreu | |
| 2015/0105638 A1 | 4/2015 | Eisen et al. | |
| 2015/0109617 A1 | 4/2015 | Gilbert et al. | |
| 2015/0148622 A1 | 5/2015 | Moyer et al. | |
| 2015/0148635 A1 | 5/2015 | Benaron | |
| 2015/0150453 A1 | 6/2015 | Abreu | |
| 2015/0182172 A1 | 7/2015 | Shelley et al. | |
| 2015/0229341 A1 | 8/2015 | Fung et al. | |
| 2015/0250404 A1 | 9/2015 | Maarek | |
| 2015/0282747 A1 | 10/2015 | Thiele | |
| 2015/0366471 A1 | 12/2015 | Leboeuf et al. | |
| 2016/0018257 A1 | 1/2016 | Mirov et al. | |
| 2016/0058308 A1 | 3/2016 | Robinson | |
| 2016/0058347 A1 | 3/2016 | Reichgott et al. | |
| 2016/0066863 A1 | 3/2016 | Thaveeprungsrporn et al. | |
| 2016/0100781 A1 | 4/2016 | Bechtel et al. | |
| 2016/0262707 A1 | 9/2016 | Devries | |
| 2016/0367154 A1 | 12/2016 | Gladshtein et al. | |
| 2017/0027521 A1 | 2/2017 | Geva et al. | |
| 2017/0050518 A1 | 2/2017 | Steeg et al. | |
| 2017/0071550 A1 | 3/2017 | Newberry | |
| 2017/0091436 A1 | 3/2017 | Cao et al. | |
| 2017/0172477 A1 | 6/2017 | Adusumilli et al. | |
| 2017/0215811 A1 | 8/2017 | Newberry | |
| 2017/0256110 A1 | 9/2017 | Divincent et al. | |
| 2017/0347894 A1 | 12/2017 | Bhushan et al. | |
| 2017/0347899 A1 | 12/2017 | Bhushan et al. | |
| 2018/0117291 A1 | 5/2018 | Netzel et al. | |
| 2018/0140210 A1 | 5/2018 | Jelfs et al. | |
| 2018/0140237 A1 | 5/2018 | Rajan et al. | |
| 2018/0177416 A1 | 6/2018 | Church et al. | |
| 2018/0177440 A1 | 6/2018 | Jelfs et al. | |
| 2018/0200433 A1 | 7/2018 | Cirit | |
| 2018/0264242 A1 | 9/2018 | Hoffman et al. | |
| 2018/0353137 A1 | 12/2018 | Balajadia et al. | |
| 2018/0358119 A1 | 12/2018 | Bhushan et al. | |
| 2019/0046039 A1 | 2/2019 | Ramesh et al. | |
| 2019/0050622 A1 | 2/2019 | Cabibihan et al. | |
| 2019/0086331 A1 | 3/2019 | Han | |
| 2019/0099114 A1 | 4/2019 | Mouradian et al. | |
| 2019/0110745 A1 | 4/2019 | Linnes et al. | |
| 2019/0125963 A1 | 5/2019 | Mou et al. | |
| 2019/0125964 A1 | 5/2019 | Mou et al. | |
| 2019/0133471 A1 | 5/2019 | Olson et al. | |
| 2019/0192085 A1 | 6/2019 | Krishna et al. | |
| 2019/0192086 A1 | 6/2019 | Krishna et al. | |
| 2019/0251238 A1 | 8/2019 | Venkatraman et al. | |
| 2019/0358387 A1 | 11/2019 | Elbadry et al. | |

FOREIGN PATENT DOCUMENTS

| | | |
|---|---|---|
| EP | 3488776 A1 | 5/2019 |
| WO | 2004047630 A1 | 6/2004 |
| WO | 2007013054 A1 | 2/2007 |
| WO | 2008006150 A1 | 1/2008 |
| WO | 2010128852 A3 | 11/2010 |
| WO | 2010147968 A1 | 12/2010 |
| WO | 2012108895 A1 | 8/2012 |
| WO | 2013052318 A1 | 4/2013 |
| WO | 2013127564 A1 | 9/2013 |
| WO | 2014163583 A1 | 10/2014 |
| WO | 2015143197 A1 | 9/2015 |
| WO | 2015200148 A1 | 12/2015 |
| WO | 2017001249 A1 | 1/2017 |
| WO | 2018206875 A1 | 11/2018 |
| WO | 2019030700 A1 | 2/2019 |
| WO | 2019118053 A1 | 6/2019 |

* cited by examiner

SYSTEM AND METHOD OF A BIOSENSOR FOR DETECTION OF HEALTH PARAMETERS

PRIOR APPLICATIONS

This application claims priority under 35 U.S.C. § 119 to U.S. Provisional Application No. 62/935,589 entitled, "SYSTEM AND METHOD OF A BIOSENSOR FOR DETECTION OF HEALTH PARAMETERS," filed Nov. 14, 2019, and hereby expressly incorporated by reference herein.

The present application claims priority under 35 U.S.C. § 120 as a continuation in part to U.S. patent application Ser. No. 16/433,947 entitled, "SYSTEM AND METHOD OF A BIOSENSOR FOR DETECTION OF MICROVASCULAR RESPONSES," filed Jun. 6, 2019, and hereby expressly incorporated by reference herein, The present application claims priority under 35 U.S.C. § 120 as a continuation in part to U.S. patent application Ser. No. 16/172,661 entitled, "SYSTEM AND METHOD OF A BIOSENSOR FOR DETECTION OF VASODILATION," filed Oct. 26, 2018, and hereby expressly incorporated by reference herein, which claims priority under 35 U.S.C. § 119(e) to:

U.S. Provisional Application No. 62/675,151 entitled, "SYSTEM AND METHOD OF A BIOSENSOR FOR DETECTION OF VASODILATION," filed May 22, 2018, and hereby expressly incorporated by reference herein;

U.S. Provisional Application No. 62/577,707 entitled, "SYSTEM AND METHOD FOR HEALTH MONITORING OF AN ANIMAL USING A MULTI-BAND BIOSENSOR," filed Oct. 26, 2017, and hereby expressly incorporated by reference herein; and U.S. Provisional Application No. 62/613,388 entitled, "SYSTEM AND METHOD FOR INFECTION DISCRIMINATION USING PPG TECHNOLOGY," filed Jan. 3, 2018, and hereby expressly incorporated by reference herein.

The present application claims priority under 35 U.S.C. § 120 as a continuation in part to U.S. patent application Ser. No. 15/898,580 entitled, "SYSTEM AND METHOD FOR OBTAINING HEALTH DATA USING A NEURAL NETWORK," filed Feb. 17, 2018, and hereby expressly incorporated by reference herein.

The present application claims priority under 35 U.S.C. § 120 as a continuation in part to U.S. patent application Ser. No. 16/239,417 entitled, "SYSTEM AND METHOD FOR MONITORING BLOOD CELL LEVELS IN BLOOD FLOW USING PPG TECHNOLOGY," filed Jan. 3, 2019, and hereby expressly incorporated by reference herein, which claims priority under 35 U.S.C. § 119(e) to U.S. Provisional Application No. 62/613,388 entitled, "SYSTEM AND METHOD FOR INFECTION DISCRIMINATION USING PPG TECHNOLOGY," filed Jan. 3, 2018, and hereby expressly incorporated by reference herein.

The present application claims priority under 35 U.S.C. § 120 as a continuation in part to U.S. patent application Ser. No. 16/208,358 entitled, "VEHICULAR HEALTH MONITORING SYSTEM AND METHOD," filed Dec. 3, 2018 which claims priority as a continuation to U.S. patent application Ser. No. 15/859,147 entitled, "VEHICULAR HEALTH MONITORING SYSTEM AND METHOD," filed Dec. 29, 2017, now U.S. Pat. No. 10,194,871 issued Feb. 5, 2019 and both of which are hereby expressly incorporated by reference herein.

The present application claims priority under 35 U.S.C. § 120 as a continuation in part application to U.S. Utility application Ser. No. 15/958,620 entitled, "SYSTEM AND METHOD FOR DETECTING A HEALTH CONDITION USING AN OPTICAL SENSOR," filed Apr. 20, 2018, now U.S. Pat. No. 10,524,720 issued Jan. 7, 2020 and hereby expressly incorporated by reference herein which claims priority under 35 U.S.C. § 120 as a continuation application to U.S. Utility application Ser. No. 15/680,991 entitled, "SYSTEM AND METHOD FOR DETECTING A SEPSIS CONDITION," filed Aug. 18, 2017, now U.S. Pat. No. 9,968,289 issued May 15, 2018 and hereby expressly incorporated by reference herein.

The present application claims priority under 35 U.S.C. § 120 as a continuation in part application to U.S. patent application Ser. No. 16/711,038 entitled, "SYSTEM AND METHOD FOR MONITORING NITRIC OXIDE LEVELS USING A NON-INVASIVE, MULTI-BAND BIOSENSOR," filed Dec. 11, 2019 and hereby expressly incorporated by reference herein, which claims priority under 35 U.S.C. § 120 as a continuation to U.S. patent application Ser. No. 15/718,721 entitled, "SYSTEM AND METHOD FOR MONITORING NITRIC OXIDE LEVELS USING A NON-INVASIVE, MULTI-BAND BIOSENSOR," filed Sep. 28, 2017, now U.S. patent Ser. No. 10/517,515 issued Dec. 31, 2019 and hereby expressly incorporated by reference herein, which claims priority as a continuation application to U.S. Utility application Ser. No. 15/622,941 entitled, "SYSTEM AND METHOD FOR MONITORING NITRIC OXIDE LEVELS USING A NON-INVASIVE, MULTI-BAND BIOSENSOR," filed Jun. 14, 2017, now U.S. Pat. No. 9,788,767 issued Oct. 17, 2017, and hereby expressly incorporated by reference herein, which claims priority under 35 U.S.C. § 119 to U.S. Provisional Application No. 62/463,104 entitled, "SYSTEM AND METHOD FOR MONITORING NITRIC OXIDE LEVELS USING A NON-INVASIVE, MULTI-BAND BIOSENSOR," filed Feb. 24, 2017, and hereby expressly incorporated by reference herein.

The present application claims priority under 35 U.S.C. § 120 as a continuation in part application to U.S. patent application Ser. No. 15/404,117 entitled, "SYSTEM AND METHOD FOR HEALTH MONITORING INCLUDING A USER DEVICE AND BIOSENSOR," filed Jan. 11, 2017 and hereby expressly incorporated by reference herein.

The present application claims priority under 35 U.S.C. § 120 as a continuation in part application to U.S. patent application Ser. No. 16/183,354 entitled, "SYSTEM AND METHOD FOR HEALTH MONITORING BY AN EAR PIECE," filed Nov. 7, 2018 and hereby expressly incorporated by reference herein, which claims priority under 35 U.S.C. § 120 as a continuation application to U.S. patent application Ser. No. 15/485,816 entitled, "SYSTEM AND METHOD FOR A DRUG DELIVERY AND BIOSENSOR PATCH," filed Apr. 12, 2017, now U.S. Pat. No. 10,155,087 issued Dec. 18, 2018 and hereby expressly incorporated by reference herein, which claims priority under 35 U.S.C. § 120 as a continuation application to U.S. Utility application Ser. No. 15/276,760, entitled, "SYSTEM AND METHOD FOR A DRUG DELIVERY AND BIOSENSOR PATCH," filed Sep. 26, 2016, now U.S. Pat. No. 9,636,457 issued May 2, 2017, which is hereby expressly incorporated by reference herein, which claims priority under 35 U.S.C. § 119 to U.S. Provisional Application No. 62/383,313 entitled, "SYSTEM AND METHOD FOR A DRUG DELIVERY AND BIOSENSOR PATCH," filed Sep. 2, 2016, and hereby expressly incorporated by reference herein.

The present application claims priority under 35 U.S.C. § 120 as a continuation in part to U.S. patent application Ser. No. 16/270,268 entitled, "SYSTEM AND METHOD FOR A BIOSENSOR INTEGRATED IN A VEHICLE," filed Feb. 7, 2019, and hereby expressly incorporated by reference herein which claims priority under 35 U.S.C. § 120 as a continuation application to U.S. patent application Ser. No. 15/811,479 entitled, "SYSTEM AND METHOD FOR A BIOSENSOR INTEGRATED IN A VEHICLE," filed Nov. 13, 2017, now U.S. Pat. No. 10,238,346 issued Mar. 26, 2019 and hereby expressly incorporated by reference herein, which claims priority under 35 U.S.C. § 120 as a continuation in part application to U.S. patent application Ser. No. 15/490,813 entitled, "SYSTEM AND METHOD FOR HEALTH MONITORING USING A NON-INVASIVE, MULTI-BAND BIOSENSOR," filed Apr. 18, 2017, now U.S. Pat. No. 9,980,676 issued May 29, 2018 which claims priority under 35 U.S.C. § 120 as a continuation application to U.S. patent application Ser. No. 15/275,388 entitled, "SYSTEM AND METHOD FOR HEALTH MONITORING USING A NON-INVASIVE, MULTI-BAND BIOSENSOR," filed Sep. 24, 2016, now U.S. Pat. No. 9,642,578 issued May 9, 2017, which claimed priority under 35 U.S.C. § 119 to:

U.S. Provisional Application No. 62/307,375 entitled, "SYSTEM AND METHOD FOR HEALTH MONITORING USING A NON-INVASIVE, MULTI-BAND BIOSENSOR," filed Mar. 11, 2016, and hereby expressly incorporated by reference herein; and U.S. Provisional Application No. 62/312,614 entitled, "SYSTEM AND METHOD FOR DETERMINING BIOSENSOR DATA USING A BROAD SPECTRUM LIGHT SOURCE," filed Mar. 24, 2016, and hereby expressly incorporated by reference herein.

The present application claims priority under 35 U.S.C. § 120 as a continuation in part application to U.S. patent application Ser. No. 15/400,916 entitled, "SYSTEM AND METHOD FOR HEALTH MONITORING INCLUDING A REMOTE DEVICE," filed Jan. 6, 2017 and hereby expressly incorporated by reference herein.

The present application claims priority under 35 U.S.C. § 120 as a continuation in part to U.S. patent application Ser. No. 16/391,175 entitled, "SYSTEM AND METHOD FOR GLUCOSE MONITORING," filed Apr. 22, 2019 which claims priority under 35 U.S.C. § 120 as a continuation application to U.S. patent application Ser. No. 14/866,500 entitled, "SYSTEM AND METHOD FOR GLUCOSE MONITORING," filed Sep. 25, 2015, now U.S. patent Ser. No. 10/321,860 on Jun. 18, 2019, and hereby expressly incorporated by reference herein, which claims priority under 35 U.S.C. § 119(e) to:

U.S. Provisional Application No. 62/194,264 entitled, "SYSTEM AND METHOD FOR GLUCOSE MONITORING," filed Jul. 19, 2015, and hereby expressly incorporated by reference herein.

FIELD

This application relates to systems and methods of non-invasive health monitoring, and in particular, a system and method for detection of glucose levels in blood flow using an optical sensor.

BACKGROUND

A person's vitals, such as temperature, blood oxygen levels, respiration rate, relative blood pressure, etc., may need to be monitored periodically. Typically, monitoring a plurality of vitals requires multiple instruments. For example, instruments for obtaining vitals of a user include blood pressure cuffs, thermometers, pulse oximeters, glucose level meters, etc.

The detection of substances and measurement of concentration level or indicators of various substances in a user's blood stream is important in health monitoring as well. Currently, detection of concentration levels of blood substances is performed by drawing blood from a blood vessel using a needle and syringe. The blood sample is then transported to a lab for analysis. This type of monitoring is invasive, non-continuous and time consuming.

One current non-invasive method is known for measuring the oxygen saturation of blood using pulse oximeters. Pulse oximeters detect oxygen saturation of hemoglobin by using, e.g., spectrophotometry to determine spectral absorbencies and determining concentration levels of oxygen. In addition, pulse oximetry may use photoplethysmography (PPG) methods for the assessment of oxygen saturation in pulsatile arterial blood flow. The subject's skin at a 'measurement location' is illuminated with two distinct wavelengths of light and the relative absorbance at each of the wavelengths is determined. For example, a wavelength in the visible red spectrum (for example, at 660 nm) has an extinction coefficient of hemoglobin that exceeds the extinction coefficient of oxihemoglobin. At a wavelength in the near infrared spectrum (for example, at 940 nm), the extinction coefficient of oxihemoglobin exceeds the extinction coefficient of hemoglobin. The pulse oximeter filters the absorbance of the pulsatile fraction of the blood (AC components), from the constant absorbance by nonpulsatile venous or capillary blood or tissue pigments (DC components), to eliminate the effect of tissue absorbance to measure the oxygen saturation of arterial blood.

For example, when the heart pumps blood to the body and the lungs during systole, the amount of blood that reaches the capillaries in the skin surface increases, resulting in more light absorption. The blood then travels back to the heart through the venous network, leading to a decrease of blood volume in the capillaries and less light absorption. The measured PPG waveform therefore comprises a pulsatile (often called "AC") physiological waveform that reflects synchronous changes in the blood volume with a cardiac cycle, which is superimposed on a much larger slowly varying quasi-static ("DC") baseline. The use of PPG techniques as heretofore been mainly used for measurement of the oxygen saturation of blood in vessels.

As such, there is a need for a non-invasive health monitoring system and method that monitors health conditions of a user non-invasively, continuously and in real time. In particular, there is a need for an improved system and method for detection of glucose levels in blood flow and vascular health.

SUMMARY

In one aspect, a biosensor includes an optical circuit configured to obtain a plurality of PPG signals at a plurality of wavelengths reflected from tissue of a user, wherein the different wavelengths have varying penetration depths of tissue. The biosensor also includes a processing circuit configured to determine a plurality of L values at a plurality of different wavelengths using the plurality of PPG signals and determine a plurality of R values using the plurality of L values. The processing circuit is further configured to determine one or more other PPG parameters using the plurality of PPG signals; and determine a glucose level in blood flow using the plurality of L values, the plurality of R values and the one or more other PPG parameters.

In another aspect, a biosensor includes an optical circuit configured to obtain a plurality of PPG signals at a plurality of wavelengths reflected from tissue of a user, wherein the different wavelengths have varying penetration depths of tissue. The biosensor further includes a processing circuit configured to determine one or more R values using the plurality of PPG signals and determine one or more other PPG parameters using the plurality of PPG signals, wherein the one or more other PPG parameters includes at least one of: a phase delay between a first PPG signal and a second PPG signal of the plurality of PPG signals, a correlation of phase shape between the first PPG signal and the second PPG signal of the plurality of PPG signals or a periodicity of first PPG signal or the second PPG signal. The processing circuit is further configured to determine a glucose level in blood flow of the user using the one or more R values and the one or more other PPG parameters.

In another aspect, the biosensor includes an optical circuit configured to obtain a plurality of PPG signals at a plurality of wavelengths reflected from tissue of a user, wherein the different wavelengths have varying penetration depths of tissue. The biosensor further includes a processing circuit configured to determine a plurality of L values at a plurality of different wavelengths using the plurality of PPG signals; determine a plurality of R values using the plurality of L values; and determine a glucose level in blood flow using the plurality of L values and the plurality of R values.

In one or more of the above aspects, the optical circuit is configured to obtain a first PPG signal at a wavelength with a high absorption coefficient for nitric oxide (NO) in blood flow and a second PPG signal at a wavelength with a low absorption coefficient for NO in blood flow.

In one or more of the above aspects, the plurality of L values includes a first L value determined using a first PPG signal at a wavelength with a high absorption coefficient for nitric oxide (NO) in blood flow and a second L value determined using second PPG signal at a wavelength with a low absorption coefficient for NO in blood flow.

In one or more of the above aspects, the plurality of R values includes an R value obtained using a first PPG signal at a first wavelength with a high absorption coefficient for nitric oxide (NO) in blood flow and a second PPG signal at a second wavelength with a low absorption coefficient for NO in blood flow; an R value obtained using the first PPG signal at a wavelength with the high absorption coefficient for nitric oxide (NO) in blood flow and a third PPG signal at a third wavelength with a different penetration depth than the first and second wavelength; and an R value obtained using the third PPG signal at the third wavelength and the second PPG signal at the second wavelength with the low absorption coefficient for NO in blood flow.

In one or more of the above aspects, the one or more other PPG parameters include at least one of: a phase delay between a first PPG signal and a second PPG signal of the plurality of PPG signals, a correlation of phase shape between the first PPG signal and the second PPG signal of the plurality of PPG signals or a periodicity of first PPG signal or the second PPG signal.

In one or more of the above aspects, the processing circuit is further configured to determine a skin temperature and determine the glucose level using the plurality of L values, the plurality of R values, the one or more other PPG parameters and the skin temperature.

In one or more of the above aspects, the plurality of L values includes a first L value determined using a first PPG signal obtained at a first wavelength in a range of 380 nm-400 nm; and a second L value determined using a second PPG signal obtained at a second wavelength equal to or above 660 nm).

In one or more of the above aspects, the plurality of R values includes an R value determined using a first PPG signal obtained at a first wavelength in a range of 380 nm-400 nm and a second PPG signal obtained at a second wavelength equal to or above 660 nm); an R value determined using the first PPG signal obtained at a first wavelength in a range of 380 nm-400 nm and a third PPG signal obtained at a third wavelength in a range of 510 nm-550 nm; or an R value determined using the third PPG signal obtained at a third wavelength in a range of 510 nm-550 nm and second PPG signal obtained at a second wavelength equal to or above 660 nm).

In one or more of the above aspects, the processing circuit implements a regression neural network processing or a classifier neural network processing to determine the glucose level.

In one or more of the above aspects, the processing circuit is further configured to determine one or more digital health parameters using the plurality of PPG signals, wherein the one or more digital health parameters includes a Vascular Health Index and wherein the processing circuit is configured to determine the Vascular Health Index using a measurement of a relative vasoconstriction of vessels during an insulin release event.

DETAILED DESCRIPTION

The word "exemplary" or "embodiment" is used herein to mean "serving as an example, instance, or illustration." Any implementation or aspect described herein as "exemplary"

or as an "embodiment" is not necessarily to be construed as preferred or advantageous over other aspects of the disclosure. Likewise, the term "aspects" does not require that all aspects of the disclosure include the discussed feature, advantage, or mode of operation.

Embodiments will now be described in detail with reference to the accompanying drawings. In the following description, numerous specific details are set forth in order to provide a thorough understanding of the aspects described herein. It will be apparent, however, to one skilled in the art, that these and other aspects may be practiced without some or all of these specific details. In addition, well known steps in a method of a process may be omitted from flow diagrams presented herein in order not to obscure the aspects of the disclosure. Similarly, well known components in a device may be omitted from figures and descriptions thereof presented herein in order not to obscure the aspects of the disclosure.

Overview

In an embodiment, a biosensor includes an optical sensor or photoplethysmography (PPG) circuit configured to transmit light at a plurality of wavelengths directed at skin tissue of a user. The user may include any animal, human or non-human. The PPG circuit detects the light reflected from the skin tissue or transmitted through the skin tissue and generates one or more PPG signals at one or more wavelengths. A processing circuit integrated in the biosensor or in communication with the biosensor processes the PPG signals to obtain a user's vitals, concentrations of substances in blood flow and/or other health information.

In an embodiment described herein, a plurality of PPG parameters are determined using PPG signals at a plurality of wavelengths. The PPG parameters include R values, L values, phase delay between two or more of the plurality of PPG signals, a correlation of phase shape between two or more of the plurality of PPG signals or a periodicity of one or more the plurality of PPG signals. Other types of parameters, such as skin temperature, may also be obtained by the biosensor. The plurality of parameters are then analyzed to determine a glucose level in blood flow of the user.

Embodiment of the Biosensor

Figure 1:
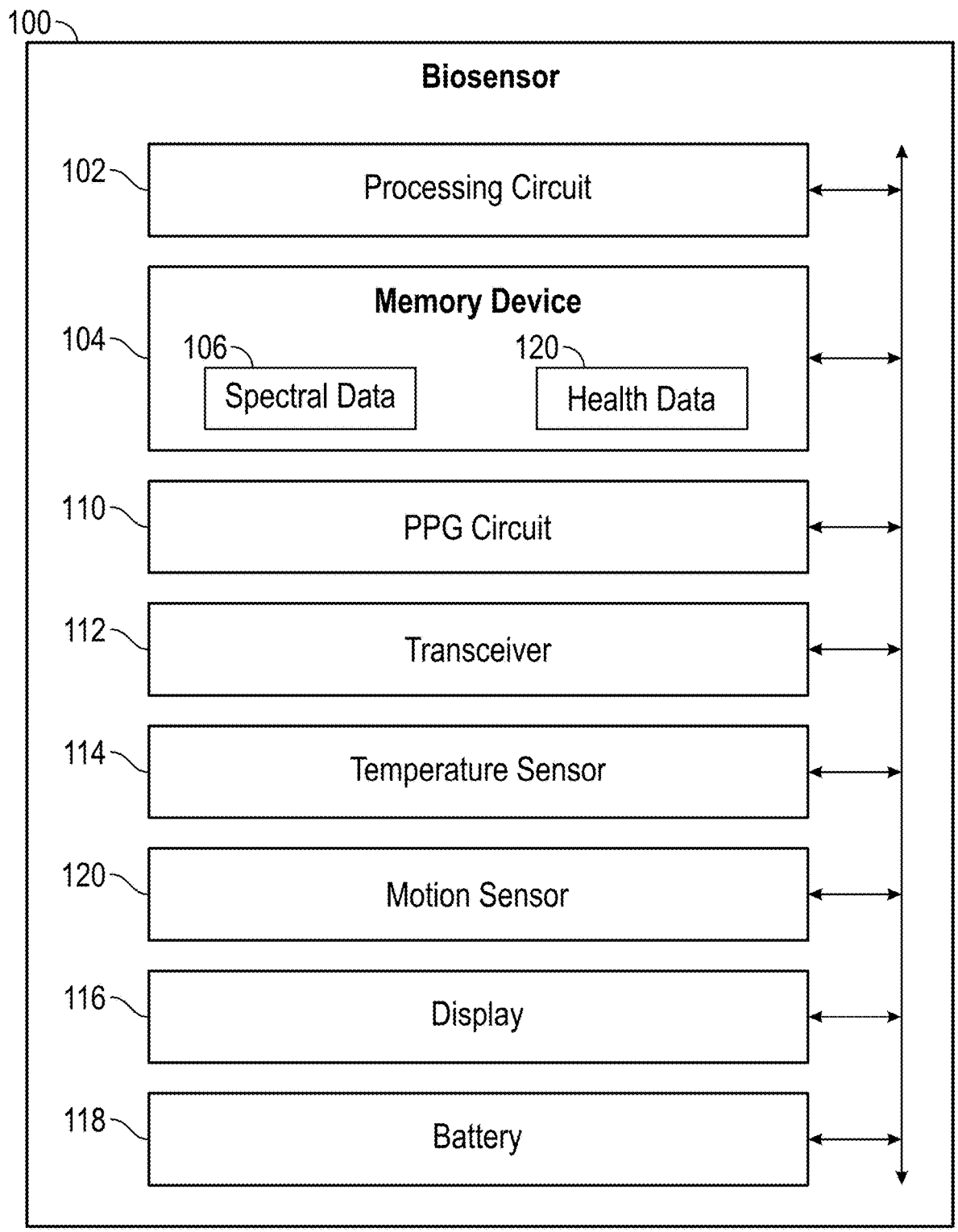
FIG. 1 illustrates a schematic block diagram of exemplary components in an embodiment of a biosensor.

FIG. 1 illustrates a schematic block diagram of exemplary components in an embodiment of the biosensor 100. The biosensor 100 may include one or more processing circuits 102 communicatively coupled to one or more memory devices 104. In one aspect, the memory device 104 may include one or more non-transitory processor readable memories that store instructions which when executed by the one or more processing circuits 102, causes the one or more processing circuits 102 to perform one or more functions described herein. The processing circuit 102 may be co-located with one or more of the other circuits of the biosensor 100 in a same physical circuit board or located separately in a different circuit board. The processing circuit 102 may also be communicatively coupled to other processing circuits, such as in another user device, a central control module or a server in a remote location, wherein the other processing circuits perform one or more functions described herein. The biosensor 100 may be battery operated and include a battery 118, such as a lithium ion battery. The memory device 104 may store spectral data 106 or health data 120 obtained by the biosensor 100.

The biosensor 100 may include a temperature sensor 114 configured to detect a temperature of a user. For example, the temperature sensor 108 may include an array of sensors (e.g., 16×16 pixels) to detect a skin temperature of a user. The temperature sensor 114 may also be used to calibrate the PPG circuit 110, such as the wavelength output of LEDs or other light sources. The biosensor 100 may include a display 116 to display biosensor data or control interfaces for the biosensor 100.

The biosensor 100 further includes a transceiver 112. The transceiver 112 may include a wireless or wired transceiver configured to communicate with or with one or more devices over a LAN, MAN and/or WAN. In one aspect, the wireless transceiver may include a Bluetooth enabled (BLE) transceiver or IEEE 802.11ah, Zigbee, IEEE 802.15-11 or WLAN (such as an IEEE 802.11 standard protocol) compliant transceiver. In another aspect, the wireless transceiver may operate using RFID, short range radio frequency, infrared link, or other short range wireless communication protocol. In another aspect, the wireless transceiver may also include or alternatively include an interface for communicating over a cellular network. The transceiver 112 may also include a wired transceiver interface, e.g., a USB port or other type of wired connection, for communication with one or more other devices over a LAN, MAN and/or WAN. The transceiver 112 may include a wireless or wired transceiver configured to communicate with a vehicle or its components over a controller area network (CAN), Local Interconnect Network (LIN), Flex Ray, Media Oriented Systems Transport (MOST), (On-Board Diagnostics II), Ethernet or using another type of network or protocol. The biosensor 100 may transmit health data using the transceiver 112 over a wide area network, such as a cellular network, to a third party service provider, such as a health care provider or emergency service provider.

The biosensor 100 may also include a motion sensor 114 configured to detect motion of the biosensor 100 or patient. In an embodiment, the motion sensor 114 includes an accelerometer. Due to motion, a signal quality of the PPG signal may decline. In an embodiment, an acceptable tolerance for a PPG signal quality indicator may be set. When a motion level exceeds a threshold, then the PPG data may be ignored to avoid measurement errors. The biosensor may be programmed to reset after a predetermined level of motion (e.g., a speed or an acceleration) is exceeded.

The biosensor 100 may be included in one or more different form factors over various types of tissue, such as a watch, ring, patch, earpiece, earbud, etc. In an embodiment, a small form factor such as a ring or patch, may include a PPG circuit 110 and transceiver to communicate via a wireless or wired connection with a remote device, such as a watch, smart phone, computer, glasses, or other user device. The remote device may include another PPG circuit 110 and/or may include the processing circuits 102 and memory 104 for processing of data received from the remote sensor.

Embodiment—PPG Circuit

Figure 2:
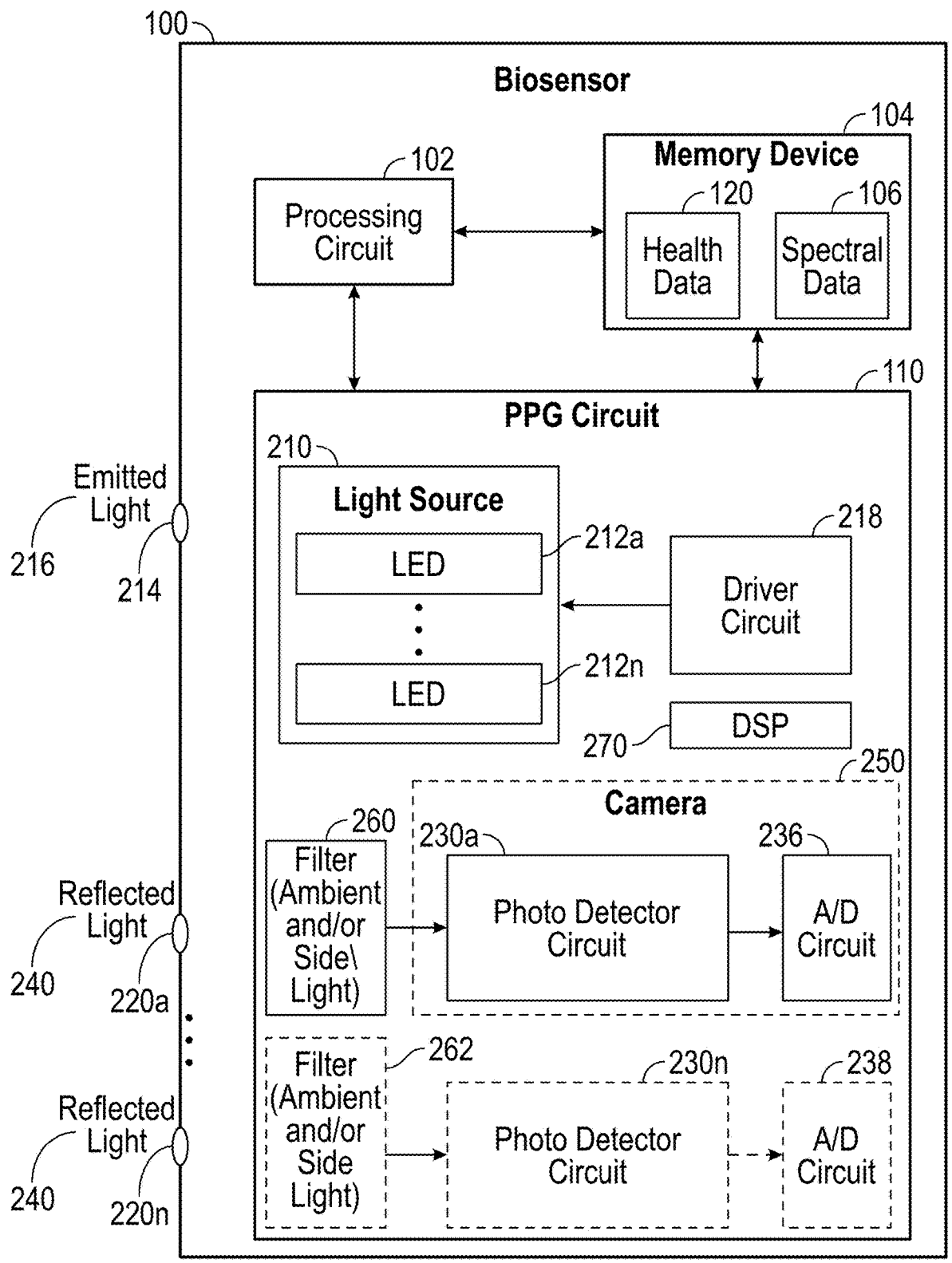
FIG. 2 illustrates a schematic block diagram of an embodiment of the PPG circuit in more detail.

FIG. 2 illustrates a schematic block diagram of an embodiment of the PPG circuit 110 in more detail. The PPG circuit 110 includes a light source 210 configured to emit a plurality of wavelengths of light across various spectrums. The plurality of LEDs 212a-n are configured to emit light in one or more spectrums, including infrared (IR) light, ultraviolet (UV) light, near IR light or visible light, in response to driver circuit 218. For example, the biosensor 100 may include a first LED 212a that emits visible light and a second LED 212b that emits infrared light and a third LED 212c that emits UV light, etc. In another embodiment, one or more of the light sources 210 may include tunable LEDs or lasers operable to emit light over one or more frequencies or ranges of frequencies or spectrums in response to driver circuit 218.

In an embodiment, the driver circuit 218 is configured to control the one or more LEDs 212a-n to generate light at one or more frequencies for predetermined periods of time. The driver circuit 218 may control the LEDs 212a-n to operate concurrently or consecutively. The driver circuit 218 is configured to control a power level, emission period and frequency of emission of the LEDs 212a-n. The driver circuit 218 may also tune a wavelength output of the LEDs 212a-n in response to a temperature or other feedback. The biosensor 100 is thus configured to emit one or more wavelengths of light in one or more spectrums that is directed at the surface or epidermal layer of the skin tissue of a user. The emitted light 216 passes through at least one aperture 214 and towards the surface or epidermal layer of the skin tissue of a user.

The PPG circuit 110 further includes one or more photodetector circuits 230a-n. The photodetector circuits 230 may be implemented as part of a camera 250. For example, a first photodetector circuit 230 may be configured to detect visible light and the second photodetector circuit 230 may be configured to detect IR light. Alternatively, a single photodetector 230 may be implemented to detect light across multiple spectrums. When multiple photodetectors 230 are implemented, the detected signals obtained from each of the photodetectors may be added or averaged. Alternatively, a detected light signal with more optimal signal to noise ratio may be selected from the multiple photodetector circuits 230a-n.

The first photodetector circuit 230a and the second photodetector circuit 230n may also include a first filter 260 and a second filter 262 configured to filter ambient light and/or scattered light. For example, in some embodiments, only light reflected at an approximately perpendicular angle to the skin surface of the user is desired to pass through the filters. The first photodetector circuit 230a and the second photodetector circuit 230n are coupled to a first analog to digital (A/D) circuit 236 and a second A/D circuit 238. Alternatively, a single A/D circuit may be coupled to each of the photodetector circuits 230a-n. The A/D circuits convert the spectral responses to digital spectral data for processing by a DSP or other processing circuit.

The one or more photodetector circuits 230a-n include one or more types of spectrometers or photodiodes or other types of light detection circuits configured to detect an intensity of light as a function of wavelength over a time period to obtain a spectral response. In use, the one or more photodetector circuits 230a-n detect the intensity of reflected light 240 from skin tissue of a user that enters one or more apertures 220a-n of the biosensor 100. In another example, the one or more photodetector circuits 230a-n detect the intensity of light due to transmissive absorption (e.g., light transmitted through tissues, such as a fingertip or ear lobe). The one or more photodetector circuits 230a-n then obtain a spectral response (a PPG signal) of the reflected or transmissive light by measuring an intensity of the light at one or more wavelengths over a period of time.

In another embodiment, the light source 210 may include a broad spectrum light source, such as a white light to infrared (IR) or near IR LED, that emits light with wavelengths across multiple spectrums, e.g. from 350 nm to 2500 nm. Broad spectrum light sources with different ranges may be implemented. In an aspect, a broad spectrum light source is implemented with a range across 100 nm wavelengths to 2000 nm range of wavelengths in the visible, IR and/or UV frequencies. For example, a broadband tungsten light source for spectroscopy may be used. The spectral response of the reflected light 240 is then measured across the wavelengths in the broad spectrum, e.g. from 350 nm to 2500 nm, concurrently. In an aspect, a charge coupled device (CCD) spectrometer may be configured in the photodetector circuit 230 to measure the spectral response of the detected light over the broad spectrum.

The PPG circuit 110 may also include a digital signal processing (DSP) circuit 270 that includes signal processing of the digital spectral data. For example, the DSP circuit may determine AC or DC components from the spectral responses (PPG signals) or diastolic and systolic points or other spectral data 106. The spectral data may then be processed by the processing circuit 102 to obtain health data 120 of a user. The spectral data 106 may alternatively or in additionally be transmitted by the biosensor 100 to a central control module for processing to obtain health data 120 of a user. The spectral data 106, PPG signals, etc. may be stored in the memory device 104 of the biosensor 100.

In use, the biosensor 100 performs PPG techniques using the PPG circuit 110 to detect the concentration levels of one or more substances in blood flow. In one aspect, the biosensor 100 receives reflected light or transmissive light from skin tissue to obtain a spectral response. The spectral response (or PPG signal) includes a spectral curve that illustrates an intensity or power or energy at a frequency or wavelength in a spectral region of the detected light over a period of time. The ratio of the resonance absorption peaks from two different frequencies can be calculated and based on the Beer-Lambert law used to obtain the levels of substances in the blood flow.

For example, one or more of the embodiments of the biosensor 100 described herein is configured to detect a concentration level of one or more substances within blood flow using PPG techniques. For example, the biosensor 100 may detect nitric oxide (NO) concentration levels and correlate the NO concentration level to a blood glucose level. The biosensor 100 may also detect oxygen saturation (SaO2 or SpO2) levels in blood flow. The biosensor may also be configured to detect a liver enzyme cytochrome oxidase (P450) enzyme and correlate the P450 concentration level to a blood alcohol level.

The spectral response of a substance or substances in the arterial blood flow is determined in a controlled environment, so that an absorption coefficient $\alpha_{g1}$ can be obtained at a first light wavelength $\lambda 1$ and at a second wavelength $\lambda 2$. According to the Beer-Lambert law, light intensity will decrease logarithmically with path length l (such as through an artery of length l). Assuming then an initial intensity $I_{in}$ of light is passed through a path length l, a concentration $C_g$ of a substance may be determined. For example, the concentration Cg may be obtained from the following equations:

At the first wavelength $\lambda_1, I_1 = I_{in1} * 10^{-(\alpha_{g1} C_{gw} + \alpha_{w1} C_w) * l}$ At the second wavelength $\lambda_2, I_2 = I_{in2} * 10^{-(\alpha_{g2} C_{gw} + \alpha_{w2} C_w) * l}$ wherein:
$I_{in1}$ is the intensity of the initial light at $\lambda_1$
$I_{in2}$ is the intensity of the initial light at $\lambda_2$
$\alpha_{g1}$ is the absorption coefficient of the substance in arterial blood at $\lambda_1$
$\alpha_{g2}$ is the absorption coefficient of the substance in arterial blood at $\lambda_2$
$\alpha_{w1}$ is the absorption coefficient of arterial blood at $\lambda_1$ $\alpha_{w2}$ is the absorption coefficient of arterial blood at $\lambda_2$
$C_{gw}$ is the concentration of the substance and arterial blood
$C_w$ is the concentration of arterial blood
Then letting R equal:

$$R = \frac{\log 10\left(\frac{I1}{Iin1}\right)}{\log 10\left(\frac{I2}{Iin2}\right)}$$

The concentration of the substance Cg may then be equal to:

$$Cg = \frac{Cgw}{Cgw + Cw} = \frac{\alpha_{w2}R - \alpha_{w1}}{(\alpha_{w2} - \alpha_{gw2})*R - (\alpha_{w1} - \alpha_{gw1})}$$

The biosensor 100 may thus determine the concentration of various substances in blood flow from the Beer-Lambert principles using the spectral responses of at least two different wavelengths.

Figure 3:
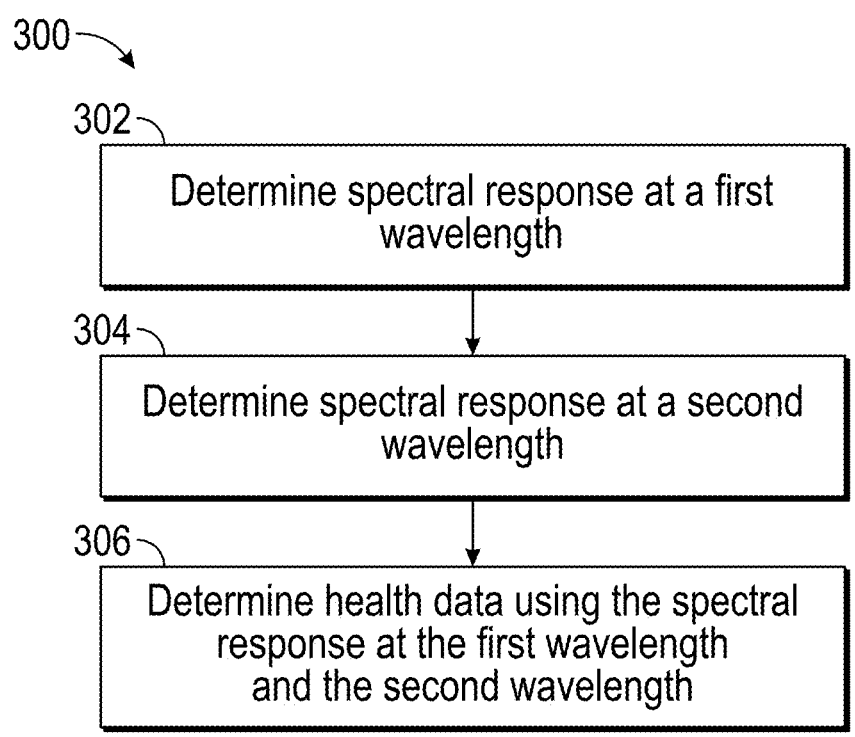
FIG. 3 illustrates a logical flow diagram of an embodiment of a method for determining concentration level of a substance in blood flow using Beer-Lambert principles.

FIG. 3 illustrates a logical flow diagram of an embodiment of a method 300 for determining concentration level of a substance in blood flow using Beer-Lambert principles. The biosensor 100 transmits light at a first predetermined wavelength and at a second predetermined wavelength. The biosensor 100 detects the light (reflected from the skin or transmitted through the skin) and determines the spectral response at the first wavelength at 302 and at the second wavelength at 304. The biosensor 100 then determines health data, such as an indicator or concentration level of substances in blood flow, using the spectral responses of the first and second wavelength at 306. In general, the first predetermined wavelength is selected that has a high absorption coefficient for the substance in blood flow while the second predetermined wavelength is selected that has a lower absorption coefficient for the substance in blood flow. Thus, it is generally desired that the spectral response for the first predetermined wavelength have a higher intensity level in response to the substance than the spectral response for the second predetermined wavelength.

In an embodiment, the biosensor 100 may detect a concentration level of nitric oxide (NO) in blood flow using a first predetermined wavelength with a high absorption coefficient for NO in a range of 380-410 nm and in particular at 390 nm or 395 nm. In another aspect, the biosensor 100 may transmit light at the first predetermined wavelength in a range of approximately 1 nm to 50 nm around the first predetermined wavelength. Similarly, the biosensor 100 may transmit light at the second predetermined wavelength in a range of approximately 1 nm to 50 nm around the second predetermined wavelength. The range of wavelengths is determined based on the spectral response since a spectral response may extend over a range of frequencies, not a single frequency (i.e., it has a nonzero linewidth). The light that is reflected or transmitted by NO may spread over a range of wavelengths rather than just the single predetermined wavelength. In addition, the center of the spectral response may be shifted from its nominal central wavelength or the predetermined wavelength. The range of 1 nm to 50 nm is based on the bandwidth of the spectral response line and should include wavelengths with increased light intensity detected for the targeted substance around the predetermined wavelength.

The first spectral response (or first PPG signal) of the light over the first range of wavelengths including the first predetermined wavelength and the second spectral response (or second PPG signal) of the light over the second range of wavelengths including the second predetermined wavelengths is then generated at 302 and 304. The biosensor 100 analyzes the first and second spectral responses to detect an indicator or concentration level of NO in the arterial blood flow at 306. In another embodiment, using absorption coefficients for both Nitric Oxide and Hemoglobin, the concentration of Nitric Oxide can be obtained in blood. A calibration table may then correlate amounts of glucose (mG/DL) in relation to R values 395/940 nm. The concentration level of NO as used herein may thus include NO in gaseous form in blood flow and/or NO attached to hemoglobin compounds in the blood flow.

In another example, the biosensor 100 may also detect vitals, such as heart rate, respiration rate and pulse pressure. The biosensor 100 may also determine a level of vasodilation and a period of vasodilation as described in more detail herein. Because blood flow to the skin can be modulated by multiple other physiological systems, the biosensor 100 may also be used to monitor vascular health, such as hypovolemia or other circulatory conditions.

Photoplethysmography (PPG) is used to measure time-dependent volumetric properties of blood in blood vessels due to the cardiac cycle. For example, the heartbeat affects the volume of blood flow and the concentration or absorption levels of substances being measured in the arterial blood flow. Over a cardiac cycle, pulsating arterial blood changes the volume of blood flow in a blood vessel. Incident light $I_O$ is directed at a tissue site and a certain amount of light is reflected or transmitted and a certain amount of light is absorbed. At a peak of blood flow or volume in a cardiac cycle, the reflected/transmitted light $I_L$ is at a minimum due to absorption by the increased blood volume, e.g., due to the pulsating blood in the vessel. At a minimum of blood volume during the cardiac cycle, the transmitted/reflected light $I_H$ 416 is at a maximum due to lack of absorption from the pulsating blood.

The biosensor 100 is configured to filter the reflected/transmitted light $I_L$ of the pulsating blood from the transmitted/reflected light $I_H$. This filtering isolates the light due to reflection/transmission of the pulsating blood from the light due to reflection/transmission from non-pulsating blood, vessel walls, surrounding tissue, etc. The biosensor 100 may then measure the concentration levels of one or more substances from the reflected/transmitted light $I_L$ 814 in the pulsating blood.

For example, incident light $I_O$ is directed at a tissue site at one or more wavelengths. The reflected/transmitted light I is detected by a photodetector or sensor array in a camera. At a peak of blood flow or volume, the reflected light $I_L$ 414 is at a minimum due to absorption by the pulsating blood, non-pulsating blood, other tissue, etc. At a minimum of blood flow or volume during the cardiac cycle, the Incident or reflected light $I_H$ 416 is at a maximum due to lack of absorption from the pulsating blood volume. Since the light I is reflected or traverses through a different volume of blood at the two measurement times, the measurement provided by a PPG sensor is said to be a 'volumetric measurement' descriptive of the differential volumes of blood present at a certain location within the user's vessels at different times during the cardiac cycle. These principles described herein may be applied to venous blood flow and arterial blood flow.

In general, the relative magnitudes of the AC and DC contributions to the reflected/transmitted light signal I may be determined. In general, AC contribution of the reflected light signal I is due to the pulsating blood flow. A difference function may thus be computed to determine the relative magnitudes of the AC and DC components of the reflected light I to determine the magnitude of the reflected light due to the pulsating blood flow. The described techniques herein for determining the relative magnitudes of the AC and DC contributions is not intended as limiting. It will be appreciated that other methods may be employed to isolate or otherwise determine the relative magnitude of the light $I_L$ due to pulsating blood flow (arterial and/or venous).

In one aspect, the spectral response obtained at each wavelength may be aligned based on the systolic 402 and diastolic 404 points in their respective spectral responses. This alignment is useful to associate each spectral response with a particular stage or phase of the pulse-induced local pressure wave within the blood vessel (which roughly mimics the cardiac cycle 406 and thus include systolic and diastolic stages and sub-stages thereof). This temporal alignment helps to determine the absorption measurements acquired near a systolic point in time of the cardiac cycle and near the diastolic point in time of the cardiac cycle 406 associated with the local pressure wave within the user's blood vessels. This measured local pulse timing information may be useful for properly interpreting the absorption measurements in order to determine the relative contributions of the AC and DC components measured by the biosensor 100. So, for one or more wavelengths, the systolic points 402 and diastolic points 404 in the spectral response are determined. These systolic points 402 and diastolic points 404 for the one or more wavelengths may then be aligned as a method to discern concurrent responses across the one or more wavelengths.

Figure 4:
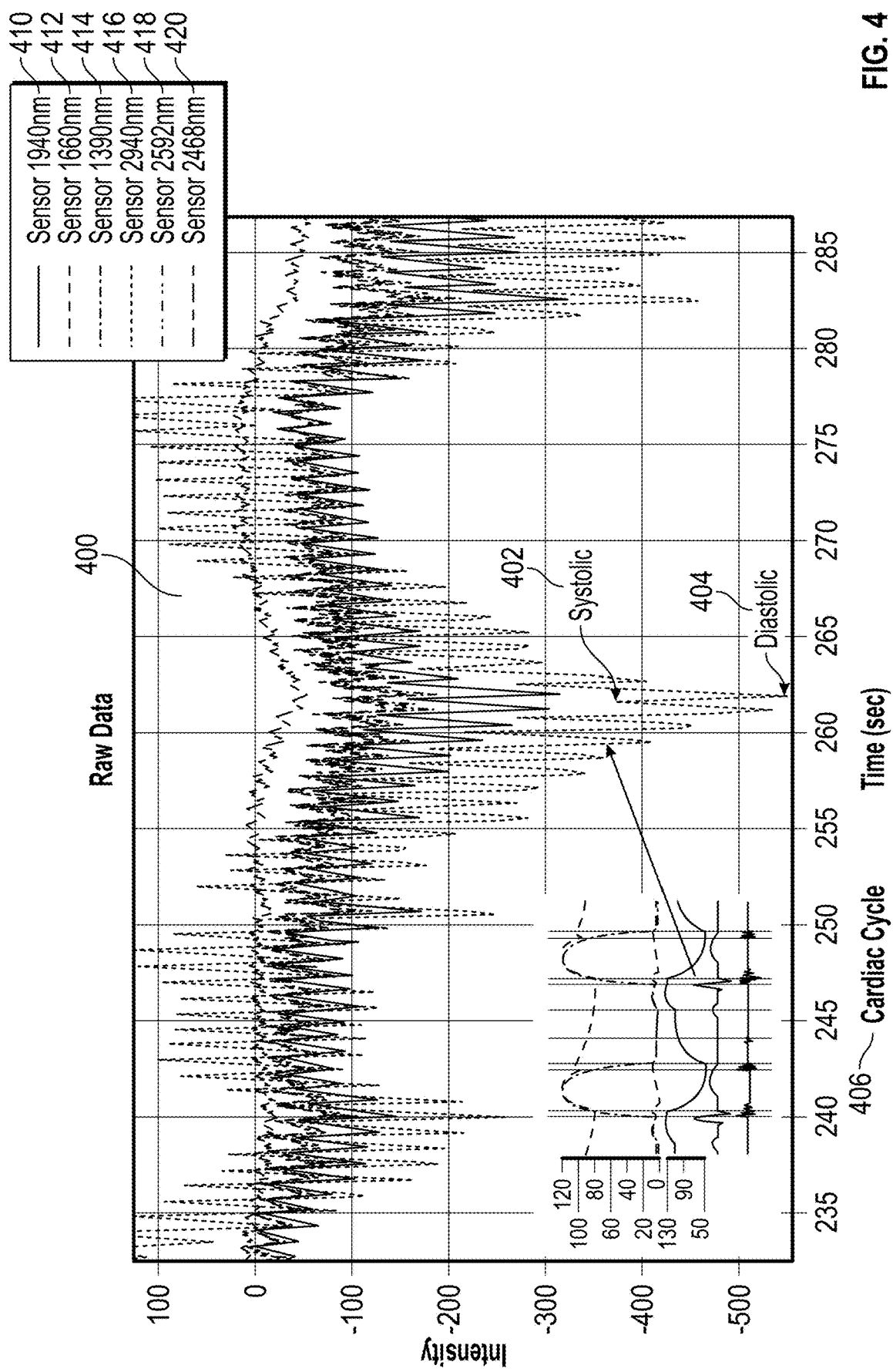
FIG. 4 illustrates the spectral response obtained at the plurality of wavelengths with the systolic points and diastolic points aligned over a cardiac cycle.

In another embodiment, the systolic points 402 and diastolic points 404 in the absorbance measurements are temporally correlated to the pulse-driven pressure wave within the blood vessels—which may differ from the cardiac cycle. In another embodiment, the biosensor 100 may concurrently measure the intensity reflected at each the plurality of wavelengths. Since the measurements are concurrent, no alignment of the spectral responses of the plurality of wavelengths may be necessary. FIG. 4 illustrates the spectral response obtained at the plurality of wavelengths with the systolic points 402 and diastolic points 404 aligned over a cardiac cycle 406.

Figure 5:
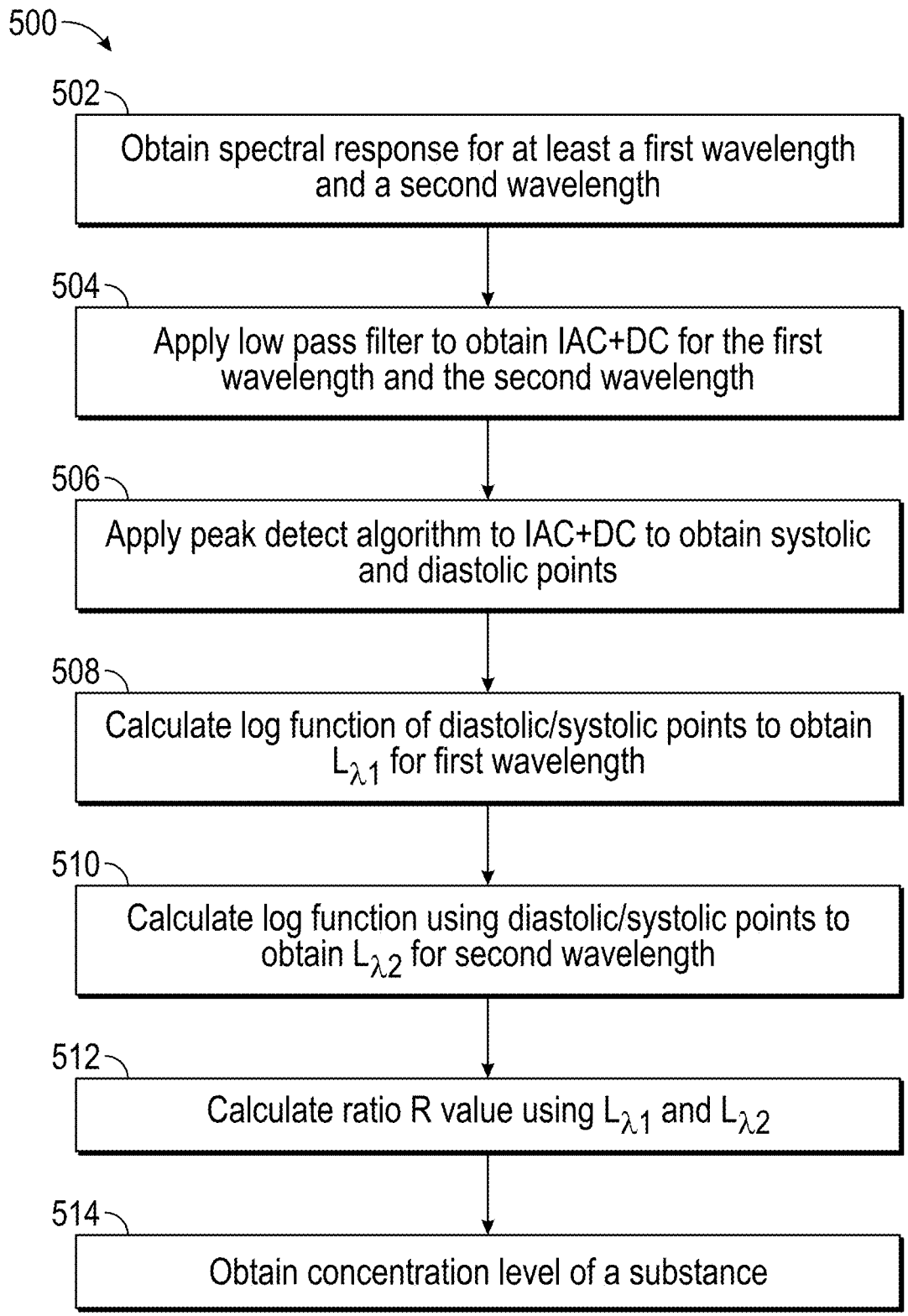
FIG. 5 illustrates a logical flow diagram of an embodiment of a method of the biosensor.

FIG. 5 illustrates a logical flow diagram of an embodiment of a method 500 of the biosensor 100. In one aspect, the biosensor 100 emits and detects light at a plurality of predetermined frequencies or wavelengths, such as approximately 940 nm, 660 nm, 390 nm, 592 nm, and 468 nm or in ranges thereof. The light is pulsed for a predetermined period of time (such as 100 usec or 200 Hz) sequentially or simultaneously at each predetermined wavelength. In another aspect, light may be pulsed in a wavelength range of 1 nm to 50 nm around each of the predetermined wavelengths. For example, for the predetermined wavelength 390 nm, the biosensor 100 may transmit light directed at skin tissue of the user in a range of 360 nm to 410 nm including the predetermined wavelength 390 nm. For the predetermined wavelength of 940 nm, the biosensor 100 may transmit light directed at the skin tissue of the user in a range of 920 nm to 975 nm. In another embodiment, the light is pulsed simultaneously at least at each of the predetermined wavelengths (and in a range around the wavelengths).

The spectral responses are obtained around the plurality of wavelengths, including at least a first wavelength and a second wavelength at 502. The spectral responses may be measured over a predetermined period (such as 300 usec.) or at least over 2-3 cardiac cycles. This measurement process is repeated continuously, e.g., pulsing the light at 10-100 Hz and obtaining spectral responses over a desired measurement period, e.g. from 1-2 seconds to 1-2 minutes or from 2-3 hours to continuously over days or weeks. The spectral data obtained by the PPG circuit 110, such as the digital or analog spectral responses, may be processed locally by the biosensor 100 or transmitted to a central control module for processing.

The systolic and diastolic points of the spectral response are then determined. Because the human pulse is typically on the order of magnitude of one 1 Hz, typically the time differences between the systolic and diastolic points are on the order of magnitude of milliseconds or tens of milliseconds or hundreds of milliseconds. Thus, spectral response measurements may be obtained at a frequency of around 10-100 Hz over the desired measurement period. The spectral responses are obtained over one or more cardiac cycles and systolic and diastolic points of the spectral responses are determined. Preferably, the spectral response is obtained over at least three cardiac cycles in order to obtain a heart rate.

A low pass filter (such as a 5 Hz low pass filter) is applied to the spectral response signal at 504. The relative contributions of the AC and DC components are obtained $I_{AC+DC}$ and $I_{AC}$. A peak detection algorithm is applied to determine the systolic and diastolic points at 506. If not detected concurrently, the systolic and diastolic points of the spectral response for each of the wavelengths may be aligned or may be aligned with systolic and diastolic points of a pressure pulse waveform or cardiac cycle.

Beer Lambert equations are then applied as described herein. For example, the $L_\lambda$ values are then calculated for the first wavelength $\lambda_1$ at 508 and the second wavelength $\lambda_2$ at 510, wherein the $L_\lambda$ values for a wavelength equals:

$$L_\lambda = \text{Log10}\left(\frac{IAC + DC}{IDC}\right)$$

wherein $I_{AC+DC}$ is the intensity of the detected light with AC and DC components and $I_{DC}$ is the intensity of the detected light with the AC component filtered by the low pass filter. The value $L_\lambda$ isolates the spectral response due to pulsating arterial blood flow, e.g. the AC component of the spectral response. Though the $L_A$ value is described in one embodiment by this equation, the L value includes alternate computations that represents the value of the AC component of the spectral response. For example, the L value may be represented alternatively by one or more of:

$$L_\lambda = \frac{IAC}{IDC} \text{ or } L_\lambda = \frac{IAC + DC}{IDC}$$

A ratio R of the $L_\lambda$ values at two wavelengths may then be determined at 512. For example, the ratio R may be obtained from the following:

$$\text{Ratio } R = \frac{L\lambda 1}{L\lambda 2}$$

The R value is thus a ratio of AC components of spectral responses at different wavelengths. The L values and R values may be determined continuously, e.g. every 1-2 seconds, and the obtained $L_\lambda$ values and/or R values averaged or meaned over a predetermined time period, such as over 1-2 minutes. The concentration level of a substance may then be obtained from the R value and a calibration database at 514. The biosensor 100 may substantially continuously monitor a user over 2-3 hours or over days or weeks.

In one embodiment, the $R_{390,940}$ value with $L_{\lambda 1=390nm}$ and $L_{\lambda 2=940}$ may be non-invasively and quickly and easily obtained using the biosensor 100 to determine a concentration level of nitric oxide NO in blood flow of a user. In particular, in unexpected results, it is believed that the nitric oxide NO levels in the blood flow is being measured at least in part by the biosensor 100 at wavelengths in the range of 380-410 and in particular at $\lambda_1=390$ nm. Thus, the biosensor 100 measurements to determine the $L_{390nm}$ values are the first time NO concentration levels in blood flow have been measured directly in vivo. These and other aspects of the biosensor 100 are described in more detail herein with clinical trial results.

Figure 6:
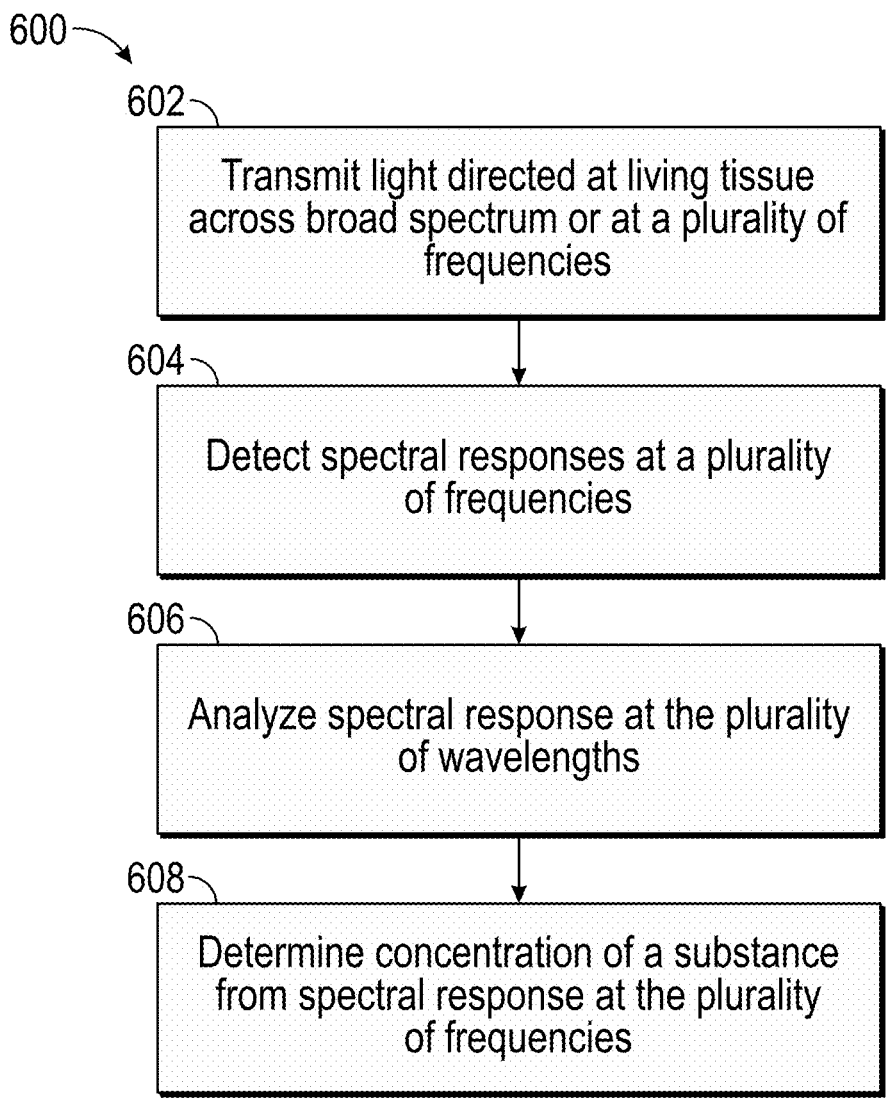
FIG. 6 illustrates a logical flow diagram of an exemplary method to determine levels of a substance in blood flow using the PPG signals at a plurality of wavelengths.

Embodiment—Determination of Concentration Level of a Substance Using PPG Signals at a Plurality of Wavelengths FIG. 6 illustrates a logical flow diagram of an exemplary method 600 to determine levels of a substance in blood flow using the PPG signals at a plurality of wavelengths. The absorption coefficient of a substance may be sufficiently higher at a plurality of wavelengths, e.g. due to isoforms or derivative compounds. For example, the increased intensity of light at a plurality of wavelengths may be due to reflectance by isoforms or other compounds in the arterial blood flow. Another method for determining the concentration levels may then be used by measuring the spectral responses and determining L and R values at a plurality of different wavelengths of light. In this example then, the concentration level of the substance is determined using spectral responses at multiple wavelengths. An example for calculating the concentration of a substance over multiple wavelengths may be performed using a linear function, such as is illustrated herein below.

$$LN(I_{1-n}) = \Sigma_{i=0}^{n} \mu i * Ci$$

wherein, $I_{1-n}$=intensity of light at wavelengths $\lambda_{1-n}$ $\mu_n$=absorption coefficient of substance 1, 2, . . . n at wavelengths $\lambda_{1-n}$ $C_n$=Concentration level of substance 1, 2, . . . n When the absorption coefficients $\mu_{1-n}$ of a substance, its isoforms or other compounds including the substance are known at the wavelengths $\lambda_{1-n}$, then the concentration level C of the substances may be determined from the spectral responses at the wavelengths $\lambda_{1-n}$ (and e.g., including a range of 1 nm to 50 nm around each of the wavelengths). The concentration level of the substance may be isolated from the isoforms or other compounds by compensating for the concentration of the compounds. Thus, using the spectral responses at multiple frequencies provides a more robust determination of the concentration level of a substance.

In use, the biosensor 100 transmits light directed at skin tissue at a plurality of wavelengths or over a broad spectrum at 602. The spectral response of light from the skin tissue may be detected at 604, and the spectral responses are analyzed at a plurality of wavelengths (and in one aspect including a range of +/−10 to 50 nm around each of the wavelengths) at 606. Then, the concentration level C of the substance may be determined using the spectral responses at the plurality of wavelengths at 608. The concentration level of the substance may be isolated from isoforms or other compounds by compensating for the concentration of the compounds. For example, using absorption coefficients for Nitric Oxide and Hemoglobin, the amount of Nitric Oxide can be obtained in arterial blood. A calibration table using human subjects may then correlate amounts of glucose (mG/DL) in relation to R values (NoHb) 395/940 nm.

Figure 7:
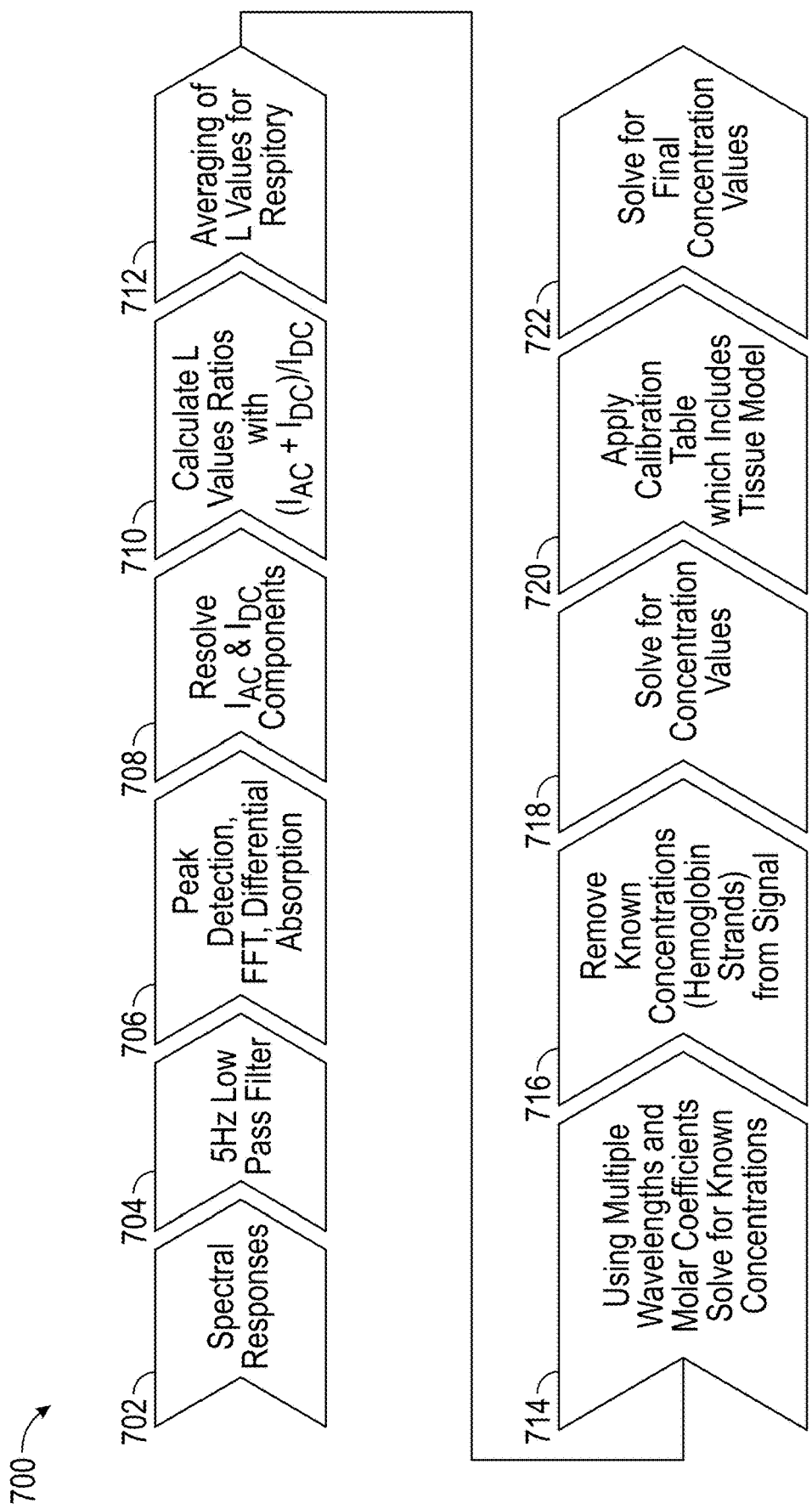
FIG. 7 illustrates a logical flow diagram of an exemplary method to determine levels of a substance using the spectral responses at a plurality of wavelengths in more detail.

FIG. 7 illustrates a logical flow diagram of an exemplary method 700 to determine levels of a substance using the spectral responses at a plurality of wavelengths in more detail. The spectral responses are obtained at 702. The spectral response signals include AC and DC components $I_{AC+DC}$. A low pass filter (such as a 5 Hz low pass filter) is applied to each of the spectral response signals $I_{AC+DC}$ to isolate the DC component of each of the spectral response signals $I_{DC}$ at 704. The AC fluctuation is due to the pulsatile expansion of the vessels due to the volume increase in pulsating blood. In order to measure the AC fluctuation, measurements are taken at different times and a peak detection algorithm is used to determine the diastolic point and the systolic point of the spectral responses at 706. A Fast Fourier transform (FFT) algorithm may also be used to isolate the DC component $I_{DC}$ and AC component of each spectral response signal at 706. A differential absorption technique may also be used as described in more detail herein. The $I_{DC}$ component is thus isolated from the spectral signal at 708.

The $I_{AC+DC}$ and $I_{DC}$ components are then used to compute the L values at 710. For example, a logarithmic function may be applied to the ratio of $I_{AC+DC}$ and $I_{DC}$ to obtain an L value for each of the wavelengths $L_{\lambda 1-n}$. Since the respiratory cycle affects the PPG signals, the L values may be averaged over a respiratory cycle and/or over another predetermined time period (such as over a 1-2 minute time period) or over a plurality of cardiac cycles at 712.

In an embodiment, isoforms of a substance may be attached in the blood stream to one or more types of hemoglobin compounds. The concentration level of the hemoglobin compounds may then need to be accounted for to isolate the concentration level of the substance from the hemoglobin compounds. For example, nitric oxide (NO) is found in the blood stream in a gaseous form and also attached to hemoglobin compounds. Thus, the spectral responses obtained around 390 nm (+/−20 nm) may include a concentration level of the hemoglobin compounds as well as nitric oxide. The hemoglobin compound concentration levels must thus be compensated for to isolate the nitric oxide. Multiple wavelengths and absorption coefficients for hemoglobin are used to determine a concentration of the hemoglobin compounds at 714. Other methods may also be used to obtain a concentration level of hemoglobin in the blood flow as well. The concentration of the hemoglobin compounds is then adjusted from the measurements at 716. The concentration values of the substance may then be obtained at 718. For example, the R values are then determined at 718.

To determine a concentration level of the substance, a calibration table or database is used that associates the obtained R value to a concentration level of the substance at 720. The calibration database correlates the R value with a concentration level. The calibration database may be generated for a specific user or may be generated from clinical data of a large sample population. For example, it is determined that the R values should correlate to similar NO concentration levels across a large sample population. Thus, the calibration database may be generated from testing of a large sample of a general population to associate R values and NO concentration levels.

In addition, the R values may vary depending on various factors, such as underlying skin tissue. For example, the R values may vary for spectral responses obtained from an abdominal area versus measurements from a wrist or finger due to the varying tissue characteristics. The calibration database may thus provide different correlations between the R values and concentration levels of a substance depending on the underlying skin tissue characteristics. The concentration level of the substance in blood flow is then obtained using the calibration table at 722. The concentration level may be expressed as mmol/liter, as a saturation level percentage, as a relative level on a scale, etc.

Embodiment—Determination of Artery Width to Obtain Concentration Levels of a Substance To obtain an estimated amount of NO in blood flow NO levels (mg/dl or mmol/l) from a density measurement of concentration level, the volume of blood needs to be determined. The volume of blood may be estimated from a diameter of the vessels and blood flow rate over a period of time. The diameter of the blood vessels may be estimated using various parameters obtained from PPG signals, as described in further detail herein.

Embodiment—Determination of Concentration Levels of a Substance Using Shifts in Absorbance Peaks In another embodiment, a concentration level of a substance may be obtained from measuring a characteristic shift in an absorbance peak of hemoglobin. For example, the absorbance peak for methemoglobin shifts from around 433 nm to 406 nm in the presence of NO. The advantage of the measurement of NO by monitoring methemoglobin production includes the wide availability of spectrophotometers, avoidance of sample acidification, and the relative stability of methemoglobin. Furthermore, as the reduced hemoglobin is present from the beginning of an experiment, NO synthesis can be measured relatively continuously (determining an NO level every 1-2 seconds or every 1-30 minutes over a predetermined time period), removing the uncertainty as to when to sample for NO.

The biosensor 100 may detect nitric oxide in vivo using PPG techniques by measuring the shift in the absorbance spectra curve of reduced hemoglobin in tissue and/or arterial blood flow. The absorbance spectra curve shifts with a peak from around 430 nm to a peak around 411 nm depending on the production of methemoglobin. The greater the degree of the shift of the peak of the curve, the higher the production of methemoglobin and NO concentration level. Correlations may be determined between the degree of the measured shift in the absorbance spectra curve of reduced hemoglobin to a concentration level of NO. The correlations may be determined from a large sample population or for a particular user and stored in a calibration database. The biosensor 100 may thus obtain an NO concentration level by measuring the shift of the absorbance spectra curve of reduced hemoglobin. A similar method of determining shifts in absorbance spectra may be implemented to determine a blood concentration level of other substances.

The biosensor 100 may obtain an NO concentration level by measuring the shift of the absorbance spectra curve of deoxygenated hemoglobin and/or by measuring the shift of the absorbance spectra curve of oxygenated hemoglobin in vivo. The biosensor 100 may then access a calibration database that correlates the measured shift in the absorbance spectra curve of deoxygenated hemoglobin to an NO concentration level. Similarly, the biosensor may access a calibration database that correlates the measured shift in the absorbance spectra curve of oxygenated hemoglobin to an NO concentration level.

Figure 8:
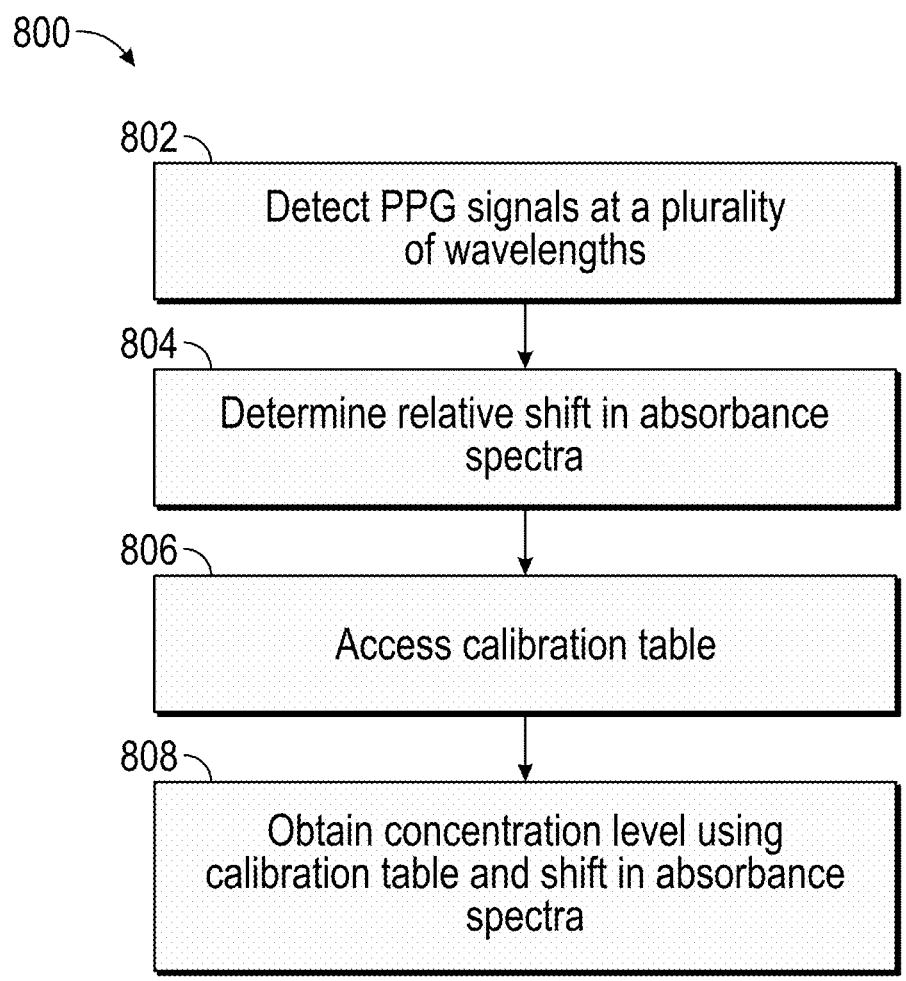
FIG. 8 illustrates a logical flow diagram of an exemplary embodiment of a method for measuring a concentration level of a substance in vivo using shifts in absorbance spectra.

FIG. 8 illustrates a logical flow diagram of an exemplary embodiment of a method 800 for measuring a concentration level of a substance in vivo using shifts in absorbance spectra. The biosensor 100 may obtain a concentration of the substance by measuring shifts in absorbance spectra of one or more substances that interact with the substance. For example, the one or more substances may include oxygenated and deoxygenated hemoglobin (HB). The PPG circuit 110 detects PPG signals at a plurality of wavelengths with a high absorption coefficient of the one or more substances that interact with the substance at 802. The biosensor 100 determines the relative shift in the absorbance spectra for the substance at 804. For example, the biosensor 100 may measure the absorbance spectra curve of deoxygenated HB and determine its relative shift or peak between the range of approximately 430 nm and 405 nm. In another example, the biosensor 100 may measure the absorbance spectra curve of oxygenated HB and determine its relative shift or peak between 421 nm and 393 nm.

The biosensor 100 accesses a calibration database that correlates the relative shift in the absorbance spectra of the substance with a concentration level of the substance at 806. The biosensor 100 may thus obtain a concentration level of the substance in blood flow using a calibration database and the measured relative shift in absorbance spectra at 808.

The biosensor 100 may be configured for measurement on a fingertip or palm, wrist, an arm, forehead, chest, abdominal area, ear lobe, or other area of the skin or body or living tissue. The characteristics of underlying tissue vary depending on the area of the body, e.g. the underlying tissue of an abdominal area has different characteristics than the underlying tissue at a wrist. The operation of the biosensor 100 may need to be adjusted in response to its positioning due to such varying characteristics of the underlying tissue. The PPG circuit 110 may adjust a power of the LEDs or a frequency or wavelength of the LEDs based on the underlying tissue. The biosensor 100 may adjust processing of the data. For example, an absorption coefficient may be adjusted when determining a concentration level of a substance based on Beer-Lambert principles due to the characteristics of the underlying tissue.

In addition, the calibrations utilized by the biosensor 100 may vary depending on the positioning of the biosensor. For example, the calibration database may include different table or other correlations between R values and concentration level of a substance depending on position of the biosensor. Due to the different density of tissue and vessels, the R value obtained from measurements over an abdominal area may be different than measurements over a wrist or forehead or fingertip. The calibration database may thus include different correlations of the R value and concentration level depending on the underlying tissue. Other adjustments may also be implemented in the biosensor 100 depending on predetermined or measured characteristics of the underlying tissue of the body part.

Embodiment—Respiration Rate, Heart Rate and Pulse Pressure

Figure 9A:
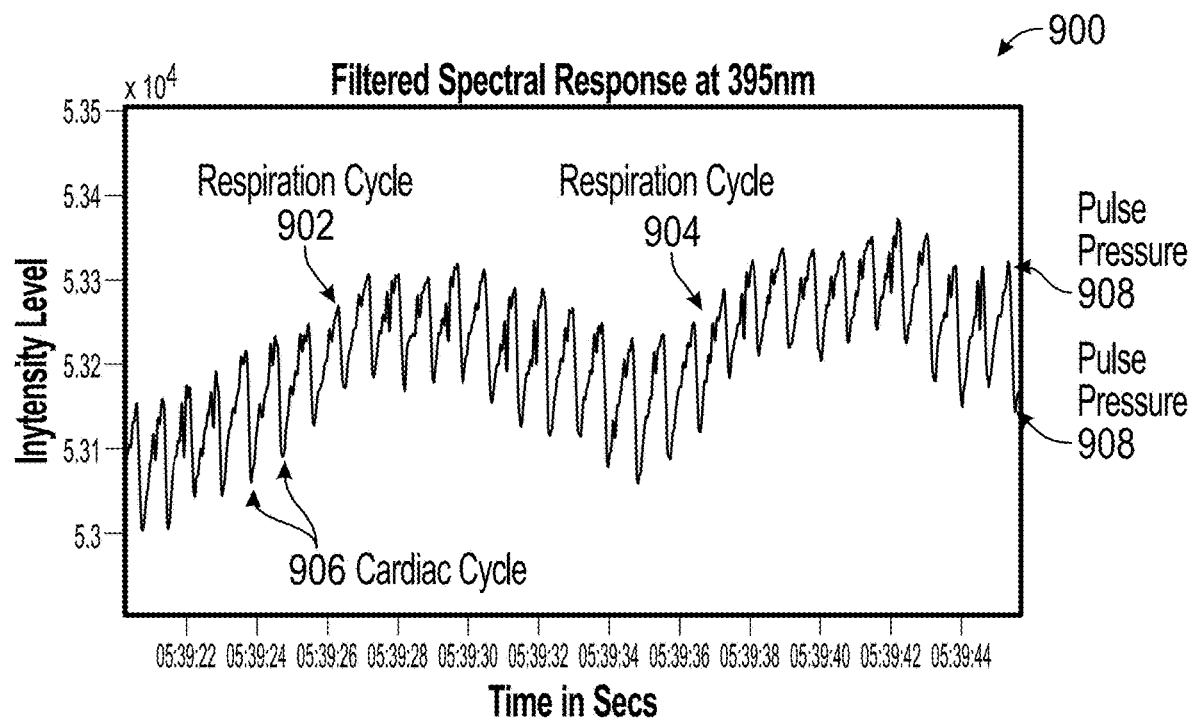
FIG. 9A illustrates a schematic drawing of an exemplary embodiment of a spectral response obtained using an embodiment of the biosensor.

FIG. 9A illustrates a schematic drawing of an exemplary embodiment of a PPG Signal 900 obtained using an embodiment of the biosensor 100 from a user. The PPG Signal 900 was obtained at a wavelength of around 395 nm and is illustrated for a time period of about 40 seconds. The PPG Signal 900 was filtered using digital signal processing techniques to eliminate noise and background interference to obtain the filtered PPG Signal 900. A first respiration cycle 902 and a second respiration cycle 904 may be obtained by measuring a low frequency component or fluctuation of the filtered PPG Signal 900. From this low frequency component, the biosensor 100 may obtain a respiratory rate of a user from the PPG Signal 900.

A heart rate may be determined from the spectral response. For example, the biosensor 100 may determine the time between diastolic points or between systolic points to determine a time period of a cardiac cycle 906. In another embodiment, to estimate the heart rate, the frequency spectrum of the PPG signal is obtained using a FFT algorithm over a predetermined period (hamming window). The pulse rate is estimated as the frequency that corresponds to the highest power in the estimated frequency spectrum. The frequency spectrum may be averaged over a time period, such as a 5-10 second window.

A pulse pressure 908 may be determined from the PPG signal 900. The pulse pressure 908 corresponds to an amplitude of the PPG signal 900 or a peak to peak value. The amplitude of the PPG signal 900 may be averaged over a time period to determine a pulse pressure 908.

Thus, a PPG signal may be used to determine heart rate, respiration rate and pulse rate. A light source in the UV range provides a PPG signal with a lower signal to noise ratio for determining heart rate and respiration rate in some tissue while a light source in the IR range provides a PPG signal with a lower signal to noise ratio in other types of tissue. The infrared range (IR) range may include wavelengths from 650 nm to 1350 nm.

Figure 9B:
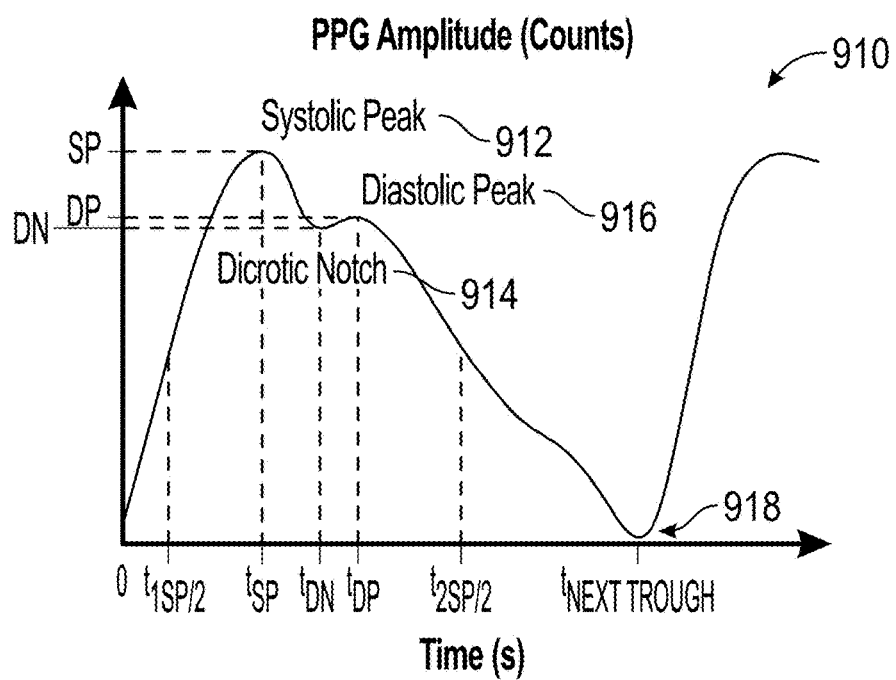
FIG. 9B illustrates a schematic drawing of an exemplary embodiment of a pressure pulse waveform.

FIG. 9B illustrates a schematic drawing of an exemplary embodiment of a pressure pulse waveform 910. After artifacts have been removed and the PPG waveform is amplified through signal processing, advanced algorithms may be used to extract and interpret its features. A peak-peak interval, or the distance between two consecutive systolic peaks, may represent a complete heart cycle, for example. In the article, "On the Analysis of Fingertip Photoplethysmogram Signals," by Mohamed Elgendi, Current Cardiology Reviews, Volume 8, pages 14-25 (2012), which is hereby incorporated by reference herein, the different characteristic features of the PPG waveform are discussed. For example, a typical PPG waveform 910 includes a systolic peak (SP) 912, a diastolic peak (DP) 916, a dicrotic notch (914), trough 918 and pulse width (tnext trough). Other characteristics include pulse pressure area (PP), systolic area (As), diastolic area (Ad), augmented pressure (AP), pulse interval, peak to peak interval, augmentation index (AI=PP/(PP−AP)×100%), crest time, etc. These or other characteristics may be determined from a PPG waveform or a first or second derivative of the PPG waveform. For example, various ratios may be derived from a second derivate of the PPG waveform, e.g., such as the early systolic negative wave to the early systolic positive wave (Ratio b/a). These and other characteristics may be measured in a PPG waveform (including its derivatives).

Figure 10:
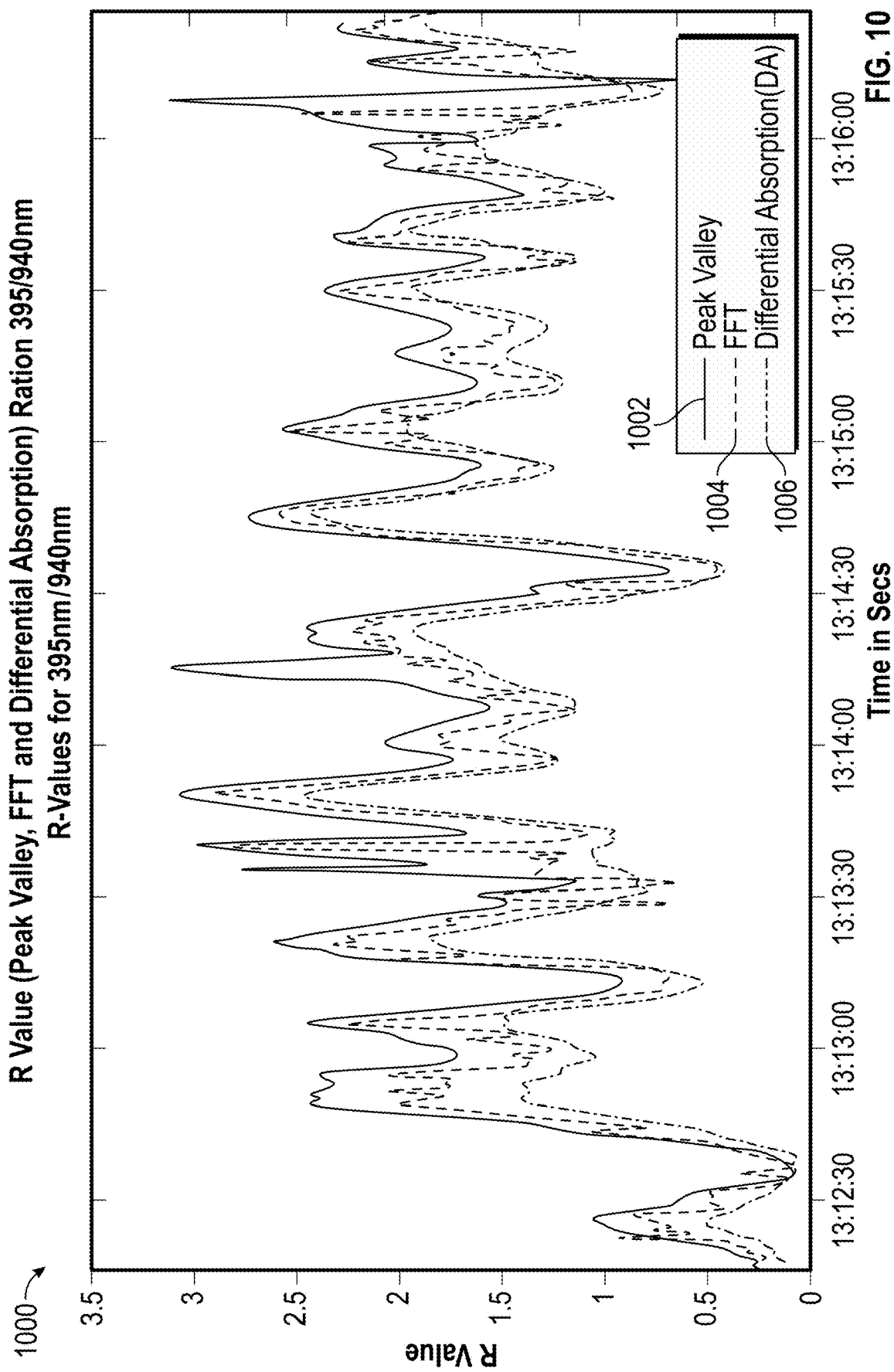
FIG. 10 illustrates a schematic drawing of an exemplary embodiment of results of R values determined using a plurality of methods.

FIG. 10 illustrates a schematic drawing of an exemplary embodiment of results of R values 1000 determined using a plurality of methods. The R values 1000 corresponding to the wavelengths of 395 nm/940 nm is determined using three methods. The R Peak Valley curve 1002 is determined using the Ratio $$R = \frac{L395}{L940}$$

as described hereinabove. The R FFT curve 1004 is obtained using FFT techniques to determine the $I_{DC}$ values and $I_{AC}$ component values of the spectral responses to determine the Ratio $$R = \frac{L395}{L940}.$$

The R differential absorption curve 1006 is determined using the shift in absorbance spectra as described in more detail in U.S. Utility application Ser. No. 15/275,388 entitled, "SYSTEM AND METHOD FOR HEALTH MONITORING USING A NON-INVASIVE, MULTI-BAND BIOSENSOR," filed Sep. 24, 2016, now U.S. Pat. No. 9,642,578 issued May 9, 2017, and hereby expressly incorporated by reference herein. The various methods thus include one or more of: Peak & Valley (e.g., peak detection), FFT, and differential absorption. Each of the methods require different amounts of computational time which affects overall embedded computing time for each signal, and therefore can be optimized and selectively validated with empirical data through large clinical sample studies. The biosensor 100 may use a plurality of these methods to determine a plurality of values for the concentration level of the substance. The biosensor 100 may determine a final concentration value using the plurality of values.

As seen in FIG. 10, the determination of the R values using the three methods provides similar results, especially when averaged over a period of time. A mean or average of the R values 1002, 1004 and 1006 may be calculated to obtain a final R value or one of the methods may be preferred depending on the positioning of the biosensor or underlying tissue characteristics.

Figure 11A:
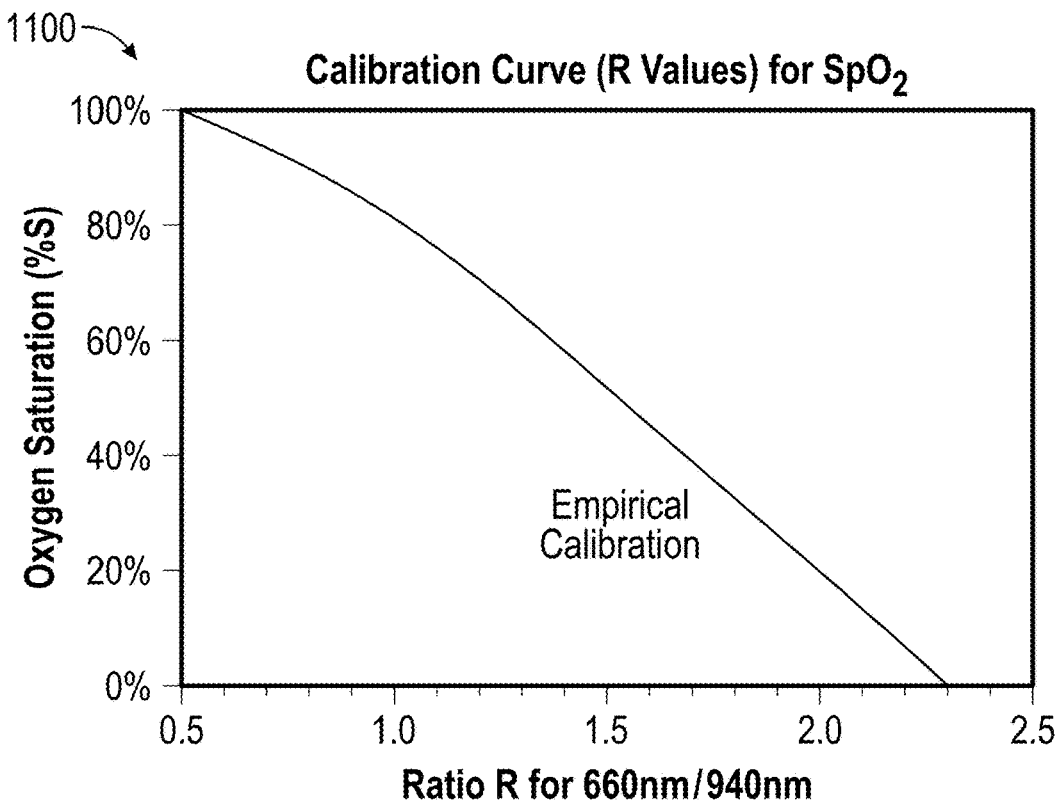
FIG. 11A illustrates a schematic drawing of an exemplary embodiment of an empirical calibration curve for correlating oxygen saturation levels ($SpO_2$) with R values.

FIG. 11A illustrates a schematic drawing of an exemplary embodiment of an empirical calibration curve 1100 for correlating oxygen saturation levels ($SpO_2$) with R values. The calibration curve 1100 may be included as part of the calibration database for the biosensor 100. For example, the R values may be obtained for $L_{660nm}/L_{940nm}$. In one embodiment, the biosensor 100 may use a light source in the 660 nm wavelength or in a range of +/−50 nm to determine $SpO_2$ levels, e.g. rather than a light source in the IR wavelength range. The 660 nm wavelength has been determined in unexpected results to have good results in measuring oxygenated hemoglobin, especially in skin tissue with fatty deposits, such as around the abdominal area.

Figure 11B:
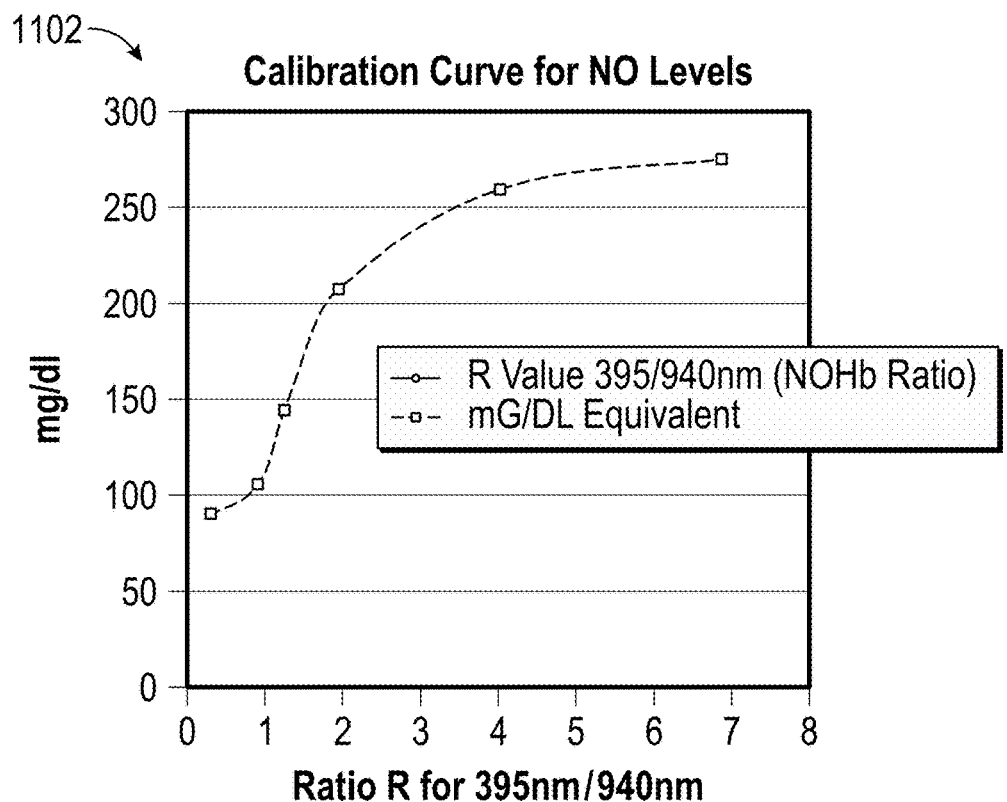
FIG. 11B illustrates a schematic drawing of an exemplary embodiment of an empirical calibration curve for correlating NO levels with R values.

FIG. 11B illustrates a schematic drawing of an exemplary embodiment of an empirical calibration curve 1102 for correlating NO levels (mg/dl) with R values. The calibration curve 1102 may be included as part of the calibration database for the biosensor 100. For example, the R values may be obtained in clinical trials from measurements of $L_{395nm}/L_{940nm}$ and the NO levels of a general sample population. The NO levels may be measured using one or more other techniques for verification to generate such a calibration curve 1102. This embodiment of the calibration curve 1102 is based on limited clinical data and is for example only. Additional or alternative calibration curves 1212 may also be derived from measurements of a general population of users at one or more different positions of the biosensor 100. For example, a first calibration curve may be obtained at a forehead, another for an abdominal area, another for a fingertip, another for a palm, etc.

From the clinical trials, the L values obtained at wavelengths around 390 nm (e.g. 380-410) are measuring nitric level (NO) levels in the arterial blood flow. The R value for L390/L940 nm may thus be used to obtain NO levels in the pulsating blood flow. From the clinical trials, it seems that the NO levels are reflected in the R values obtained from L390 nm/L940 nm and wavelengths around 390 nm such as L395 nm/L940 nm. The NO levels may thus be obtained from the R values and a calibration database that correlates the R value with known concentration levels of NO.

In other embodiments, rather than $L\lambda 1=390$ nm, the L value may be measured at wavelengths in a range from 410 nm to 380 nm, e.g., as seen in the graphs wherein $L\lambda 1=395$ nm is used to obtain a concentration level of NO. In addition, $L\lambda 2$ may be obtained at any wavelength at approximately 660 nm or above. Thus, R obtained at approximately $L\lambda 1=380$ nm-400 nm and $L\lambda 2 \geq 660$ nm may also be obtained to determine concentration levels of NO.

Figure 12:
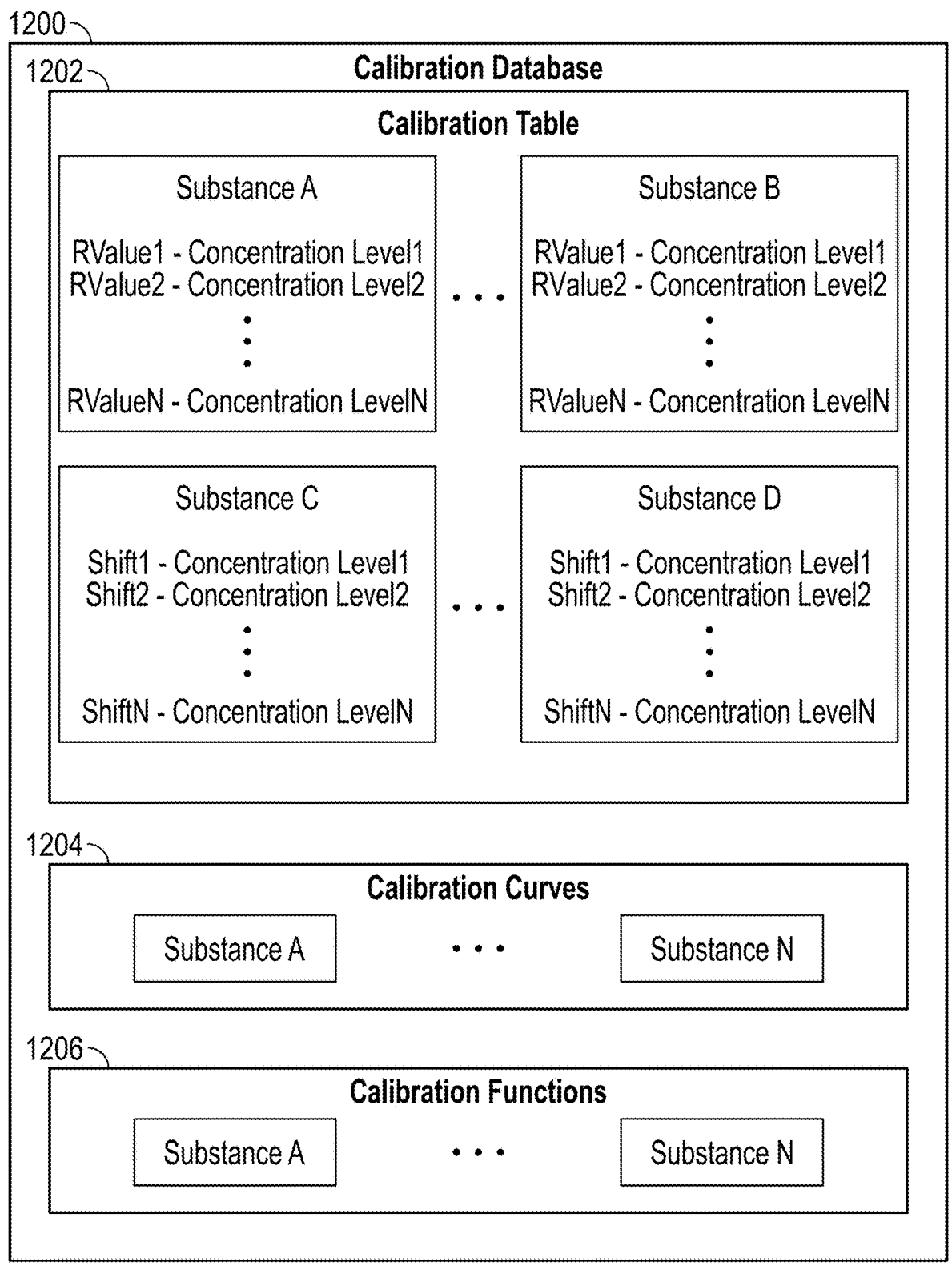
FIG. 12 illustrates a schematic block diagram of an embodiment of a calibration database.

FIG. 12 illustrates a schematic block diagram of an embodiment of a calibration database 1200. The calibration database 1200 includes one or more calibration tables 1202, calibration curves 1204 or calibration functions 1206 for correlating obtained values to concentration levels of one or more substances A-N. The concentration level of the substances may be expressed in the calibration tables 1202 as units of mmol/liter, as a saturation level or percentage, as a relative level on a scale (e.g., 0-10), etc. For example, the concentration level of NO may be determined and expressed as (mg/dl) as a saturation level or percentage (SpNO %) or a relative level on a scale (e.g., 0-10).

The calibration database 1200 may also include one or more calibration tables for one or more underlying skin tissue types. In one aspect, the calibration database 1200 may correlate an R value to a concentration level of a substance for a plurality of underlying skin tissue types.

In another aspect, a set of calibration tables 1202 may correlate an absorption spectra shift to a concentration level of one or more substances A-N. For example, a first table may correlate a degree of absorption spectra shift of oxygenated hemoglobin to NO concentration levels. The degree of shift may be for the peak of the absorbance spectra curve of oxygenated hemoglobin from around 421 nm. In another example, the set of table 1202 may correlate a degree of absorption spectra shift of deoxygenated hemoglobin to NO concentration levels. The degree of shift may be for the peak of the absorbance spectra curve of deoxygenated hemoglobin from around 430 nm.

The calibration database 1200 may also include a set of calibration curves 1204 for a plurality of substances A-N. The calibration curves may correlate L values or R values or degree of shifts of spectral data to concentration levels of the substances A-N.

The calibration database 1200 may also include calibration functions 1206. The calibration functions 1206 may be derived (e.g., using regressive functions) from the correlation data from the calibration curves 1204 or the calibration tables 1202. The calibration functions 1206 may correlate L values or R values or degree of shifts in spectral data to concentration levels of the substances A-N for one or more underlying skin tissue types.

Embodiment—Neural Network

One or more types of artificial neural networks (a.k.a. machine learning algorithms) may be implemented herein to determine health data from PPG signals. For example, neural networks may be used to obtain a concentration level of NO or glucose or other health data from input data derived from PPG signals. Neural network models can be viewed as simple mathematical models defining a function $f$ wherein $f:X \rightarrow Y$ or a distribution over X or both X and Y. Types of neural network engines or APIs currently available include, e.g. TensorFlow™, Keras™, Microsoft® CNTK™, Caffe™, Theano™ and Lasagne™.

Sometimes the various machine learning techniques are intimately associated with a particular learning rule. The function $f$ may be a definition of a class of functions (where members of the class are obtained by varying parameters, connection weights, thresholds, etc.). The neural network learns by adjusting its parameters, weights and thresholds iteratively to yield desired output. The training is performed using defined set of rules also known as the learning algorithm. Machine learning techniques include ridge linear regression, a multilayer perceptron neural network, support vector machines and random forests. For example, a gradient descent training algorithm is used in case of supervised training model. In case, the actual output is different from target output, the difference or error is determined. The gradient descent algorithm changes the weights of the network in such a manner to minimize this error. Other learning algorithms include back propagation, least mean square (LMS) algorithm, etc. A set of examples or a training set is used for learning by the neural network. The training set is used to identify the parameters [e.g., weights] of the network.

Figure 13:
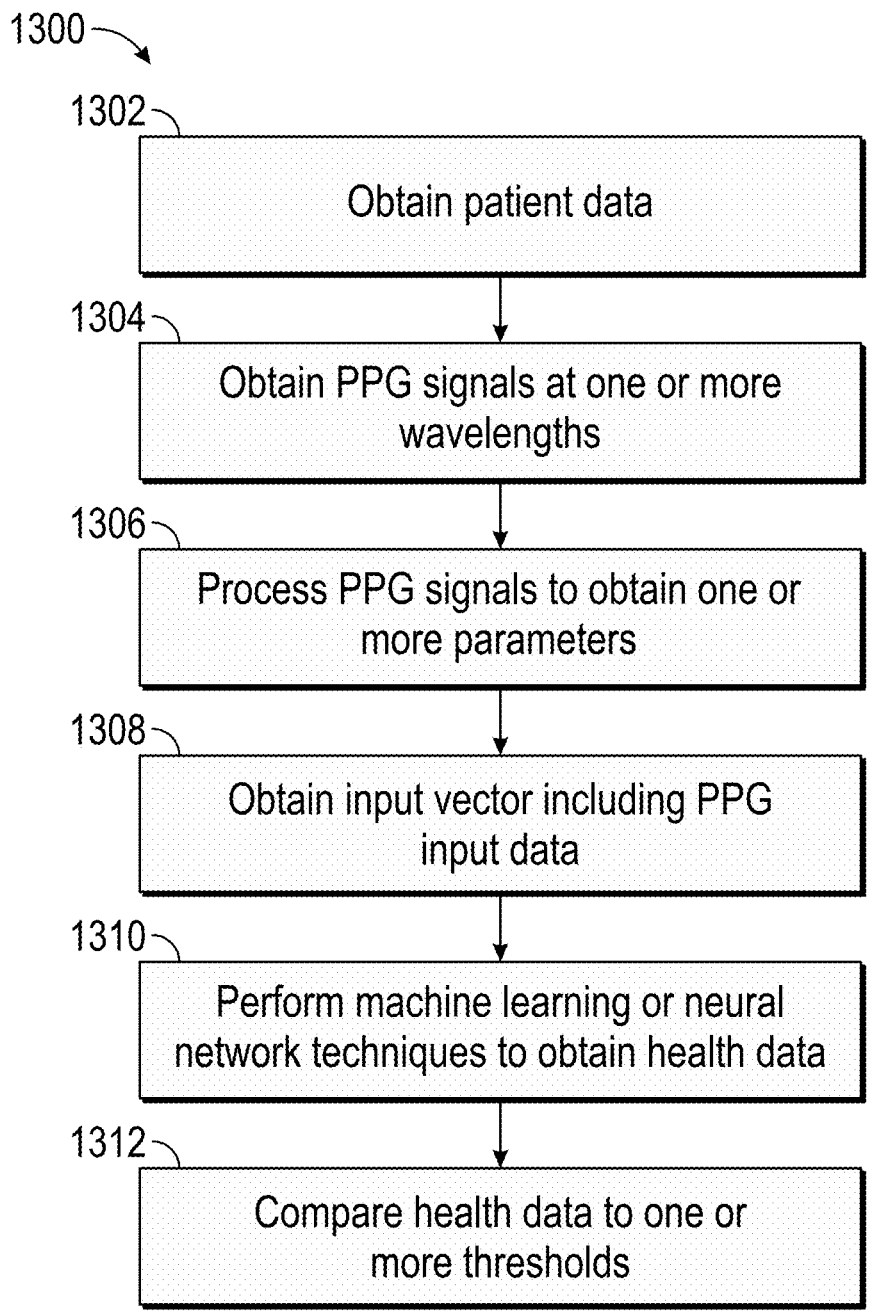
FIG. 13 illustrates a logical flow diagram of an embodiment of a method for using a machine learning neural network technique for detection of health data.

FIG. 13 illustrates a logical flow diagram of an embodiment of a method 1300 for using a machine learning neural network technique for detection of health data. In an embodiment, patient data is obtained at 1302. The patient data may include one or more of: age, weight, body mass index, temperature, blood pressure, pre-existing medical conditions, trauma events, mental conditions, injuries, demographic data, physical examinations, laboratory tests, diagnosis, treatment procedures, prescriptions, radiology examinations, historic pathology, medical history, surgeries, etc. PPG signals at one or more wavelengths are obtained at 1304.

Various parameters of the PPG signals may be determined or measured at 1306 These parameters include the diastolic and systolic points, transfer functions, timing differences between wavelengths, the L values, R values, pulse shape (measured by autoregression coefficients and moving averages), characteristic features of the shape of the PPG waveform, the average distance between pulses, variance, instant energy information, energy variance, etc. Other parameters may be extracted by representing the PPG signal as a stochastic auto-regressive moving average (ARMA). Parameters also may be extracted by modeling the energy of the PPG signal using the Teager-Kaiser operator, calculating the heart rate and cardiac synchrony of the PPG signal, and determining the zero crossings of the PPG signal. These and other parameters may be obtained using a PPG signal. The PPG input data may include the PPG signals, and/or one or more parameters derived from the PPG signals.

An input vector is obtained at 1308. The input vector includes the PPG input data, such as the PPG signals at one or more wavelengths and/or one or more parameters generated from the PPG signals at the one or more wavelengths. Since the PPG signal is of variable duration, a fixed dimension vector for a measurement of the PPG signal may be obtained. The input vector may also include patient data.

The input vector is processed by a processing device executing a neural network (aka machine learning algorithm). The processing device executes the machine learning algorithm or neural network techniques using the input vector to determine health data at 1310. The health data includes one or more of heart rate, period of vasodilation, level of vasodilation, respiration rate, blood pressure, oxygen saturation level, NO level, liver enzyme level, Glucose level, Blood alcohol level, blood type, sepsis risk factor, infection risk factor, cancer, virus detection, creatinine level or electrolyte level. The health data may also include blood viscosity, blood pressure, arterial stiffness, vascular health, cardiovascular risk, atherosclerosis, etc. The health data may be generated as an output fixed length vector.

The obtained health data may be compared to expected ranges or thresholds in a calibration table at 1312. Alarms or warnings may be issued based on the comparison.

Embodiment—Measurement of Vasodilation/Vasoconstriction Using PPG Signals

Vasodilation and vasoconstriction are different from blood volume changes due to the cardiac cycle. Vasodilation is the widening of blood vessels due to relaxation of smooth muscle cells within the vessel walls, in particular in the large veins, large arteries, and smaller arterioles. For example, the release of the Endothelium-derived relaxing factor (EDRF) causes the arteries to expand in diameter and change elasticity. This process is the opposite of vasoconstriction, which is the narrowing of blood vessels due to constriction of the smooth muscle cells within the vessels walls. The vascular endothelium is crucially involved in the fundamental regulation of blood flow matching demand and supply of tissue. After transient ischemia, arterial inflow increases. As a response to increased shear forces during reactive hyperemia, healthy arteries dilate via release of NO or other endothelium-derived vasoactive substances. This endothelium-dependent flow-mediated vasodilation (FMD) is impaired in atherosclerosis.

The capacity of blood vessels to respond to physical and chemical stimuli in the lumen confers the ability to self-regulate tone and to adjust blood flow and distribution in response to changes in the local environment. Many blood vessels respond to an increase in flow, or more precisely shear stress, by dilating. This phenomenon is designated flow-mediated vasodilation (FMD). A principal mediator of FMD is endothelium-derived NO—an example of an EDRF.

Although the precise mechanism by which vasodilation occurs during reactive hyperemia in FMD measurement has not been fully elucidated, nitric oxide (NO) has been proposed as a principal mediator of FMD. The NO, produced as a result of an increase of endothelial NO synthase activity induced by shear stress, diffuses into the tunica media, leading to relaxation of smooth muscle cells and subsequent vasodilation. The assessment of endothelial function by FMD, therefore, presupposes a normal structural condition. Impaired endothelium-independent vasodilation is thought to be associated with structural vascular alterations and alterations in smooth muscle cells, e.g. as a result of atherosclerosis.

As the presence of endothelial dysfunction is closely associated with cardiovascular risk and outcome, the measurement of FMD in the brachial artery has become a standard method for the assessment of endothelial function in patients and to evaluate therapeutic interventions targeting atherosclerosis. For example, in healthy humans, the relative increase in brachial artery diameter during vasodilation is typically in the 5% to 10% range.

Flow-mediated vasodilation measurements have been performed in human studies and are of diagnostic and prognostic importance. Prior techniques for measuring vasodilation require using high-frequency ultrasound to visually inspect vessels, most commonly the brachial artery. For example, one ultrasound technique evaluates flow-mediated vasodilation (FMD), an endothelium-dependent function, in the brachial artery. This process includes applying a stimulus to provoke the endothelium to release nitric oxide (NO) with subsequent vasodilation that is then imaged using high resolution ultrasonography and quantitated as an index of vasomotor function. This process of high-resolution ultrasonography of the brachial artery to evaluate vasomotor function has limitations. It must be performed in a clinical setting by a medical clinician using expensive ultrasonography equipment. Thus, there is a need for an improved system and method for detection of vasodilation or vasoconstriction and vascular health.

Thus, there is a need for an improved system and method for detection of vasodilation/vasoconstriction and conditions affected by vasodilation and conditions that affect vasodilation. The systems and methods described herein for detection of levels of vasodilation and periods of vasodilation may be used to determine levels of vasoconstriction and periods of vasoconstriction.

In various embodiments described herein, vasodilation or vasoconstriction and characteristics thereof may be measured using PPG signals obtained by the biosensor. The effects of vasodilation may be observed in PPG signals in one or more of a plurality of wavelengths across different spectrums, such as IR, visible and UV. For example, PPG signals across the spectrum may vary in shape, intensity level and timing due to vasodilation/vasoconstriction. In one example, the effect of vasodilation is observed from phase differences between PPG signals of different wavelengths, especially between wavelengths in different spectrums. Vasodilation also causes subtle skin movement which may be observed in PPG signals, especially in lower frequency components of PPG signals (e.g. frequencies that do not reflect the pulsatile blow flow). Using one or more characteristics of the PPG signals, a level of vasodilation/vasoconstriction may be obtained. The level of vasodilation/vasoconstriction may be measured as a relative change in the size of vessels, such as percentage increase/decrease in a baseline diameter or planar area, or in a range such as 1-10, or in other manners.

In addition, an arterial stiffness or elasticity index may be obtained using the PPG signals. The PPG signals may predict vascular health, such as atherosclerosis. For example, a timing or period to change from a state of vasodilation to normal width may be obtained using phase differences between different wavelengths. The rate of change may indicate vascular stiffness and a prediction of vascular health.

In another embodiment, the level of vasodilation may be used to calibrate measurement of oxygen saturation SpO2 or other measurements of concentration of substances in blood flow. For example, measurements of oxygen saturation levels may be in error during periods of vasodilation. These measurements of oxygen saturation during vasodilation may be identified and flagged and/or the measurements may be calibrated in response to a level of vasodilation.

The biosensor described herein obtains PPG signals and measures a relative level of vasodilation of vessels and a period of vasodilation. For example, the PPG signal measures the pressure wave of blood flow through vessels. Vasodilation changes the propagation properties of blood flow through vessels, and thus the PPG signal changes. The changes in PPG signals due to the changing propagation properties is reflected in a transfer function generated from the PPG signals, e.g. time differences and wave shape differences between PPG signals. The transfer function may be measured to determine a level of vasodilation in real time.

Figure 14:
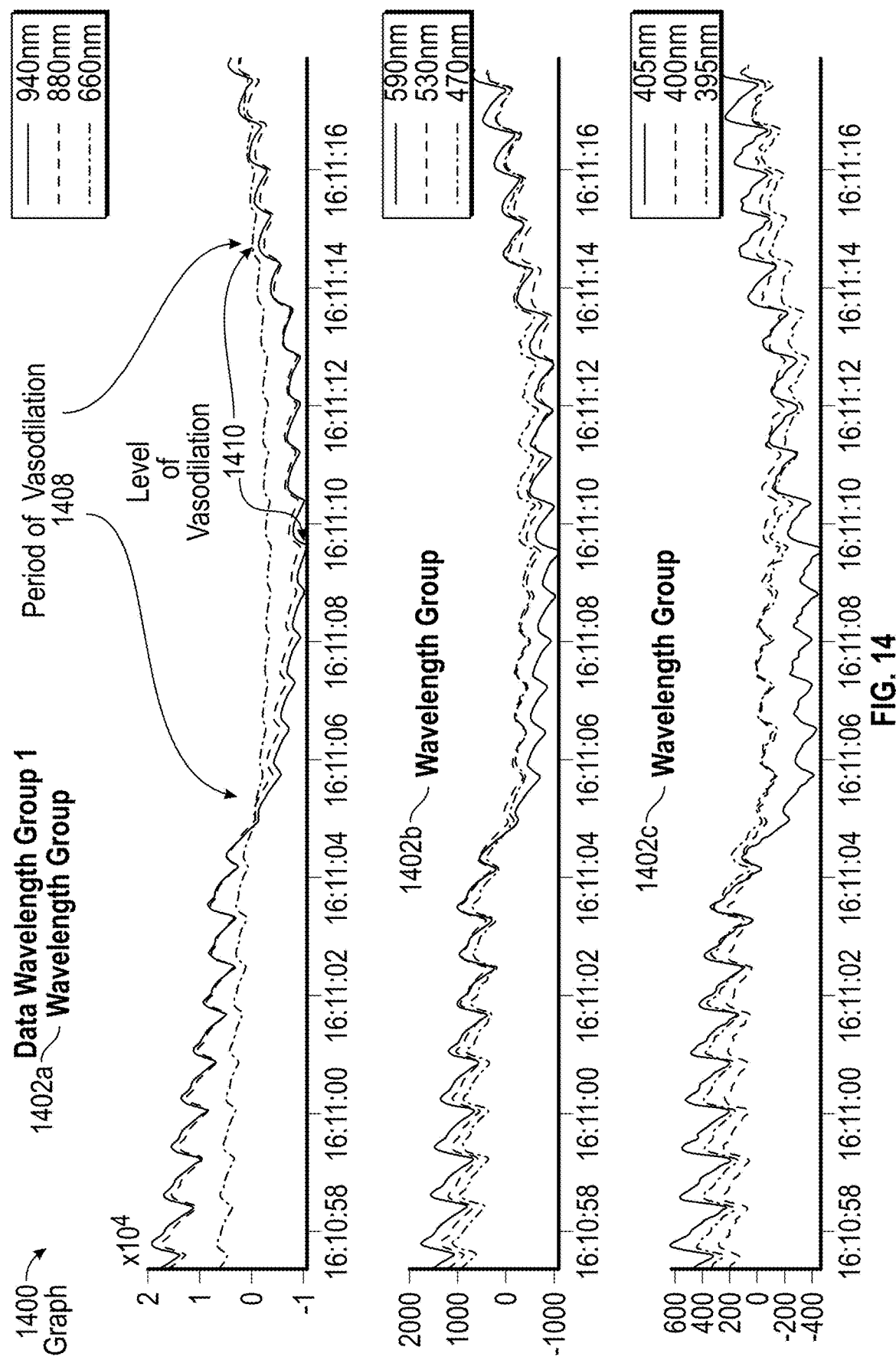
FIG. 14 illustrates a schematic diagram of a graph of PPG signals during a period of vasodilation in vessels.

FIG. 14 illustrates a schematic diagram of a graph 1400 of PPG signals during a period of vasodilation in vessels. At "rest", as the body processes food, insulin is dispensed, and nitric oxide is released into the blood. The arteries expand due to the NO causing the outer muscle of the arteries to expand temporarily. This vasodilation is reflected in the PPG signal, and highly visible in the signal to noise ratio.

The biosensor 100 obtained a PPG signal during vasodilation after caloric intake for a wavelength at 940 nm, a wavelength at 880 nm and a wavelength at 660 nm as shown in the PPG Signals for Wavelength Group 1402a. The biosensor 100 also obtained the spectral response for a wavelength at 590 nm, a wavelength at 530 nm and a wavelength at 470 nm as shown in the PPG Signals for Wavelength Group 1402b. The biosensor 100 further obtained the spectral response for a wavelength at 405 nm, a wavelength at 400 nm and a wavelength at 395 nm as shown in the PPG Signals for Wavelength Group 1402c.

As shown in the graphs, the PPG signals reflect a period of vasodilation 1408. The vasodilation 1408 is reflected in the PPG signals during a time period between approximately 16.11.04 secs through approximately 16.11.17 secs. In particular, a lower frequency component of the PPG signals changes during the period of vasodilation 1408. This lower frequency component of the PPG signals includes the lower frequencies not affected by the pulsating blood flow (pressure wave) due to the cardiac cycle.

During vasodilation, the arteries and other vessels widen changing the absorption properties of the vascular tissue. These changes in absorption properties are due, e.g., by the increase in blood in the vascular tissue and the compression of surrounding tissue due to the widening vessels. The PPG signals across wavelengths in the IR, visible and UV spectrums are affected by the changing absorption properties of the vascular tissue due to vasodilation.

The level of vasodilation 1410 may be obtained from the PPG signals. For example, the amplitude changes in a low frequency component from the PPG signal may be correlated to a level of vasodilation. The level of vasodilation may be expressed as a percentage change of the diameter or planar area of the vessel or percentage increase in blood flow during the period of vasodilation. The level of vasodilation may alternatively be measured in a range such as 1-10, or in other manners. A level of vasoconstriction may be similarly detected and measured.

The duration of the vasodilation may also be obtained from the PPG signals. The beginning of vasodilation and end of vasodilation may be identified from a change in amplitude, especially of low frequency components, of the PPG signals. For example, the vasodilation begins at approximately 16.11.04 secs and ends at approximately 16.11.17 secs in Graph 1400 and so indicates a period of vasodilation of 13 seconds.

Figure 15:
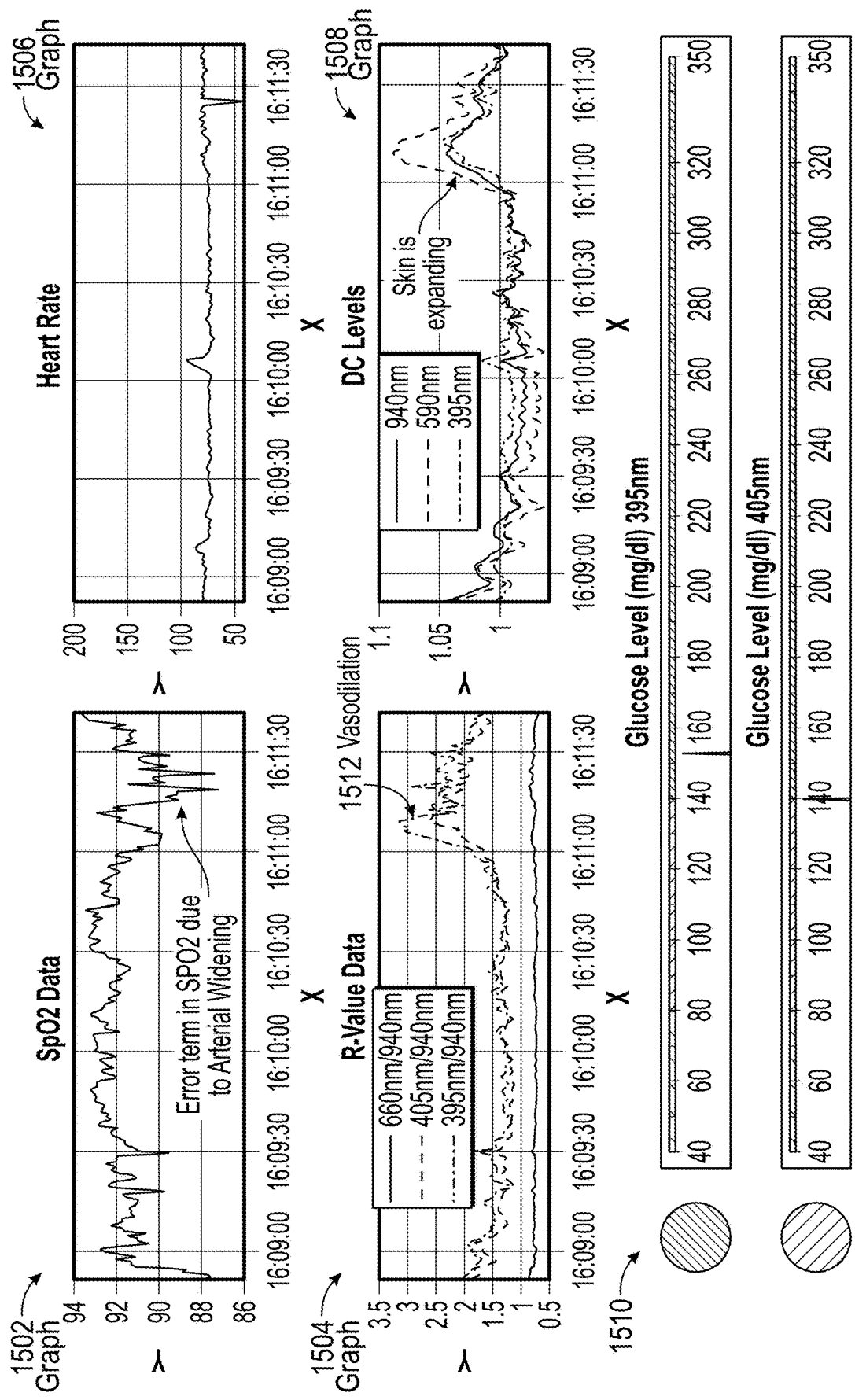
FIG. 15 illustrates a schematic diagram of a series of graphs illustrating the effects of vasodilation in PPG signals.

FIG. 15 illustrates a schematic diagram of a series of graphs illustrating the effects of vasodilation using the PPG signals shown in FIG. 14. The first graph 1502 illustrates $R_{660/940}$ values that may be used to obtain a measurement of oxygen saturation $SpO_2$. The vasodilation period 1512, seen at approximately 16.11.04 secs through approximately 16.11.17 secs, affects the R values and thus the $SpO_2$ measurements. Other measurements based on R values or relative amplitudes of PPG signals are also affected by vasodilation. In an embodiment, an error value or calibration may be determined for measurements of oxygen saturation $SpO_2$ during a period of vasodilation. The error value or calibration may depend on the level of vasodilation or change in R values due to the vasodilation.

The second graph 1504 illustrates R values at $R_{660/940}$, $R_{405/940}$ and $R_{395/940}$. The vasodilation period 1512, seen at approximately 16.11.04 secs through approximately 16.11.17 secs, affects the R values, especially R values using PPG signals in the UV or near UV range. The R values may be affected during the vasodilation period since the ratio of the amplitude of different wavelengths is used to obtain the R values. This may cause errors in the measurement of blood component levels. The R values and/or measurements of blood component levels may be compensated due to the effect of vasodilation to correct errors during periods of vasodilation.

For example, during the expansion of vessels during a vasodilation period (e.g., due to NO or other EDRF), it may not be practical to measure the SpO2 due to the error term present in the 940 & 660 nm PPG signals. This effect of vasodilation is likely being observed by current SpO2 meters. Errors in the measurement of SpO2 may be caused by undetected periods of vasodilation in current SpO2 meters. Vasodilation may also cause errors in determinations of other blood components using PPG signals. The measurement of the respiratory cycle in a PPG signal is also affected during vasodilation.

The duration of the vasodilation effect may depend on the individual, the amount of the food ingested and the arterial rigidity. For example, the vessels of diabetic subjects are likely to expand less and have much less change in amplitude of PPG signals during vasodilation/vasoconstriction due to inelasticity of the arteries due to arterial rigidity and endothelial dysfunction.

The graph 1506 illustrates the higher frequencies of the PPG signal at 660 nm that may be used to determine whether the heart rate remains relatively unaffected during the period of vasodilation. The graph 1510 illustrates an elevated glucose level during the vasodilation period of about 140-152 mg/dl.

The graph 1508 illustrates the lower frequencies of PPG signals at 940 nm, 590 nm and 395 nm (e.g., the frequencies not affected by pulsatile blood flow). The characteristics of the lower frequencies of the PPG signals change during the vasodilation period. The absorption properties of the vascular tissue vary due to changes in volume of blood. In addition, the widening of the vessels compresses the surrounding tissue. And the epidermis, the upper layer of the skin, may expand in response to the widening vessels during vasodilation. The PPG signals are thus affected by this change in absorption properties of the tissue, as seen in graph 1508.

The graph 1508 also illustrates that the PPG signals in different spectrums exhibit a time or phase delay. For example, the PPG signal at 940 nm in the IR range, the PPG signal at 590 nm in the visible range, and the PPG signal at 395 nm in the UV range have timing differences. This time delay is due in part to the different penetration depths of the wavelengths. Preferably, to determine this time delay, PPG signals in an infrared range (IR) range from 650 nm to 1350 nm and PPG signals outside the IR range are compared to determine the time or phase delay.

The pressure pulse wave propagates from deeper tissue to shallower tissue, and thus a phase difference is generated between the pressure pulse wave in the IR and UV signals. As the arteries vasodilate and vasoconstrict, the resistance to the pressure pulse wave changes and changes the propagation time from the deeper tissue to the shallower tissue. This change in propagation time also changes the phase difference between the pressure pulse wave in the IR and UV signals. This phase difference provides a measure of the effects of vasodilation and vasoconstriction. By comparing changes in the phase difference between the UV & IR, the effects of vasodilation and vasoconstriction may be measured.

At a same input power, light at higher wavelengths (IR light) penetrates vascular tissue deeper than light at lower wavelengths (UV light). The optical properties of the tissue are affected by many factors, including but not limited to, skin-tone, tissue hydration, and tissue chemistry. In a sensor configuration where the light from the light source is backscattered to a sensor on the same surface, the optical signal at the sensor includes a sum of all light backscattered that makes it to the focal surface after interacting with the tissue. With the optical power being the same across all wavelengths, some of the light backscattered from the IR light penetrates deeper into the tissue than the UV light does. This means that the different wavelengths of light probe different depths of tissue. Near the surface of the skin, the density of arterial blood vessels is much higher (i.e. the amount of arterial blood) than at the deeper tissue depths. This means that while the IR light is affected by the arterial blood at the shallower depths, the majority of the IR signal is reflected from the deeper arterial blood.

When the heart beats, the arteries swell as fluid is pushed out of the heart. The leading edge of the swelling or pressure wave moves like a "bulge" through the arterial system. This system can be thought of as an elastically dampened hydraulic system. The pressure wave or bulge in the pulsatile blood flow moves from the lower tissue to the upper tissue. Thus, the deeper penetrating wavelengths (such as IR light) detect a pressure wave first followed by the lesser penetrating wavelengths (such as visible then UV light). The time delay in the "bulge" or pressure wave moving from the lower tissue into the upper tissue thus creates a time delay in a pressure waveform seen in the PPG signals at different wavelengths. For example, as seen in FIG. 15, a waveform in the UV range has a time delay compared to a waveform in the IR range and a waveform in the visible range (390 nm to 700 nm). This time delay in the different wavelengths is thus due to the depth of penetration into the skin of each wavelength.

Vasodilation/vasoconstriction changes the propagation of the pressure wave starting in the deeper, larger arteries and then moving to the shallower, smaller ones. In addition, the UV light at 395 nm is absorbed by blood more than at 940 nm. Thus, less blood is needed to obtain the same intensity to sample the PPG signal. Because the deeper arteries are "closer" in the arterial structure to the main arteries supplying blood to the tissue site, they are less rigid than the arterioles that are closer to the surface of the skin (where the majority of the UV signal is reflected). The deeper arteries are more affected by vasodilation and vasoconstriction.

In an embodiment described herein, this change in propagation of the pressure wave can be measured in the change in transfer function from a wavelength that penetrates the tissue deeply (e.g. in the IR range) to a wavelength that penetrates tissue much less deeply (e.g. in the visible or UV range). This means that by measuring the change in shape and time delay of PPG signals of two or more wavelengths with different penetration depths (e.g., wherein at least one is in the near-IR window and one is not), information about vasodilation/vasoconstriction may be determined. Also, because the transfer function between the two depths of penetration is affected by blood pressure, blood viscosity, tissue absorption, and, in general, cardiovascular health, these other parameters can be characterized as well. Features or parameters of the PPG signal that can be examined include, but are not limited to, the time delay between the systolic points and diastolic points in different wavelengths and the difference in dicrotic notch suppression between wavelengths.

Vasoconstriction forces a greater volume of blood out of the tissue site. This will lead to a decrease in absorption in the field of view of the sensor because in general, blood absorbs more light than tissue. There will be an increase in the intensity of the reflected light detected at the biosensor because less light is being absorbed (because there is less blood to absorb it). This will lead to a sharp increase in the "DC" signal. Additionally, because the surface area of the blood vessels is decreased, the intensity of the pulsating signal due to the pressure pulse wave (the AC signal) is decreased.

In tests, a patient consumed vasodilators and PPG signals were measured. The PPG signals at different wavelengths exhibited a decrease in time delay (phase difference), an increase in the DC levels, and decreased in the AC levels. The research described herein has thus confirmed that in general, the time delay (phase difference) increases, the DC levels spike, and AC signals decrease during vasoconstriction.

Vasodilation or vasoconstriction may also change the color or hue of the skin tissue due to expansion or contraction of the vessels. This increase or decrease of blood flow may change the hue of the skin. By monitoring the hue of the skin, the biosensor 100 may detect vasodilation or other changes in blood circulation in the tissue. For example, a PPG signal in a visible light range such as at a yellow (590 nm-560 nm) or Red (564 nm-580 nm) or Blue (490 nm-450 nm) wavelength may be used to detect a change in hue of the skin.

Figure 16:
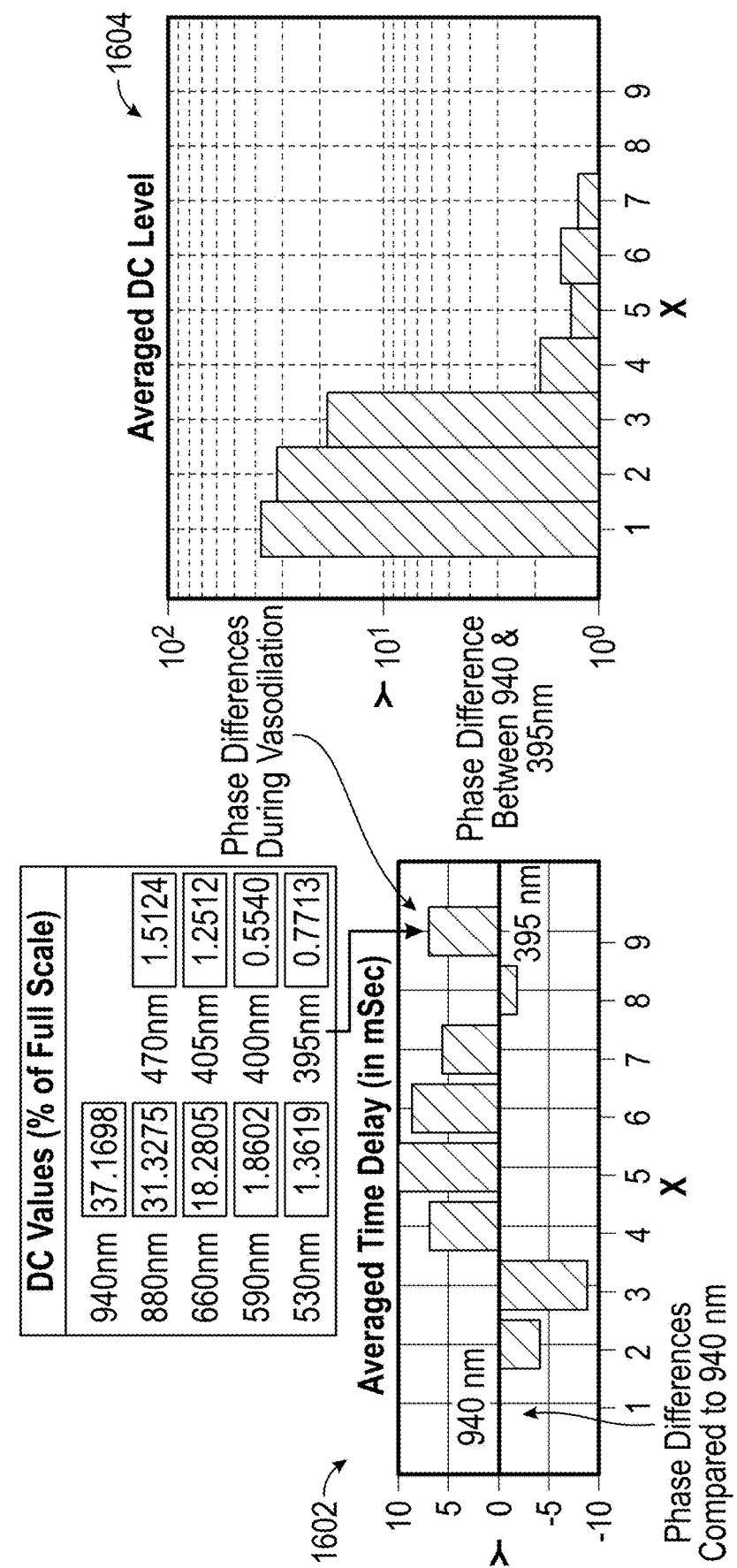
FIG. 16 illustrates a schematic diagram illustrating phase differences and average low frequency levels during vasodilation of PPG signals of various wavelengths.

FIG. 16 illustrates a schematic diagram 1600 illustrating phase differences and average low frequency levels during vasoconstriction using the PPG signals of various wavelengths from FIG. 14. The Graph 1602 illustrates the average phase difference between a PPG signal at 940 nm and PPG signals of various wavelengths during the period of vasodilation. The first time difference equal to 0 is between 940 and itself. The last shown time difference is between 395 nm and 940 nm. The phase difference or the timing difference between PPG signals in graph 1602 illustrates a negative to positive timing which corresponds to the constrictions and expansion of the arteries during vasodilation/vasoconstriction. A change in the phase delay between the PPG signals at different wavelengths is thus seen during a period of vasoconstriction.

The second graph 1604 illustrates the average "DC values" in PPG signals of various wavelengths during the period of vasodilation. The "DC values" include DC components and/or low frequency components not generally affected by the pulsatile blood flow. The graph 1604 illustrates that the average DC values $I_{DC}$ are above a baseline normal during the period of vasoconstriction. The average DC values increase due to vasoconstriction, changing tissue characteristics of contracting or expanding muscles and is proportional to the force applied to the muscle. So, the DC value (low frequencies not generally affected by the pulsatile blood flow) can be used to determine periods and levels of vasodilation/vasoconstriction.

The endothelium lines the walls of vessels and helps to regulate vascular function. In the vasculature, insulin is released in response to ingestion or hunger. The insulin activates two distinct signaling path-ways in the endothelium that result in secretion of nitric oxide (NO) and endothelin (ET-1), respectively.

Figure 17B:
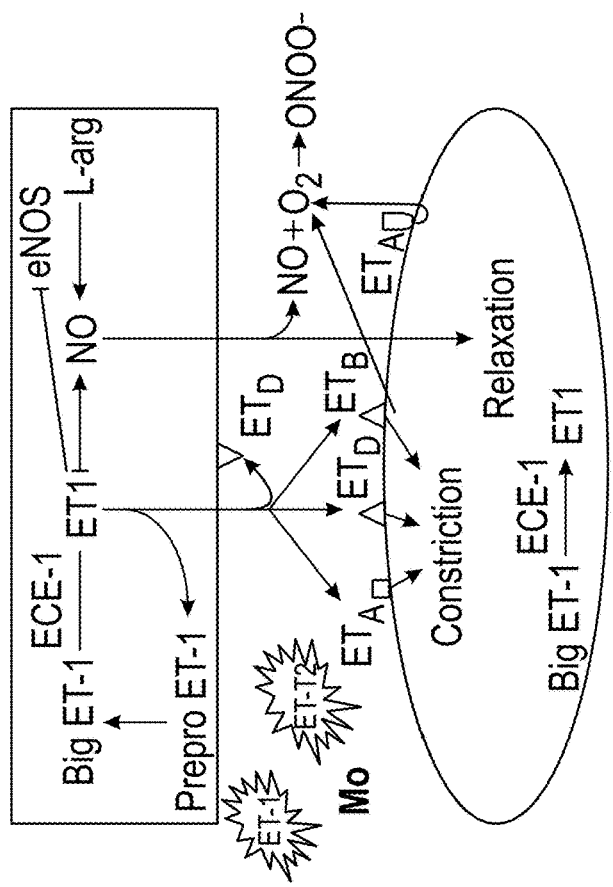
FIG. 17B illustrates a schematic block diagram of an arterial wall with vascular dysfunction.
Figure 17A:
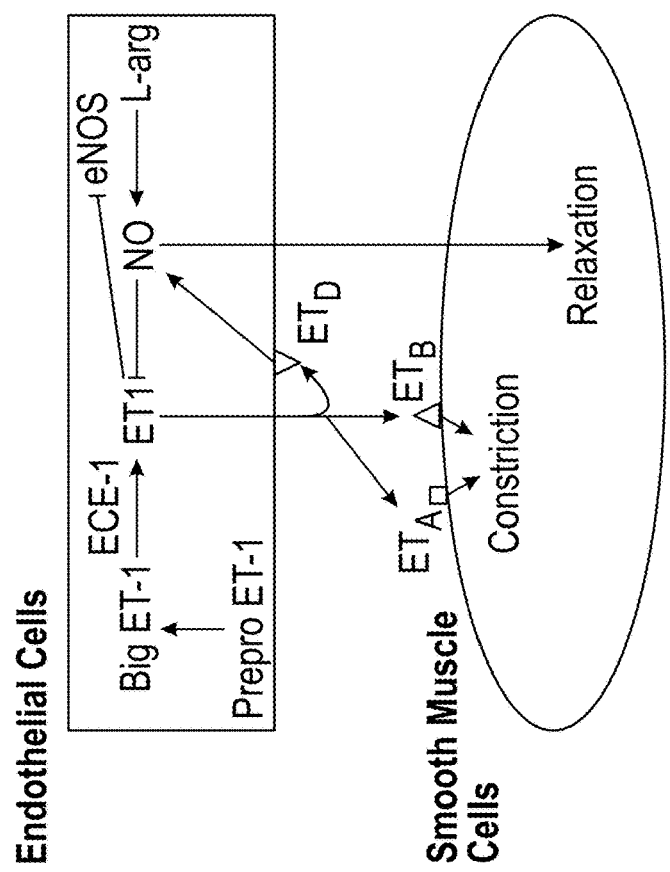
FIG. 17A illustrates a schematic block diagram of an arterial wall under healthy conditions.

FIG. 17A illustrates a schematic block diagram of an arterial wall under healthy conditions 1702. Smooth muscle cells respond to NO as a vasodilator and endothelin (ET-1) as a vasoconstrictor. ET-1 incites constriction in the smooth muscle cells by binding to $ET_A$ and $ET_B$ receptors. In the vasculature, the $ET_A$ receptor is mainly located on vascular smooth muscle cells and mediates vasoconstriction. The $ET_B$ receptor is primarily located on endothelial cells but may also be present on vascular smooth muscle cells. Stimulation of the endothelial $ET_B$ receptor results in release of NO and prostacyclin which causes vasodilatation, whereas stimulation of the vascular smooth muscle cell $ET_B$ receptor results in vasoconstriction. Thus, the net effect produced by ET-1 is determined on the receptor localization and the balance between $ET_A$ and $ET_B$ receptors.

Endothelial cells also mediate rapid responses to neural signals for blood vessel dilation, by releasing NO to make smooth muscles relax in the vessel wall. Production of NO counteracts or mediates the constricting effects of ET-1 in response to insulin in vasculatures. Insulin stimulates NO production in endothelial cells by subsequently activating the intracellular enzymes 1-phosphatidylinositol 3-kinase (PI3-ki-nase) and Akt, which activates endothelial NO synthase. NO, stimulated by higher insulin doses, is thought to be the underlying agent in insulin-mediated, endothelium-dependent vasodilation. In healthy arteries, smaller levels of ET-1 are produced in comparison to NO levels, and so the bioavailability of NO is preserved.

FIG. 17B is a schematic block diagram of an arterial wall with vascular dysfunction. In vascular dysfunction, there is an increased expression of ET-1 in smooth muscle cells and macrophages. There is also an increased expression of $ET_B$ receptors on smooth muscle cells mediating vasoconstriction. In addition, ET-1 may decrease endothelial NO synthase (eNOS) expression, thereby reducing NO production. Both the $ET_A$ and the $ET_B$ receptors on smooth muscle cells may mediate formation of superoxide (O2) in endothelial dysfunction. Superoxide will decrease the biological activity of NO by forming peroxynitrate (ONOO—). This increases the effect of ET-1 and decreases the effect of NO on smooth muscle cells. Clinical evidence in obesity and diabetes suggest Endothelial dysfunction as a failure to vasodilate adequately after application of an endothelium-dependent vasodilator but also excess vasoconstrictor tone. Thus, ET-1 contributes to endothelial dysfunction both directly, through its vasoconstrictor effects, and indirectly, through inhibitory effects on NO production.

Collectively, the balance of these effects in endothelial dysfunction is shifted towards more vasoconstriction, inflammation and oxidative stress. This pathogenic role of the altered expression and biological actions of ET-1 in vascular dysfunction may lead to the development of cardiovascular disease, atherosclerosis and hypertension. For example, dysfunction of the vascular endothelium is an early finding in the development of cardiovascular disease and is closely related to clinical events in patients with atherosclerosis and hypertension.

As discussed above, in the vascular system, insulin stimulates both ET-1 and NO activity. An imbalance between the efficacy of these substances may be involved in the pathophysiology of heart disease, hypertension and atherosclerosis. Thus, a device and method to determine the balance of these substances in vivo would be important in determining insulin-resistance and vascular health.

Figure 18:
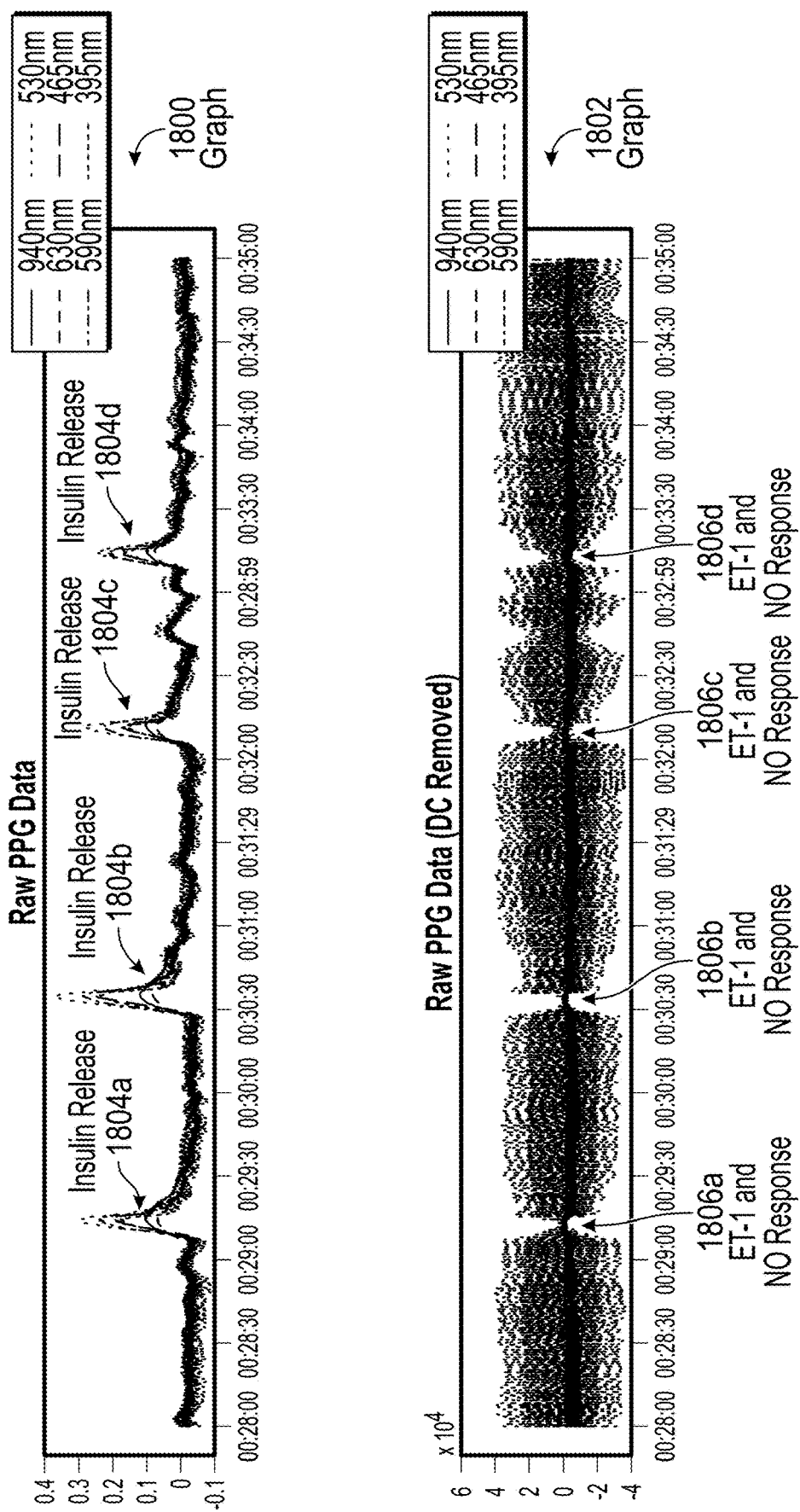
FIG. 18 illustrates a schematic diagram of PPG signals obtained during periods of insulin release in vessels.

FIG. 18 illustrates a schematic diagram of PPG signals obtained during periods of insulin release events in vessels. At "rest", a body responds to caloric intake by releasing insulin into the blood stream. This insulin release stimulates ET-1 and NO activity.

In the example of Graph 1800, the biosensor 100 obtained PPG signals over a seven minute period between 28 mins and 35 mins around a plurality of wavelengths at 940 nm, 630 nm, 590 nm, 530 nm, 465 nm and 395 nm. The PPG signals reflect "pulses" of insulin in the blood flow in response to discrete release of insulin by the pancreas in the bloodstream. The PPG signals reflect the insulin release events at a first pulse 1804a around 29.15 mins, a second pulse 1804b around 30.35 mins, a third pulse 1804c around 32.10 mins, and a fourth pulse 1804d around 33 mins. Vascular strain occurs during release of localized insulin (insulin release events) as part of the glucose regulation processes. This vascular strain impairs the PPG signals temporarily during the interaction of the ET-1 and NO agents released during the insulin release events.

Graph 1802 illustrates the PPG signals due to pulsatile blood flow $I_{AC}$. The $I_{DC}$ signal has been filtered from the PPG signals in this example. The $I_{AC}$ signal reflects the ET-1 and NO response in the vessels due to the insulin release events at a first pulse around 29.15 mins, a second pulse around 30.35 mins, a third pulse around 32.10 mins, and a fourth pulse around 33 mins. The smooth muscle cells of arterial walls tighten during chemical reactions of each insulin pulse. This temporary stiffing of the arterial structure causes a dampening effect on the PPG signals during the insulin release event. The 630 nm & 940 nm optical wavelengths are probing at deeper arterial/venous tissue structures wherein the smooth muscle walls are thicker and exhibit a higher stiffness factor under chemical induced strain such as an insulin release. The blood flow of the outer tissues (microvacuoles) include less smooth muscle tissue thickness and therefore respond with a more pronounced PPG signal pulse at 395 nm, 465 nm, 530 nm and 590 nm. Thus, the PPG pulses at these wavelengths are less pronounced.

Due to the higher level of insulin release, the ET-1 and NO response at the first pulse 1806a and the second pulse 1806b have a greater constricting effect on the vessels. The vasoconstriction decreases in the third and fourth pulses due to the decrease in insulin release at ET-1 and NO responses 1806c and 1806d. In addition, the NO levels may also have accumulated to further mediate the effects of ET-1. Thus, the vasoconstriction is lessened in response to the later insulin release events 1804c and 1804d.

The vasoconstriction in response to insulin release is thus affected by the balance of ET-1 and NO as well as vascular disease such as atherosclerosis. By measuring the relative vasoconstriction or relative change in arterial diameter in response to insulin release, vascular health may be assessed using the biosensor 100.

Figure 19:
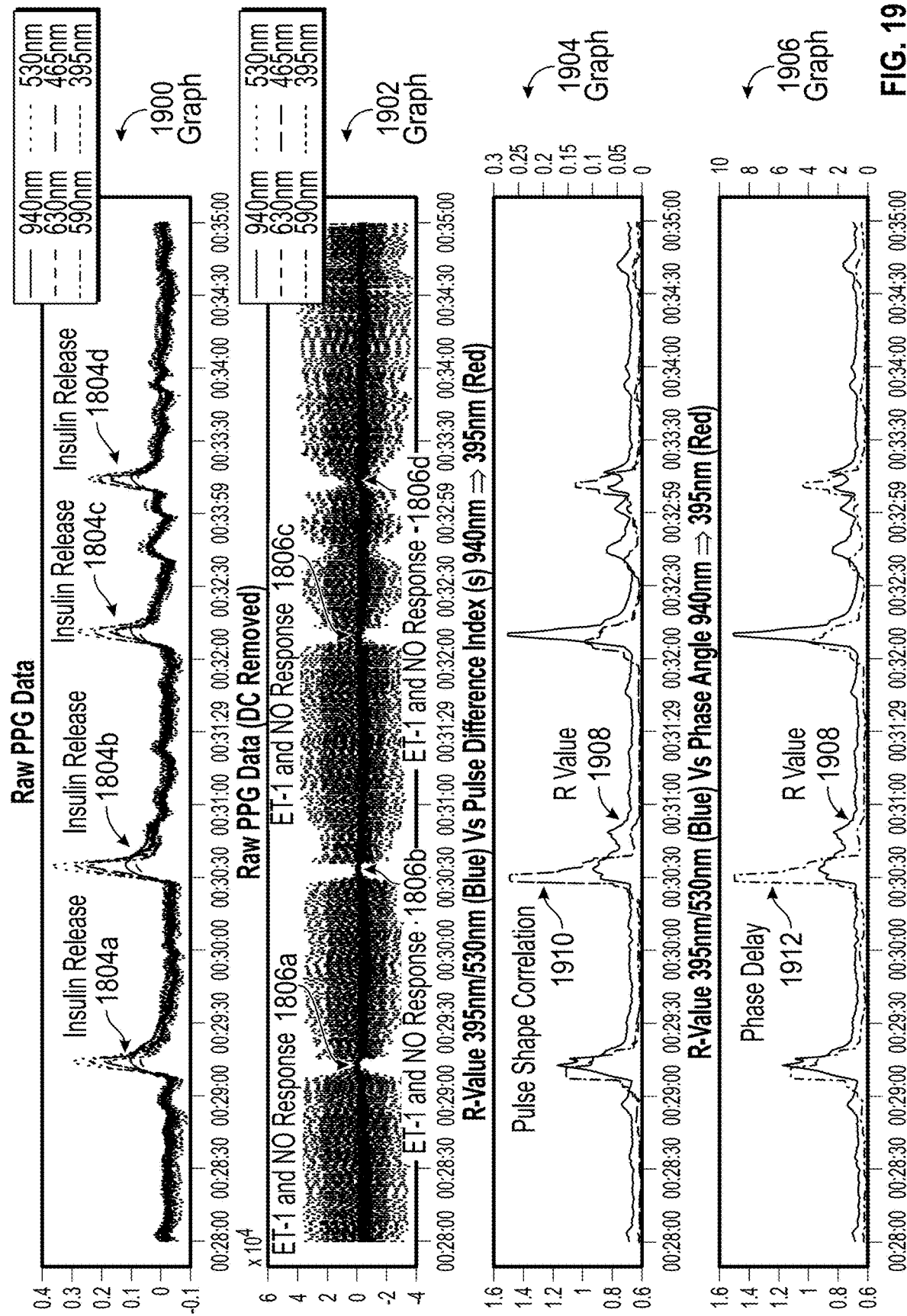
FIG. 19 illustrates a schematic diagram of graphs comparing phase offset and pulse shape waveform in a plurality of PPG signals during insulin release in vivo.

FIG. 19 illustrates a schematic diagram of graphs comparing phase delay and pulse shape correlation in a plurality of PPG signals during insulin release in vivo. As shown in Graph 1800, in the example of Graph 1900, the biosensor 100 obtained PPG signals over a seven minute period between 28 mins and 35 mins around a plurality of wavelengths at 940 nm, 630 nm, 590 nm, 530 nm, 465 nm and 395 nm. The PPG signals reflect "pulses" in response to discrete release of insulin in the bloodstream. Graph 1902 illustrates the PPG signals due to pulsatile blood flow $I_{AC}$ with low frequency signals $I_{DC}$ filtered therefrom.

In Graph 1904 and 1906, the R value 1908 of 395 nm/530 nm is illustrated. In addition, a correlation is computed between the PPG waveform at 940 nm and the PPG waveform at 395 nm to obtain a Pulse Shape Correlation 1910 and a Phase Delay 1912. The PPG signals are processed using, e.g., a cross correlation function or a Hilbert transformation or another algorithm that provides a comparison of pulse shape and temporal relationship between PPG signals. For example, the time delay between the two PPG signals at 395 nm and 940 nm can also be calculated at each time instant from the phase shift of their wavelet transforms.

The Pulse Shape Correlation 1910 and Phase Delay 1912 include effects of outer and inner tissue layers of vessels on the PPG signal. When the muscle cells constrict during vasoconstriction, the optical properties are altered. In addition, the change in NO level affects the PPG signal around 395 nm.

In healthy persons, arterial walls are more flexible and thus have a greater relative change in diameter in response to insulin. The Pulse Shape Correlation 1910 and Phase Delay 1912 signals reflect a greater change in signal levels in response to insulin. The R value pulses are correspondingly more pronounced. The phase timing is inversely proportional to the arterial diameters.

In patients having endothelium dysfunction, the arteries exhibit stiffness with a decreased relative change in diameter. Endothelium dysfunction may be found in patients with diseases such as atherosclerosis, hypertension and diabetes. The Pulse Shape Correlation 1910 and Phase Delay 1912 respond with a decreased relative amplitude change during an insulin release event. The Pulse Shape Correlation 1910 and Phase Delay 1912 may thus be used to determine arterial stiffness and vascular health.

In an embodiment, the phase delay 1912, pulse shape correlation 1910 and R value 1908 may also be used to determine whether ET-1 or NO is more dominant in response to insulin. For example, the average or mean range of one or more of these measurements in a healthy population is measured. Then, an individual measurement is compared to the average or mean range of one or more of phase delay 1912, pulse shape correlation 1910 and R value 1908. The comparison may be used to obtain whether an imbalance is present between the effects of ET-1 and NO. An imbalance in the effects of the two substances has an increased vasoconstrictor effect on vessels due to an increase in ET-1 activity.

In addition, this change in propagation of the pressure wave can be measured in the change in transfer function from a wavelength that penetrates the tissue deeply (e.g. in the IR range) to a wavelength that penetrates tissue much less deeply (e.g. in the visible or UV range). This means that by measuring the change in pulse shape and phase delay of the PPG signals at two or more wavelengths with different penetration depths (e.g., wherein at least one is in the near-IR window and one is not), information about a level of vasoconstriction/vasodilation may be determined.

Figure 20:
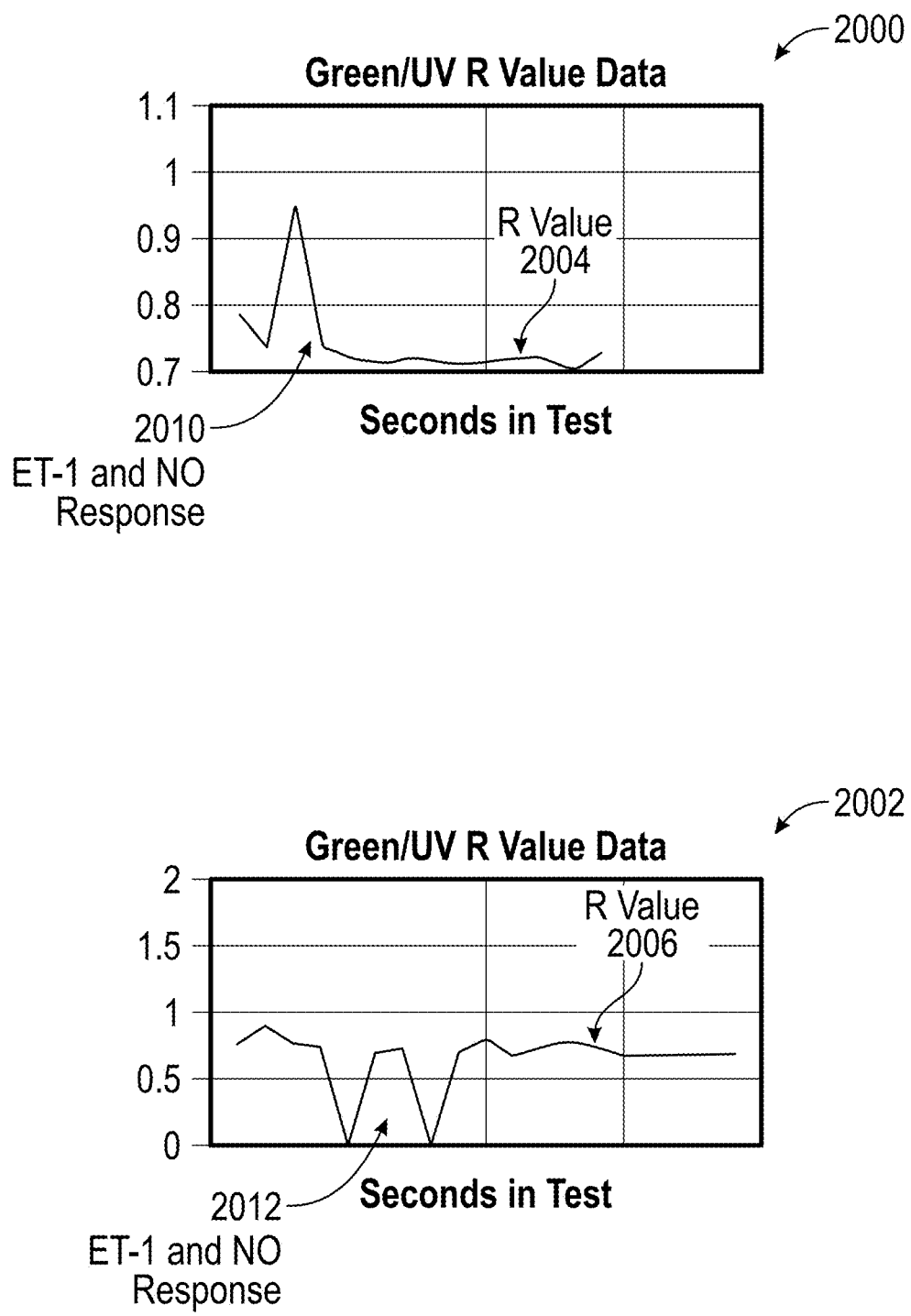
FIG. 20 illustrates a schematic block diagram of an insulin response of a young healthy male and a middle-aged male.

Embodiment—Biosensor Detection of Vascular Health During an Insulin Release Event FIG. 20 illustrates a schematic block diagram of an insulin response of a young healthy male and a middle-aged male. The Graph 2000 illustrates an R value 2004 of 395 nm/530 nm during an insulin response in a middle-aged male patient obtained using the biosensor 100. In the ET-1 and NO response 2010, the R values 2004 shows a subdued response due to an increased arterial stiffness and/or ET-1 prominence. The ET-1/NO response 2010 is more typical of vasoconstriction.

The Graph 2002 illustrates an R value 2006 of 395 nm/530 nm during an insulin response in a young male patient. In the ET-1 and NO response 2012, the R values 2006 have a relatively greater range due to a healthy vascular system. The ET-1/NO response 2012 is more typical of vasodilation. Thus, by comparing the R value data of healthy persons in a general population with an individual's measurement, the presence of an increased arterial stiffness and/or ET-1 prominence may be determined.

Figure 21:
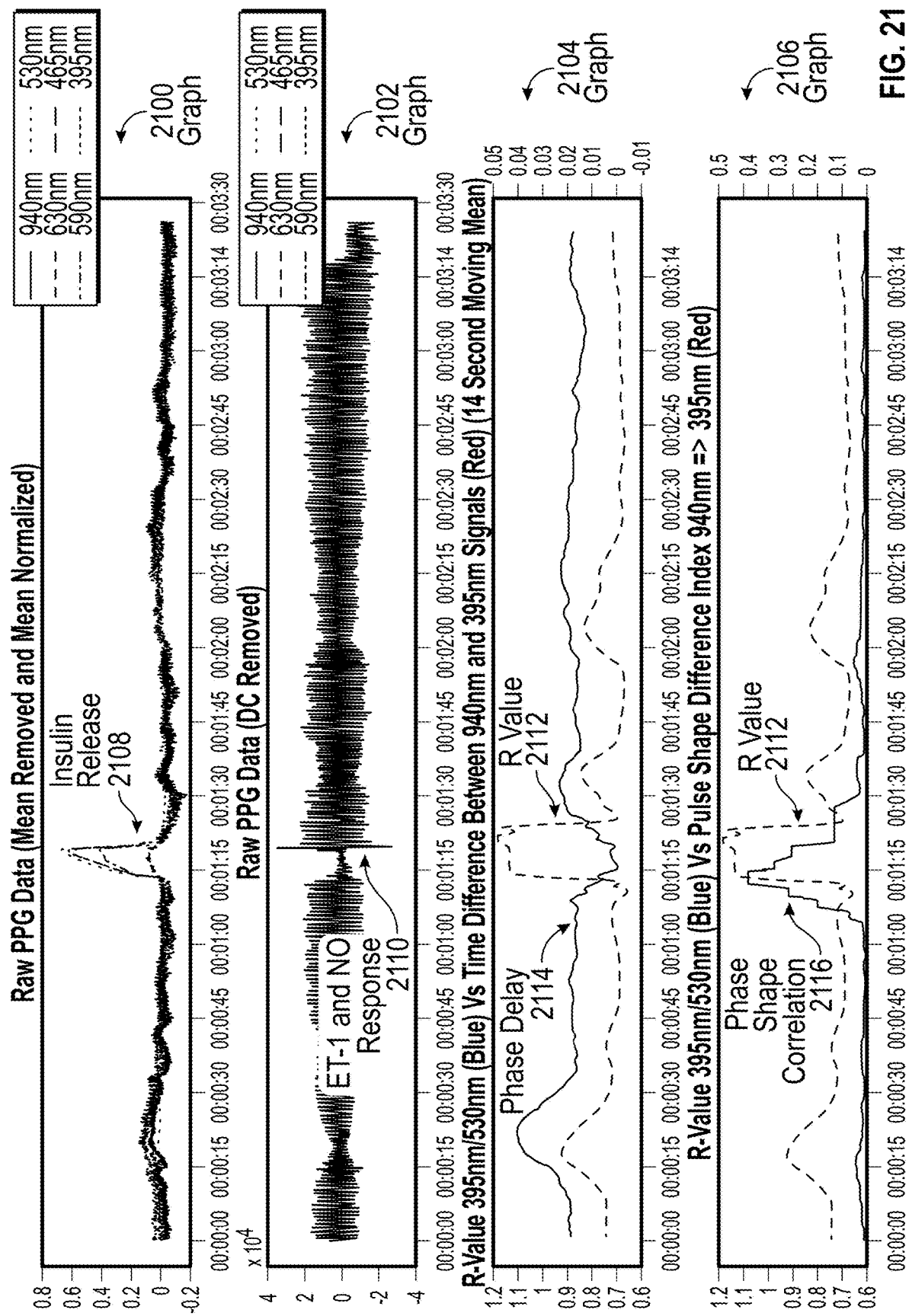
FIG. 21 illustrates a schematic diagram of graphs comparing phase offset and pulse shape waveform in a plurality of PPG signals during insulin release in an adolescent male.

FIG. 21 illustrates a schematic diagram of graphs comparing phase offset and pulse shape waveform in a plurality of PPG signals during insulin release in an adolescent male. In the example of Graph 2100, the biosensor 100 obtained PPG signals over an approximately three minute period around a plurality of wavelengths at 940 nm, 630 nm, 590 nm, 530 nm, 465 nm and 395 nm. The PPG signals reflect a discrete insulin release event 2108 in the bloodstream. The insulin release 2108 includes a marked PPG pulse in a first wavelength having a high absorption coefficient for NO, (e.g. 395 nm) wherein the amplitude of the pulse is at least greater than twice expected from a heart rate pulse.

Graph 2102 illustrates the PPG signals due to pulsatile blood flow $I_{AC}$. The $I_{AC}$ signal reflects an ET-1 and NO response 2110. The $I_{AC}$ signal has at least a 50% decrease in amplitude during the insulin release event 2108. One reason for the decrease in amplitude includes the constriction of the smooth muscle cells in vessels that affects the absorption properties of the tissue.

In Graph 2104 and 2106, the R value 2112 of 395 nm/530 nm is illustrated. In addition, a correlation between the PPG waveform at 940 nm and the PPG waveform at 395 nm is also illustrated. The correlation includes a Phase Delay 2114 and a Pulse Shape Correlation 2116. The PPG signals are processed using a cross correlation function or a Hilbert transformation or another algorithm that determines similarities in pulse shape and temporal relationship between the PPG signals. For example, the time delay between the two signals can also be calculated at each time instant from the phase shift of their wavelet transforms.

The Phase Delay 2114 and a Pulse Shape Correlation 2116 includes effects of outer and inner tissue layers of vessels on the PPG signal, e.g. muscle cells during vasoconstriction. The Phase Delay 2114 and a Pulse Shape Correlation 2116 may be mapped to a vessel diameter or level of vasoconstriction/vasodilation.

Figure 22:
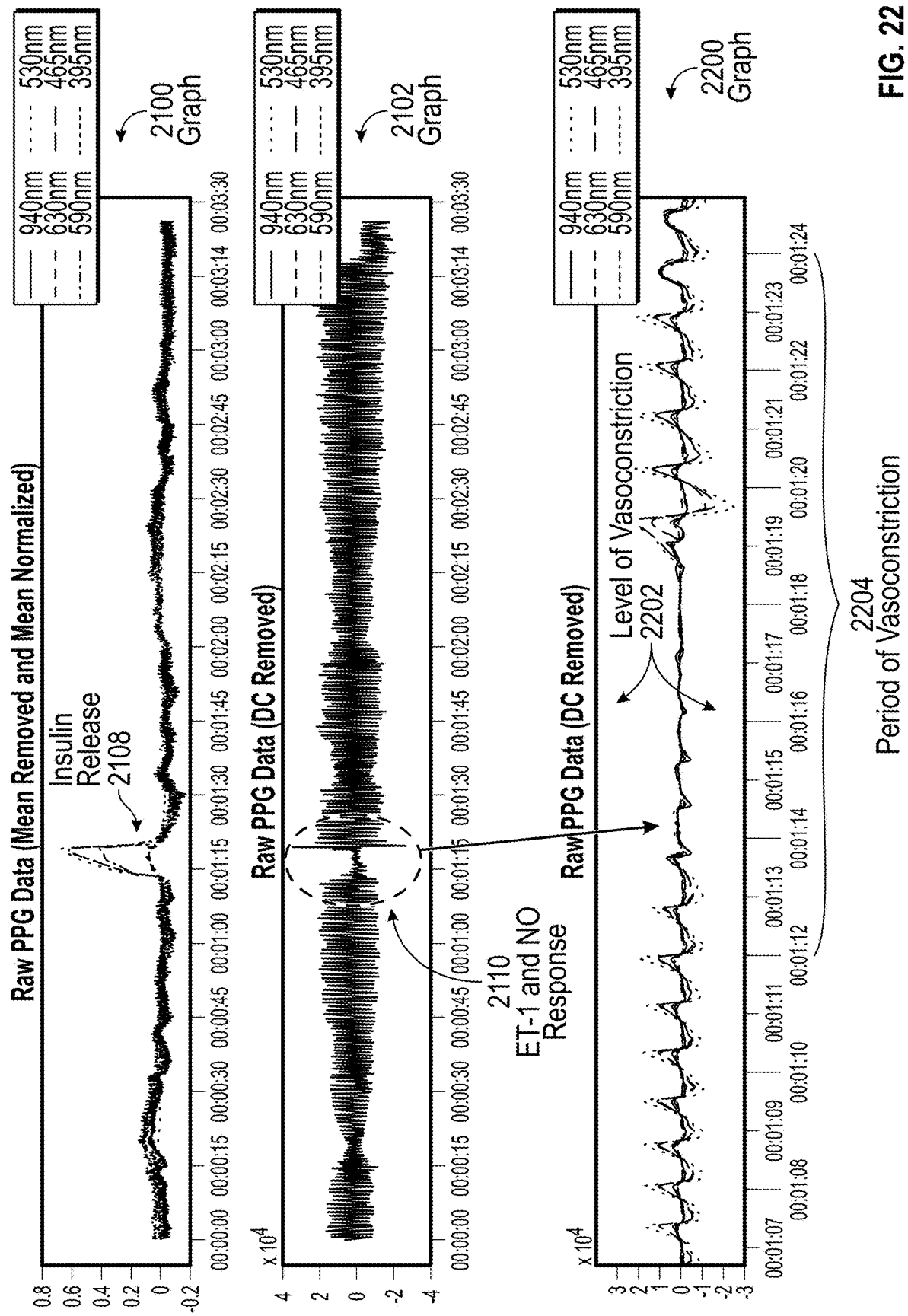
FIG. 22 illustrates a schematic diagram of an insulin response in the adolescent male in greater detail.

FIG. 22 illustrates a schematic diagram of an insulin response in the adolescent male in greater detail. Graph 2200 illustrates the PPG signals due to pulsatile blood flow $I_{AC}$ during the period of insulin release 2108. The ET-1 and NO response 2110 creates a chemical stress in the endothelium from competing forces of arterial dilation and constriction. With a healthy ET-1 and NO efficacy, the endothelium should exhibit arterial stiffening and/or vasoconstriction. The constricting shallow muscle cells affect the optical properties of the PPG signals during this interval. Thus, the period of vasoconstriction 2204 may include one or more of increased arterial stiffness and/or vasoconstriction due to the effects of ET-1 and NO activity.

The period of vasoconstriction 2204 may be determined based on the amplitude changes of the PPG signals. At the beginning of the period of vasoconstriction 2204, the amplitudes of the $I_{AC}$ signal begin to decrease and then to slowly increase until the amplitudes of the $I_{AC}$ signal return to average at the end of the period of vasoconstriction 2204. The period of vasoconstriction 2304 is approximately between 21 sec and 31 sec. in this example.

A level of vasoconstriction 2202 may be determined, e.g., from an average peak to peak amplitude of the PPG signals prior to or after the period of vasoconstriction and the lowest peak to peak amplitude of the PPG signals during the period of vasoconstriction. The level of vasoconstriction may be measured in other manners, such as average peak value to lowest peak value during the period of vasoconstriction.

Figure 23:
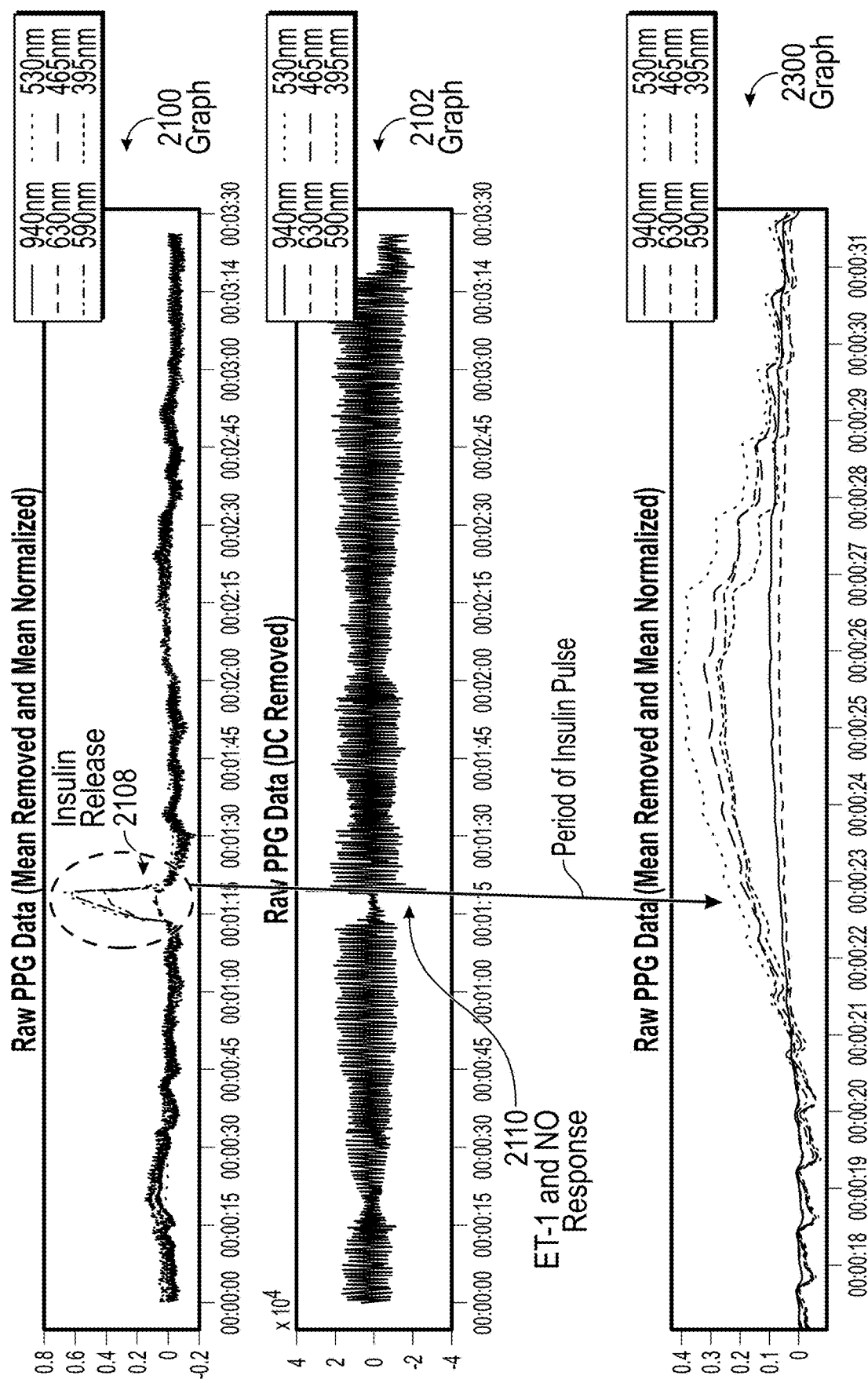
FIG. 23 illustrates a schematic diagram of an insulin response in the adolescent male in greater detail.

FIG. 23 illustrates a schematic diagram of an insulin response in the adolescent. Graph 2300 illustrates the PPG signals during the insulin release event 2108 in greater detail. The Graph 2300 illustrates that the insulin release generates a constricting response in the vessels over an approximately 10 second interval during the period of vasoconstriction 2204. The period of vasoconstriction 2204 may include one or more of increased arterial stiffness and vasoconstriction due to the effects of the ET-1 and NO response 2110.

Figure 24:
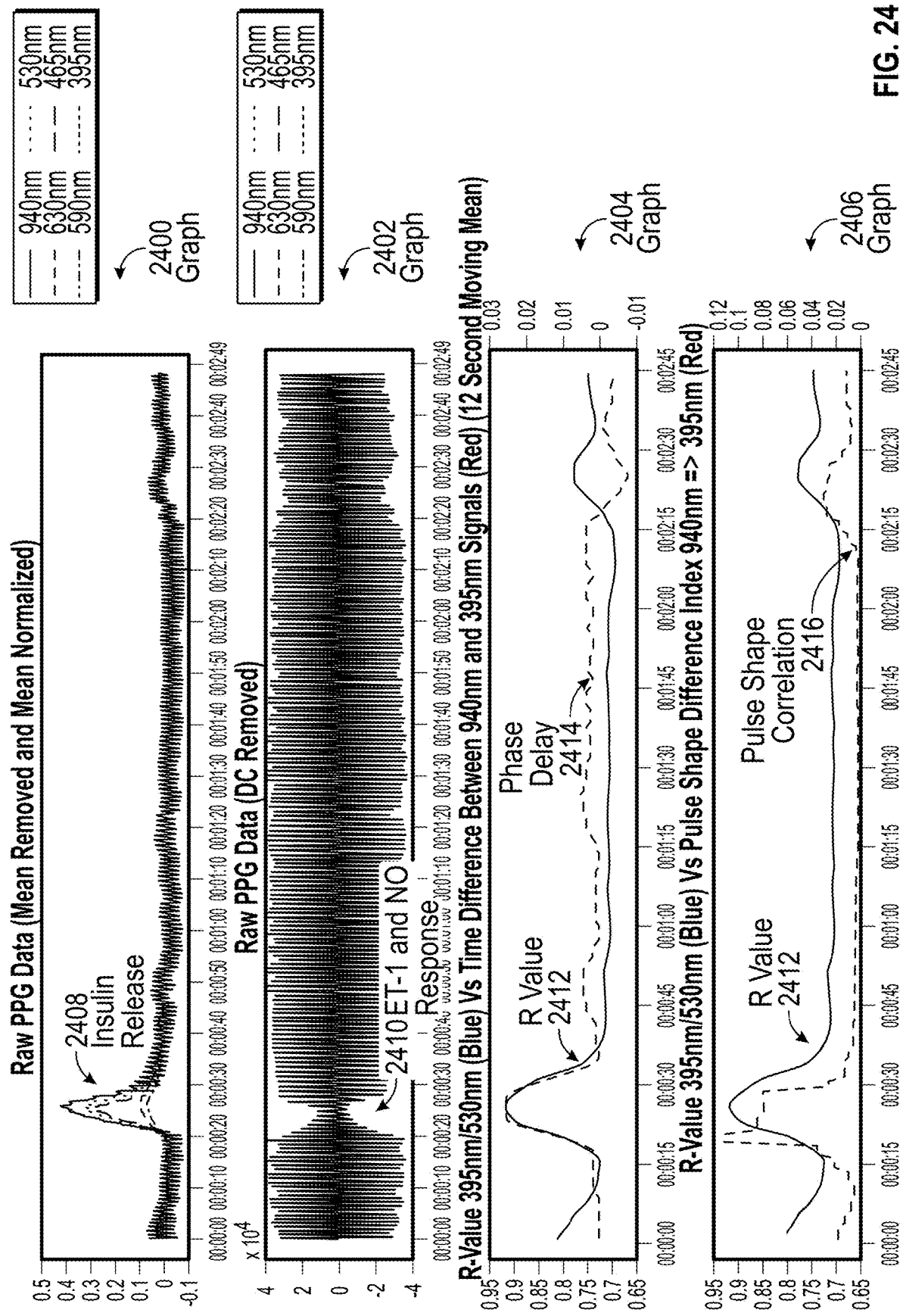
FIG. 24 illustrates a schematic diagram of graphs comparing phase offset and pulse shape waveform in a plurality of PPG signals during insulin release in a middle-aged male.

FIG. 24 illustrates a schematic diagram of graphs comparing phase offset and pulse shape waveform in a plurality of PPG signals during an insulin release event in a middle-aged male. In the example of Graph 2400, the biosensor 100 obtained PPG signals over a 2:49 minute period around a plurality of wavelengths at 940 nm, 630 nm, 590 nm, 530 nm, 465 nm and 395 nm. The PPG signals reflect a pulse in response to a discrete insulin release 2408 in the bloodstream. The insulin release 2108 includes a marked PPG pulse in a first wavelength having a high absorption coefficient for NO, wherein the amplitude of the pulse is at least greater than twice expected from a heart rate pulse.

Graph 2402 illustrates the PPG signals due to pulsatile blood flow $I_{AC}$. The $I_{AC}$ signal reflects an ET-1 and NO response 2410 in the vessels due to the insulin release 2408. The $I_{AC}$ signal has at least a 50% decrease in amplitude during the insulin release event 2408.

In Graph 2404 and 2406, the R value 2412 of 395 nm/530 nm is illustrated. In addition, a correlation between the PPG waveform at 940 nm and the PPG waveform at 395 nm is illustrated as Phase Delay 2414 and Pulse Shape Correlation 2416. The PPG signals are processed using a cross correlation function or a Hilbert transformation or another algorithm that determines similarities in pulse shape and temporal relationship between PPG signals. For example, the time delay between the two signals can also be calculated at each time instant from the phase shift of their wavelet transforms.

The Phase Delay 2414 and a Pulse Shape Correlation 2416 includes effects of outer and inner tissue layers of vessels on the PPG signal, e.g. muscle cells during vasoconstriction. The Phase Delay 2414 and a Pulse Shape Correlation 2416 may be mapped to a vessel diameter or level of vasoconstriction/vasodilation.

Figure 25:
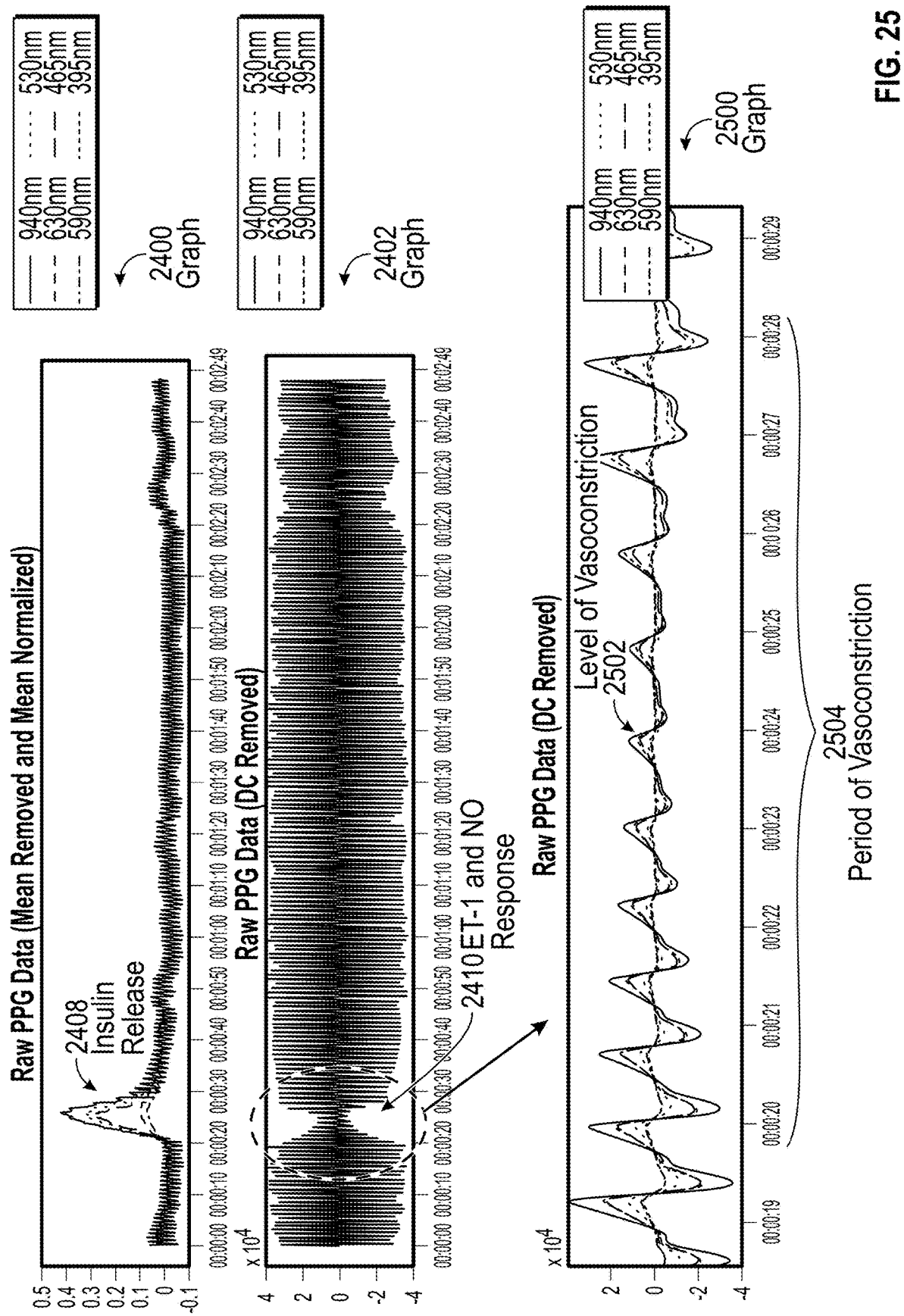
FIG. 25 illustrates a schematic diagram of an insulin response in a middle-aged male in greater detail.

FIG. 25 illustrates a schematic diagram of an insulin response in a middle aged male in greater detail. From FIG. 24, graph 2402 illustrates the PPG signals due to pulsatile blood flow $I_{AC}$ during the period of insulin release 2408. The Graph 2500 illustrates that the ET-1 and NO response 2410 from graph 2402 in greater detail. Graph 2500 reflects the decrease in amplitude of the $I_{AC}$ signal due to vasoconstriction. When smooth muscles cells tighten causing vasoconstriction, the $I_{AC}$ signal amplitude decreases in magnitude. The constricting shallow muscle cells affect the optical properties of the PPG signals during this interval.

The period of vasoconstriction in this example is from about 20 seconds to at least 28 seconds, e.g. the period of vasoconstriction 2504. The period of vasoconstriction 2504 may include one or more of increased arterial stiffness and vasoconstriction due to the effects of the ET-1 and NO response. A level of vasoconstriction 2502 may be determined, e.g., from an average peak to peak amplitude of the PPG signals prior to or after the period of vasoconstriction and the lowest peak to peak amplitude of the PPG signals during the period of vasoconstriction. The level of vasoconstriction 2502 may be measured in other manners, such as average peak value to lowest peak value during the period of vasoconstriction.

Figure 26:
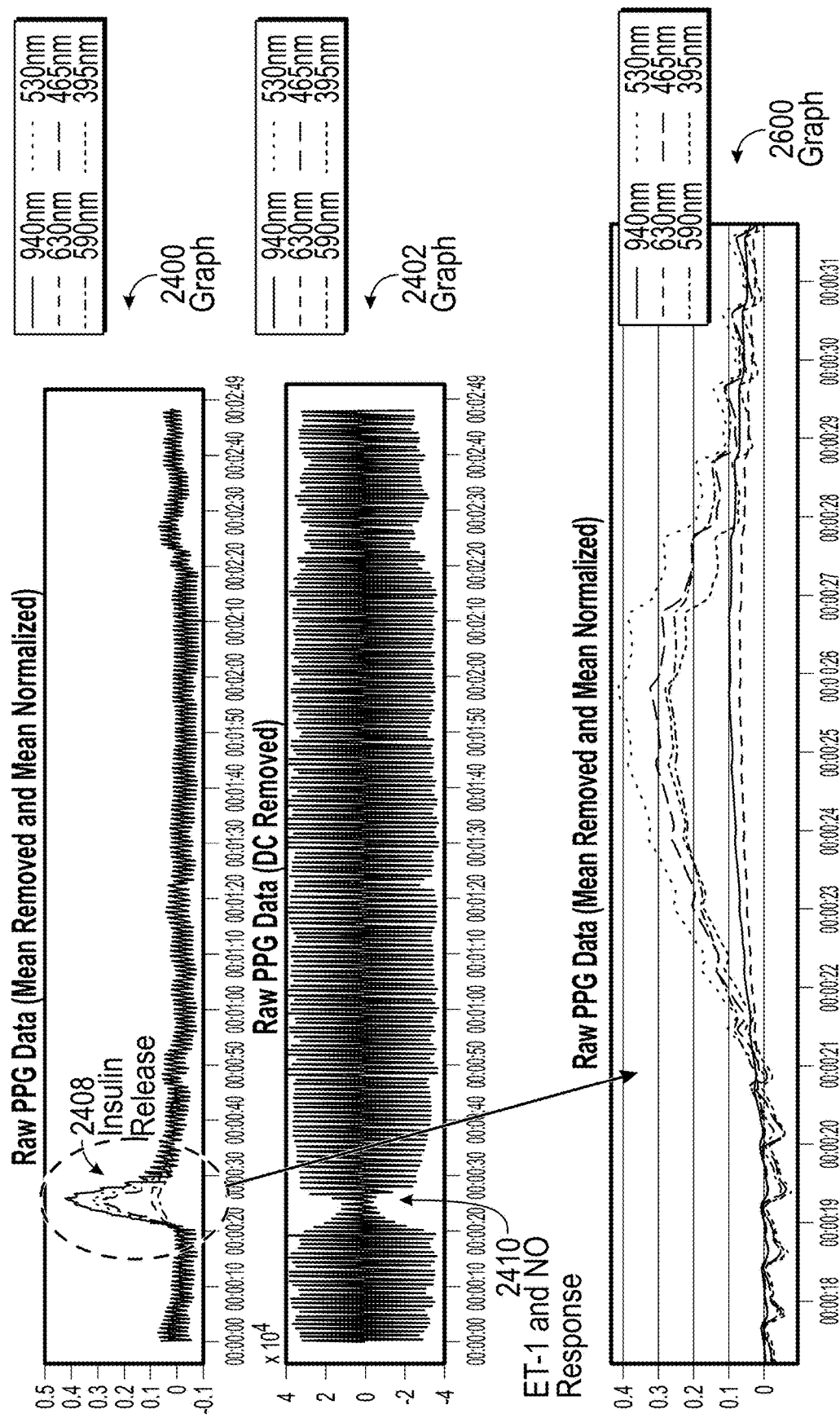
FIG. 26 illustrates a schematic diagram of an insulin response in a middle-aged male in greater detail.

FIG. 26 illustrates a schematic diagram of an insulin response in a middle aged male in greater detail. Graph 2600 illustrates the PPG signals during the period of insulin release 2408. The Graph 2600 illustrates that the insulin release generates a constricting response in the vessels during the period of vasoconstriction. The constricting shallow muscle cells affect the optical properties of the PPG signals during this interval.

Comparing the PPG signals detected during the insulin release between the adolescent male and the middle aged male, the PPG signals indicate that the vasoconstriction is relatively less in the middle aged male. The decrease in vasoconstriction is expected due to age related arterial stiffness and arteriosclerosis. This age-related difference in vasoconstriction can be due to decreased elastic production from fibrinogen, associated with ageing, or hypertension or pathological conditions such as atherosclerosis. The smooth muscle cells of the adolescent male may also be stronger, and the elastic lamina that surrounds the lumen of the artery may be more resilient and flexible at that age. This demonstrates that a level of vasoconstriction may be determined from the PPG signals and compared to healthy values (such as in the adolescent male) to determine vascular health.

Figure 27:
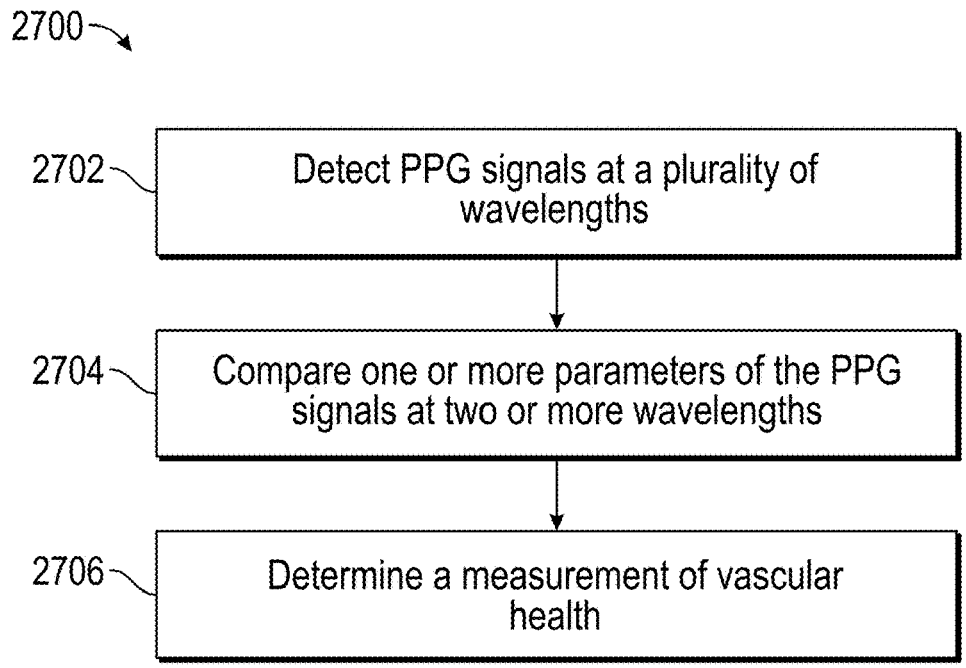
FIG. 27 illustrates a schematic flow diagram of an embodiment of a method for determining vascular health using the biosensor.

FIG. 27 illustrates a schematic flow diagram of an embodiment of a method 2700 for determining vascular health using the biosensor 100. The biosensor 100 detects PPG signals at a plurality of wavelengths reflected from skin tissue at 2702. Preferably, the first wavelength has a high absorption coefficient for NO and is approximately 395 nm or in a range from 380 to 410 and a lower depth of penetration into the tissue. The second wavelength has a lower absorption coefficient for NO and is approximately in a range from 510 nm to 550 nm or is in an IR range such as 940 nm and has a greater depth of penetration into the tissue.

The PPG signals are measured over a period of time that preferably includes one or more insulin release events, such as after ingestion, wherein insulin is released into the blood stream. The insulin release is reflected by a marked PPG pulse in the first wavelength having a high absorption coefficient for NO. The pulse has a 5-10 second duration, wherein the amplitude of the pulse is at least greater than twice expected from a heart rate pulse. The pulses due to insulin release also have a much lower frequency than a heart rate. The insulin release event may thus be identified in the PPG signals using one or more of these characteristics.

One or more parameters derived using the PPG signals during the insulin release event is determined and compared at 2704. For example, a cross correlation function may determine a phase offset between the PPG signals and/or pulse shape correlations during the insulin release event. The PPG signals may also be processed using other cross correlation functions or a Hilbert transformation or another algorithm that determine similarities in pulse shape and temporal relationship between PPG signals.

A measurement of vascular health is obtained using the one or more parameters at 2706. For example, a measurement of vasoconstriction or vasodilation may be obtained, such as a vessel diameter or percentage of change in diameter. The relative efficacy of ET-1 and NO may be estimated based on the measurement of diameter change and level of insulin release. A level of arterial stiffness may be determined using the measurement of the diameter change and level of insulin release and comparing to such measurements in a general sampling of healthy persons without vascular dysfunction.

Figure 28:
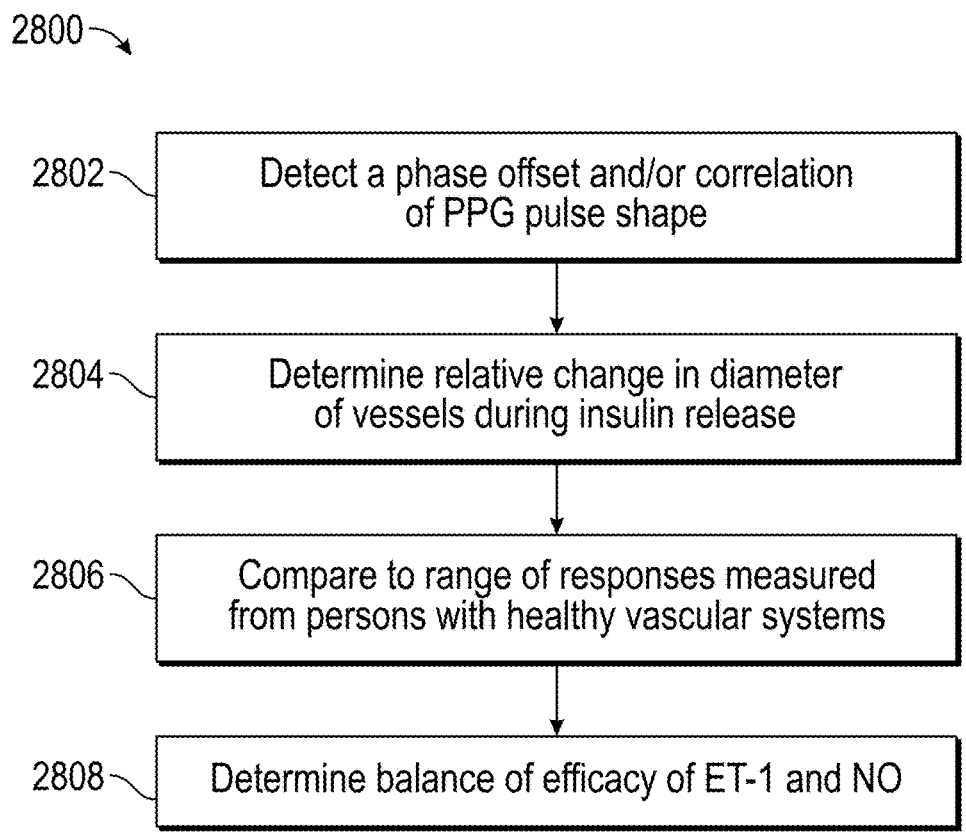
FIG. 28 illustrates a schematic flow diagram of an embodiment of a method for determining an efficacy balance of ET-1 and NO in smooth muscle cells of vessels.

FIG. 28 illustrates a schematic flow diagram of an embodiment of a method 2800 for determining an efficacy balance of ET-1 and NO in smooth muscle cells of vessels. The vasoconstriction or vasodilation in response to insulin release is affected by the balance of ET-1 and NO as well as vascular disease such as atherosclerosis. By measuring the relative vasoconstriction or change in arterial diameter or stiffness in response to insulin release, the relative efficacy and balance of ET-1 and NO may be assessed using the biosensor 100.

The phase offset and/or correlation of pulse shape of two or more PPG signals is determined over the period of time including the insulin release at 2802. For example, the first wavelength has a high absorption coefficient for NO and a lower penetration depth into tissue, and the second wavelength has a lower absorption coefficient for NO and a higher penetration depth into tissue. A cross correlation function may be used to determine the phase offset and/or pulse shape correlations or a Hilbert transformation or another algorithm that determine similarities in pulse shape and temporal relationship between PPG signals.

An imbalance in the effects of the two substances has an increased vasoconstrictor effect on vessels due to an increase in ET-1 activity and suppression of NO efficacy. The change in diameter of vessels during insulin release may be determined at 2804 and compared to a healthy individual of similar age with no vascular dysfunction at 2804. Increased relative levels of vasoconstriction may be indicative of increased ET-1 activity due to an imbalance of ET-1 and NO efficacy caused by insulin-resistance disease such as diabetes.

The phase delay may also provide an indication of the balance of ET-1 and NO in response to insulin. For example, the R value is compared to systolic peaks of the phase delay to determine a relative level of vasoconstriction or change in diameter of vessels. The phase offset between two or more of the PPG signals in different spectrums, or having different depths of penetration of tissue, is measured. The phase offset may be used to determine presence of vasodilation/vasoconstriction in the tissue. For example, in normal tissue, the PPG signals exhibit only a slight difference in phase or timing when nominal vasodilation is occurring in the tissue. When the PPG signals have a greater difference in phase or timing, this indicates that blood flow in the tissue near the surface is decreased, e.g. due to vasoconstriction, due to low blood circulation level or an imbalance of NO and ET-1 or arterial stiffness. When blood flow is increased to the tissue, the PPG signals at UV and IR wavelengths exhibit a lower variance in pulse shape and a higher correlation value. This decrease in the difference in the pulse shape of the PPG signals at the different wavelengths indicates an increase of blood flow, e.g. due to vasodilation.

The phase offset and pulse shape correlation may be mapped to a level of vasodilation/vasoconstriction, e.g. using a calibration table or function. The level of vasodilation/vasoconstriction and a period of vasodilation/vasoconstriction may thus be determined using the phase differences and pulse shape correlations between the PPG signals at the different wavelengths. The above described parameters of the PPG signals may also be used to determine a period of vasoconstriction using similar methods.

In another aspect, R values are determined using the PPG signals at least two wavelengths, such as $R_{660nm/940nm}$ or $R_{405/940}$ or $R_{395nm/940nm}$. The level of vasodilation or period of vasodilation may be determined using changes in amplitude of one or more R values.

The level of vasoconstriction/vasodilation may be compared to an insulin level to determine the balance of the effects of ET-1 and NO at 2808. For example, the level of vasoconstriction/vasodilation for a known insulin level or during an average insulin release event may be determined in individuals with healthy vascular function. A calibration table or function may store a mapping of a range of vasoconstriction/vasodilation and/or an average period of vasoconstriction/vasodilation for one or more levels of insulin release by testing a general population of healthy individuals. The level of vasodilation may be represented as a measurement of one or more of: a percentage of change in arterial width, diameter or planar area or a change in blood flow or volume, etc. These comparisons may thus indicate a balance of efficacy between ET-1 and NO at 2808.

In addition, arterial stiffness may decrease a relative level of vasodilation compared to an average or normal range. The rate of change of the width of the artery at a beginning or end of vasodilation may be used as an indicator of arterial stiffness. A reduction in elasticity of arteries may decrease the rate of change in the width of the artery and thus the rate of change in the level of vasodilation. These comparisons of the rate of change of the width of vessels may also be used to indicate a measurement of arterial stiffness. These determinations may also factor in the determination of whether the cause of reduced vasoconstriction/vasodilation is due to an imbalance of ET-1 and NO or due to arterial stiffness during an insulin release event.

Embodiment—Measurement of Insulin Levels

Figure 29:
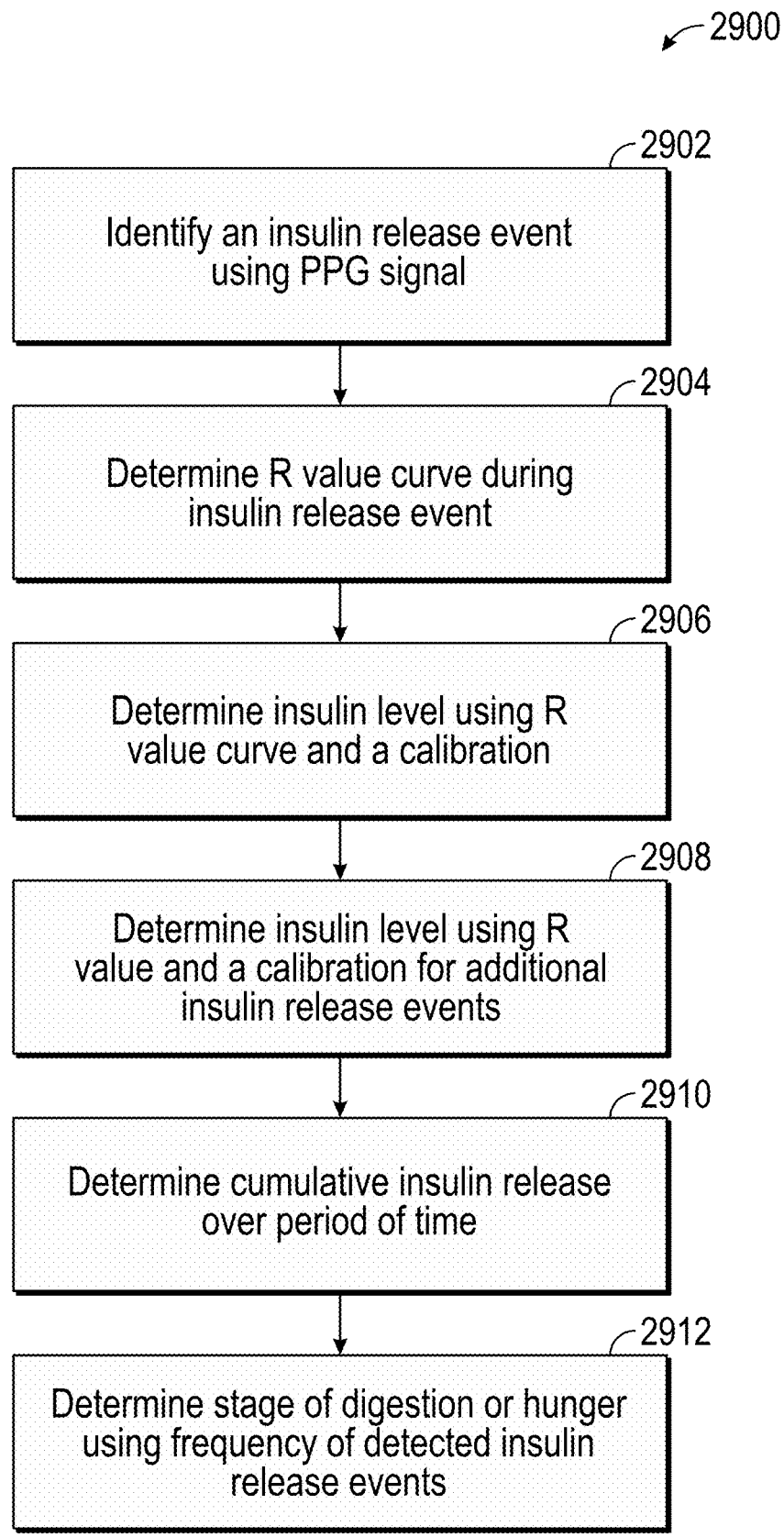
FIG. 29 illustrates a schematic flow diagram of an embodiment of a method for determining an insulin level in blood flow.

FIG. 29 illustrates a schematic flow diagram of an embodiment of a method 2900 for determining an insulin level in blood flow. The biosensor 100 monitors PPG signals at a plurality of wavelengths reflected from skin tissue over a period of time, such as 5 minutes to 24 hours. Preferably, a first wavelength has a high absorption coefficient for NO and is approximately 395 nm or in a range from 380 to 410. A second wavelength has a lower absorption coefficient for NO and is approximately 530 nm or in a range from 510 nm to 550 nm or is in an IR range such as 940 nm.

The PPG signals are analyzed to identify one or more insulin release events at 2902. For example, after ingestion, insulin is naturally released into the blood stream. The insulin release effects a marked PPG pulse in the first wavelength having a high absorption coefficient for NO. The PPG pulse, e.g., has a longer duration than a PPG pulse of a heart rate. For example, the PPG pulse during an insulin release event has an approximately 5-10 second duration, wherein the change in amplitude of the PPG pulse is at least greater than twice expected from a heart rate pulse. Signal analysis using pattern recognition may be employed with the PPG signals to identify the insulin pulse.

An R value curve is obtained over the period of the insulin release event, using PPG signals having the first and second wavelength, such as an R value of 395 nm/530 nm or 395 nm/940 nm at 2904. The R value curve during the insulin release event is analyzed to determine an insulin level at 2906. For example, an area under the R value curve is determined during the insulin release event. A calibration table or curve is tabulated that associates the area to the insulin level. The calibration may be performed on an individual using a blood test to determine insulin levels during a calibration phase of the biosensor. Alternatively, the calibration may be predetermined from testing of a general population. Though an area under the R value curve is described for the calibration, other parameters obtained from the pulse of the PPG signals during the insulin release event may be used to determine insulin levels, such as an average R value or $I_{AC}$ value.

Insulin is usually secreted in discrete amounts one or more times depending on the stage of digestion. Thus, multiple insulin release events may be detected within a short time period after ingestion. The insulin level may be determined for additional insulin release events using the R value curve and calibration table at 2908. The cumulative insulin released over a time period may then be determined at 2910 by summation of the individual insulin release events during the time period.

The stage of digestion may also be determined using identification of the insulin release events from the PPG signals. For example, the insulin release events are more frequent after ingestion during stage 1 and stage 2 of digestion and are less frequent when hungry. Correspondingly, the frequency of PPG pulses due to insulin release events increases in response to different stages of digestion. In contrast, the frequency of the PPG pulses due to insulin release events decreases in response to fasting or hunger. Thus, by measuring the frequency or time between insulin release events using the PPG signals, a stage of digestion may be identified or a level of fasting or hunger may be identified at 2912.

Embodiment—Measurement of Glucose Levels

As described herein, the biosensor may determine a glucose level by averaging an R value over a short period of time (e.g., around 2-3 minutes) and using a calibration to obtain a glucose level associated with the R value. This method has predictable results for healthy persons with little to no vascular dysfunction. However, for persons with certain diseases, e.g. affecting arterial health, this method may not provide accurate results due to unhealthy vasoconstriction of arterioles near the surface of the skin or tissue. For example, diabetes creates extreme vasoconstriction that affects the R value and results in inaccurate correlations to NO and glucose levels.

Figure 30:
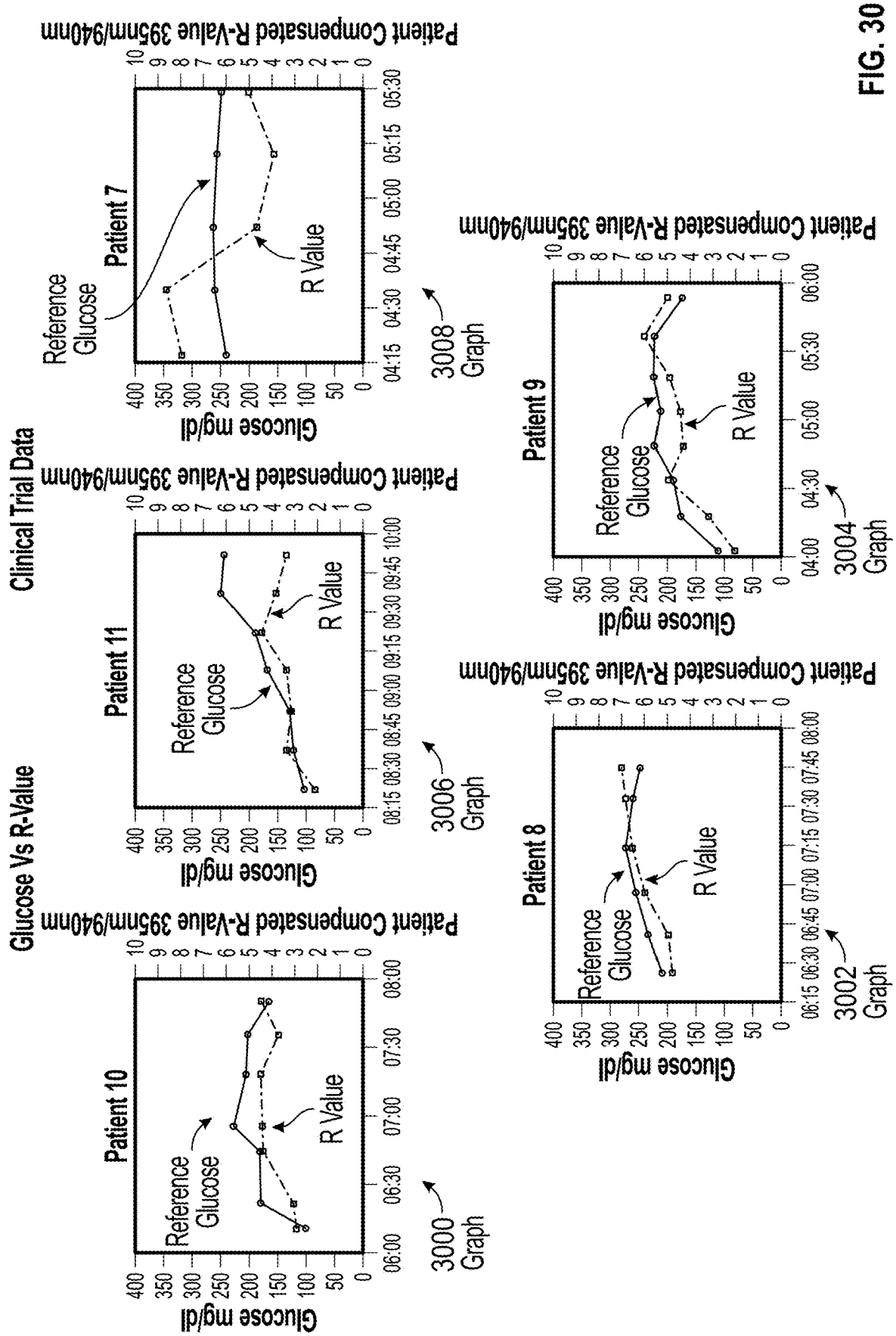
FIG. 30 illustrates schematic diagrams of measurements of glucose levels in a plurality of patients obtained using the biosensor in a clinical trial.

FIG. 30 illustrates schematic diagrams of measurements of glucose levels in a plurality of patients using the biosensor in a clinical trial. In this example, the patients ingested a caloric intake, and then a reference glucose was tested at discrete points using a blood test. In addition, the biosensor 100 detected an R value at 395 nm/940 nm at the discrete points. The patients in graphs 3000, 3002 and 3004 had a seemingly healthy vascular function and NO response. The R value approximately tracked the trend in the reference glucose. Thus, the R value provides a predictable tracking of trends in glucose, and a universal calibration table or curve may be compiled to correlate R values and glucose levels in these patients.

However, the patients in graphs 3006 and 3008 exhibited vascular dysfunction. The R value diverged from the reference glucose at one or more of the discrete points. For example, the vasodilation effect during phase 2 of digestion created unexpected results in the R values. Thus, in patients with atypical vascular responses, individual calibration of glucose levels to R values may need to be performed.

Figure 31:
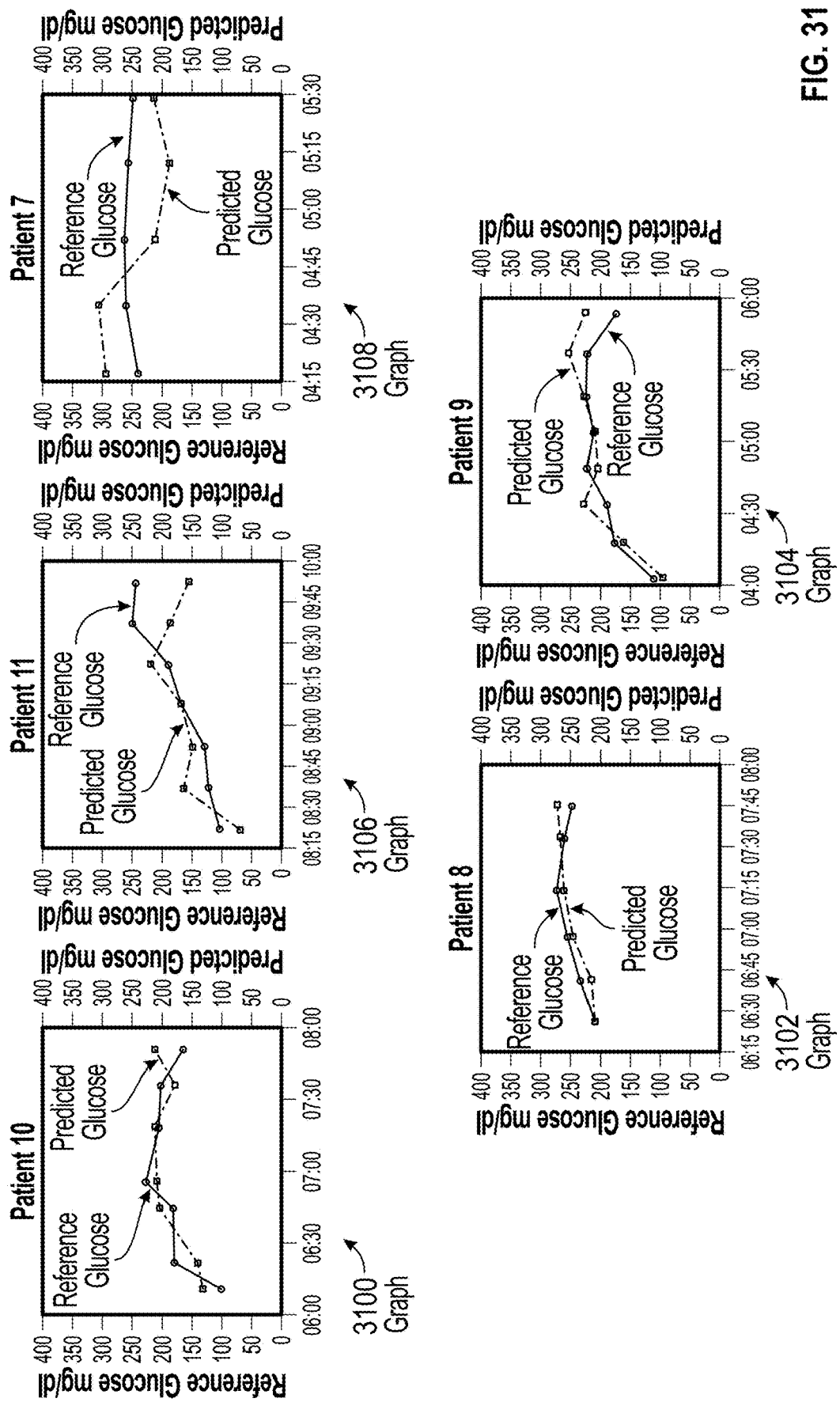
FIG. 31 illustrates schematic diagrams of measurements of glucose levels in a plurality of patients obtained using the biosensor in a clinical trial.

FIG. 31 illustrates schematic diagrams of measurements of glucose levels in a plurality of patients using the biosensor 100 in a clinical trial. In this example, the reference glucose is displayed with a predicted glucose value that is obtained using the $R_{395nm/940nm}$ values shown in FIG. 30. The R values for patients in graphs 3000, 3002 and 3004 with a seemingly healthy vascular function and NO response were correlated to the predicted glucose values using a universal calibration. The universal calibration correlates R values and glucose values based on a clinical testing from a general sample population of persons with healthy vascular systems. The universal calibration may include a table, equation, factor or curve. Thus, the R value provides a predictable tracking of trends in glucose for patients with a relatively healthy vascular response, and a universal calibration may be compiled to correlate R values and glucose levels in these patients.

However, the R values for patients in graphs 3106 and 3108 are correlated to the predicted glucose values using individual calibrations. For example, the R value is obtained, and an interim glucose value is estimated using the universal calibration. The interim glucose value is then adjusted using an individual calibration. A difference or other correlation between the interim glucose value and the reference glucose is determined at one or more points of time. The difference or other correlation is used as an individual calibration to adjust the interim glucose value to the predicted glucose levels shown in Graphs 3106 and 3108. Thus, for patients with vascular dysfunction, an individual calibration is used to obtain the predicted glucose levels from the R values In another embodiment, the individual calibration directly correlates the R values to the predicted glucose level for patients with vascular dysfunction. The reference glucose at one or more discrete points is compared to the $R_{395nm/940nm}$ values at the same discrete points, and the individual calibration is obtained.

The individual calibration should be recalculated at least every 2-3 months due to potential change in vascular function. For example, arteriolosclerosis or insulin resistance may further deteriorate the vascular health such that the vessels exhibit increased vasoconstriction. This deterioration may affect the level of vasoconstriction in vessels and the correlation between R values and glucose levels.

Figure 32:
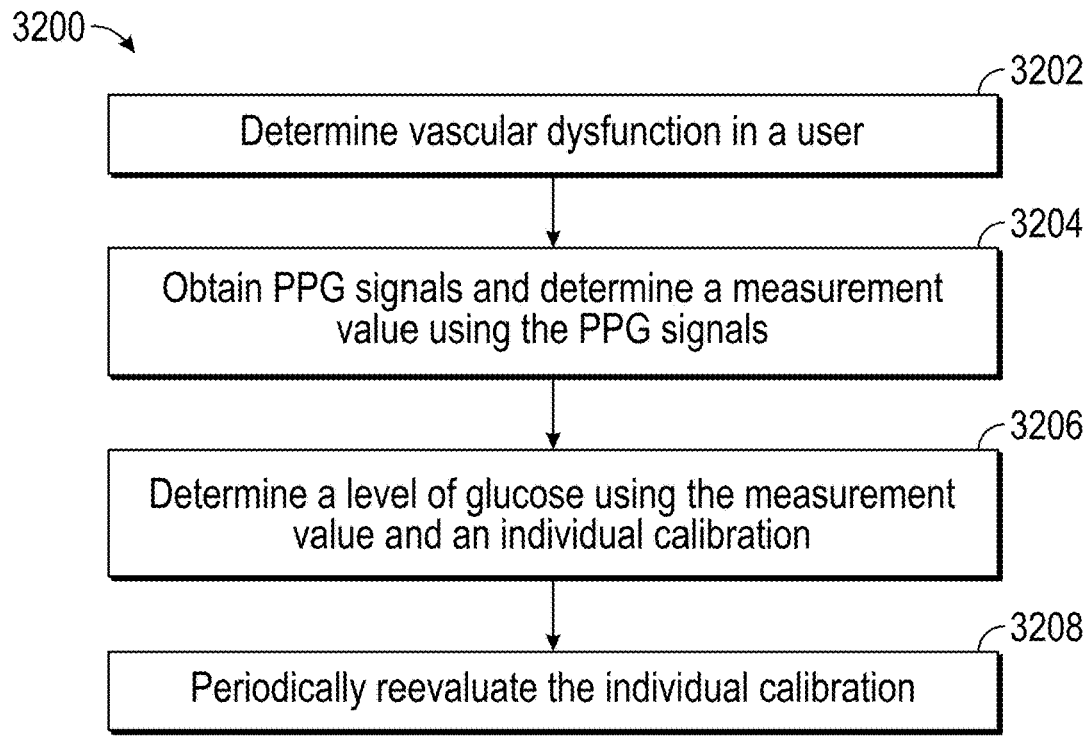
FIG. 32 illustrates a schematic flow diagram of an embodiment of a method for determining glucose levels of a patient with atypical vascular function.

FIG. 32 illustrates a schematic flow diagram of an embodiment of a method 3200 for determining glucose levels of a patient with atypical vascular function. The biosensor 100 determines that a user has vascular dysfunction or a disease that typically leads to vascular dysfunction, such as diabetes, heart disease or arteriolosclerosis, at 3202. The user may input or request individual calibration. The PPG signals are obtained, preferably at a first wavelength with a high absorption coefficient for NO, such as 395 nm or in a range around 380 nm to 410 nm and determining a measurement value using the PPG signals at 3204. The measurement value may include, e.g., an R value at 395/940 or 395/530 wavelength ratios.

The biosensor 100 may then determine a level of glucose using the measurement value and an individual calibration at 3206. For example, the R value is obtained, and an interim glucose value is estimated using the universal calibration. The interim glucose value is then adjusted using an individual calibration. In another embodiment, the individual calibration directly correlates the R values to the predicted glucose level for patients with vascular dysfunction. Thus, for patients with vascular dysfunction, an individual calibration is used to obtain the predicted glucose levels from the R values.

The individual calibration should be re-evaluated periodically at 3208. For example, the individual calibration should be updated at least every 2-3 months due to potential changes in vascular function.

Figure 33:
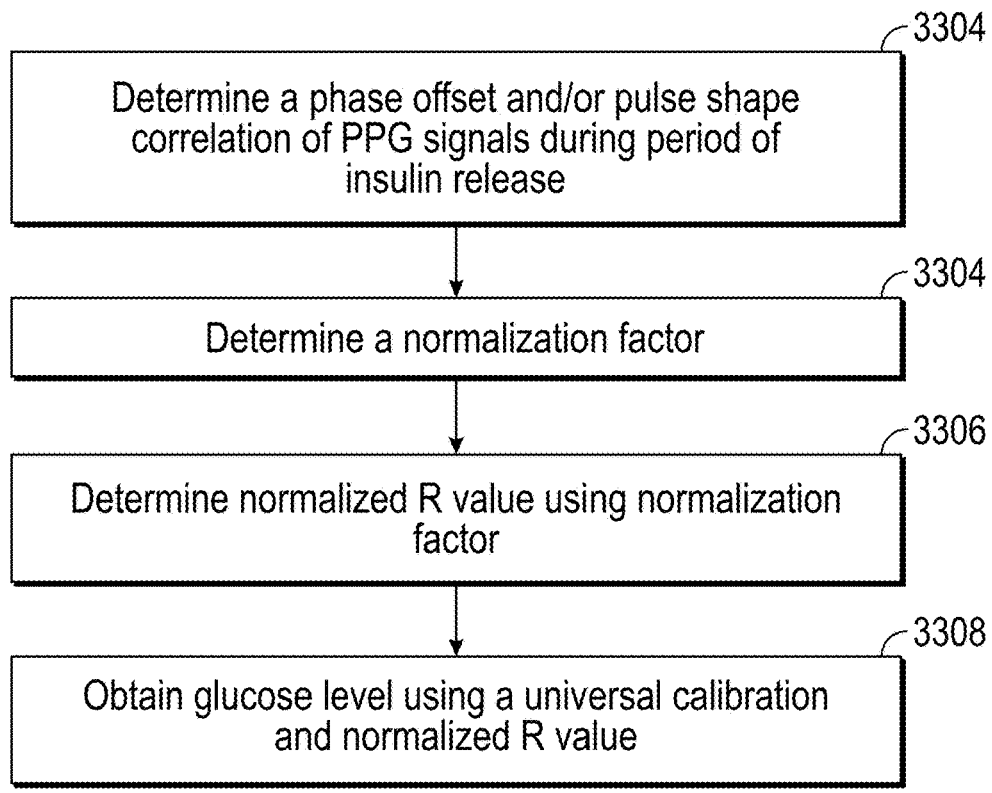
FIG. 33 illustrates a schematic flow diagram of another embodiment of a method for determining glucose levels of a patient with atypical vascular function.

FIG. 33 illustrates a schematic flow diagram of another embodiment of a method 3300 for determining glucose levels of a patient with atypical vascular function. As shown in the example of Graph 1900, the biosensor 100 obtains PPG signals over a time period between around a plurality of wavelengths at 940 nm, 630 nm, 590 nm, 530 nm, 440 nm and 395 nm. The "pulses" in response to discrete release of insulin in the bloodstream are identified in the PPG signals. Then a correlation is computed between the PPG waveform with a low absorption coefficient for NO (e.g., 440 nm, 530 nm or another wavelength in the visible range or in the IR range) and the PPG waveform with a high absorption coefficient for NO (e.g., at 395 nm or in a range of +/−10 nm of 395 nm) during the period of release of insulin in to obtain a Pulse Shape Correlation and a Phase Delay at 3302. The PPG signals are processed using, e.g., a cross correlation function or a Hilbert transformation or another algorithm that determines similarities in pulse shape and temporal relationship between the PPG signals.

The phase offset or waveform correlation may then be used to determine a factor to "normalize" an R value to obtain a normalized R value at 3306. Thus, the normalization factor may account for increased vasoconstriction due to vascular dysfunction. For example, the R value may be divided by an averaged phase offset factor or an averaged pulse shape correlation to determine the "normalized" R value. The normalized R value is then correlated to a glucose level using a universal calibration table or curve at 3308. The normalization factor compensates the R value in patients with vascular dysfunction.

In another embodiment, a plurality of calibrations may be implemented, each assigned to one or more different normalization factors. The glucose level is determined using the calibration table associated with the determined normalization factor.

Embodiment—Identification of Deep Inhalation

Figure 34:
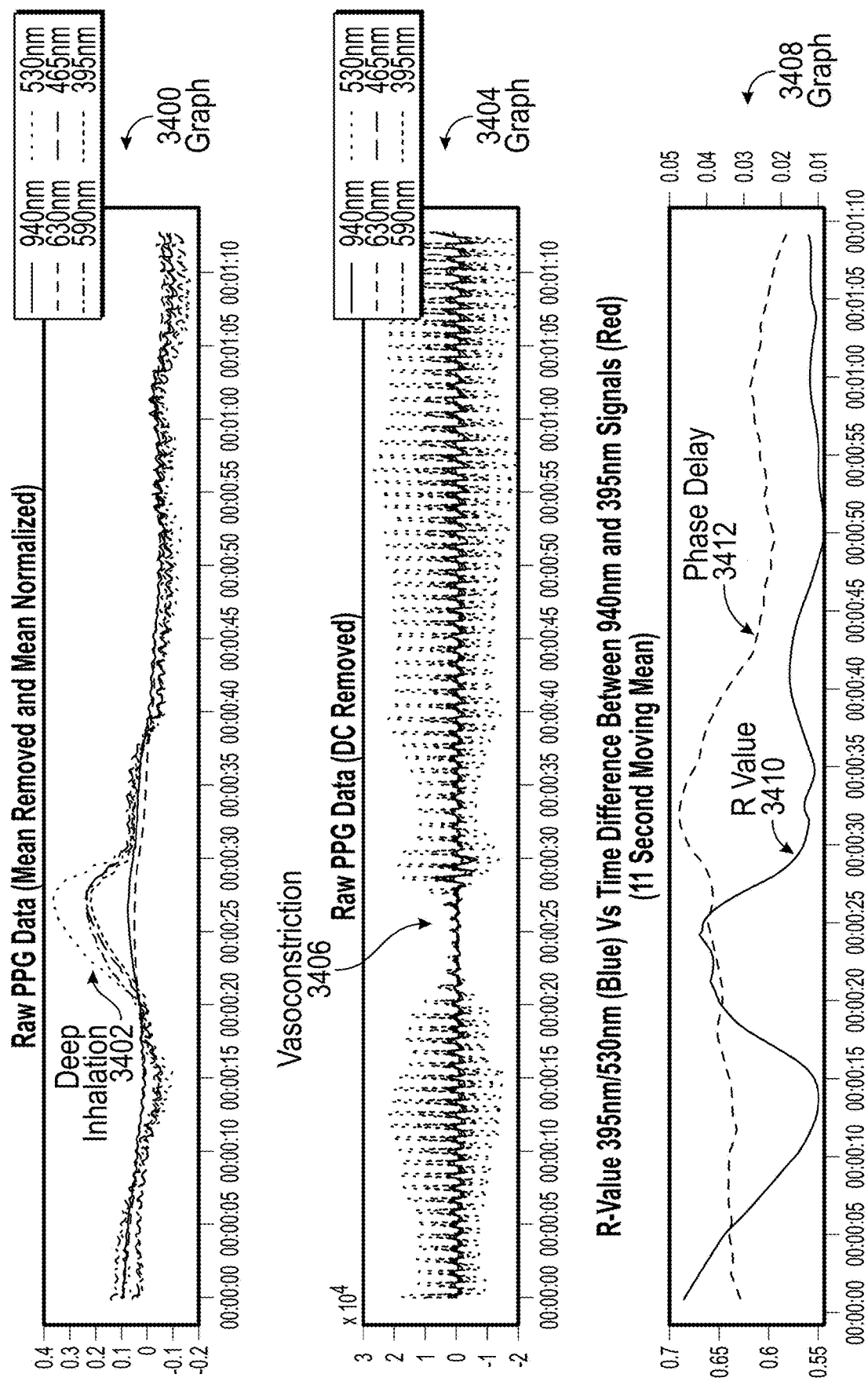
FIG. 34 illustrates a schematic diagram of graphs of PPG signals during deep inhalation.

FIG. 34 illustrates a schematic diagram of graphs of PPG signals during deep inhalation. A rapid, deep inspiration is also known to induce vasoconstriction of skin arterioles. In particular, a deep inhalation may vastly reduce the amplitude of PPG pulse waveforms and also introduce marked low-frequency components as a consequence of vasoconstriction and subsequent vasodilatation. These changes due to deep inspiration may create difficulties in accurately identifying PPG waveform features, such as insulin release periods. This also increases the error when computing physiological measures.

Graph 3400 illustrates PPG signal obtained during a deep inhalation 3402 around a plurality of wavelengths at 940 nm, 630 nm, 590 nm, 530 nm, 465 nm and 395 nm. The deep inhalation caused a decrease in the PPG pulse amplitude along with a characteristic low-frequency trend as seen in Graph 3404. Graph 3404 shows the $I_{AC}$ signal due to pulsatile blood flow. Because of the excessively low amplitude indicative of vasoconstriction 3406, the deep inhalation may be mistaken for an insulin release event.

Graph 3408 illustrates the R value 3410 of 395 nm/530 nm is illustrated. In addition, a correlation is computed between the PPG waveform at 940 nm and the PPG waveform at 395 nm to obtain a Phase Delay 3412. The PPG signals are processed using, e.g., a cross correlation function or a Hilbert transformation or another algorithm that determines similarities in pulse shape and temporal relationship between PPG signals. For example, the time delay between the two signals can also be calculated at each time instant from the phase shift of their wavelet transforms.

The R value 3410 has a low amplitude indicative of vasoconstriction 3406, such as in insulin release or deep inhalation. However, the phase delay 3412 does not indicate an insulin release. As seen in Graph 2404 in FIG. 24, the phase delay 2414 in response to an insulin release has a corresponding pulse with a large amplitude change. The phase delay 3412 in response to the deep inhalation 3402 fails to include such a pulse at a time corresponding to the vasoconstriction 3406. Thus, the vasoconstriction 3406 may be identified as an inhalation or other vasoconstriction causing event and not due to insulin release. Such pattern recognition may be performed to identify insulin release events recorded by the PPG signals.

Embodiment—Detection of a Risk of Sepsis or Other Infection Based on NO Levels

In an embodiment, the biosensor 100 may detect a risk of sepsis using NO concentration levels. In this embodiment, an R value derived from $L_{395}$ and $L_{940}$ is used to determine a NO measurement though other parameters may be obtained, such as $R_{390/940}$ or $L_{390}$. In the clinical trials herein, the $R_{395/940}$ value for a person without a sepsis condition was in a range of 0.1-8. In addition, it was determined that the $R_{395/940}$ value of 30 or higher is indicative of a patient with a sepsis condition and that the $R_{395/940}$ value of 8-30 was indicative of a risk of sepsis in the patient. In general, the $R_{395/940}$ value of 2-3 times a baseline of the $R_{395/940}$ value was indicative of a risk of sepsis in the patient. These ranges are based on preliminary clinical data and may vary. In addition, a position of the biosensor, pre-existing conditions of a patient or other factor may alter the numerical values of the ranges of the $R_{395/940}$ values described herein.

The R values are determined by using a wavelength in the UV range with high absorption coefficient for NO, e.g. in a range of 380 nm-410 nm. These R values have a large dynamic range from 0.1 to 300 and above. The percentage variance of R values in these measurements is from 0% to over 3,000%. The R values obtained by the biosensor 100 are thus more sensitive and may provide an earlier detection of septic conditions than blood tests for serum lactate or measurements based on MetHb.

For example, an optical measurement of MetHb in blood vessels is in a range of 0.8-2. This range has a difference of 1.1 to 1.2 between a normal value and a value indicating a septic risk. So, these measurements based on MetHb have less than a 1% percentage variance. In addition, during a septic condition, MetHb may become saturated due to the large amount of NO in the blood vessels. So, an optical measurement of MetHb alone or other hemoglobin species alone is not able to measure these excess saturated NO levels. The R values determined by measuring NO level directly using a wavelength in the UV range are thus more sensitive, accurate, have a greater dynamic range and variance, and provide an earlier detection of septic conditions.

A baseline NO measurement in blood vessels of a healthy general population is obtained. For example, the biosensor 100 may obtain R values or other NO measurements using the biosensor 100. For example, the biosensor 100 may measure an L395 value or determine SpNO % based on an R value for a general population over a period of time, such as hours or days. These NO measurements are then averaged to determine a baseline NO measurement. The NO measurement in blood vessels is then obtained for a general population with a diagnosis of sepsis. For example, the biosensor 100 may obtain R values or other NO measurements (such as an L395 value or SpNO %) for patients diagnosed with sepsis using traditional blood tests, such as serum lactate blood tests. The biosensor 100 may monitor the patients throughout the diagnosis and treatment stages. The NO measurements are then averaged to determine a range of values that indicate a septic condition.

Predetermined thresholds may then be obtained from the NO measurements. For example, a threshold value indicative of a non-septic condition may be obtained. A threshold value for a septic condition may also be obtained. The biosensor 100 is then configured with the predetermined thresholds for the NO measurement.

The predetermined thresholds may be adjusted based on an individual patient's pre-existing conditions. For example, a patient with diabetes may have lower R values. A baseline NO value for a patient may also be determined based on monitoring of the patient during periods without infections. The predetermined thresholds stored in the bio sensor 100 may then be adjusted based on any individual monitoring and/or pre-existing conditions.

In addition, the predetermined thresholds may be determined and adjusted based on positioning of the biosensor 100. For example, different R values or other NO measurements may be obtained depending on the characteristics of the underlying tissue, such as tissue with high fatty deposits or with dense arterial blood flow. The thresholds and other configurations of the biosensor 100 may thus be adjusted depending on the underlying skin tissue, such as a forehead, chest, arm, leg, finger, abdomen, etc.

Figure 35A:
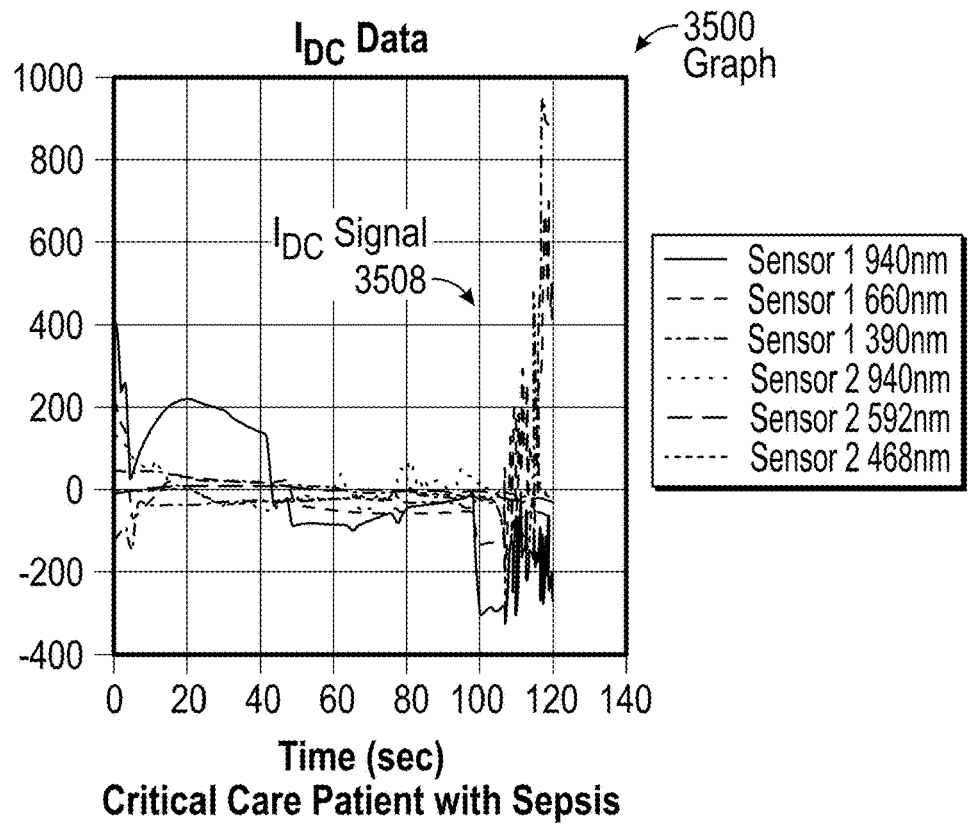
FIG. 35A illustrates a schematic diagram of graphs of PPG signals detected from a critical care patient diagnosed with sepsis.
Figure 35A:
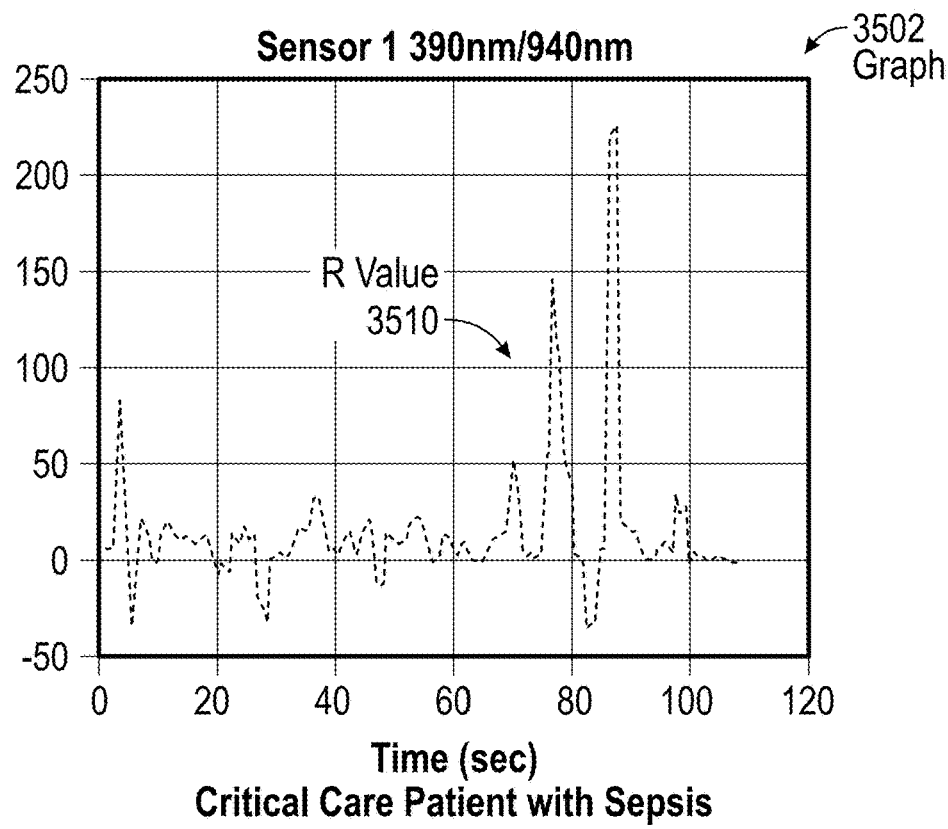

FIG. 35A illustrates graphical representations of PPG signals detected from a critical care patient diagnosed with sepsis. The biosensor 100 obtained PPG signals over a time period of approximately two minutes around a plurality of wavelengths at 940 nm, 630 nm, 590 nm, 530 nm, 440 nm and 390 nm. Graph 3500 illustrates the $I_{DC}$ signal 3508 of low frequency signals with the $I_{AC}$ signal filtered. The $I_{AC}$ signal has erratic frequency pulses with high amplitude peaks, especially at the 390 nm with a high absorption coefficient for NO. Graph 3502 illustrates the R value 3510 obtained for 390 nm/940 nm. The R value 3510 also has an erratic signal that fluctuates between positive and negative values with extremely high amplitude peaks. The R value in this example exceeds 200.

These large peaks in sepsis patients may initially create difficulties in accurately identifying PPG waveform features, such as insulin release periods. However, in patients with sepsis, the PPG responses are erratic in frequency with peaks exceeding amplitudes typically seen in insulin release periods. In addition, the R values for 390 nm/940 nm has abnormally high values exceeding 10 times normal and then may also have negative values.

Figure 35B:
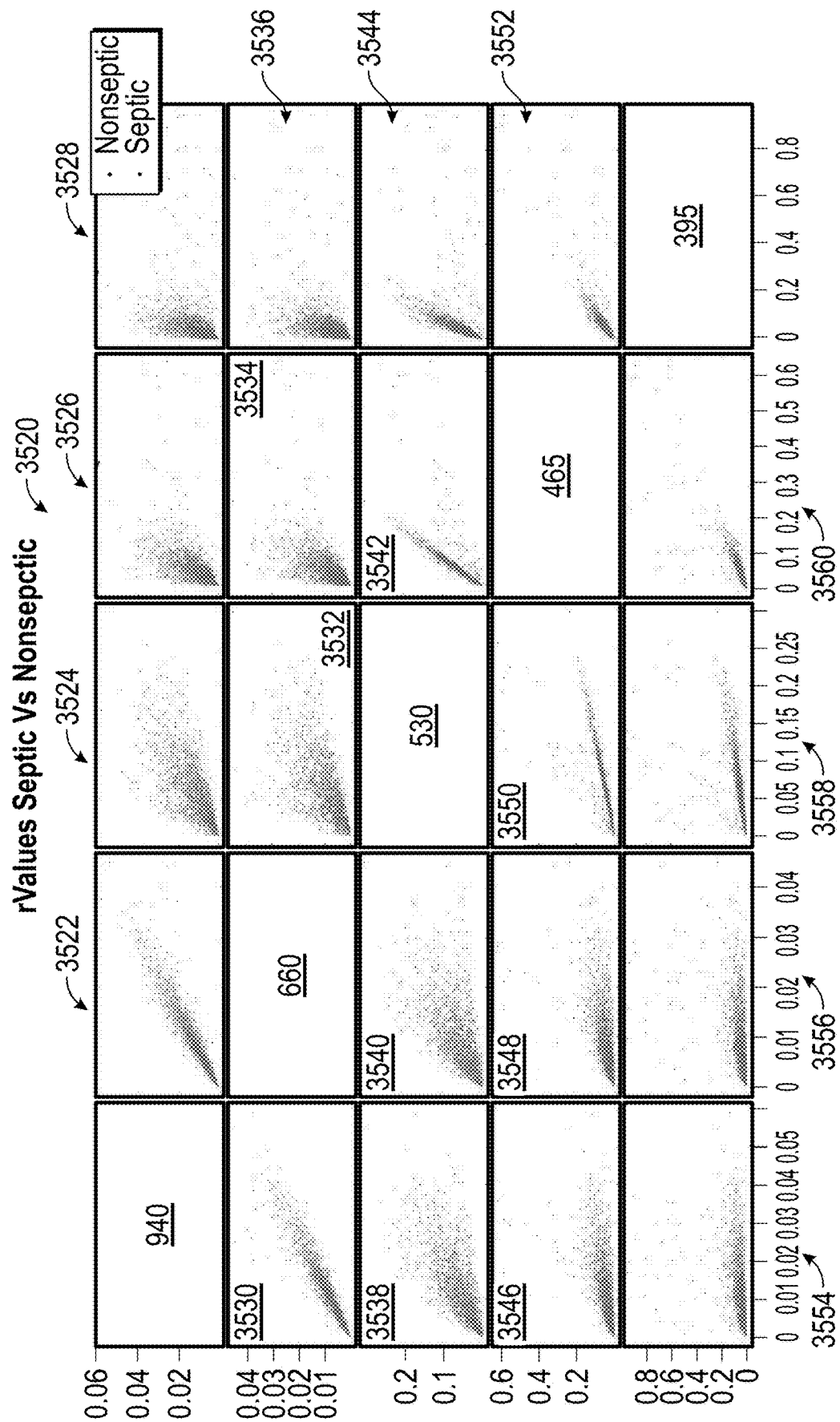
FIG. 35B illustrates graphical representations 3520 of PPG signals detected from a clinical trial of patients.

FIG. 35B illustrates graphical representations 3520 of PPG signals detected from a clinical trial of patients. A first set of patients were diagnosed as septic using an industry accepted blood test. A second set of patients were diagnosed as non-septic using an industry accepted blood test. PPG signals at a plurality of wavelengths (940 nm, 660 nm, 530 nm, 465 nm, 395 nm) are obtained from patients in a clinical trial. PPG signals were concurrently obtained from the first set and second set of patients. Various R values are then obtained from the plurality of wavelengths and then normalized. Graph 3522 illustrates the R values at 660 nm/940 nm for the first set of patients and second set of patients. Graph 3524 illustrates the R values at 530 nm/940 nm for the first set of patients and the second set of patients. Graph 3526 illustrates the R values at 465 nm/940 nm for the first and second set of patients. Graph 3528 illustrates the R values at 395 nm/940 nm for the first and second set of patients. Graph 3530 illustrates the R values at 940 nm/660 nm for the first and second set of patients. Graph 3532 illustrates the R values at 530/660 nm for the first and second set of patients.

Graph 3534 illustrates the R values at 465 nm/660 nm for the first set of patients and second set of patients. Graph 3536 illustrates the R values at 395 nm/660 nm for the first and second set of patients. Graph 3538 illustrates the R values at 940 nm/530 nm for the first set of patients and the second set of patients. Graph 3540 illustrates the R values at 660 nm/530 nm for the first and second set of patients. Graph 3542 illustrates the R values at 465 nm/530 nm for the first set of patients and the second set of patients. Graph 3544 illustrates the R values at 395/530 nm for the first and second set of patients.

Graph 3546 illustrates the R values at 940 nm/465 nm for the first set of patients and the second set of patients. Graph 3548 illustrates the R values at 660 nm/465 nm for the first set of patients and the second set of patients. Graph 3550 illustrates the R values at 530 nm/465 nm for the first and second set of patients. Graph 35 illustrates the R values at 395 nm/940 nm for the first and second set of patients. Graph 3552 illustrates the R values at 395 nm/6465 nm for the first and second set of patients.

Graph 3554 illustrates the R values at 940/395 nm for the first and second set of patients. Graph 3556 illustrates the R values at 660 nm/395 nm for the first and second set of patients. Graph 3558 illustrates the R values at 530 nm/395 nm for the first and second set of patients. Graph 3560 illustrates the R values at 465 nm/395 nm for the first and second set of patients.

If the variance in R values in a graph are not statistically significant for the first set of patients and the second set of patients, then the R value is not a good measure of sepsis. Graph 3528 and the inverse Graph 3554 illustrates a good variance in R values between the first set of patients and second set of patients using PPG signals at 395 nm and 940 nm. In addition, Graph 3536 (and the inverse Graph 3556) illustrate a good variance in R values between the first set of patients and second set of patients using PPG signals at 395 nm and 660 nm. Thus, the R values of PPG signals at 395 nm and 940 nm or R values of PPG signals at 395 and 660 nm may be used to determine a septic condition in a patient.

Embodiment—Detection of Digestion or Hunger

Figure 36:
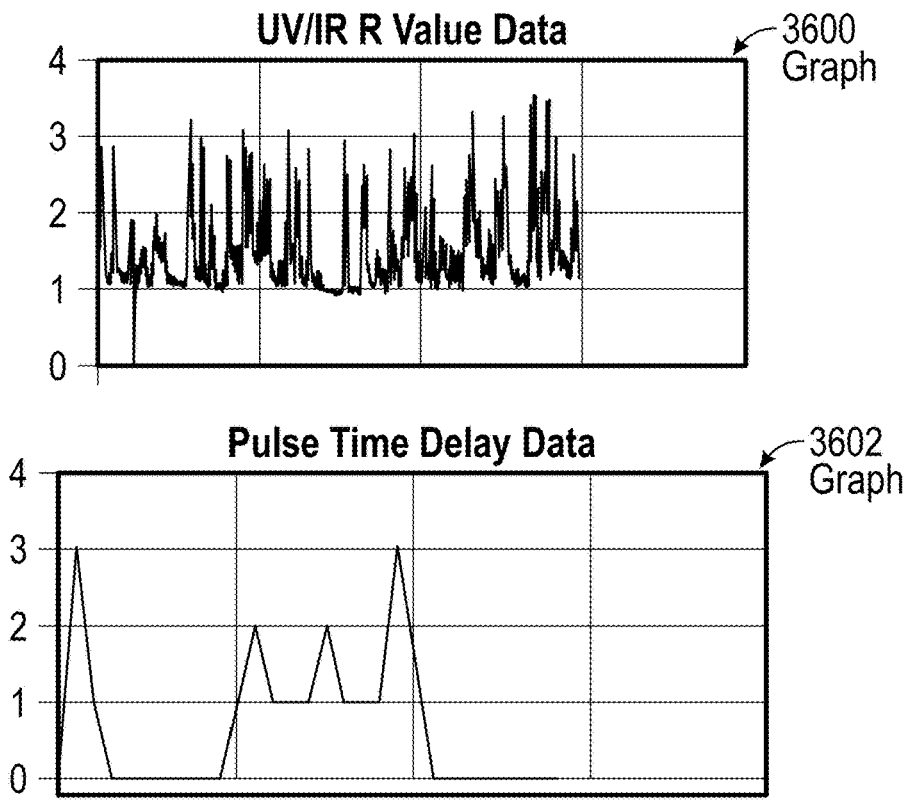
FIG. 36 illustrates a schematic diagram of graphs of PPG signals during periods of ingestion and fasting.

FIG. 36 illustrates a schematic diagram of graphs of PPG signals during periods of ingestion and fasting. Graph 3600 illustrates an R value obtained from PPG signals at 395 nm and 940 nm over an approximate 88 minute time period. The patient ingested food at approximately 19 minutes. The Graph 3600 shows insulin release pulses with a frequency of approximately every 2-3 minutes after ingestion. In contrast, Graph 3602 shows PPG signal response over an approximately 102 minute period. The patient has not ingested caloric intake. The insulin release pulses have a frequency of approximately every 10-20 minutes. Thus, by determining a frequency or average period between insulin release pulses, an ingestion time or digestion stage may be determined. In addition, a hunger level or time from ingestion may also be determined from the time between insulin release pulses.

The stage of digestion may thus be determined using identification of the insulin release events from the PPG signals. For example, the insulin release events are more frequent after ingestion during stage 1 and stage 2 of digestion and are less frequent in response to fasting or hunger. Thus, by measuring the frequency or time between insulin release events using the PPG signals, a stage of digestion may be identified or a level of fasting or hunger may be identified.

Embodiment—Calibration During Ingestion Periods

During ingestion, a greater frequency of insulin release pulses may affect the PPG signals. The walls of the blood vessels are constricting and harden due to muscle tension and may generate false readings of arterial stiffness or blood flow. The calibration for determining glucose levels may need to be adjusted during such ingestion periods.

In addition, during insulin release, vascular imaging or tests, such as a CT Scan or ultrasound or MRI of the blood flow of the vascular system should be avoided. The walls of the vessels may not exhibit normal behavior during insulin release. By measuring the frequency or time between insulin release events using the PPG signals, a stage of digestion may be identified. Depending on the stage of digestion and frequency of insulin release events, the vascular imaging or tests may be performed or delayed.

Figure 37:
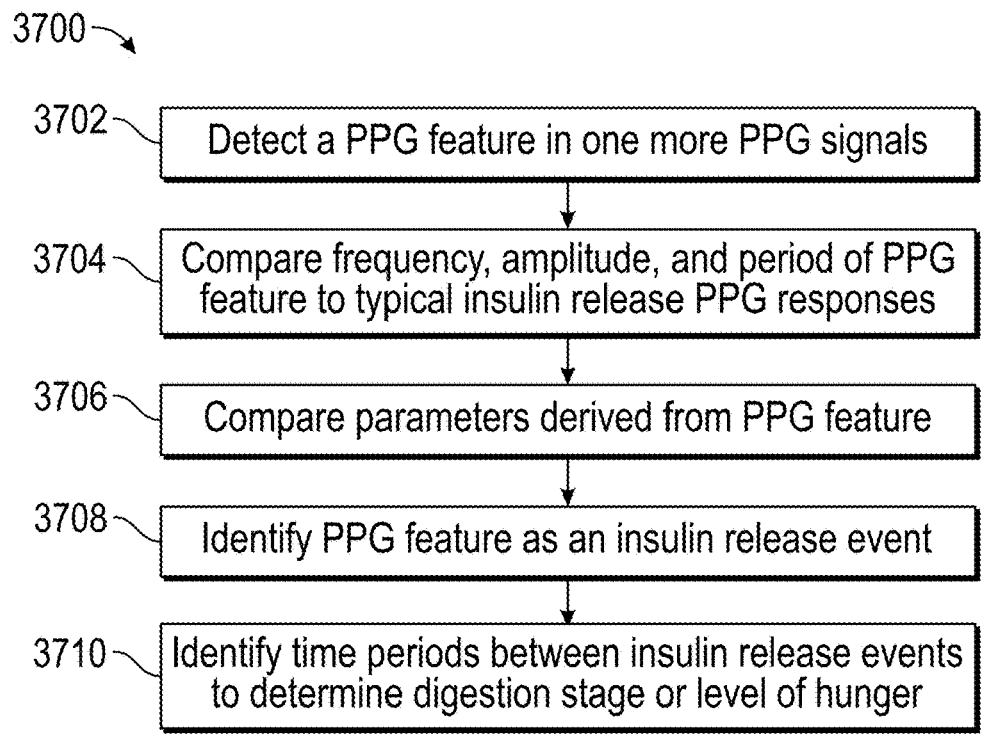
FIG. 37 illustrates a schematic flow diagram of an embodiment of a method for identifying a PPG feature, such as an insulin release pulse or deep inhalation pulse.

FIG. 37 illustrates a schematic flow diagram of an embodiment of a method 3700 for identifying a PPG feature, such as an insulin release event. A pulse or amplitude peak is detected in PPG signals at one or more wavelengths at 3702. The frequency, amplitude and period of the PPG feature are compared to typical or average responses or characteristics of PPG signals during an insulin release event at 3704. For example, PPG pulses due to an insulin release have a much lower frequency than a heart rate. The frequency increases after ingestion and then decreases with hunger. The period of the pulse for an insulin pulse is longer than a typical heartbeat, for example lasting over 4-10 seconds and have an IAC amplitude that is at least 50% less than a heartbeat pulse. Thus, the biosensor 100 may determine a change in amplitude of the PPG signals and compare the change in the amplitude of the PPG signals to a predetermined range of the amplitude of PPG signals during an insulin release event. The predetermined range may include an average or mean of the amplitude or a percentage of change during the insulin release event. The predetermined range of the amplitude may be obtained from testing of a general population with a healthy vascular system.

Additionally, the biosensor 100 may determine a period of the pulse and compare to a predetermined range of periods of PPG pulses during an insulin release event. The predetermined range may include an average or mean of the period of the pulse during an insulin release event. The predetermined range of the period may be obtained from testing of a general population with a healthy vascular system.

Furthermore, a frequency or time between pulses may also be determined and compared to predetermined frequencies or a count of a number of pulses typically found during digestion or hunger. This comparison may be used to determine a stage of digestion or level of hunger or estimated time since ingestion of caloric intake.

The frequency, amplitude and period of the PPG feature may also be compared to typical responses of PPG signals during other events, such as deep inhalation, sepsis or other types of features. Thus, other types of PPG responses may also be identified.

In addition, one or more parameters derived from the PPG signals may be compared to known patterns or characteristics to identify an insulin release pulse at 3706. For example, the IAC signal, an L value curve or an R value curve (such as 390 nm/940 nm) is determined from the PPG signals. These parameters are then compared to predetermined ranges for the corresponding parameter during an insulin release event. For example, an R value for an insulin pulse is much lower than R values in a sepsis patient. In addition, the R value has a similar pulse shape and timing as the PPG signal of IAC for an insulin release event while there is less correlation between the R value and the IAC signal with deep inhalation. Other parameters such as integrals or derivatives or wavelet transforms or correlations between PPG signals may be determined and compared to predetermined normal ranges during insulin release events. The PPG feature is then identified at 3708 as an insulin release event or may be identified as a sepsis condition, deep inhalation or other feature.

When the PPG feature is identified as an insulin release event, the frequency or time between insulin release events may be measured using the PPG signals to determine a stage of digestion or a level of hunger at 3710. A time since ingestion of caloric intake may also be estimated.

In an embodiment, substantially continuous detection of PPG signals during a time period, e.g. over a plurality of hours, is more likely to capture and identify an insulin release event in a patient. Periodic measurements, such as a sampling window of PPG signals for one to three minutes, during the same time period is less likely to capture an insulin release event in the patient. Since the substantially continuous measurements are more likely to capture the occurrence of insulin release events, subsequent glucose level measurements are more accurate as well.

Embodiment—Measurement of Heart Rate Variations Due to Insulin Pulses

Figure 38:
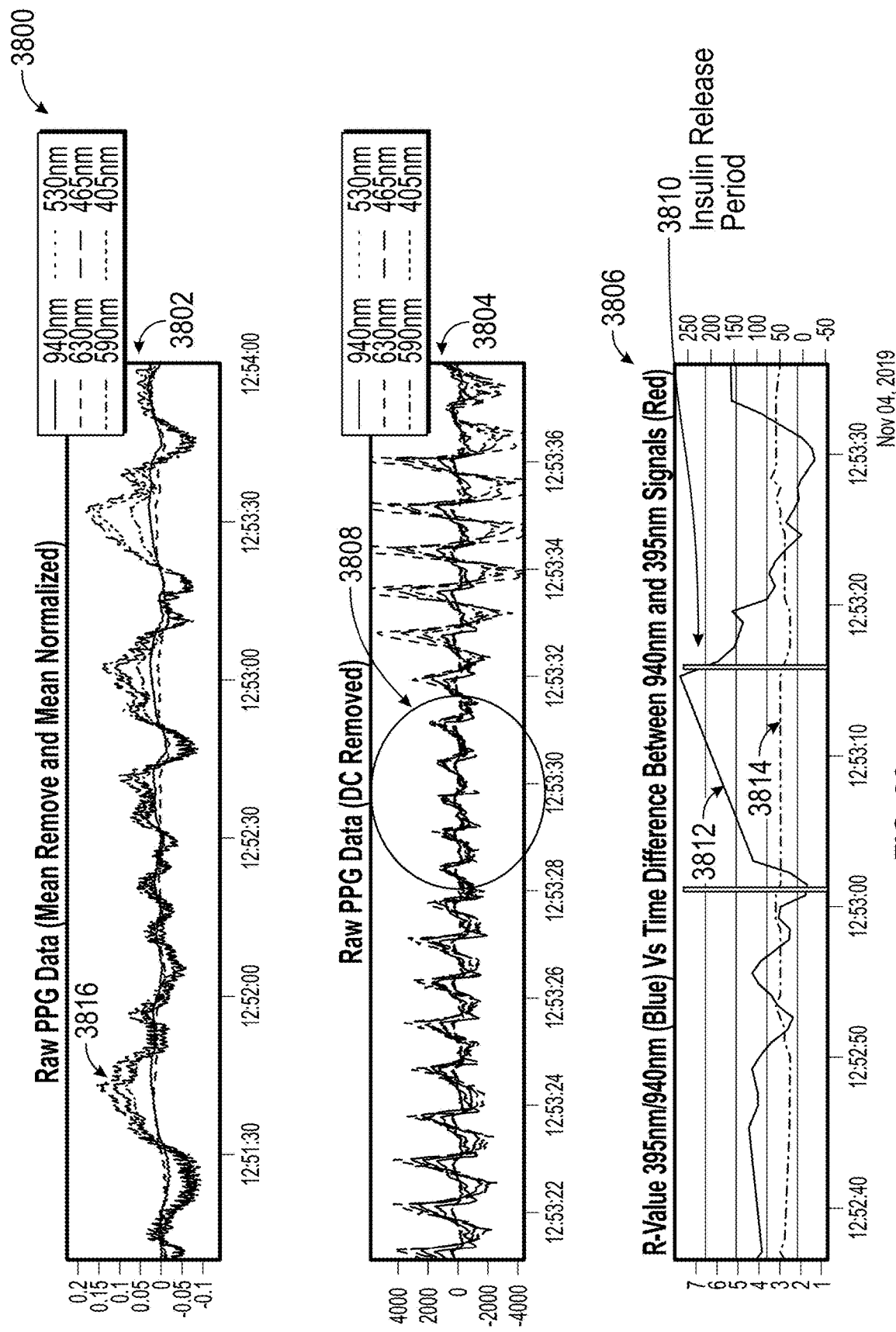
FIG. 38 illustrates a graphical representations of test results obtained from an embodiment of the biosensor.

FIG. 38 illustrates a graphical representations 3800 of test results obtained from an embodiment of the biosensor 100. In this experiment, the PPG signals were obtained from a biosensor 100 configured on a finger of a healthy patient with no known pre-conditions affecting vascular health. The graph 3802 depicts normalized PPG signals 3816 obtained from a healthy patient at a plurality of wavelengths including 940 nm, 630 nm, 590 nm, 530 nm, 465 nm, and 405 nm over a period of about three minutes. The PPG signals have been mean removed and normalized so that the wavelengths may be displayed on the same graph to compare relative changes in the shape of the signals.

The second graph 3804 depicts an AC component of the PPG signals 3816 with a DC component filtered over an approximate 15 second period. The pressure pulse wave (HR pulse) pattern in vessels may be seen during an insulin release event or period 3808. The insulin release period 3808 is due to the release of insulin into the bloodstream. The pancreas releases insulin into the blood stream in discrete pulses. These pulses of insulin in the blood stream affect the vasodilation of the vessels. The insulin release event 3808 includes a time period having a pulse of insulin in the blood stream or a marked increase of insulin in the blood stream. As seen in the graph 3804, the pressure pulse wave pattern and thus cardiac cycle, is affected at least in part due to the insulin release event 3808.

The third graph 3806 illustrates an R value 3812 obtained from the PPG signals 3816 at a first wavelength of 395 nm and a second wavelength 940 nm. A phase difference 3814 is also depicted between the PPG signals 3816 at the first wavelength of 395 nm and the second wavelength 940 nm. The R value 3812 is affected by the insulin release event or period 3810 as shown in the graph 3808. The R value 3812 increases during the insulin release period 3810 perhaps in part due to the vasodilation of the vessels caused by the insulin pulse.

Figure 39:
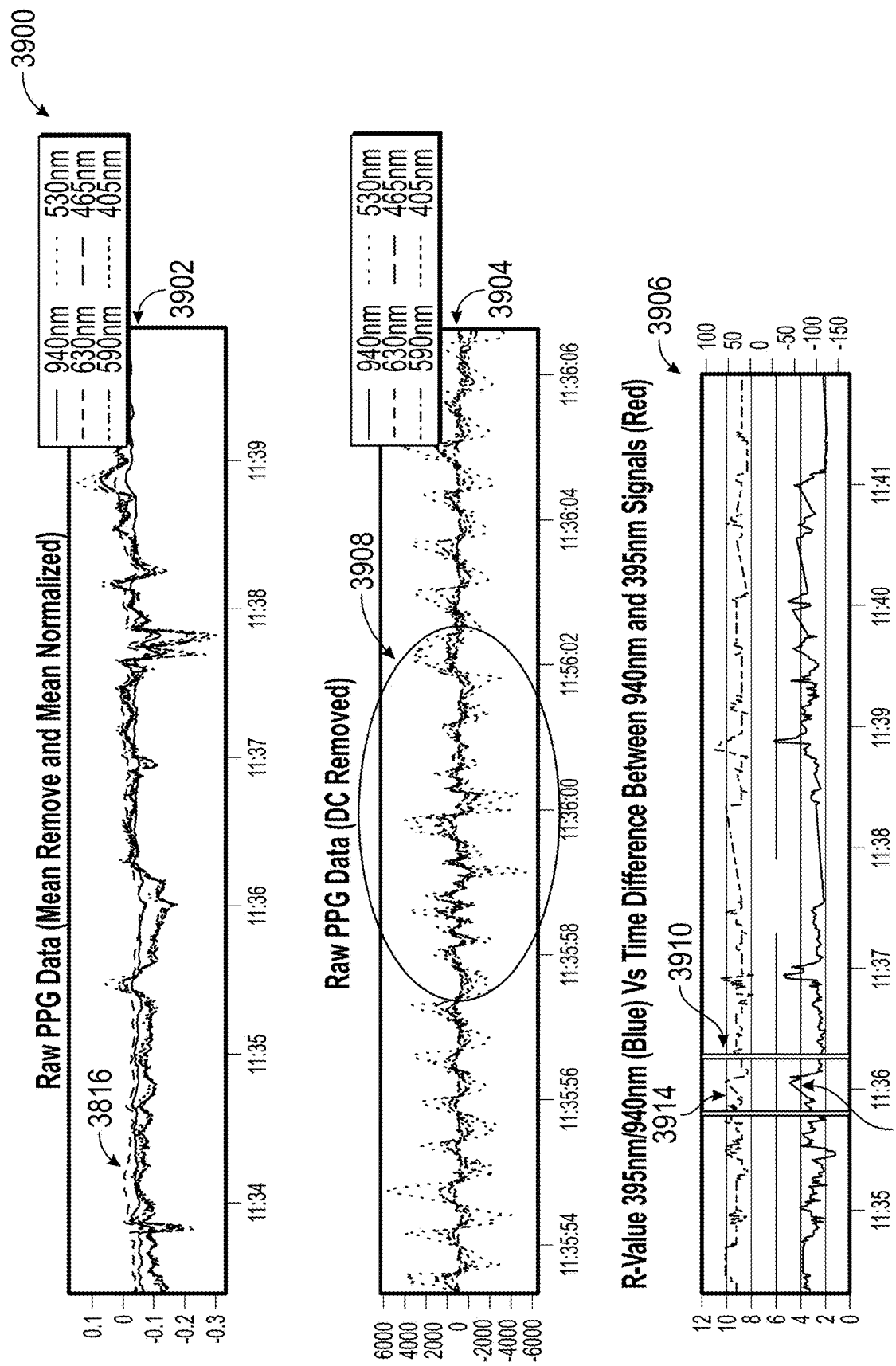
FIG. 39 illustrates graphical representations of additional test results obtained from an embodiment of the biosensor.

FIG. 39 illustrates graphical representations 3900 of additional test results obtained from an embodiment of the biosensor 100. In this experiment, the PPG signals were obtained from a biosensor 100 configured on a finger of a second healthy patient with no known pre-conditions affecting vascular health. The graph 3902 depicts normalized PPG signals 3916 obtained from a healthy patient at a plurality of wavelengths including 940 nm, 630 nm, 590 nm, 530 nm, 465 nm, and 405 nm over a period of about five minutes.

The second graph 3904 depicts an AC component of the PPG signals 3916 with a DC component filtered over an approximate 12 second period. The pressure pulse wave (HR pulse) pattern in vessels may be seen during an insulin release event or period 3908. The insulin release period 3908 is due to the release of insulin into the bloodstream. The insulin release event 3908 includes a time period having a pulse of insulin in the blood stream or a marked increase of insulin in the blood stream. As seen in the graph 3904, the pressure pulse wave pattern and thus cardiac cycle, is affected at least in part due to the insulin release event 3908.

The third graph 3906 illustrates an R value 3912 obtained from the PPG signals 3916 at a first wavelength of 395 nm and a second wavelength 940 nm. A phase difference 3914 is also depicted between the PPG signals 3916 at the first wavelength of 395 nm and the second wavelength 940 nm. The R value 3912 is affected by the insulin release event or period 3910 as shown in the graph 3908. The R value 3912 increases during the insulin release period 3910 perhaps in part due to the vasodilation of the vessels caused by the insulin pulse.

Figure 40:
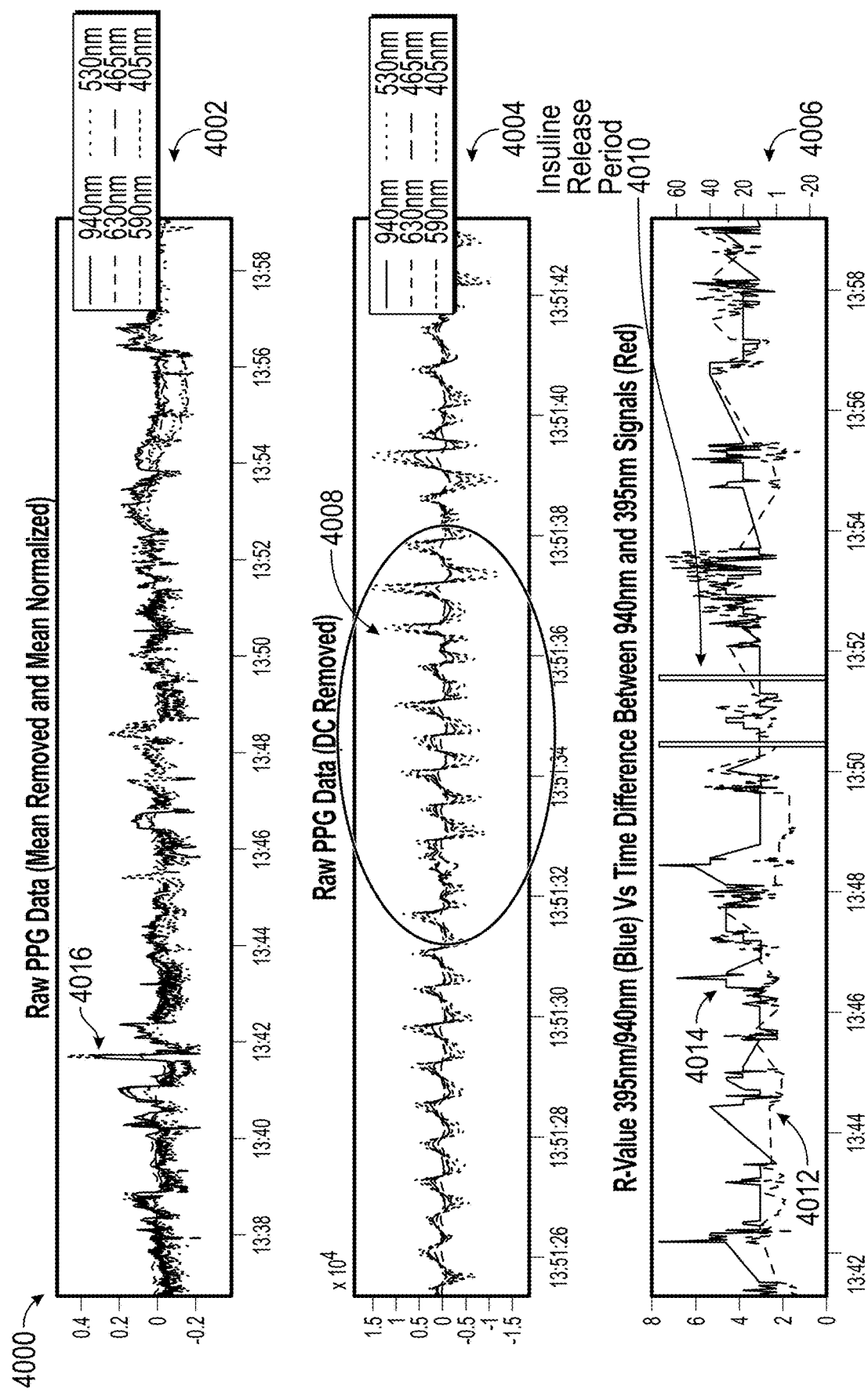
FIG. 40 illustrates graphical representations of additional test results obtained from an embodiment of the biosensor.

FIG. 40 illustrates graphical representations 4000 of additional test results obtained from an embodiment of the biosensor 100. In this experiment, the PPG signals were obtained from a biosensor 100 configured on a finger of a third healthy patient with no known pre-conditions affecting vascular health. The graph 4002 depicts normalized PPG signals 4016 obtained from the third healthy patient at a plurality of wavelengths including 940 nm, 630 nm, 590 nm, 530 nm, 465 nm, and 405 nm over a period of about twenty minutes.

The second graph 4004 depicts an AC component of the PPG signals 4016 with a DC component filtered over an approximate 16 second period. The pressure pulse wave (HR pulse) pattern in vessels may be seen during an insulin release event or period 4008. The insulin release period 4008 is due to the release of insulin into the bloodstream. The insulin release event 4008 includes a time period having a pulse of insulin in the blood stream or a marked increase of insulin in the blood stream. As seen in the graph 4004, the pressure pulse wave pattern, and thus cardiac cycle, is affected at least in part due to the insulin release event 4008.

The third graph 4006 illustrates an R value 4012 obtained from the PPG signals 4016 at a first wavelength of 395 nm and a second wavelength 940 nm. A phase difference 4014 is also depicted between the PPG signals 4016 at the first wavelength of 395 nm and the second wavelength 940 nm. The R value 4012 is affected by the insulin release event or period 4010 as shown in the graph 4006. The R value 4012 increases during the insulin release period 4010 perhaps in part due to the vasodilation of the vessels caused by the insulin pulse.

Using the PPG signals, the biosensor 100 may thus identify an insulin release event in vessels in a healthy patient. The biosensor 100 may use one or more PPG parameters, such as a comparison (such as a cross correlation) of the pressure pulse wave pattern in an AC component of a PPG signal or changes in the R value to identify the insulin release event. The biosensor 100 may also use other PPG parameters derived from the PPG signals to identify an insulin release period, such a phase difference between PPG signals, L values, etc. For example, a typical PPG waveform 910 includes a systolic peak (SP) 912, a diastolic peak (DP) 916, a dicrotic notch (914), trough 918 and pulse width (tnext trough). Other characteristics include pulse pressure area (PP), systolic area (As), diastolic area (Ad), augmented pressure (AP), pulse interval, peak to peak interval, augmentation index (AI=PP/(PP−AP)×100%), crest time, etc. These or other characteristics may be determined from a PPG waveform or a first or second derivative of the PPG waveform. For example, various ratios may be derived from a second derivate of the PPG waveform, e.g., such as the early systolic negative wave to the early systolic positive wave (Ratio b/a). These and other characteristics may be measured in a PPG waveform (including its derivatives) and be included as PPG parameters.

Figure 41:
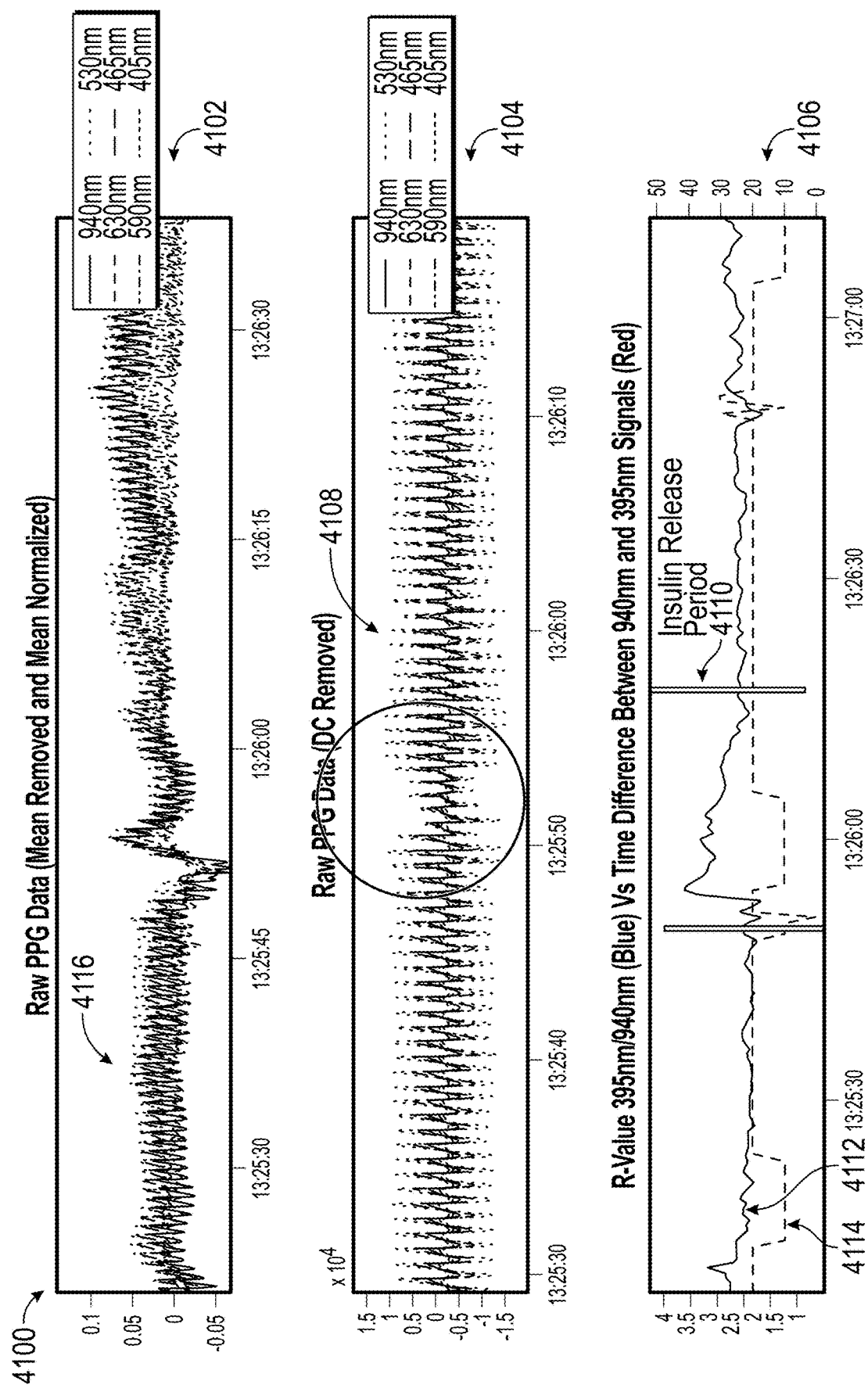
FIG. 41 illustrates graphical representations of additional test results obtained from an embodiment of the biosensor.

FIG. 41 illustrates graphical representations 4100 of additional test results obtained from an embodiment of the biosensor 100. In this experiment, the PPG signals 4116 were obtained from a biosensor 100 configured on a finger of a patient with Type I Diabetes. The graph 4102 depicts normalized PPG signals 4116 obtained from the patient at a plurality of wavelengths including 940 nm, 630 nm, 590 nm, 530 nm, 465 nm, and 405 nm over a period of about two minutes.

The second graph 4104 depicts an AC component of the PPG signals 4116 with a DC component filtered over an approximate fifty second period. The pressure pulse wave (HR pulse) pattern in vessels may be seen during an insulin release event or period 4108. The insulin release event 4108 includes a time period having a pulse of insulin in the blood stream or a marked increase of insulin in the blood stream. As seen in the graph 4104, the pressure pulse wave pattern and thus cardiac cycle, is affected at least in part due to the insulin release event 4108. Thus, the insulin release event may affect the HR pulse pattern during the insulin release period in a patient with Type 1 Diabetes.

The third graph 4106 illustrates an R value 4112 obtained from the PPG signals 4116 at a first wavelength of 395 nm and a second wavelength 940 nm. A phase difference 4114 is also depicted between the PPG signals 4116 at the first wavelength of 395 nm and the second wavelength 940 nm. The R value 4112 is affected by the insulin release event or period 4108 as shown in the graph 4006. The R value 4112 increases during the insulin release period 4010 perhaps in part due to the vasodilation of the vessels caused by the insulin pulse. In addition, the phase difference 4114 increases during the insulin release period 4010.

Figure 42:
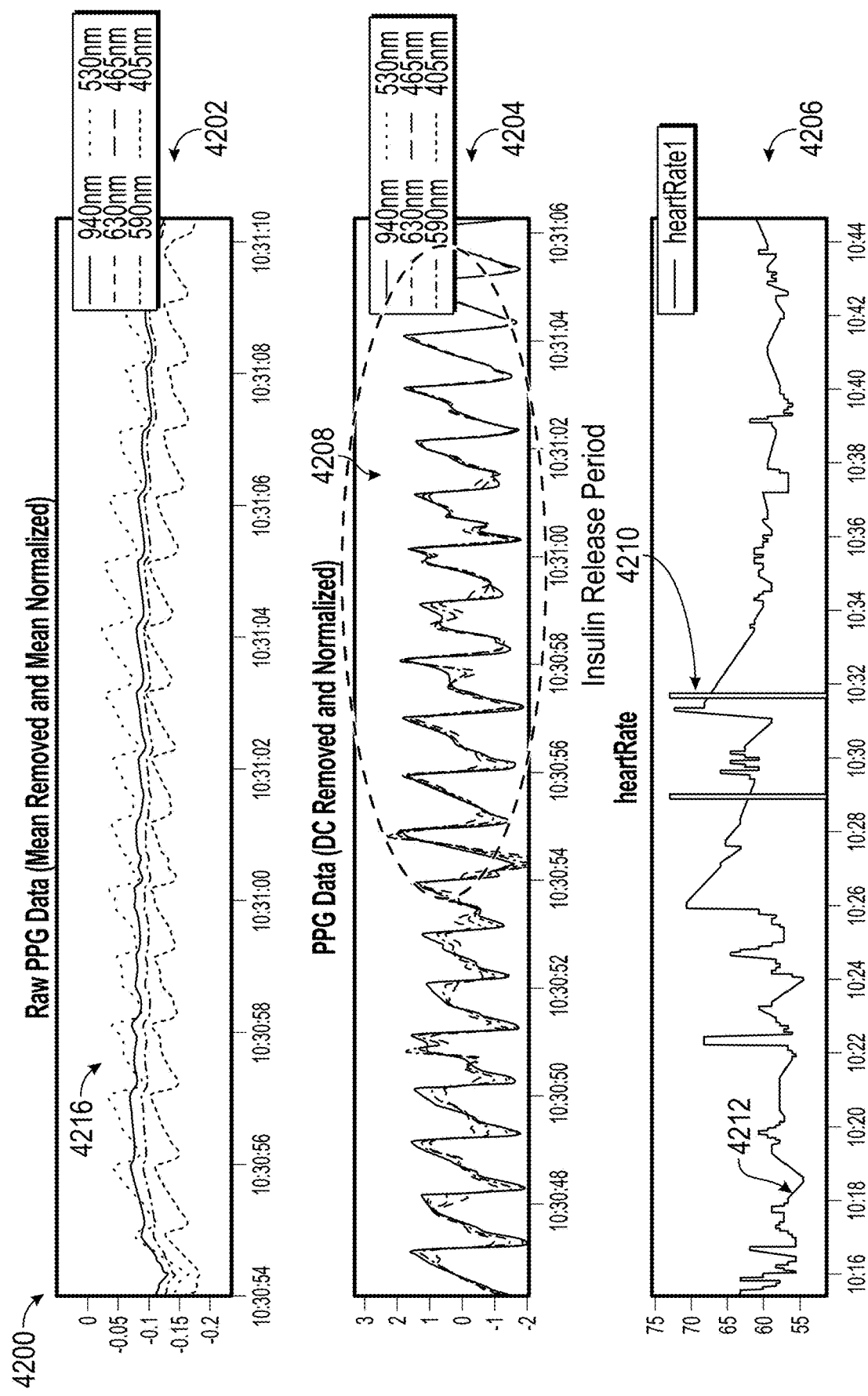
FIG. 42 illustrates graphical representations of additional test results obtained from an embodiment of the biosensor.

FIG. 42 illustrates graphical representations 4200 of additional test results obtained from an embodiment of the biosensor 100. In this experiment, the PPG signals 4216 were obtained from a biosensor 100 configured on a finger of a patient with Type II Diabetes. The graph 4202 depicts normalized PPG signals 4216 obtained from the patient at a plurality of wavelengths including 940 nm, 630 nm, 590 nm, 530 nm, 465 nm, and 405 nm over a period of about sixteen seconds.

The second graph 4204 depicts an AC component of the PPG signals 4216 with a DC component filtered over an approximate twenty second period. The pressure pulse wave (cardiac cycle) pattern in vessels may be seen during an insulin release event or period 4208. The insulin release event 4208 includes a time period having a pulse of insulin in the blood stream or a marked increase of insulin in the blood stream. As seen in the graph 4204, the pressure pulse wave pattern and thus cardiac cycle, is affected at least in part due to the insulin release event 4208. Thus, the insulin release event may affect the HR pulse pattern during the insulin release period in a patient with Type 1I Diabetes.

The third graph 4206 illustrates the heart rate 4212 determined from the PPG signals 4216. The heart rate during the insulin release period 4210 fluctuates as well. The insulin release event 4210 affects the pressure pulse wave pattern, cardiac cycle and heart rate in the patient with Type 2 Diabetes.

A comparison of the variability of the cardiac cycle or pressure pulse wave pattern in PPG signals during an insulin release event was performed. In general, healthy patients who are NOT diabetic exhibit greater variations in pressure pulse wave patterns during insulin release events. A comparison of periodicity of the PPG signals in graph 4100 of the patient with Type 1 Diabetes was made with the periodicity of the PPG signals in graphs 3800, 3900, 4000 of healthy patients. The pressure pulse wave pattern exhibited less variability during the insulin release event in the patient with Type I Diabetes than the pressure pulse wave patterns for the healthy patients.

As diabetes progresses in patients, the variability in the heart rate and/or pulse wave pattern decreases during insulin release events. It is assumed that the endothelium dysfunction increases due to the disease progression, and that the blood vessels are hardening. This atherosclerosis decreases the vasodilation in vessels which in turn decreases the variability in PPG signals during an insulin release event. Patients with Type 1 diabetes who are long time insulin users have the least amount of heart rate variability. The variability of the heart rate and/or pulse wave pattern during an insulin release event may thus be used in evaluating vascular health.

Eventually though, as diabetes progresses in patients to later stages, the heart itself tends to have much more heart irregularities and non-rhythmic patterns that may affect pressure pulse waves. When a patient with Type I and Type II diabetes is affected by such heart disease, then the extent of variability in PPG signals may increase (rather than decrease) during an insulin release event.

An insulin release event may affect both the vessels and the heart in the vascular system. During insulin release events, a chemical reaction releases ET-1 & NO from the endothelium cells lining walls of vessels in the vascular system. These endothelium cells also line the inner heart chambers and generate insulin releases in the heart. The heart exhibits altered electrical activity during insulin release events that affects the cardiac cycle and heart rate (including the bpm and/or heart rate pulse pattern) and pressure pulse wave pattern in vessels. So insulin release events are affecting both the heart and vascular structures.

Insulin release events may occur from 1 minute to 20 minutes apart depending on the person, activity, and caloric intake. Thus, insulin release events may occur during a health screening, physical exam or diagnostic test. These tests may be adversely affected by the variability in the pressure pulse wave and heart rate during an insulin release event. For example, a blood pressure measurement during an insulin release event may indicate a false reading of high blood pressure. In another example, an ECG (also known as an EKG) or stethoscopic exam performed during an insulin release event may result in a false indication of a heart arrhythmia. Other tests that may be affected by an insulin release event include an echocardiogram, heart rate measurement, MRI of the heart or vessels, electromyography (EMG), etc.

Thus, in an embodiment, to prevent errors in these health tests or screenings, insulin release events in vessels or the heart are identified and monitored, e.g. using PPG signals as described herein or by other means. During an insulin release event, the health testing may be suspended, or test results occurring during such an insulin release event may be highlighted as such.

Figure 43:
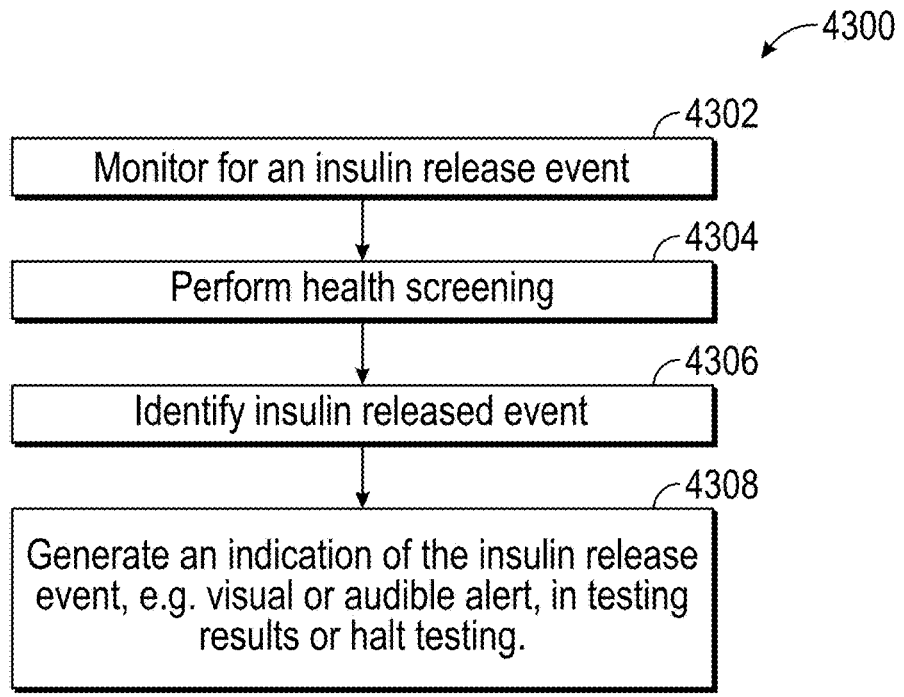
FIG. 43 illustrates a schematic flow diagram of an embodiment of a method for performing a health screening.

FIG. 43 illustrates a schematic flow diagram of an embodiment of a method 4300 for performing a health screening. The health screening may include a test affected by an insulin release event, such as one or more of an ECG, EKG, EMG, stethoscopic exam, blood pressure measurement, heart rate measurement, MRI, CATSCAN, echocardiogram, etc. During all or part of the health screening, the heart and/or other vascular tissue is monitored for an insulin release event at 4302. The biosensor 100 described herein may monitor for the insulin release event using PPG signals or other means may be employed (such as using ECG readings). The health screening is performed at 4304. The health screening may be for a short period (such as a 1 minute ECG) or continuous monitoring over hours or days (such as a heart monitor). An insulin release event is identified at 4306, and an indication of the insulin release event is generated at 4308. The indication may include an audible and/or visual alert. The health provider performing the health screening is then aware that the testing may not be accurate due to the insulin release event. The health provider may choose to reperform the health screening or ignore the test results for the period during the insulin release event.

In another embodiment, the indication may alternatively or additionally include halting the health screening, e.g. such as an ECG. The health screening may resume after the insulin release event. In another embodiment, the indication of the insulin release event may alternatively or additionally be generated as part of the testing results, e.g. an indication that the results may not be accurate due to the insulin release event or an indication of the period of the insulin release event on the test results.

This process helps to prevent errors in health screenings due to anomalies in heart rate and pressure pulse wave patterns during an insulin release event. The insulin release event in vessels or the heart are identified and monitored, e.g. using PPG signals as described herein or by other means. During an insulin release event, the health testing may be suspended or indicated as occurring during such insulin release event. The insulin release event monitoring may also be performed to help control pacemakers or other devices.

Embodiment—Determination of Glucose Levels in Blood Flow Using a Plurality of Parameters As previously discussed, an R value obtained using $L\lambda 1=380$ nm-400 nm and $L\lambda 2 \geq 660$ nm may be used to determine concentration levels of NO in blood flow. In an embodiment, the concentration level of NO may be used to determine a diabetic risk or a blood glucose level. In another example, the R value obtained at $L\lambda 1=380$ nm-400 nm and $L\lambda 2 \geq 660$ nm is determined over a period of time and used with a calibration table to determine the level of glucose in blood flow, e.g. without determining a level of NO.

In addition to the R value obtained using $L\lambda 1=380$ nm-400 nm and $L\lambda 2 \geq 660$ nm, other parameters may be considered in addition to and/or alternatively to this R value in determining a glucose level in blood flow. For example, one or more of the following parameters may be used in determining a glucose level in blood flow:

R value obtained using PPG signals at 395 nm (or in a range of 380 nm-400 nm) and at 940 nm (or equal to or above 660 nm)

R value obtained using PPG signals at 395 nm (or in a range of 380 nm-400 nm) and at 530 nm (or in a range of 510 nm-550 nm)

R value obtained using PPG signals at 530 nm (or in a range of 510 nm-550 nm) and at 940 nm (or equal at or above 660 nm)

L value determined using PPG signals around 395 nm (or in a range of 380 nm-400 nm)

L value determined using PPG signals around 940 nm (or equal at or above 660 nm)

Measurement of a Time or Phase Delay between PPG signals at 395 nm (or in a range of 380 nm-400 nm) and at 940 nm (or equal at or above 660 nm)

Measurement of Correlation of Phase Shape between PPG signals at 395 nm (or in a range of 380 nm-400 nm) and at 940 nm (or equal at or above 660 nm)

Periodicity of a PPG signal at 395 nm (or in a range of 380 nm-400 nm) or at 940 nm (or equal at or above 660 nm)

Skin Temperature

The above parameters are exemplary and additional or alternate parameters may also be considered in determining a glucose level in blood flow.

In an embodiment, the parameters include L values and/or R values obtained using wavelengths having different depths of penetration into the tissue, e.g. 395 nm, 530 nm, 940 nm. The R and L values may thus reflect the level of circulation at various layers of tissue. Poor circulation results in varying R and L values measured using the different wavelengths while good circulation results in less variable R and L values. The differences in good and bad circulation affect the R and L values, and thus the glucose level readings.

Other parameters may also include a time delay and/or pulse shape correlation between PPG signals at different depths of tissue, e.g. between PPG signals at 395 nm and 940 nm. For example, the PPG signals may be processed using a cross correlation function or a Hilbert transformation or another algorithm that determines similarities in pulse shape and temporal relationship between the PPG signals. The time delay between the two PPG signals may also be calculated from the phase shift of their wavelet transforms. The Phase Delay and Pulse Shape Correlation provides a measurement of the effects of outer and inner tissue layers of vessels on the PPG signal, e.g. muscle cells during vasoconstriction. The Phase Delay and a Pulse Shape Correlation provide information on a level of vasoconstriction or vasodilation, circulation and arterial stiffness.

When the PPG signals have a greater difference in phase or timing, this indicates that blood flow in the tissue near the surface is decreased, e.g. due to vasoconstriction, due to low blood circulation level or an imbalance of NO and ET-1 or arterial stiffness. When blood flow is increased to the tissue, the PPG signals at the UV and IR wavelengths exhibit a lower variance in pulse shape and a higher correlation value. This decrease in the difference in the pulse shape of the PPG signals at the different wavelengths indicates an increase of blood flow, e.g. due to vasodilation. The vascular flow at the different tissue depths thus provides information on circulation. In addition, when the correlation between pulse shapes decreases, it may indicate an activity such as digestion or circulation issues are occurring.

Another parameter may also include a measurement of periodicity of a PPG signal, e.g. at 395 nm and/or at 940 nm. For example, the periodicity of a PPG signal may include a frequency domain analysis, using a Discrete Fourier Transform (DFT)/determining the periodogram of a signal or using an autocorrelation (cross-product measures similarity across time). Specific measurements or the PPG signal may be determined and input as parameters or compared, e.g. a time between systolic and diastolic points of the PPG signal, e.g. a stroke length, stroke period, amplitude, etc. During moments of stress, the PPG signal exhibits decreased periodicity or similarity. Blood volume may change with heart rate as well.

Temperature of the patient, such as skin temperature, during PPG signal readings may also be used as an input. The skin temperature is associated with circulation and arterial diameter. For example, a cold skin temperature of extremities in a normal temperature room with a normal heart rate, may indicate low circulation.

One or more of these parameters may be used to obtain glucose levels or other health data. Additional parameters may also be employed in such determinations.

Figure 44:
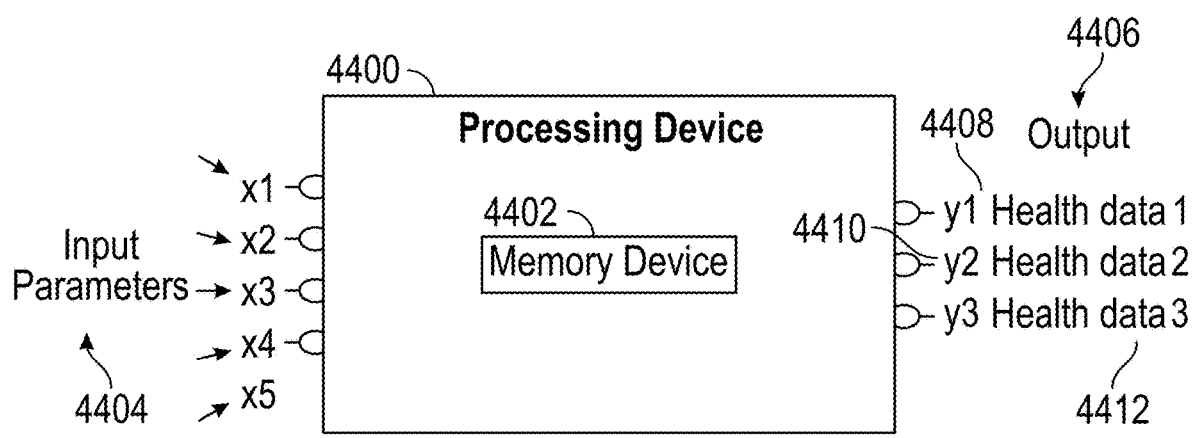
FIG. 44 illustrates a schematic block diagram of an embodiment of a processing device for processing the one or more parameters.

FIG. 44 illustrates a schematic block diagram of an embodiment of a processing device for processing the one or more parameters. The processing device 4400 performs one or more of the functions described herein in response to instructions stored in a memory device 4402 and/or other storage devices, either local or remote.

In an embodiment, one or more types of artificial intelligence or neural network processing models may be implemented by the processing device 4300 to determine health data from one or more of the parameters. For example, the processing device 4300 may implement a regression model or classifier type model. A regression module neural network may be trained using one or more learning vectors with similar types of input parameters and known outputs as described further hereinabove. A classifier neural network may be applied to the one or more parameters to determine a glucose level or other health data. The glucose level may be expressed as within one or more ranges, such as normal, above normal, below normal, etc. (Region 1, 2, 3, 4 of glucose range—normal, below or above).

In another embodiment, a custom algorithm or correlation may be applied to one or more of the parameters to determine a glucose level or other health data. Additional or alternate parameters may be included in these determinations. In addition, other types of AI processing, custom algorithms or quantum processing may be applied to determine health data from one or more of these parameters.

Figure 45A:
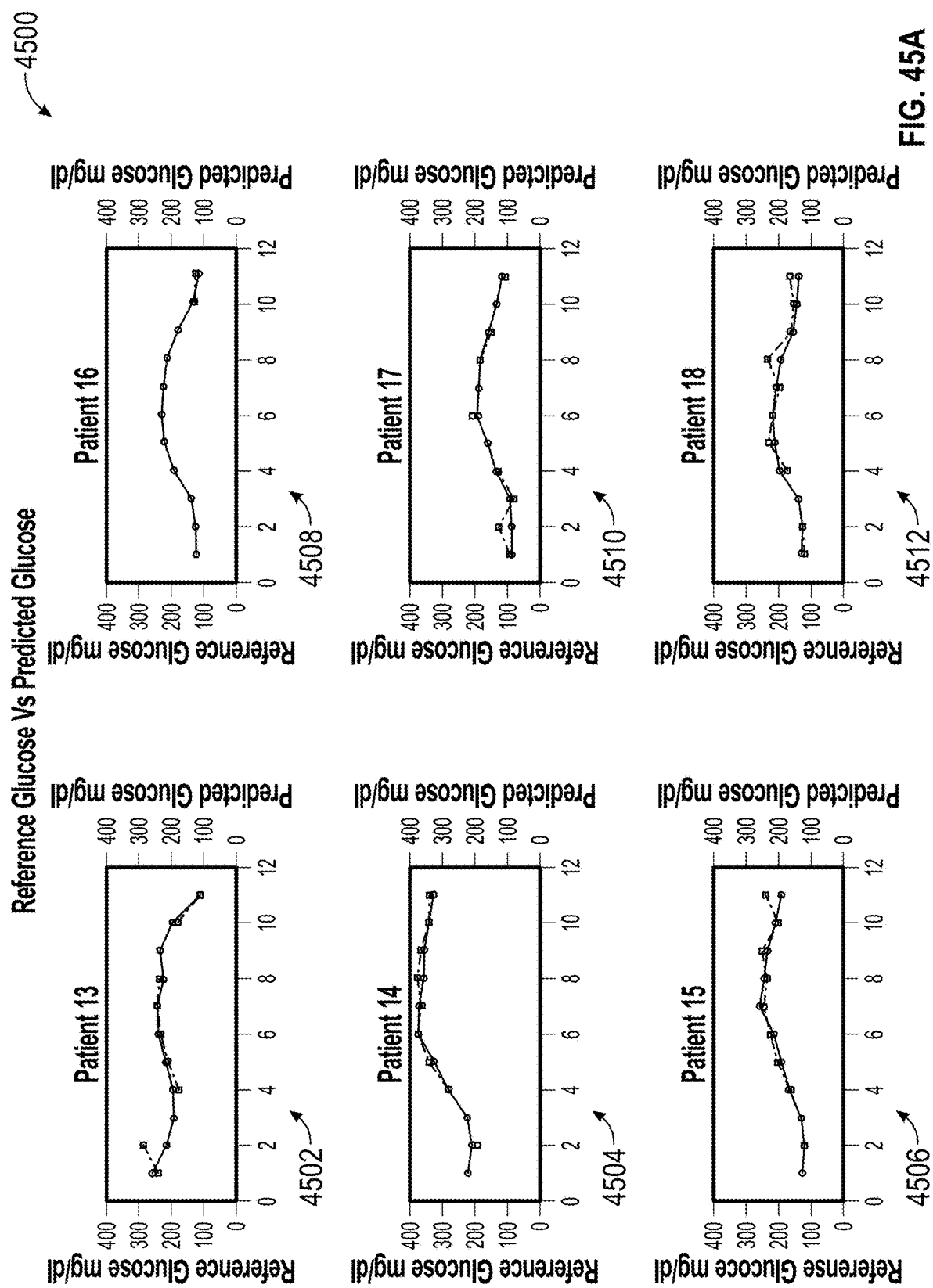
FIG. 45 illustrates graphical representations of clinical test results for a plurality of patients.
Figure 45B:
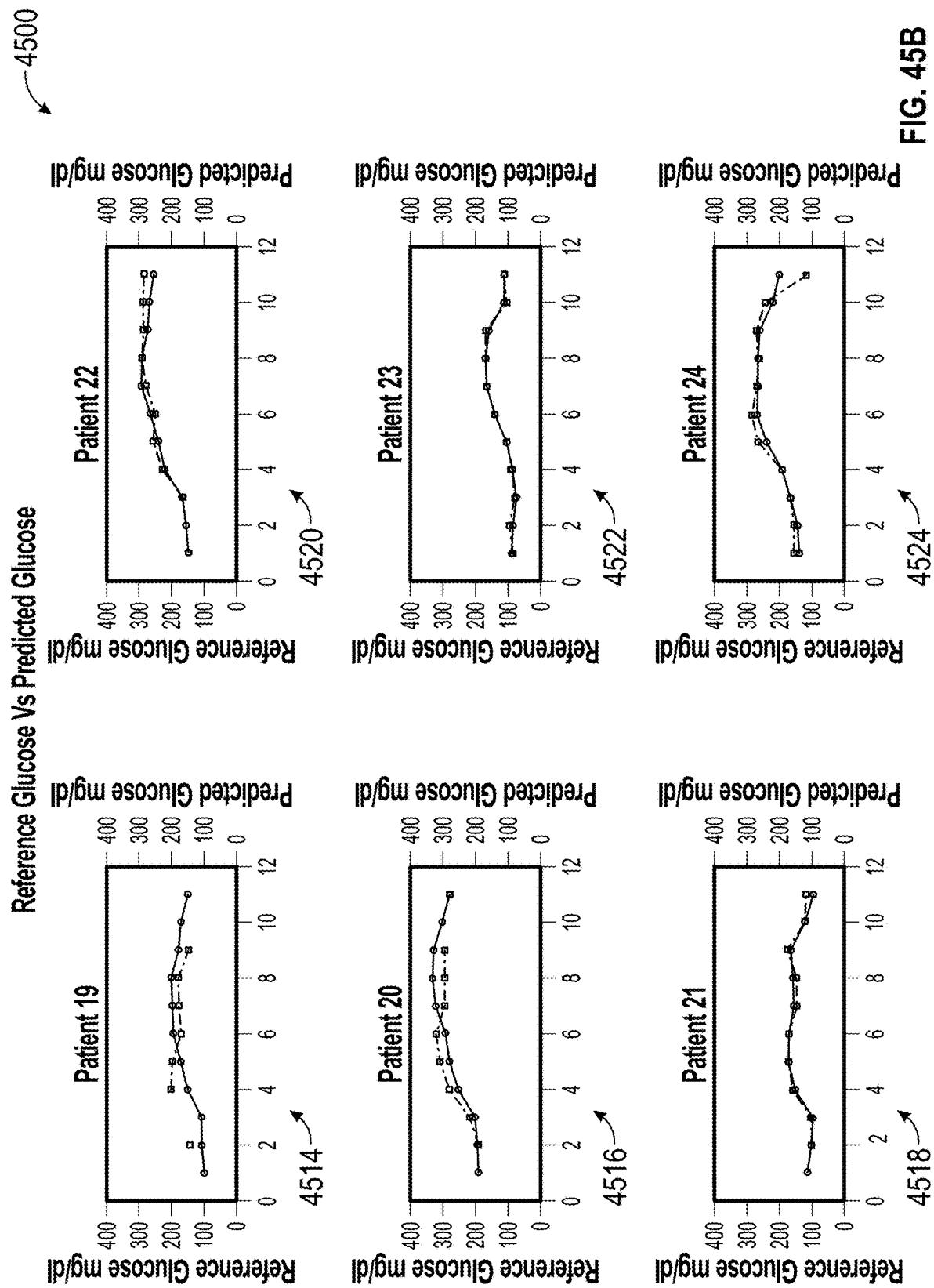

FIG. 45 illustrates graphical representations 4500 of clinical test results for a plurality of patients. The test results are predicted glucose levels obtained by the biosensor 100 using a plurality of parameters. The predicted glucose levels are compared with reference glucose levels that were obtained using a standard blood test. As seen in the graphs, the predicted glucose levels in testing are very similar to the reference glucose levels.

Figure 46:
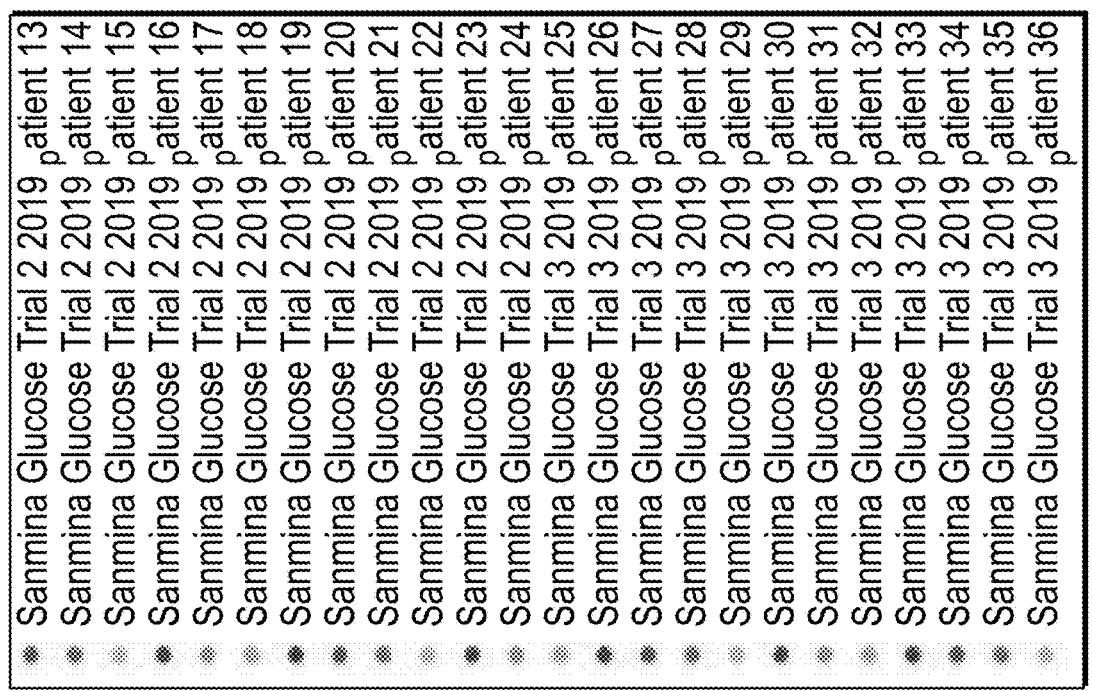
FIG. 46 illustrates a graphical representation of a distribution of errors between the predicted glucose levels and the reference glucose levels.
Figure 46:
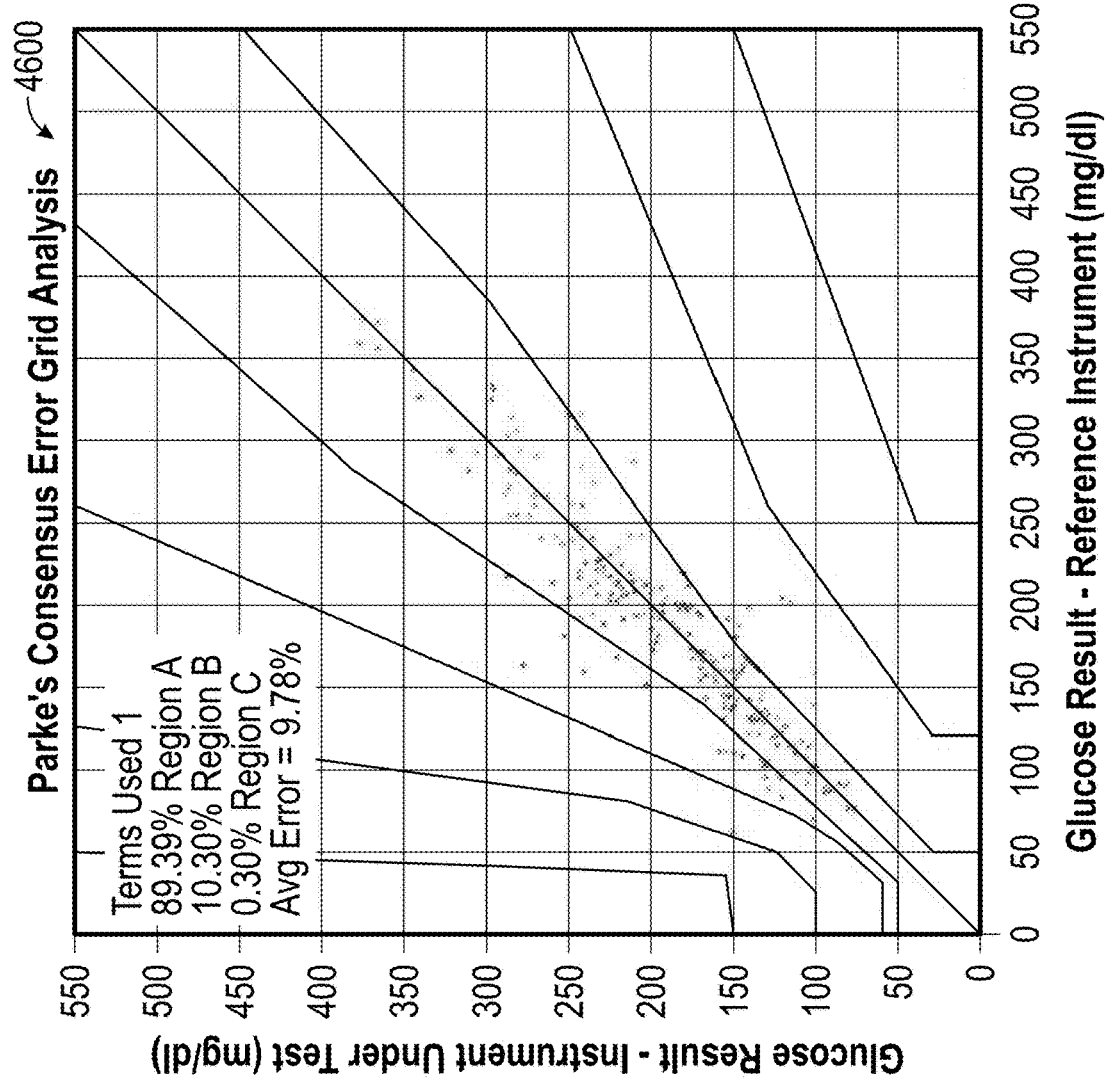

FIG. 46 illustrates a graphical representation of a distribution of errors between the predicted glucose levels and the reference glucose levels from FIG. 45. The graph 4600 illustrates Parke's consensus error grid analysis between the predicted glucose levels and the reference glucose levels for the plurality of patients 4602. The graph 4600 shows that 89.39% of the error was within region A, 10.30% in region B, and 0.30% in region C. The average error is 9.78%. Thus, the predicted glucose levels obtained using the plurality of parameters were under an average 10% error from the reference glucose levels.

Figure 47:
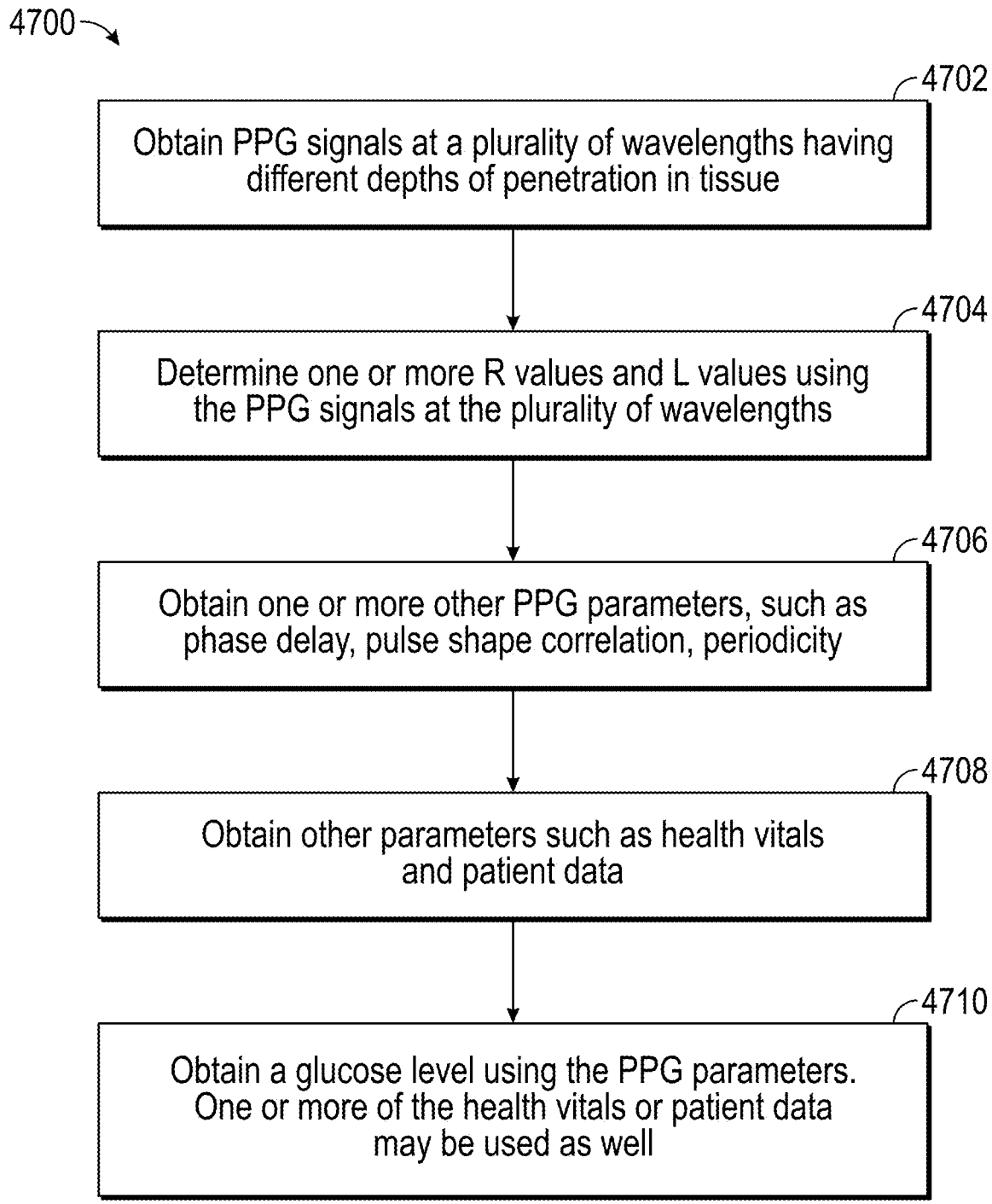
FIG. 47 illustrates a schematic flow diagram of an embodiment of a method for determining a concentration level of glucose using a plurality of parameters.

FIG. 47 illustrates a schematic flow diagram of an embodiment of a method 4700 for determining glucose levels using a plurality of parameters. PPG signals are obtained at a plurality of wavelengths having different depths of penetration in tissue at 4702. For example, optical signals are reflected from tissue of a patient at wavelengths in a range of 380 nm-400 nm, and/or in a range of 510 nm-550 nm and/or at a wavelength greater than 660 nm. The optical signals are detected and converted to electrical PPG signals. One or more PPG parameters are determined using the plurality of wavelengths at 4704. For example, the following PPG parameters may be determined:

R value obtained using PPG signals at 395 nm (or in a range of 380 nm-400 nm) and at 940 nm (or equal to or above 660 nm)

R value obtained using PPG signals at 395 nm (or in a range of 380 nm-400 nm) and at 530 nm (or in a range of 510 nm-550 nm)

R value obtained using PPG signals at 530 nm (or in a range of 510 nm-550 nm) and at 940 nm (or equal to or above 660 nm)

L value determined using PPG signals around 395 nm (or in a range of 380 nm-400 nm)

L value determined using PPG signals around 940 nm (or equal to or above 660 nm)

The above L values and R values are exemplary only. As described below with respect to FIG. 49 and FIG. 50, PPG signals at other wavelengths may be employed to determine L values and R values that are used to determine glucose levels.

In addition, one or more other PPG parameters may be determined, such as a phase delay between a plurality of the PPG signals at different wavelengths, a correlation of phase shape between a plurality of PPG signals at different wavelengths or a periodicity of one or more of the PPG signals at 4706. For example, the following may be determined:

A measurement of a time or phase delay between PPG signals at 395 nm (or in a range of 380 nm-400 nm) and at 940 nm (or equal to or above 660 nm), A measurement of correlation of Phase Shape between PPG signals at 395 nm (or in a range of 380 nm-400 nm) and at 940 nm (or equal to or above 660 nm), or A periodicity of a PPG signal at 395 nm (or in a range of 380 nm-400 nm) or at 940 nm (or equal to or above 660 nm).

These PPG parameters obtained using the PPG signals at one or more wavelengths may be used in the determination of the concentration level of glucose in blood flow. The above PPG parameters are exemplary and additional or alternate PPG parameters may also be obtained. For example, a typical PPG waveform 910 includes a systolic peak (SP) 912, a diastolic peak (DP) 916, a dicrotic notch (914), trough 918 and pulse width (tnext trough). Other characteristics include pulse pressure area (PP), systolic area (As), diastolic area (Ad), augmented pressure (AP), pulse interval, peak to peak interval, augmentation index (AI=PP/(PP−AP)×100%), crest time, etc. Additional PPG parameters may include the pulse shape (measured by autoregression coefficients and moving averages), variance, instant energy information, energy variance, etc. Other parameters may be extracted by representing the PPG signal as a stochastic auto-regressive moving average (ARMA). Parameters also may be extracted by modeling the energy of the PPG signal using the Teager-Kaiser operator, calculating the heart rate and cardiac synchrony of the PPG signal, or determining the zero crossings of the PPG signal. These or other characteristics may be determined from a PPG waveform or a first or second derivative of the PPG waveform, e.g., such as the early systolic negative wave to the early systolic positive wave (Ratio b/a) and be included as PPG parameters.

In addition to the PPG parameters obtained using PPG signals, other parameters may also be used, such as a user's vitals (skin temperature, blood pressure, etc.) and user data (such as age, pre-existing conditions, etc.) at 4708. The above parameters are exemplary and additional or alternate parameters may also be obtained.

In 4710, a concentration level of glucose is obtained using the PPG parameters. The concentration level of glucose may also be obtained using the user's vitals and user data.

Figure 48:
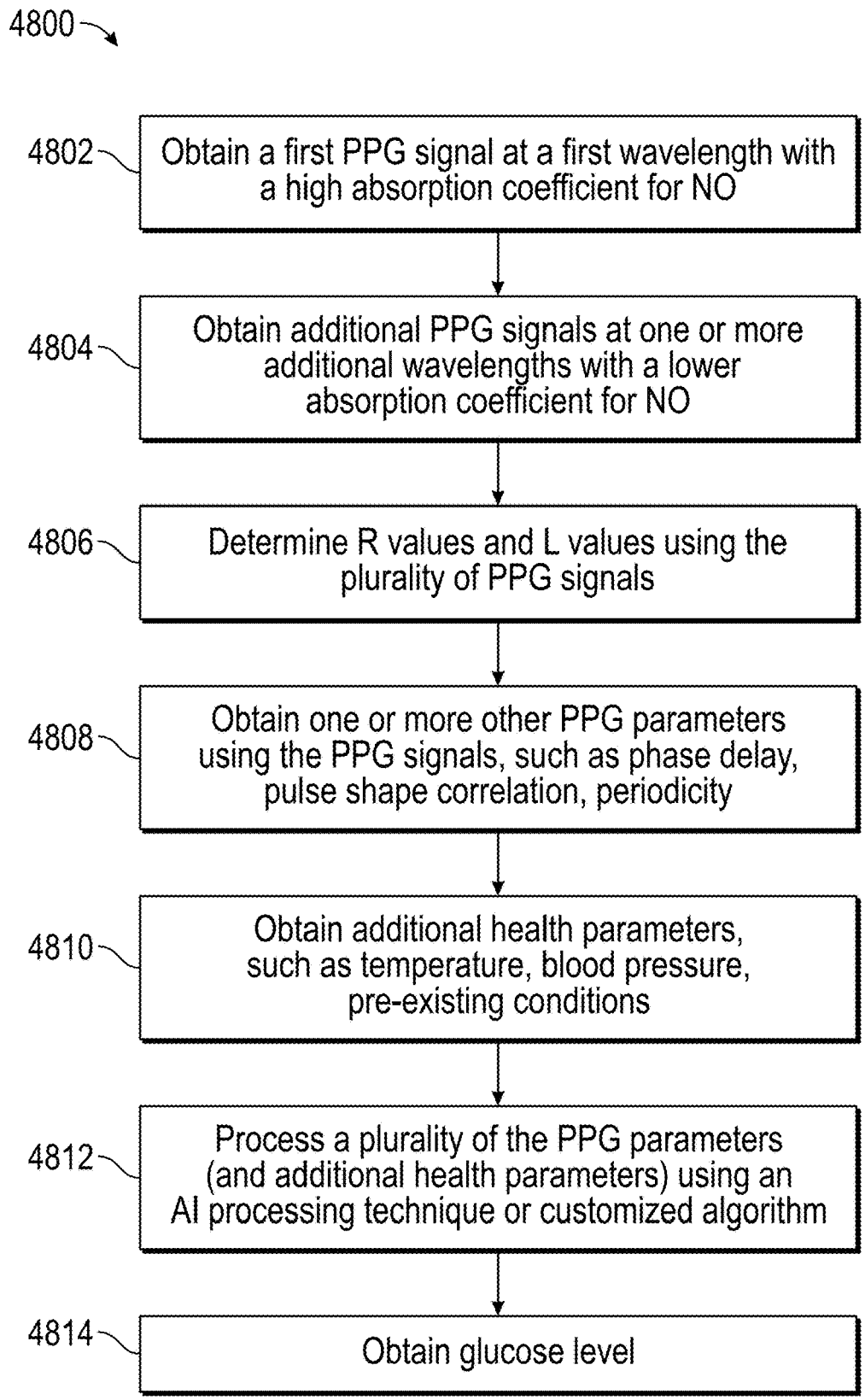
FIG. 48 illustrates a schematic flow diagram of an embodiment of a method for determining a concentration of glucose in blood flow using a plurality of parameters in more detail.

FIG. 48 illustrates a schematic flow diagram of an embodiment of a method 4800 for determining a concentration of glucose in blood flow using a plurality of parameters in more detail. At 4802, a first PPG signal is obtained at a first wavelength with a high absorption coefficient for NO in a range of 380-410 nm, preferably 390-395 nm. A second PPG signal is obtained at a second wavelength with a low absorption coefficient for NO, such as equal to or above 660 nm and preferably 940 nm. One or more additional PPG signals are obtained at one or more additional wavelengths with a lower absorption coefficient for NO, preferably with a different penetration depth than the first and second wavelength, such as in a range of 510 nm-550 nm or otherwise below 660 nm.

At 4806, the PPG signal at a wavelength with a high absorption coefficient for NO is used to obtain a first L value, and a PPG signal at a wavelength with a low absorption coefficient for NO is used to obtain a second L value. Additional L values may be obtained, such as using a PPG signal in a range of 510 nm-550 nm. The first and second L values are used to determine a first R value. A second R value may be obtained using PPG signals at 395 nm (or in a range of 380 nm-400 nm) and at 530 nm (or in a range of 510 nm-550 nm). A third R value may be obtained using PPG signals at 530 nm (or in a range of 510 nm-550 nm) and at 940 nm (or equal to or above 660 nm). As described below with respect to FIG. 49 and FIG. 50, PPG signals at other wavelengths may be obtained to determine L values and R values that are then used to determine glucose levels.

One or more other PPG parameters may be obtained using the PPG signals at the plurality of wavelengths at 4808. For example, other PPG parameters may include a measurement of a time or phase delay between PPG signals at 395 nm (or in a range of 380 nm-400 nm) and at 940 nm (or equal to or above 660 nm), a measurement of correlation of phase shape between PPG signals at 395 nm (or in a range of 380 nm-400 nm) and at 940 nm (or equal to or above 660 nm), or a periodicity of a PPG signal at 395 nm (or in a range of 380 nm-400 nm) or at 940 nm (or equal to or above 660 nm). The above PPG parameters are exemplary and additional or alternate PPG parameters may also be obtained. For example, a typical PPG waveform 910 includes a systolic peak (SP) 912, a diastolic peak (DP) 916, a dicrotic notch (914), trough 918 and pulse width (tnext trough). Other characteristics include pulse pressure area (PP), systolic area (As), diastolic area (Ad), augmented pressure (AP), pulse interval, peak to peak interval, augmentation index (AI=PP/(PP−AP)×100%), crest time, etc. Additional PPG parameters may include the pulse shape (measured by autoregression coefficients and moving averages), variance, instant energy information, energy variance, etc. Other parameters may be extracted by representing the PPG signal as a stochastic auto-regressive moving average (ARMA). Parameters also may be extracted by modeling the energy of the PPG signal using the Teager-Kaiser operator, calculating the heart rate and cardiac synchrony of the PPG signal, or determining the zero crossings of the PPG signal. These or other characteristics may be determined from a PPG waveform or a first or second derivative of the PPG waveform, e.g., such as the early systolic negative wave to the early systolic positive wave (Ratio b/a) and be included as PPG parameters.

Other health parameters may also be obtained at 4810, such as a user's vitals (skin temperature, blood pressure, etc.) and user data (such as age, pre-existing conditions, etc.).

A plurality of the parameters are processed at 4812 to obtain a concentration level of glucose at 4814. The parameters may be processed using an artificial intelligence (AI) or machine learning technique. The AI processing device executes a machine learning algorithm with the parameters as inputs and determines the concentration level of glucose.

The AI processing device may be pre-configured with weights, parameters or other learning vectors derived from a training set. The training set preferably includes the same input parameters and known values of the glucose levels. For example, glucose levels may be obtained in a clinical setting using a known standard blood test. The PPG signals and parameters are also obtained. This training set is provided to a neural network training algorithm to generate the learning vectors. The training set may include further patient data such as age, weight, BMI, pre-existing conditions (diabetes), medical history (family members with diabetes), etc.

During a learning stage, the neural network adjusts parameters, weights and thresholds iteratively to yield a known output from the input parameters (PPG parameters, patient vitals and/or patient data). The training is performed using defined set of rules also known as the learning algorithm. For example, a gradient descent training algorithm is used in case of supervised training model. In case the actual output is different from target output, the difference or error is determined. The gradient descent algorithm changes the weights of the network in such a manner to minimize this error. Other learning algorithms that may be implemented include back propagation, least mean square (LMS) algorithm, a "random forest", deep belief network trained using restricted Boltzmann machines, or support vector machine. The analysis may use any known regression analysis technique, such as, for example and without limitation, random forests, support vector machines, or a deep belief network trained using restricted Boltzmann machines. In another embodiment, the machine learning process may include a classifier type algorithm. Other types of AI processing models may also be implemented to analyze the plurality of parameters (PPG parameters, patient vitals and/or patient data) to obtain a concentration level of glucose in blood flow.

Alternatively to AI processing, the plurality of parameters may also be processed using a custom algorithm or processing model to obtain the concentration level of glucose in 4814.

Personal calibration of the biosensor 100 may be performed as well. For example, a person may input a glucose measurement obtained using a blood test with a strip meter. The biosensor 100 may then determine PPG signals and perform calibration if needed. This self-calibration may be requested as well if a glucose measurement is abnormal, e.g. outside expected ranges for a user.

Figure 49:
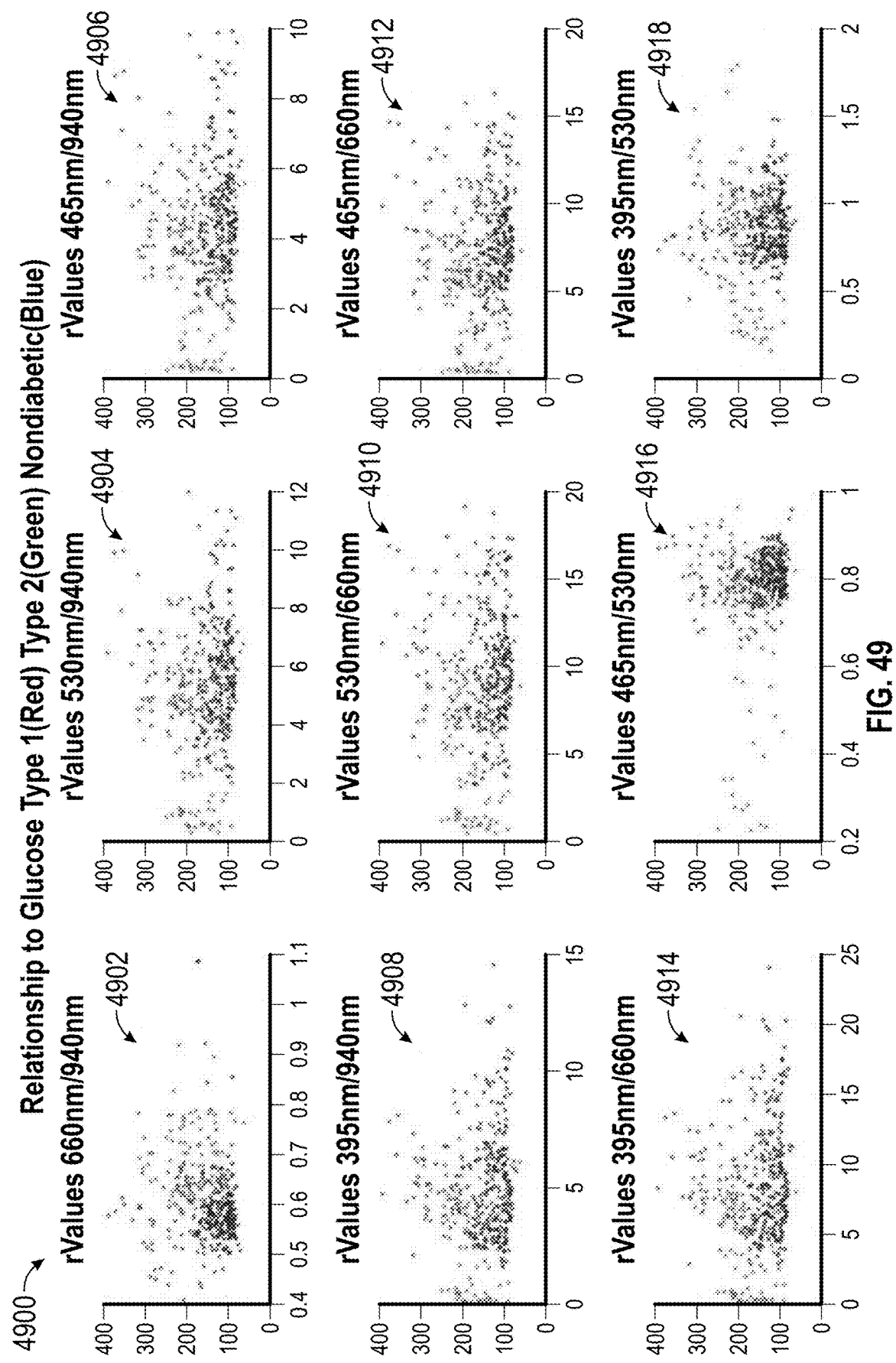
FIG. 49 illustrates graphical representations of additional test results obtained from an embodiment of the biosensor.

FIG. 49 illustrates graphical representations 4900 of additional test results obtained from an embodiment of the biosensor 100. The graphical representations 4900 illustrate R values obtained using a plurality of wavelengths. A first set of R values are obtained from patients with Type 1 Diabetes, a second set of R values are obtained from patients with Type 2 Diabetes and a third set of R values are obtained from patients that are non-Diabetic. A first graph 4902 illustrates R values from the different set of patients obtained using PPG signals at 660 nm and 940 nm. A second graph 4904 illustrates R values obtained using PPG signals at 530 nm and 940 nm. A third graph 4906 illustrates R values obtained using PPG signals at 495 nm and 940 nm. A fourth graph 4908 illustrates R values obtained using PPG signals at 395 nm and 940 nm. A fifth graph 4910 illustrates R values obtained using PPG signals at 530 nm and 660 nm. A sixth graph 4912 illustrates R values obtained using PPG signals at 465 nm and 660 nm. A seventh graph 4914 illustrates R values obtained using PPG signals at 395 nm and 660 nm. An eighth graph 4916 illustrates R values obtained using PPG signals at 465 nm and 530 nm. A ninth graph 4918 illustrates R values obtained using PPG signals at 395 nm and 530 nm. One or more of these R values may be used to determine a concentration level of glucose as described herein, e.g., with respect to FIG. 48.

Figure 50:
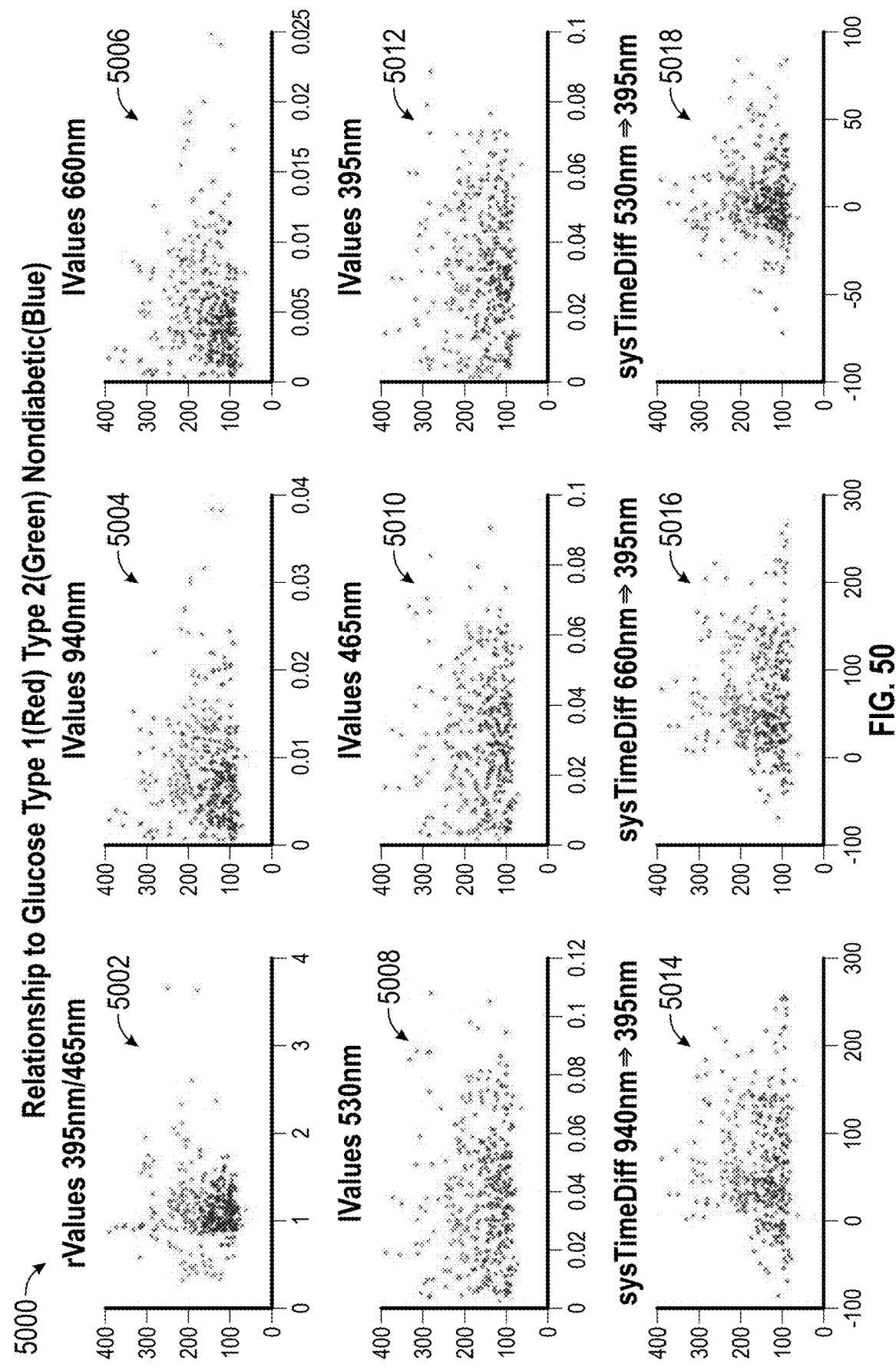
FIG. 50 illustrates graphical representations of additional test results obtained from an embodiment of the biosensor.

FIG. 50 illustrates graphical representations 5000 of additional test results obtained from an embodiment of the biosensor 100. The graphical representations 5000 illustrate various PPG parameters obtained using a plurality of wavelengths. A first set of measurements are obtained from patients with Type 1 Diabetes, a second set of measurements are obtained from patients with Type 2 Diabetes and a third set of measurements are obtained from patients that are non-Diabetic. A first graph 5002 illustrates R values obtained using PPG signals at 395 nm and 465 nm. This R value may be used with one or more of the R values in FIG. 49 to determine a concentration level of glucose as described herein, e.g., with respect to FIG. 48. A second graph 5004 illustrates L values obtained using PPG signals at 940 nm, a third graph 5006 illustrates L values obtained using PPG signals at 660 nm, a fourth graph 5008 illustrates L values obtained using PPG signals at 530 nm, and a fifth graph 5010 illustrated L values obtained using PPG signals at 465 nm. The sixth graph 5012 illustrates L values obtained using PPG signals at 395 nm. The L values obtained using PPG signals at 940 nm, 660 nm, 530 nm, 465 nm may be used with L values obtained using PPG signals at 395 nm to determine a concentration level of glucose as described herein, e.g., with respect to FIG. 48.

FIG. 50 also illustrates other PPG parameters obtained using the biosensor 100. For example, graph 5014 illustrates a phase delay or time difference between systolic points of the pressure pulse wave in the PPG signals obtained at 940 nm and 395 nm for a plurality of patients. Graph 5016 illustrates a phase delay or time difference between systolic points of the pressure pulse wave of PPG signals obtained at 660 nm and 395 nm for a plurality of patients. Graph 5018 illustrates a phase delay or time difference between systolic points of the pressure pulse wave of PPG signals obtained at 530 nm and 395 nm for a plurality of patients. These phase delay measurements between the different PPG signals may be used as PPG parameters to determine a concentration level of glucose as described herein, e.g., with respect to FIG. 48.

Figure 51:
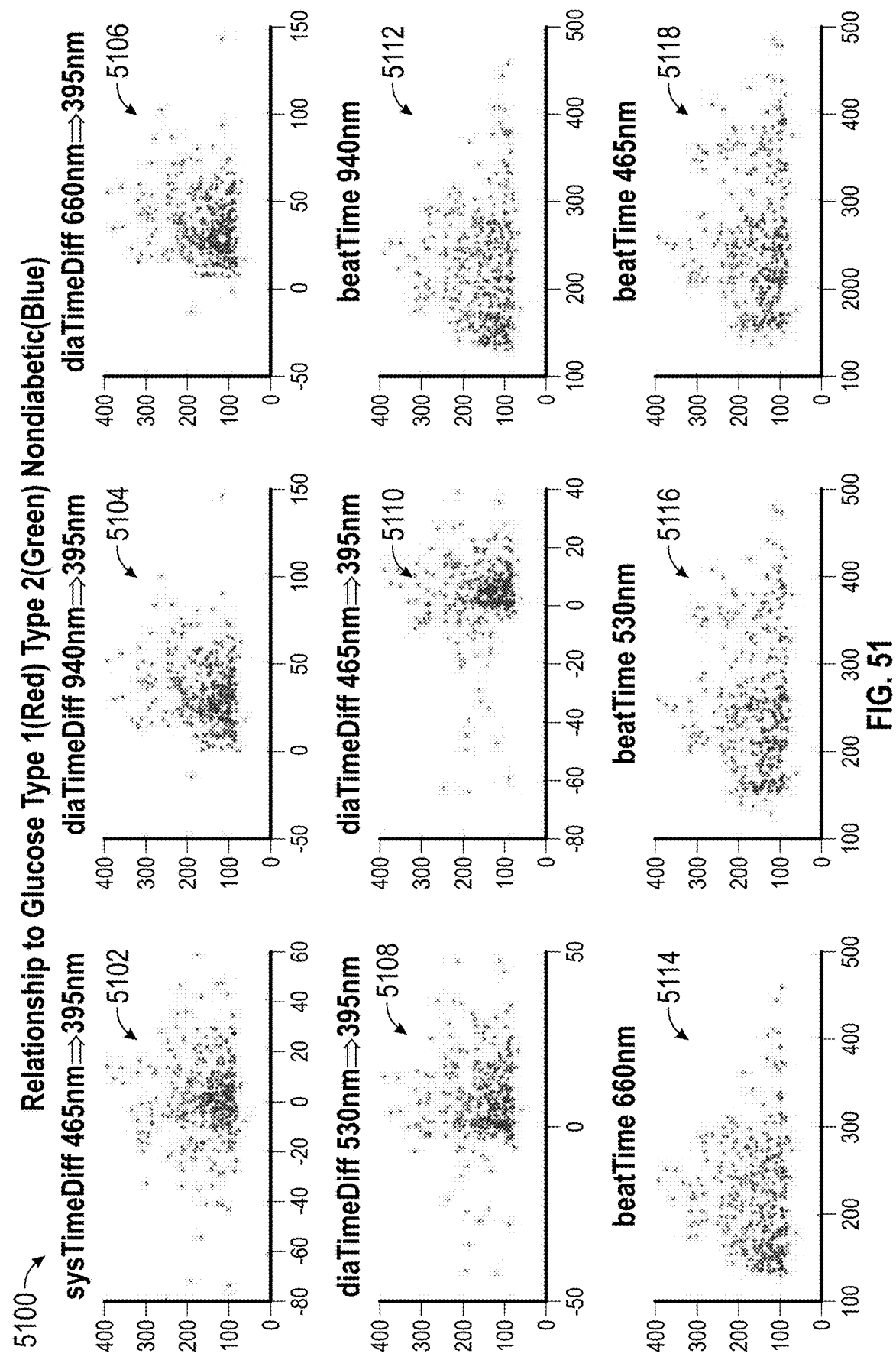
FIG. 51 illustrates graphical representations of additional test results obtained from an embodiment of the biosensor.

FIG. 51 illustrates graphical representations 5100 of additional test results obtained from an embodiment of the biosensor 100. The graphical representations 5100 illustrate various other PPG parameters obtained using a plurality of wavelengths. A first set of measurements are obtained from patients with Type 1 Diabetes, a second set of measurements are obtained from patients with Type 2 Diabetes and a third set of measurements are obtained from patients that are non-Diabetic.

Graph 5102 illustrates a phase delay or time difference between systolic points of the pressure pulse wave of PPG signals obtained at 465 nm and 395 nm for a plurality of patients. Graph 5104 illustrates a phase delay or time difference between diastolic points of the pressure pulse wave of PPG signals obtained at 940 nm and 395 nm for a plurality of patients. Graph 5106 illustrates a phase delay or time difference between diastolic points of the pressure pulse wave of PPG signals obtained at 660 nm and 395 nm for a plurality of patients. Graph 5108 illustrates a phase delay or time difference between diastolic points of the pressure pulse wave of PPG signals obtained at 530 nm and 395 nm for a plurality of patients. Graph 5110 illustrates a phase delay or time difference between diastolic points of the pressure pulse wave of PPG signals obtained at 465 nm and 395 nm for a plurality of patients. These phase delay measurements between the different PPG signals may be used as PPG parameters to determine a concentration level of glucose as described herein, e.g., with respect to FIG. 48.

Figure 52:
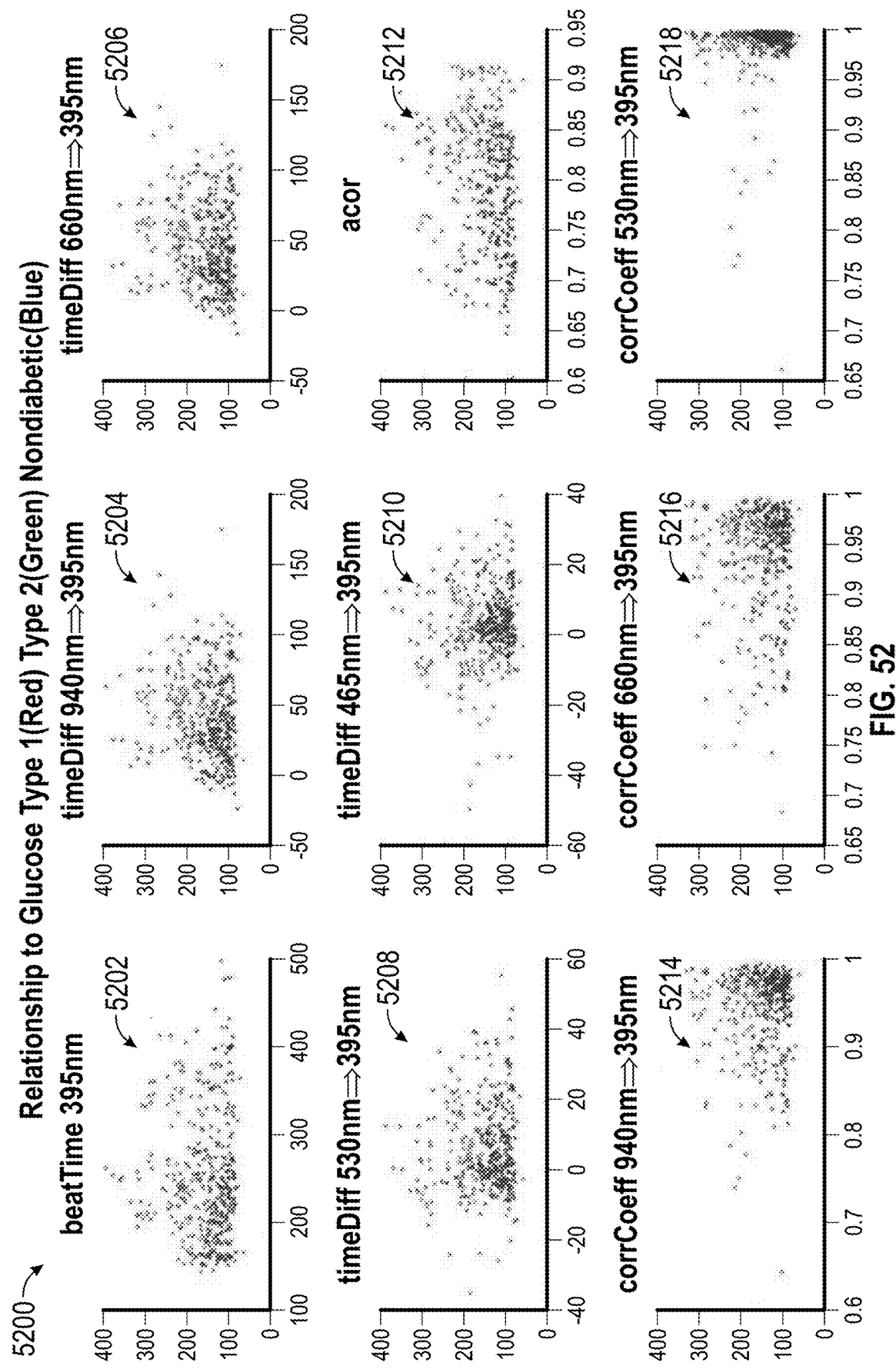
FIG. 52 illustrates graphical representations of additional test results obtained from an embodiment of the biosensor.

The graph 5112 illustrates beat time measurements obtained from PPG signals at 940 nm. The beat time measurements is a measurement of the time from the diastolic to systolic points of the pressure pulse wave. The graph 5114 illustrates the beat time measurements obtained using PPG signals at 660 nm, graph 5116 illustrates the beat time measurements obtained using PPG signals at 530 nm and graph 5118 illustrates beat time measurements obtained using PPG signals at 465 nm. As seen in these graphs, the wavelength of the PPG signal may affect the signal to noise ratio and measurement of the cardiac cycle and heart rate. Though the systolic phase difference, diastolic phase difference and beat time are described herein, other parameters of the pressure pulse wave may be used as PPG parameters, such as dicrotic notch FIG. 52 illustrates graphical representations 5200 of additional test results obtained from an embodiment of the biosensor 100. The graphical representations 5200 illustrate various other PPG parameters obtained using PPG signals at a plurality of wavelengths. A first set of measurements are obtained from patients with Type 1 Diabetes, a second set of measurements are obtained from patients with Type 2 Diabetes and a third set of measurements are obtained from patients that are non-Diabetic. Graph 5202 illustrates a beat time measured at 395 nm. As described with respect to FIG. 51, the wavelength of the PPG signal may affect the measurement of the cardiac cycle and heart rate. The underlying tissue affects the absorption properties and quality of the PPG signals. Thus, the wavelength of the PPG signal for detection of heart rate may be selected depending on the underlying tissue and quality of the signal.

Graph 5204 illustrates a phase delay measurement between 940 nm and 395 nm. Graph 5206 illustrates a phase delay measurement between PPG signals at 660 nm and 395 nm for a plurality of patients. Graph 5208 illustrates a phase delay measurement between PPG signals at 530 nm and 395 nm for a plurality of patients. Graph 5210 illustrates a phase delay measurement between PPG signals at 465 nm and 395 nm. Graph 5212 illustrates autocorrelation measurements of PPG signals at 940 nm. Graph 5214 illustrates a correlation coefficient between PPG signals at 940 nm and 395 nm for a plurality of patients. Graph 5216 illustrates a correlation coefficient between PPG signals at 660 nm and 395 nm for a plurality of patients. Graph 5218 illustrates a correlation coefficient between PPG signals at 530 nm and 395 nm for a plurality of patients. These heart rate, phase delay and correlation measurements may be used as PPG parameters to determine a concentration level of glucose as described herein, e.g., with respect to FIG. 48.

Figure 53:
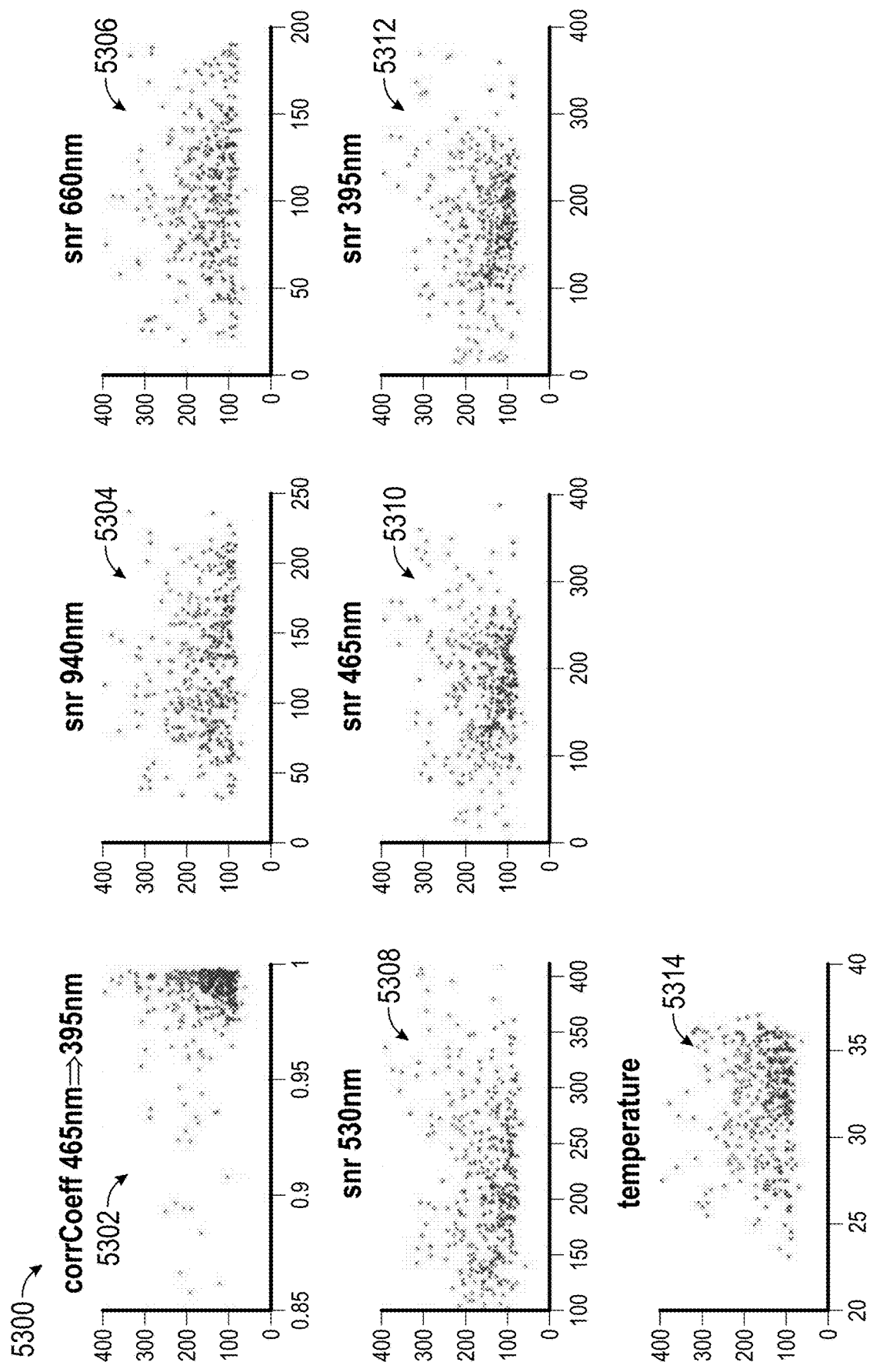
FIG. 53 illustrates graphical representations of additional test results obtained from an embodiment of the biosensor.

FIG. 53 illustrates graphical representations 5300 of additional test results obtained from an embodiment of the biosensor 100. The graphical representations 5300 illustrate various other PPG parameters obtained using a plurality of wavelengths. A first set of measurements are obtained from patients with Type 1 Diabetes, a second set of measurements are obtained from patients with Type 2 Diabetes and a third set of measurements are obtained from patients that are non-Diabetic. Graph 5302 illustrates a correlation coefficient between PPG signals at 465 nm and 395 nm for the plurality of patients. Graph 5304 illustrates a measurement of signal to noise ratio (SNR) of PPG signals at 940 nm for the plurality of patients. Graph 5306 illustrates a measurement of signal to noise ratio (SNR) of PPG signals at 660 nm for the plurality of patients. Graph 5308 illustrates a measurement of signal to noise ratio (SNR) of PPG signals at 530 nm for the plurality of patients. Graph 5310 illustrates a measurement of signal to noise ratio (SNR) of PPG signals at 465 nm for the plurality of patients. Graph 5312 illustrates a measurement of signal to noise ratio (SNR) of PPG signals at 395 nm for the plurality of patients. Graph 5314 illustrates a temperature measurement for the plurality of patients. These correlation measurements, SNR measurements, and temperature measurements may be used as parameters to determine a concentration level of glucose as described herein, e.g., with respect to FIG. 48.

The SNR measurements may be used to select a wavelength for use, e.g. a PPG signal with a higher SNR may be used over a PPG signal with a lower SNR depending on the measurement (such as heart rate). The SNR measurement may also be used to determine motion or neural activity present in the PPG signal. When a SNR measurement for a PPG signal is below a threshold, the PPG signal may not be used or measurements based on the PPG signal may be flagged as unreliable.

One or more of the parameters in FIGS. 49-53 may also be used to detect a diabetic risk or a diabetic condition of a user. When a diabetic risk or diabetic condition is determined, the biosensor 100 may then determine a Type I diabetic risk or a Type II diabetic risk.

Figure 54:
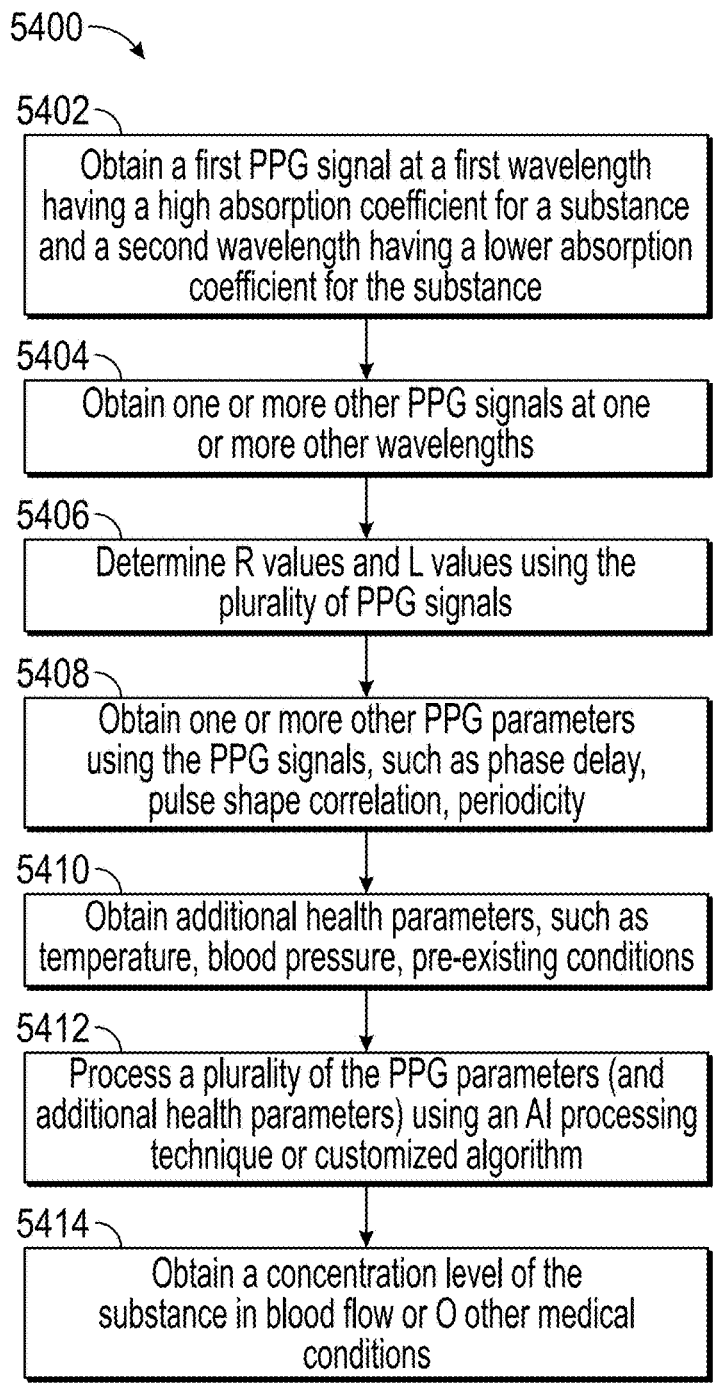
FIG. 54 illustrates a schematic flow diagram of an embodiment of a method for determining a concentration of a substance in blood flow using a plurality of parameters.

FIG. 54 illustrates a schematic flow diagram of an embodiment of a method 5400 for determining a concentration of a substance in blood flow using a plurality of parameters. The concentration level of substances other than glucose may also be obtained using the plurality of parameters described herein (PPG parameters, patient vitals and/or patient data).

At 5402, a first PPG signal is obtained at a wavelength with a high absorption coefficient for the substance and a second PPG signal is obtained at a wavelength with a lower absorption coefficient for the substance. For example, absorption coefficients for one or more frequencies that have an intensity level responsive to concentration level of the substance in blood flow may be determined. Other frequencies with a lower response to the substance in the blood flow are then determined.

For example, the biosensor 100 may also determine alcohol levels in the blood using wavelengths at approximately 390 nm and/or 468 nm. For example, an R468,940 value (obtained from a ratio of L468 nm and L940 nm) may be used as a liver enzyme indicator, e.g. P450 enzyme indicator. The P450 liver enzyme is generated in response to alcohol levels. Thus, the measurement of the spectral response for the wavelength at approximately 468 nm may be used to obtain blood alcohol levels from the concentration levels of P450 and a calibration database.

In another aspect, the biosensor 100 may measure creatinine levels using the PPG circuit by detecting a PPG signal with a wavelength around 530 nm. Creatinine is produced by the kidneys and various factors can affect the kidney production levels of creatinine. The biosensor 100 may detect a high absorption coefficient for creatinine, e.g. at 530 nm or in ranges +/−20 nm.

In another aspect, the biosensor 100 may detect various electrolyte concentration levels or blood analyte levels, such as bilirubin and sodium and potassium. In another aspect, the biosensor 100 may detect sodium NACL concentration levels in the arterial blood flow to determine dehydration.

In another aspect, the PPG sensor may detect white blood cell counts to determine a risk of infection. For example, the biosensor 100 may detect the various types of white blood cells based on the spectral response of the wavelengths, e.g. using one or more wavelengths shown in Table 1 below.

TABLE 1

| White Blood Cell Type | Diameter | Color | Spectral Absorption Wavelengths |
|---|---|---|---|
| Neutrophil | 10-12 um | Pink - Red, Blue, White | Red - 660 nm Blue - 470 nm Green - 580 nm |
| Eosinophil | 10-12 um | Pink Orange | 660 nm, 470 nm, 580 nm 600 nm |
| Basophil | 12-15 um | Blue | 470 nm |
| Lymphocyte | 7-15 um | | 633 nm |
| Monocyte | 15-30 um | | 580 nm |

In yet another aspect, abnormal cells or proteins or compounds that are present or have higher concentrations in the blood with persons having cancer, may be detected using similar PPG techniques described herein at one or more other wavelengths. Thus, cancer risk may then be obtained through non-invasive testing by the biosensor 100. Since the biosensor 100 may operate in multiple frequencies, various health monitoring tests may be performed concurrently.

In another aspect, the biosensor 100 may detect cholesterol levels, such as LDL-Cholesterol, HDL-Cholesterol, and Triglycerides. In a first embodiment, the biosensor 100 detects cholesterol from PPG signals around a first wavelength with a high absorption coefficient for cholesterol, such as 440 nm or 550 nm. The wavelengths 440 nm and 550 nm may be used by the biosensor 100 to detect cholesterol as well as 468 nm. PPG signals around a second wavelength with a lower absorption coefficient for cholesterol are also obtained, such as 880 nm or 940 nm. Other substances that may be obtained include bilirubin (using L460 nm) and iron (using L510 nm, L651 nm, L300 nm) and potassium (using L550 nm). In another embodiment, an R592,940 value (obtained from a ratio of L592 nm and L940 nm) may be used as a digestive indicator to measure digestive responses, such as phase 1 and phase 2 digestive stages.

Additional PPG signals are obtained at one or more additional wavelengths having a different depth of penetration from the first and second wavelengths, such as in a range of 510 nm-550 nm or below 660 nm at 5404.

At 5406, the PPG signal at a wavelength with a high absorption coefficient for the substance is used to obtain a first L value, and a PPG signal at a wavelength with a lower absorption coefficient for the substance is used to obtain a second L value. Additional L values may be obtained using the one or more other wavelengths, such as using a PPG signal in a range of 510 nm-550 nm. The first and second L values are used to determine a first R value. A second R value may be obtained using PPG signals at the high absorption coefficient for the substance (or in a range of +/−20 nm) and at 530 nm (or in a range of 510 nm-550 nm). A third R value may be obtained using PPG signals obtained at the one or more additional wavelengths, e.g. at 530 nm (or in a range of 510 nm-550 nm) and at 940 nm (or equal to or above 660 nm).

One or more other PPG parameters may be obtained using the PPG signals at the plurality of wavelengths at 5408. For example, other PPG parameters may include a measurement of a time or phase delay between PPG signals with a high absorption coefficient for the substance (or in a range of +/−20 nm) and at a low absorption coefficient for the substance (or equal to or above 660 nm), a measurement of correlation of phase shape between PPG signals with a high absorption coefficient for the substance (or in a range of +/−20 nm) and at a low absorption coefficient for the substance (or equal to or above 660 nm), or a periodicity of a PPG signal with a high absorption coefficient for the substance (or in a range of +/−20 nm). Additional PPG parameters may include the diastolic and systolic points, the pulse shape (measured by autoregression coefficients and moving averages), characteristic features of the shape of the PPG waveform, the average distance between pulses, variance, instant energy information, energy variance, etc. Other parameters may be extracted by representing the PPG signal as a stochastic auto-regressive moving average (ARMA). Parameters also may be extracted by modeling the energy of the PPG signal using the Teager-Kaiser operator, calculating the heart rate and cardiac synchrony of the PPG signal, or determining the zero crossings of the PPG signal. These and other parameters may be obtained using the PG signals.

Other health parameters may also be obtained at 5410, such as a user's vitals (skin temperature, blood pressure, etc.) and user data (such as age, pre-existing conditions, etc.).

A plurality of the parameters are processed at 5412 to obtain a concentration level of the substance in blood flow at 5414. The plurality of parameters may be processed using an artificial intelligence (AI) or machine learning technique, e.g. using a regression model to determine the concentration levels. Alternatively, the parameters may be processed using a customized algorithm or processing models.

The plurality of the parameters may also be used to identify an insulin release event, ET-1/NO efficacy balance, or vasodilation/vasoconstriction level. In addition, the plurality of parameters may also be analyzed to determine one or more health indices described hereinbelow.

Embodiment—Health Indices

The biosensor 100 may determine one or more health indices using the parameters described herein. Example indices are provided below but additional or alternate indicators may be determined as well. The health indices may include digital health parameters that include discrete levels in numbers or letters. For example, the health indices described herein may be within a numerical range (e.g., 1-10) or a level (e.g., below, above, average, normal or abnormal) or a letter grade (e.g., A, B, C).

Vascular Health Index—A vascular health index may be determined by the biosensor 100 that indicates a vascular health of a user. The vascular health index may be determined using one or more of the parameters described herein including one or more of the following:

A relative vasoconstriction during an insulin release event
Arterial Stiffness
Level of Insulin Release The measurement of relative vasoconstriction during an insulin release event includes, e.g. a phase difference and/or pulse shape differences between PPG signals, wherein the PPG signals are measured at wavelengths with various depths of penetration. Vasoconstriction is affected by the balance of ET-1 and NO as well as vascular disease such as atherosclerosis. By measuring the relative vasoconstriction or change in vessel diameter in response to insulin release, a vascular health index may be assessed using the biosensor 100. The level of arterial stiffness may be determined using the measurement of the diameter change and level of insulin in the blood flow and comparing such measurements to a general sampling of healthy persons without vascular dysfunction. For example, a timing or period to change from a state of vasodilation to normal width may be obtained using phase differences between different wavelengths. The rate of change may indicate vascular stiffness and a prediction of vascular health. Circulation may also be considered when determining the vascular health index. Alternative or additional measurements may also be included in determining the vascular health index.

Pulse width and pulse area also correlate with the systemic vascular resistance, which could reflect drug interaction of the patient or blood viscosity. Another indicator of aortic stiffness is the augmentation index, which is the ratio between the diastolic peak and systolic peak. The time delay between the systolic and diastolic peaks shortens with the subject's age and, given the subject's height, provides an indicator for large artery stiffness. Both of these indicators could inform a subject's vascular health.

Figure 55:
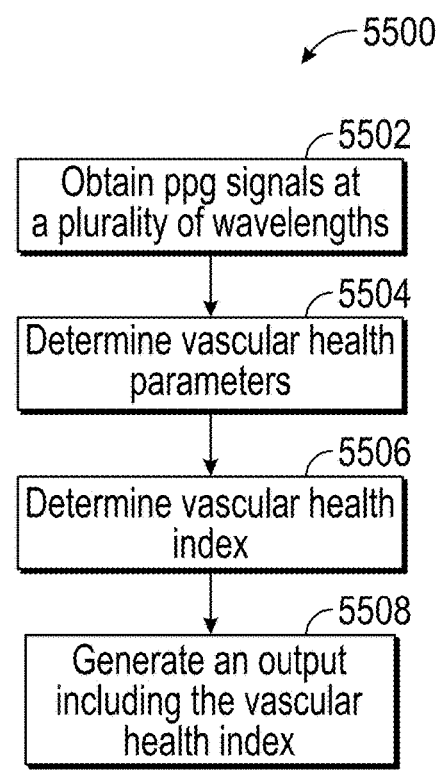
FIG. 55 illustrates a schematic flow diagram of an embodiment of a method for determining a vascular health index.

FIG. 55 illustrates a schematic flow diagram of an embodiment of a method 5000 for determining a vascular health index. At 5502, PPG signals are obtained at a plurality of wavelengths, including a wavelength with a high absorption coefficient for NO in a range of 380-410 nm, preferably 390-395 nm. Additional PPG signals are obtained at one or more additional wavelengths with a lower absorption coefficient for NO, such as in a range of 510 nm-550 nm or equal to or above 660 nm (such as 940 nm).

Vascular health parameters are then determined using the PPG signals at the plurality of wavelengths at 5504. For example, an insulin release event is identified in the PPG signals, e.g. as described with respect to FIG. 37. The insulin levels and the relative change in diameter of vessels during the insulin release event is obtained, as described with respect to FIG. 27 and FIG. 28. Other health parameters may also be obtained, such as a user's vitals (skin temperature, blood pressure, etc.) and user data (such as age, pre-existing conditions, etc.). The relative vasoconstriction or change in vessel diameter in response to insulin release event and level of insulin in the blood flow is compared to such measurements in a sampling of healthy persons without vascular dysfunction in a general population.

At 5506, the vascular health index is then determined. The vascular health index may be a numerical range, percentage, letter grade or other indicator that provides an indication of vascular health of a user, e.g. compared to a in a sampling of healthy persons without vascular dysfunction in a general population. The vascular health index is then displayed or otherwise output at 5508.

Endothelial Dysfunction Index (or NO & ET-1 Peptide Index)—The endothelial dysfunction index provides an indication of the functioning or health of the endothelial layer of vessels. The Endothelial Dysfunction Index (EDI) is a measurement of the level of functioning of the endothelial layer. The EDI is an important parameter in determining the overall health of a patient. Endothelial Vascular dysfunction is a precursor or a symptom of various conditions, including without limitation diabetes, renal disease, sepsis, high blood pressure, sleep apnea, hearing loss, heart failure, stroke, dementia, Alzheimer's disease, COPD and sepsis. Since Endothelial Vascular dysfunction is either a precursor or a symptom of various conditions, the EDI may provide an early warning of such conditions.

Figure 56:
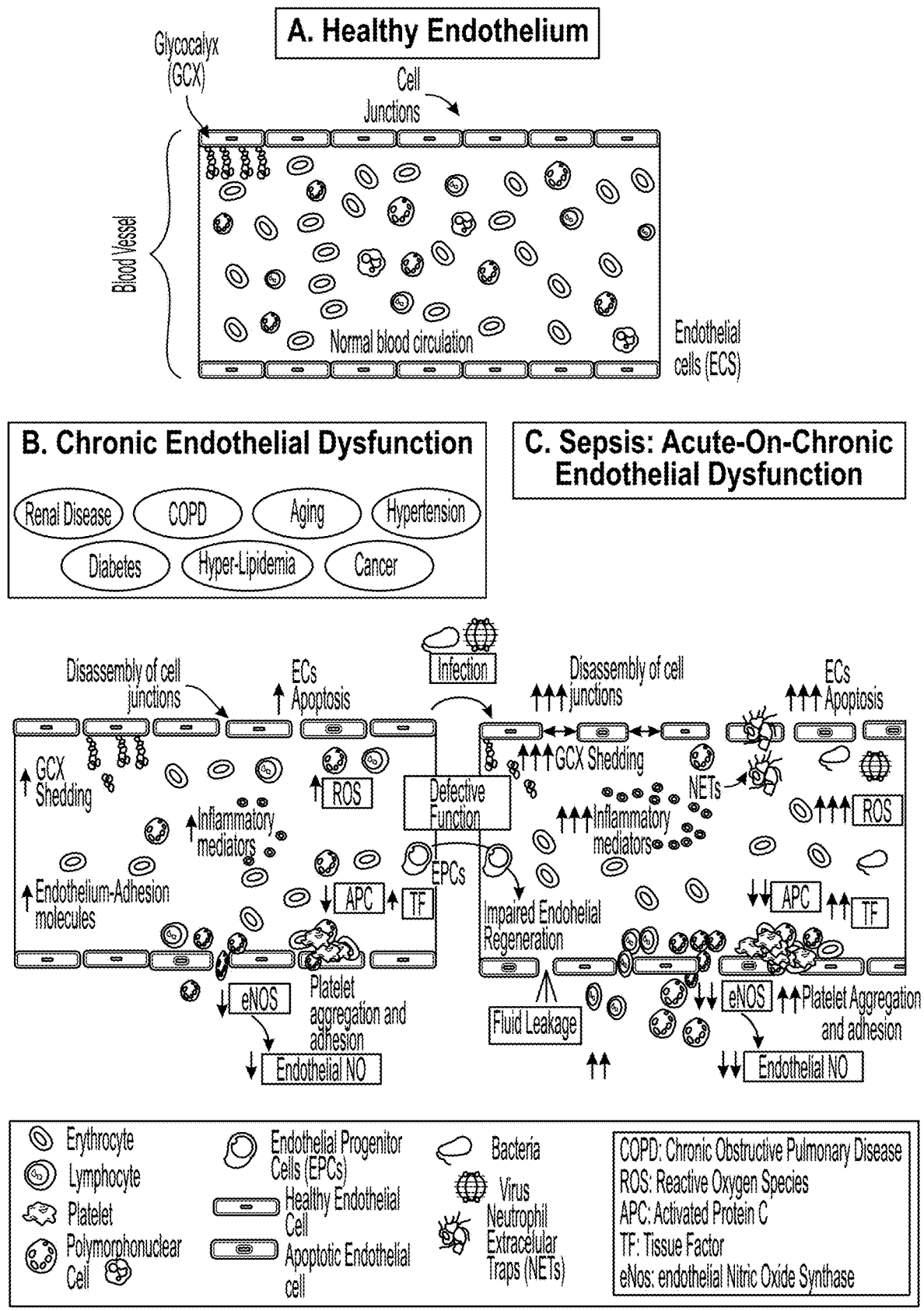
FIG. 56 illustrates a schematic diagram of endothelial dysfunction.

FIG. 56 illustrates a schematic diagram of endothelial dysfunction. The diagram is from the article entitled, "Shared Features of Endothelial Dysfunction between Sepsis and Its Preceding Risk Factors (Aging and Chronic Disease)", Bermejo-Martin J F, Martín-Fernandez M, López-Mestanza C, Duque P, Almansa R., J Clin Med. 2018; 7(11):400, Published 2018 Oct. 30, doi:10.3390/jcm7110400, incorporated by reference herein. The diagram illustrates healthy endothelium at A. In A, the endothelial cells are lining a blood vessel with normal blood circulation. The diagram illustrates chronic endothelial dysfunction at B. Endothelial cells are becoming disjointed with disassembly of cell junctions. Endothelial NO is leaking from the vessels into the tissue creating an increase in NO. The diagram further illustrates acute or chronic endothelial dysfunction as occurs with sepsis at C. In C, the disassembly of cell junctions is further aggravated resulting in fluid leakage from the blood vessels. The level of NO in acute dysfunction may now be double or triple the levels in healthy endothelial of A.

Figure 57:
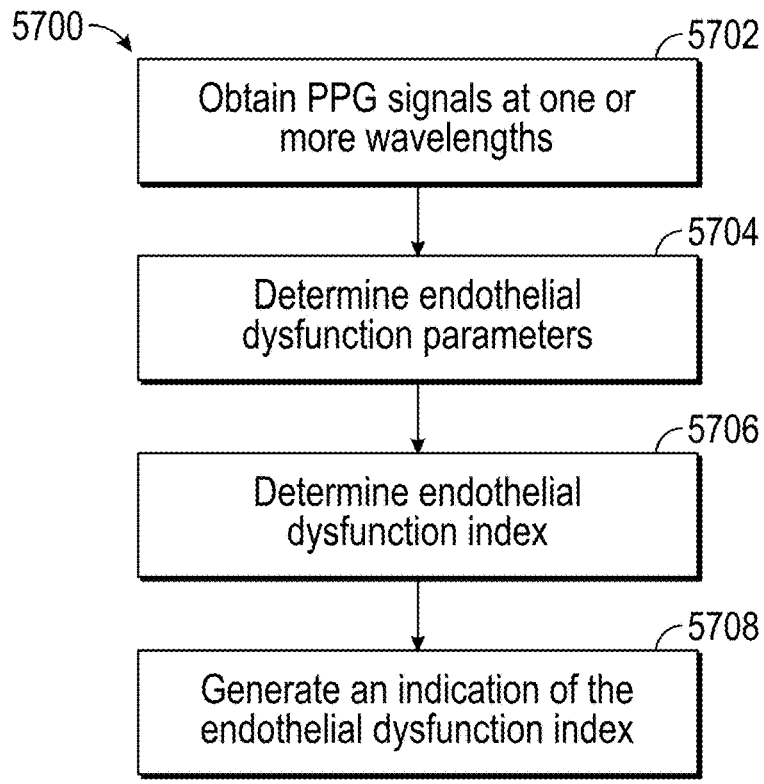
FIG. 57 illustrates a schematic flow diagram of an embodiment of a method for determining the endothelial dysfunction index.

FIG. 57 illustrates a schematic flow diagram of an embodiment of a method 5200 for determining the endothelial dysfunction index. At 5702, PPG signals are obtained at a plurality of wavelengths, including a wavelength with a high absorption coefficient for NO in a range of 380-410 nm, preferably 390-395 nm. Additional PPG signals are obtained at one or more additional wavelengths with a lower absorption coefficient for NO, such as in a range of 510 nm-550 nm or equal to or above 660 nm (such as 940 nm).

Endothelial dysfunction parameters are then determined using the PPG signals at the plurality of wavelengths at 5704. In an embodiment, the phase delay, pulse shape correlation and R values determined using PPG signals may be used to determine a balance of ET-1 or NO in response to insulin in blood flow as described herein with respect to FIG. 28. For example, the average or mean range of one or more of these measurements in a healthy population is measured. Then, an individual measurement is compared to the average or mean range of one or more of phase delay, pulse shape correlation and R values. The comparison may be used to determine a level of balance between the effects of ET-1 and NO.

In another embodiment, a patient may be requested to fast for 5-6 hours. A fasting NO level and glucose level is then obtained. After ingestion or caloric intake, the NO level and glucose level are again obtained and compared with the fasting measurements.

Alternative or additional measurements may also be included in determining the Endothelial Dysfunction Index. For example, malondialdehyde (MDA) levels in a blood sample may be measured as well as NO in plasma serum. The following blood measurements may also provide information on vascular health: MRP: mid regional proadrenomedullin, bioadrenomedullin, angiopoietin, syndecan-1. Other blood measurements may include Endocan (ESM1), Intercellular Adhesion Molecule 1 (ICAM-1), E-Selectin (SEL-E), P-Selectin (SEL-P), Vascular Cell Adhesion Molecule 1 (VCAM-1) or Thrombomodulin (THBD). In particular of the above, a blood measurement of MRP provides a good basis for prediction of Endothelium health. These measurements may provide a baseline for testing of the Endothelial Dysfunction Index determined using PPG signals. In another embodiment, one or more of these blood measurements may also be included as additional parameters in determining the Endothelial Dysfunction Index along with measurements obtained using PPG signals.

At 5706, the endothelial dysfunction index is then determined. The endothelial dysfunction index may be a numerical range, percentage, letter grade or other indicator that provides an indication of endothelial dysfunction of a user, e.g. compared to a in a sampling of healthy persons without vascular dysfunction in a general population. The endothelial dysfunction index is then displayed or otherwise output at 5708.

Arterial stiffness (or Atherosclerosis) Index—The arterial stiffness index provides an indication of a level or degree of atherosclerosis. The arterial stiffness index may be determined, e.g., by measuring the relative vasoconstriction or change in arterial diameter during an insulin release event. The phase difference between PPG signals during an insulin release event is measured, wherein the PPG signals are obtained at wavelengths with various depths of tissue penetration. A greater phase difference between the PPG signals indicates that the circulation is varying at the different depths of tissue. The vessels are not responding, e.g. due to arterial stiffness. A normal range for phase differences in the PPG signals may be measured using a general population of healthy patients.

Alternative or additional measurements may also be included in determining the arterial stiffness index. The arterial stiffness index may be a numerical range, percentage, letter grade or other indicator that provides an indication of arterial stiffness of a user, e.g. compared to a sampling of healthy persons without vascular dysfunction in a general population.

Insulin Release & Glucose Index—The biosensor may identify a number and duration of insulin release events during a time period and measure a glucose level over the time period as described herein. The insulin release & Glucose index may be a numerical range, percentage, letter grade or other indicator that provides an indication of insulin release and glucose level compared to a normal or average range of insulin release events and glucose levels in a healthy population.

Heart Atrial Fibrillation Risk—Atrial Fibrillation is a quivering or irregular heartbeat (arrhythmia) that can lead to blood clots, stroke, heart failure and other heart-related complications. The biosensor 100 may measure the pressure pulse wave pattern (and so the cardiac cycle) using the PPG circuit. The biosensor 100 may determine a heart rate variability and/or pulse wave shape variability. Using these comparisons, the biosensor 100 may determine a risk of atrial fibrillation.

Sleep Quality Index—The biosensor 100 may measure heart rate and pressure pulse wave pattern (and so the cardiac cycle) during sleep or rest using the PPG circuit. In addition, the biosensor 100 may measure respiration rate and oxygen saturation during sleep or rest. Other factors such as sleep duration, sleep disturbances, waking episodes, etc. may also be obtained. Using these factors, the biosensor 100 may determine a sleep quality index. Alternative or additional measurements may also be included in determining the Sleep Quality Index.

Neural Activity—As described in U.S. patent application Ser. No. 16/103,876, hereby incorporated by reference herein, the biosensor 100 may detect movement of different body parts using fluctuation patterns in PPG signals. Neural activation or stimulus generates noise superimposed on the PPG signal. Neural activity may thus be determined using autocorrelation patterns and S/N ratio.

Hydration Index—The biosensor 100 may determine a hydration index, e.g. by measuring a level of sodium in the blood stream. For example, the PPG sensor may detect a sodium chloride (NACL) concentration levels in the blood flow using a PPG signal at a wavelength of 450 nm with a high absorption coefficient for NACL in blood flow. Hydration decreases with increasing levels of NACL in blood flow. The biosensor 100 may thus generate a hydration index to indicate a level of hydration based on the measured NACL levels.

Stress Index—The biosensor 100 may determine a stress index based on one or more parameters, such as NO levels, heart rate, variability of the pressure pulse wave, and/or S/N ratio of PPG signals. Alternative or additional measurements may also be included in determining the Stress Index.

Digestive Information and Reactive Calorie Intake Estimation—The biosensor may determine a number and duration of insulin release events during a period (such as 12 hours). The number and duration of the insulin pulses may be correlated to digestion and caloric intake. For example, integrals of the PPG signals during insulin release events may be used to calibrate a calorie count. The frequency or time between insulin release events may be measured using the PPG signals to determine a stage of digestion or a level of hunger. A time since ingestion of caloric intake may also be estimated.

Figure 58:
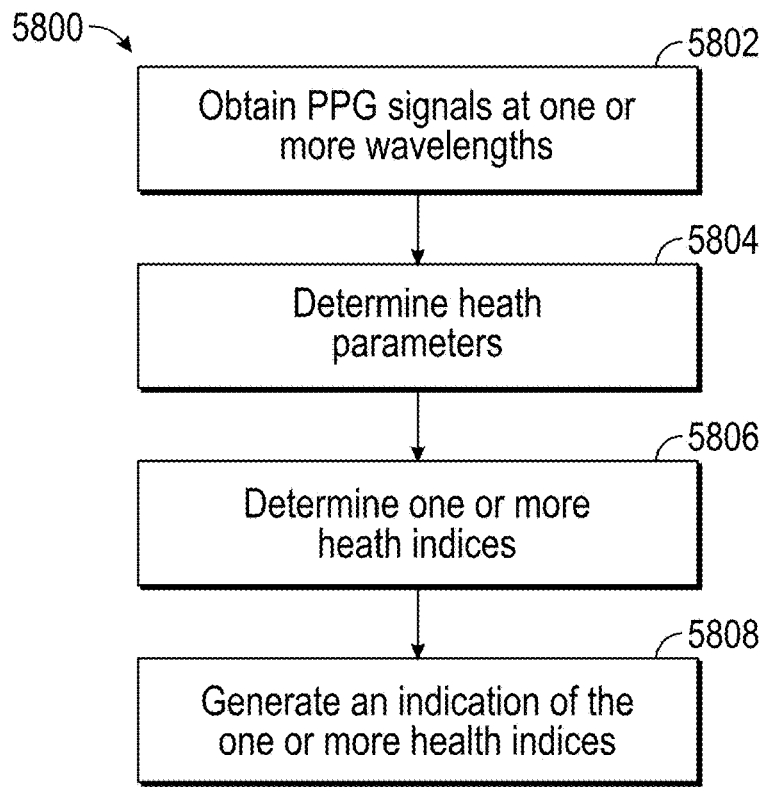
FIG. 58 illustrates a logical flow diagram of an embodiment of a method for determining one or more health indices.

FIG. 58 illustrates a logical flow diagram of an embodiment of a method for determining one or more health indices. At 5802, PPG signals are obtained at one or more wavelengths. Health parameters are determined at 5804. The health parameters may include R values, L values, NO levels, glucose levels, insulin level, insulin release events, ET-1/NO efficacy balance, vasodilation/vasoconstriction level, levels of other analytes (such as NACL), skin temperature, periodicity of PPG signals or other parameters described herein. The health parameters are then used to determine one or more health indices at 5806. In an embodiment, the health parameters may be compared to average values or ranges of similar parameters measured in a general healthy population. In another embodiment, the health parameters may be compared to a personal baseline of the user to obtain the health index.

An indication of the one or more health indices is then provided at 5808. The health indices may include digital health parameters, e.g. the health indexes expressed in a numerical or alphabetical range or a level (such as above, below, average, normal, abnormal, etc.). The biosensor 100 may thus determine one or more health indices using the measurements described herein. The indices described herein are exemplary and additional or alternate indicators may be determined as well. The health indices may provide an indication when further testing is needed of a user.

Embodiment—Diagnosis of a Health Condition

This multi-parameter approach may also be used to diagnose other health conditions, such as kidney function, heart failure, atrial fibrillation, other heart conditions, pneumonia, staph infections, sepsis, other types of infections, respiratory function, COPD, diabetes, Type I diabetes, or Type II diabetes. A plurality of PPG parameters are input into a neural network or AI classifier model that has been trained with data of patients clinically diagnosed with the target health condition. The plurality of parameters preferably includes a multiplicity of R values each obtained using different wavelength ratios and a multiplicity of L values obtained at different wavelengths.

Figure 59:
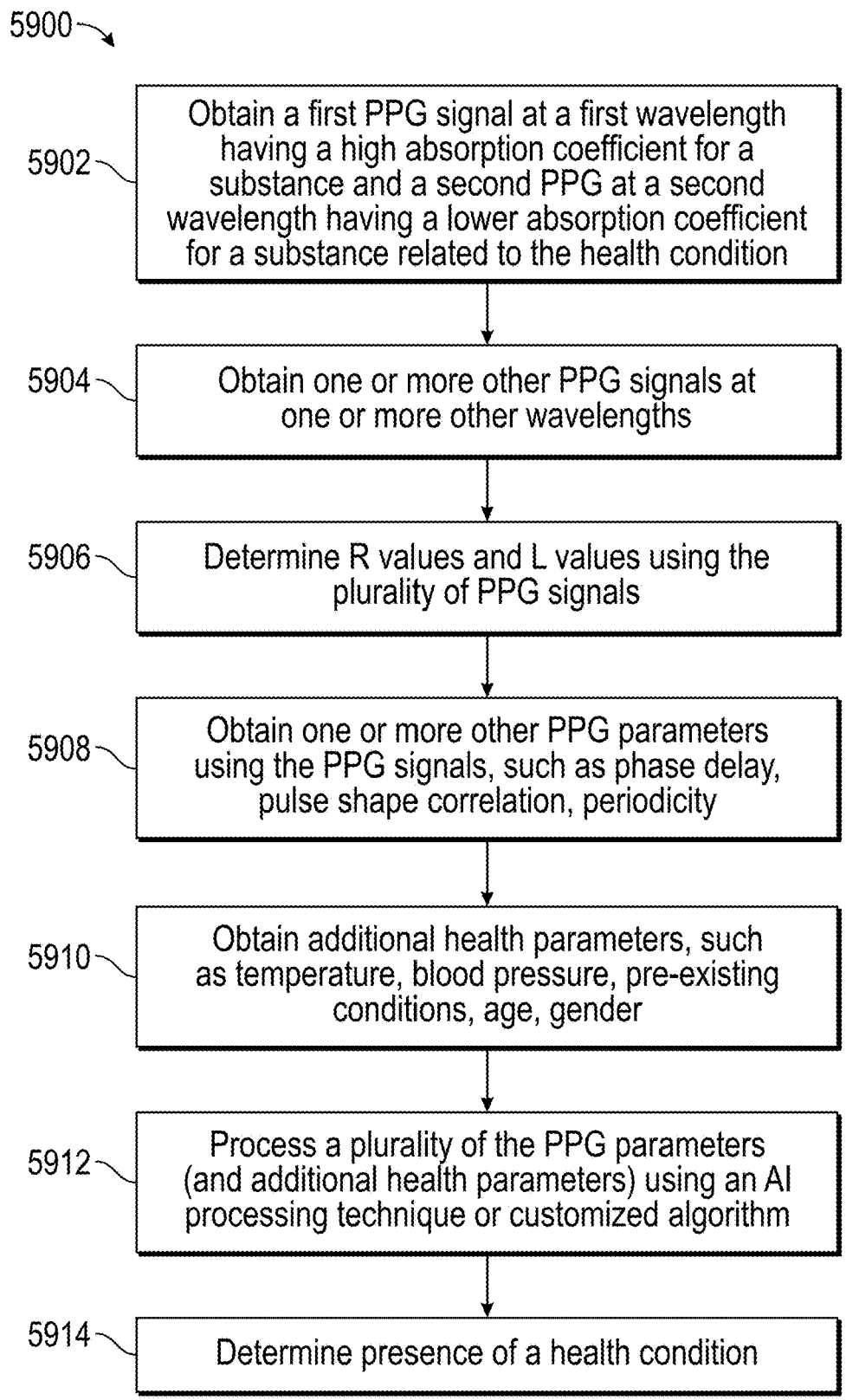
FIG. 59 illustrates a logical flow diagram of an embodiment of a method for determining a health condition using a plurality of PPG parameters.

FIG. 59 illustrates a logical flow diagram of an embodiment of a method 5900 for determining a health condition using a plurality of PPG parameters. At 5902, a first PPG signal is obtained at a wavelength with a high absorption coefficient for a substance related to the health condition and a second PPG signal is obtained at a wavelength with a lower absorption coefficient for the substance. For example, the substance related to the health condition may be a substance that may help diagnose the health condition. For example, creatinine is produced by the kidneys and various factors can affect levels of creatinine in blood flow, including kidney failure. The biosensor 100 may thus obtain a PPG signal with a high absorption coefficient for creatinine, e.g. a wavelength around 530 nm or in ranges +/−20 nm in step S902.

In another aspect, the biosensor 100 may determine PPG signals having a high absorption coefficient for NO (e.g., a wavelength of 395 nm or in ranges +/−20 nm of 395 nm) to help diagnose sepsis or other infections, as well as diabetes, Type I diabetes, or Type II diabetes or even PTSD. In another aspect, the biosensor 100 may diagnose infections by detecting PPG signals at wavelengths with high absorption coefficient for various types of white blood cells shown in Table 1 above. In yet another aspect, PPG signals at wavelengths with high absorption coefficient for various types of abnormal cells or proteins or compounds that are present or have higher concentrations in the blood with persons having cancer, may be detected to aid in a cancer diagnosis.

In another aspect, PPG signals are detected at wavelengths with high absorption coefficient for various types of cholesterol, such as LDL-Cholesterol, HDL-Cholesterol, and Triglycerides to determine normal or abnormal cholesterol levels. In another example, PPG signals at wavelengths with high absorption coefficient for iron (510 nm, 651 nm, 300 nm) are determined to detect anemia in a patient. In another aspect, to detect heart conditions or respiratory conditions (such as COPD), PPG signals may be detected at wavelengths with high absorption coefficient for oxygen, such as 660 nm or in ranges +/−20 nm thereof.

Additional PPG signals are obtained at one or more additional wavelengths having a different depth of penetration from the first and second wavelengths, such as in a range of 510 nm-550 nm or below 660 nm at 5904.

At 5906, the PPG signal at a first wavelength with a high absorption coefficient for the related substance is used to obtain a first L value, and a PPG signal at a second wavelength with a lower absorption coefficient for the related substance is used to obtain a second L value. Additional L values may be obtained using the one or more other wavelengths, such as using a PPG signal in a range between the first and second wavelength or other wavelengths with a different penetration depth. The first and second L values are used to determine a first R value. A second R value may be obtained using PPG signals at the high absorption coefficient for the substance (or in a range of +/−20 nm) and at a different wavelength with a different penetration depth. A third R value may be obtained using PPG signals obtained at the one or more additional wavelengths.

One or more other PPG parameters may be obtained using the PPG signals at the plurality of wavelengths at 5908. For example, other PPG parameters may include a measurement of a time or phase delay between PPG signals with a high absorption coefficient for the substance (or in a range of +/−20 nm) and at a low absorption coefficient for the substance (or equal to or above 660 nm), a measurement of correlation of phase shape between PPG signals with a high absorption coefficient for the substance (or in a range of +/−20 nm) and at a low absorption coefficient for the substance (or equal to or above 660 nm), or a periodicity of a PPG signal with a high absorption coefficient for the substance (or in a range of +/−20 nm). Additional PPG parameters may include the diastolic and systolic points, the pulse shape (measured by autoregression coefficients and moving averages), characteristic features of the shape of the PPG waveform, the average distance between pulses, variance, instant energy information, energy variance, etc. Other parameters may be extracted by representing the PPG signal as a stochastic auto-regressive moving average (ARMA). Parameters also may be extracted by modeling the energy of the PPG signal using the Teager-Kaiser operator, calculating the heart rate and cardiac synchrony of the PPG signal, or determining the zero crossings of the PPG signal. These and other parameters may be obtained using the PG signals.

Other health parameters may also be obtained at 5910, such as a user's vitals (skin temperature, blood pressure, etc.) and user data (such as age, pre-existing conditions, gender, etc.).

A plurality of the parameters are processed at 5912 to obtain a determination or diagnosis of the health condition or a risk of the health condition. The plurality of parameters may be processed using an artificial intelligence (AI) or machine learning technique, e.g. using a classifier model to determine the diagnosis. Alternatively, the parameters may be processed using a customized algorithm or processing models.

Embodiment—Biosensor Configurations

The largest blood vessels are arteries and veins, which have a thick, tough wall of connective tissue and many layers of smooth muscle cells. The wall is lined by an exceedingly thin single sheet of endothelial cells, the endothelium, separated from the surrounding outer layers by a basal lamina. The inner layer (tunica intima) is the thinnest layer, formed from a single continuous layer of endothelial cells and supported by a subendothelial layer of connective tissue and supportive cells.

Farther from the heart, where the surge of blood has dampened, the percentage of elastic fibers in an artery's tunica intima decreases and the amount of smooth muscle in its tunica media increases. The artery at this point is described as a muscular artery. The diameter of muscular arteries typically ranges from 0.1 mm to 10 mm. Their thick tunica media allows muscular arteries to play a leading role in vasoconstriction. In contrast, their decreased quantity of elastic fibers limits their ability to expand.

The radial artery and the proper digital artery to the index finger are muscular arteries with greater smoother muscle cells. Their thick tunica media allows these muscular arteries to play a leading role in vasoconstriction. In contrast, their decreased quantity of elastic fibers limits their ability to expand. The radial artery extends to arterioles and capillaries in the fingertip of the index finger. An arteriole is a small-diameter blood vessel in the microcirculation that extends and branches out from an artery and leads to capillaries. An arteriole is a very small artery that leads to a capillary. Arterioles have the same three tunics as the larger vessels, but the thickness of each is greatly diminished. The critical endothelial lining of the tunica intima is intact. The tunica media is restricted to one or two smooth muscle cell layers in thickness. The tunica externa remains but is very thin. The precise diameter of the lumen of an arteriole at any given moment is determined by neural and chemical controls, and vasoconstriction and vasodilation in the arterioles are the primary mechanisms for distribution of blood flow.

Capillaries consist only of the thin endothelial layer of cells with an associated thin layer of connective tissue. The amounts of connective tissue and smooth muscle in the vessel wall vary according to the vessel's diameter and function, but the endothelial lining is always present. In the finest branches of the vascular tree—the capillaries and sinusoids—the walls consist of nothing but endothelial cells and a basal lamina, together with a few scattered—but functionally important—pericytes. These are cells of the connective-tissue family, related to vascular smooth muscle cells, that wrap themselves round the small vessels. Capillaries consist of a single layer of endothelium and associated connective tissue without smooth muscle cells.

Due to the different vascular structure at different depths, the use of an R value of 395 nm/530 nm wavelengths may be preferred in obtaining results from tissues in a finger or other tissues wherein vessels are closer to the surface. For example, in some instances it may be preferred that wavelengths penetrate the tissue at similar depths due to variations in the vascular profile at different depths. The R value described herein may also be computed using wavelengths with a low absorption coefficient for NO at 440 nm, 530 nm, 940 nm or another wavelength in the visible range or in the IR range) and a wavelength with a high absorption coefficient for NO (e.g., at 395 nm or in a range of +/−20 nm of 395 nm).

In addition, due to the different vascular structure at different tissue sites, the biosensor 100 is preferably calibrated for the type of tissue at a detection site. The same detection site is preferably maintained throughout a measurement period because vascular structure and dynamics varies between different tissue sites. The variation may affect the calibration and relative amplitude of the PPG signals.

The biosensor may be included in one or more different form factors over various types of tissue, such as a watch, ring, patch, earpiece, earbud, etc. In an embodiment, a small form factor such as a ring or patch, may communicate via a wireless or wired connection with a remote device, such as a watch, smart phone, wrist band, computer, glasses, or other user device. The remote device may include a PPG circuit and/or may include a processing device for processing of PPG signals obtained by the remote sensor.

In one or more aspects herein, a processing module or circuit includes at least one processing device, such as a microprocessor, micro-controller, digital signal processor, microcomputer, neural network or AI processor, Quantum processor, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing circuit further includes a memory device. The memory device is a non-transitory memory and may be an internal memory or an external memory, and the memory may be a single memory device or a plurality of memory devices. The memory may be a read-only memory, random access memory, volatile memory, non-volatile memory, static memory, dynamic memory, flash memory, cache memory, and/or any non-transitory memory device that stores digital information. The processing device performs one or more of the functions described herein in response to instructions stored in a memory device.

As may be used herein, the term "operable to" or "configurable to" indicates that an element includes one or more of circuits, instructions, modules, data, input(s), output(s), etc., to perform one or more of the described or necessary corresponding functions and may further include inferred coupling to one or more other items to perform the described or necessary corresponding functions. As may also be used herein, the term(s) "coupled", "coupled to", "connected to" and/or "connecting" or "interconnecting" includes direct connection or link between nodes/devices and/or indirect connection between nodes/devices via an intervening item (e.g., an item includes, but is not limited to, a component, an element, a circuit, a module, a node, device, network element, etc.). As may further be used herein, inferred connections (i.e., where one element is connected to another element by inference) includes direct and indirect connection between two items in the same manner as "connected to".

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, frequencies, wavelengths, component values, integrated circuit process variations, temperature variations, rise and fall times, and/or thermal noise. Such relativity between items ranges from a difference of a few percent to magnitude differences.

Note that the aspects of the present disclosure may be described herein as a process that is depicted as a schematic, a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function.

The various features of the disclosure described herein can be implemented in different systems and devices without departing from the disclosure. It should be noted that the foregoing aspects of the disclosure are merely examples and are not to be construed as limiting the disclosure. The description of the aspects of the present disclosure is intended to be illustrative, and not to limit the scope of the claims. As such, the present teachings can be readily applied to other types of apparatuses and many alternatives, modifications, and variations will be apparent to those skilled in the art.

In the foregoing specification, certain representative aspects of the invention have been described with reference to specific examples. Various modifications and changes may be made, however, without departing from the scope of the present invention as set forth in the claims. The specification and figures are illustrative, rather than restrictive, and modifications are intended to be included within the scope of the present invention. Accordingly, the scope of the invention should be determined by the claims and their legal equivalents rather than by merely the examples described. For example, the components and/or elements recited in any apparatus claims may be assembled or otherwise operationally configured in a variety of permutations and are accordingly not limited to the specific configuration recited in the claims.

Furthermore, certain benefits, other advantages and solutions to problems have been described above with regard to particular embodiments; however, any benefit, advantage, solution to a problem, or any element that may cause any particular benefit, advantage, or solution to occur or to become more pronounced are not to be construed as critical, required, or essential features or components of any or all the claims.

As used herein, the terms "comprise," "comprises," "comprising," "having," "including," "includes" or any variation thereof, are intended to reference a nonexclusive inclusion, such that a process, method, article, composition or apparatus that comprises a list of elements does not include only those elements recited, but may also include other elements not expressly listed or inherent to such process, method, article, composition, or apparatus. Other combinations and/or modifications of the above-described structures, arrangements, applications, proportions, elements, materials, or components used in the practice of the present invention, in addition to those not specifically recited, may be varied or otherwise particularly adapted to specific environments, manufacturing specifications, design parameters, or other operating requirements without departing from the general principles of the same.

Moreover, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is intended to be construed under the provisions of 35 U.S.C. § 112(f) as a "means-plus-function" type element, unless the element is expressly recited using the phrase "means for" or, in the case of a method claim, the element is recited using the phrase "step for."

The invention claimed is:

1. A biosensor, comprising:
an optical circuit configured to obtain a plurality of PPG signals at a plurality of wavelengths reflected from tissue of a user, wherein the different wavelengths have varying penetration depths of tissue;
one or more processing circuits configured to:
determine a plurality of L values at a plurality of different wavelengths using the plurality of PPG signals, wherein a first L value of the plurality of L values is determined using a first PPG signal obtained at a first wavelength in a range of 380 nm-410 nm and a second L value of the plurality of L values is determined using a second PPG signal obtained at a second wavelength equal to or above 660 nm and a third L value of the plurality of L values is determined using a third PPG signal obtained at a third wavelength in a range of 510 nm-550 nm;
determine a plurality of R values using the plurality of L values, wherein a first R value is determined from a ratio of the first L value and the second L value and a second R value is determined from a ratio of the first L value and the third L value;
determine one or more other PPG parameters using the plurality of PPG signals; and
determine a glucose level in blood flow using the plurality of L values, the plurality of R values and the one or more other PPG parameters.

2. The biosensor of claim 1, wherein the at least one processing circuit includes a first processing circuit configured to implement a regression neural network processing or a classifier neural network processing and wherein the plurality of L values, the plurality of R values and the one or more other PPG parameters are input into the first processing circuit to determine the glucose level.

3. The biosensor of claim 1, wherein the one or more other PPG parameters include at least one of: a phase delay between a first PPG signal and a second PPG signal of the plurality of PPG signals, a correlation of phase shape between the first PPG signal and the second PPG signal of the plurality of PPG signals or a periodicity of first PPG signal or the second PPG signal.

4. The biosensor of claim 1, wherein the processing circuit is further configured to determine a skin temperature and determine the glucose level using the plurality of L values, the plurality of R values, the one or more other PPG parameters and the skin temperature.

5. The biosensor of claim 1, wherein the plurality of R values further includes:
a third R value determined from a ratio of the second L value and the third L value.

6. A biosensor, comprising:
an optical circuit configured to obtain a plurality of PPG signals at a plurality of wavelengths reflected from tissue of a user, wherein the different wavelengths have varying penetration depths of tissue;
one or more processing circuits configured to:
determine one or more R values using the plurality of PPG signals, wherein an R value is determined from a ratio of AC components of a first PPG signal obtained from a first wavelength and a second PPG signal obtained at second wavelength;
determine a plurality of PPG parameters using the plurality of PPG signals, wherein the plurality of PPG parameters includes: a phase delay between the first PPG signal and the second PPG signal of the plurality of PPG signals, a correlation of phase shape between the first PPG signal and the second PPG signal of the plurality of PPG signals and a periodicity of at least the first PPG signal or the second PPG signal; and
determine a glucose level in blood flow of the user using the one or more R values and the plurality of PPG parameters.

7. The biosensor of claim 6, wherein the optical circuit is configured to obtain the first PPG signal at the first wavelength with a high absorption coefficient for nitric oxide (NO) in blood flow and the second PPG signal at the second wavelength with a low absorption coefficient for NO in blood flow.

8. The biosensor of claim 7, wherein the one or more R values include:
a first R value obtained using the first PPG signal at the first wavelength with the high absorption coefficient for nitric oxide (NO) in blood flow and the second PPG signal at the second wavelength with a low absorption coefficient for NO in blood flow;
a second R value obtained using the first PPG signal at the wavelength with the high absorption coefficient for nitric oxide (NO) in blood flow and a third PPG signal at a third wavelength with a different penetration depth than the first and second wavelength; and
a third R value obtained using the third PPG signal at the third wavelength and the second PPG signal at the second wavelength with the low absorption coefficient for NO in blood flow.

9. The biosensor of claim 6, wherein the processing circuit is further configured to determine the glucose level in blood flow of the user using the one or more R values, the plurality of PPG parameters and a plurality of L values, wherein the plurality of L values include:
a first L value determined using the first PPG signal at the first wavelength with a high absorption coefficient for nitric oxide (NO) in blood flow; and
a second L value determined using the second PPG signal at the second wavelength with a low absorption coefficient for NO in blood flow.

10. The biosensor of claim 6, wherein the one or more processing circuits are further configured to determine a skin temperature and determine the glucose level using the one or more R values, the plurality of PPG parameters and the skin temperature.

11. The biosensor of claim 6, wherein the one or more processing circuits implement a regression neural network processing or a classifier neural network processing to determine the glucose level.

12. The biosensor of claim 6, wherein the one or more processing circuits are further configured to determine one or more digital health parameters using the plurality of PPG signals.

13. The biosensor of claim 12, wherein the one or more digital health parameters includes a Vascular Health Index and wherein the processing circuit is configured to determine the Vascular Health Index using a measurement of a relative vasoconstriction of vessels during an insulin release event.

14. A biosensor, comprising:
an optical circuit configured to obtain a plurality of PPG signals at a plurality of wavelengths reflected from tissue of a user, wherein a first PPG signal is obtained at a first wavelength in a range of 380 nm-410 nm, a second PPG signal is obtained at a second wavelength equal to or above 660 nm, and a third PPG signal is obtained at a third wavelength in a range of 510 nm-550 nm;
a signal processing circuit configured to:
determine a plurality of L values at a plurality of different wavelengths using the plurality of PPG signals, wherein a first L value is determined by isolating an alternating current (AC) component of the first PPG signal and a second L value is determined by isolating an AC component of the second PPG signal and a third L value is determined by isolating an AC component of the third PPG signal;
determine a plurality of R values using the plurality of L values, wherein a first R value is determined from a ratio of the first L value and the second L value and a second R value is determined from a ratio of the first L value and the third L value; and
a neural network processing circuit that is configured to:
receive the plurality of L values and the plurality of R values as input; and
determine a glucose level in blood flow using the plurality of L values and the plurality of R values.

15. The biosensor of claim 14, wherein the optical circuit is configured to obtain a third PPG signal at a third wavelength with a different penetration of depth from the first wavelength and the second wavelength.

16. The biosensor of claim 14, wherein the neural network processing circuit is a regression neural network processing circuit or a classifier neural network processing circuit.

17. The biosensor of claim 16, wherein the signal processing circuit is further configured to:
determine a plurality of PPG parameters using the plurality of PPG signals, wherein the plurality of PPG parameters include at least: a phase delay between the first PPG signal and the second PPG signal of the plurality of PPG signals, a correlation of phase shape between the first PPG signal and the second PPG signal of the plurality of PPG signals and a periodicity of at least the first PPG signal or the second PPG signal.

18. The biosensor of claim 17, wherein the neural network processing circuit is further configured to determine the glucose level in blood flow using the plurality of L values, the plurality of R values, and the plurality of PPG parameters.

19. The biosensor of claim 14, wherein the processing circuit is further configured to determine one or more digital health parameters using the plurality of PPG signals.

20. The biosensor of claim 19, wherein the one or more digital health parameters includes a Vascular Health Index and wherein the processing circuit is configured to determine the Vascular Health Index using a measurement of a relative vasoconstriction of vessels during an insulin release event.

* * * * *